United States Patent
Sawada et al.

(10) Patent No.: US 9,000,186 B2
(45) Date of Patent: Apr. 7, 2015

(54) RING-FUSED HETEROCYCLIC DERIVATIVE

(75) Inventors: Takashi Sawada, Shizuoka (JP);
Tomohiro Danjo, Shizuoka (JP); Keiichi Motosawa, Shizuoka (JP); Takayuki Furuta, Yokohama (JP); Maki Ichioka, Shizuoka (JP); Masamori Sugawara, Mishima (JP); Noriaki Uesaka, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 13/983,248

(22) PCT Filed: Feb. 1, 2012

(86) PCT No.: PCT/JP2012/052224
§ 371 (c)(1),
(2), (4) Date: Oct. 21, 2013

(87) PCT Pub. No.: WO2012/105594
PCT Pub. Date: Aug. 9, 2012

(65) Prior Publication Data
US 2014/0038941 A1 Feb. 6, 2014

(30) Foreign Application Priority Data
Feb. 1, 2011 (JP) .................................. 2011-019742

(51) Int. Cl.
| C07D 235/02 | (2006.01) |
| C07D 471/04 | (2006.01) |
| A61K 31/4184 | (2006.01) |
| A61K 31/42 | (2006.01) |
| A61K 31/4355 | (2006.01) |
| A61K 31/4439 | (2006.01) |
| A61K 31/4525 | (2006.01) |
| A61K 31/497 | (2006.01) |
| A61K 31/519 | (2006.01) |
| C07D 487/04 | (2006.01) |
| C07D 519/00 | (2006.01) |

(52) U.S. Cl.
CPC .......... *C07D 471/04* (2013.01); *A61K 31/4184* (2013.01); *A61K 31/42* (2013.01); *A61K 31/4355* (2013.01); *A61K 31/4439* (2013.01); *A61K 31/4525* (2013.01); *A61K 31/497* (2013.01); *A61K 31/519* (2013.01); *C07D 487/04* (2013.01); *C07D 519/00* (2013.01)

(58) Field of Classification Search
USPC ..................................................... 548/302.7
See application file for complete search history.

(56) References Cited

U.S. PATENT DOCUMENTS

| 5,047,411 A | 9/1991 | Takasugi et al. |
| 5,420,138 A | 5/1995 | Corbier et al. |
| 5,498,774 A | 3/1996 | Mitsudera et al. |
| 8,236,841 B2 | 8/2012 | Sawada et al. |

(Continued)

FOREIGN PATENT DOCUMENTS

| EP | 0356234 A2 | 2/1990 |
| EP | 404190 A1 | 12/1990 |

(Continued)

OTHER PUBLICATIONS

Shin et al., "T-type $Ca^{2+}$ channels as therapeutic targets in the nervous system", Current Opinion in Pharmacology, vol. 8, 2008, p. 33-41.
Bezprozvanny et al., "Voltage-Dependent Blockade of Diverse Types of Voltage-Gated $Ca^{2+}$ Channels Expressed in *Xenopus* Oocytes by the $Ca^{2+}$ Channel Antagonist Mibefradil (Ro 40-5967)", Molecular Pharmacology, vol. 48, 1995, pp. 540-549.
Jagodic et al., "Cell-Specific Alterations of T-Type Calcium Current in Painful Diabetic Neuropathy Enhance Excitability of Sensory Neurons", The Journal of Neuroscience, 27(12):3305-3316 (2007).
Yasui et al., "Pathophysiological Significance of T-type $Ca^{2+}$ Channels: Expression of T-type $Ca^{2+}$ channels in Fetal and Diseased Heart", *Journal of Pharmacological Sciences* 99, 205-210 (2005).

(Continued)

*Primary Examiner* — James O Wilson
*Assistant Examiner* — Oluwafemi Masha
(74) *Attorney, Agent, or Firm* — Mintz Levin Cohn Ferris Glovsky and Popeo, P.C.; David G. Conlin

(57) ABSTRACT

A ring-fused heterocyclic derivative represented by the following general formula (I) or a pharmaceutically acceptable salt thereof having a T-type calcium channel regulatory effect and useful as a pruritus therapeutic and/or preventive agent, and the like are provided. In the general formula (I), $R^1$ represents optionally substituted lower alkyl, and the like; $R^2$ represents an optionally substituted cycloalkyl, and the like; Q represents a hydrogen atom, and the like; $R^3$ represents —C(=O)$NR^8R^9$ (wherein $R^8$ and $R^9$ may be the same or different, and each represents a hydrogen atom, and the like), and the like; $L^1$ represents —$CR^{11A}R^{11B}$— (wherein $R^{11A}$ and $R^{11B}$ may be the same or different, and each represents a hydrogen atom, and the like), and the like; and $W^1$ and $W^2$ may be the same or different, and each represents C—$R^{12}$ (wherein $R^{12}$ represents a hydrogen atom, and the like), and the like.

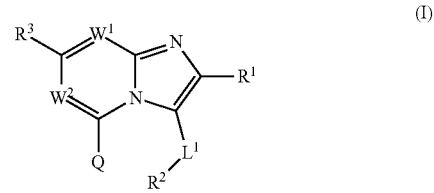

(I)

29 Claims, No Drawings

(56) References Cited

U.S. PATENT DOCUMENTS

| | | |
|---|---|---|
| 2003/0004181 A1 | 1/2003 | Hauel et al. |
| 2003/0236264 A1 | 12/2003 | Rogers et al. |
| 2004/0180947 A1 | 9/2004 | Kayakiri et al. |
| 2005/0197351 A1 | 9/2005 | Lee et al. |
| 2005/0239822 A1 | 10/2005 | Hennies et al. |
| 2006/0003985 A1 | 1/2006 | Renger et al. |
| 2006/0030610 A1 | 2/2006 | Koch et al. |
| 2006/0148801 A1 | 7/2006 | Hsieh et al. |
| 2006/0281750 A1 | 12/2006 | Li et al. |
| 2007/0049604 A1 | 3/2007 | Nam et al. |
| 2007/0173504 A1 | 7/2007 | Pacofsky et al. |
| 2008/0070888 A1 | 3/2008 | McKittrick et al. |
| 2008/0085896 A1 | 4/2008 | Lee et al. |
| 2008/0167287 A1 | 7/2008 | Zhuo et al. |
| 2009/0124612 A1 | 5/2009 | Albrecht et al. |
| 2009/0143376 A1 | 6/2009 | Milburn et al. |
| 2009/0234019 A1 | 9/2009 | Gray et al. |
| 2009/0239853 A1 | 9/2009 | Sawada et al. |
| 2010/0168084 A1 | 7/2010 | Huber et al. |
| 2010/0184800 A1 | 7/2010 | Pracitto et al. |
| 2010/0222387 A1 | 9/2010 | Barrow et al. |
| 2011/0053960 A1 | 3/2011 | Wu |
| 2011/0071128 A1 | 3/2011 | Alberati et al. |
| 2011/0112064 A1 | 5/2011 | Barrow et al. |
| 2012/0220457 A1 | 8/2012 | Miller et al. |
| 2013/0085133 A1 | 4/2013 | Severson et al. |

FOREIGN PATENT DOCUMENTS

| | | |
|---|---|---|
| EP | 1277754 | 1/2003 |
| EP | 01568695 A1 | 8/2005 |
| EP | 01757590 A1 | 2/2007 |
| FR | 2647451 | 5/1989 |
| JP | 10324688 | 12/1998 |
| JP | 2011-140452 | 7/2011 |
| WO | WO-91/08211 | 6/1991 |
| WO | WO-98/37075 A1 | 8/1998 |
| WO | WO-99/00372 A1 | 1/1999 |
| WO | WO-01/83481 A1 | 11/2001 |
| WO | WO-02/066477 | 8/2002 |
| WO | WO-02/066478 | 8/2002 |
| WO | WO-03/070732 | 8/2003 |
| WO | WO-2004/035000 A2 | 4/2004 |
| WO | WO-2006/023883 A2 | 3/2006 |
| WO | WO-2006/094235 A1 | 9/2006 |
| WO | WO-2006/101455 | 9/2006 |
| WO | WO-2007/002361 A2 | 1/2007 |
| WO | WO-2007/075852 A2 | 7/2007 |
| WO | WO-2007/120729 A2 | 10/2007 |
| WO | WO-2008/008539 A2 | 1/2008 |
| WO | WO-2008/032764 | 3/2008 |
| WO | WO-2008/032764 A1 | 3/2008 |
| WO | WO-2008/033447 A1 | 3/2008 |
| WO | WO-2008/064157 A1 | 5/2008 |
| WO | WO-2009/108798 | 9/2009 |
| WO | WO-2010/110428 | 9/2010 |
| WO | WO-2011/057145 A2 | 5/2011 |
| WO | WO-2011/097607 A1 | 8/2011 |

OTHER PUBLICATIONS

Sanfilippo et al., "Synthesis of (aryloxy)alkylamines. 2. Novel imidazo-fused heterocycles with calcium channel blocking and local anesthetic activity", Journal of Medicinal Chemistry, 1988, vol. 31, No. 11, pp. 2221-2227.

International Search Report mailed Mar. 13, 2012, in corresponding PCT Application No. PCT/JP2012/052224.

Perez-Reyes, "Molecular Physiology of Low-Voltage-Activated T-type Calcium Channels", Physiological Review, vol. 83, 2003, p. 117.

Iftinca et al., Regulation of neuronal T-type calcium channels,Trends in Pharmacological Science, vol. 30., 2009, p. 32.

Anderson et al., "Thalamic Cav3.1 T-type2+ channel plays a crucial role in stabilizing sleep", Proceedings of the National Academy of Science of the United States of America, vol. 102, 2005, p. 1743.

Lee et al., "Lack of delta waves and sleep disturbances during non-rapid eye movement sleep in mice lacking α1G-subunit of T-type calcium channels",Proceedings of the National Academy of Science of the United States of America, vol. 101, 2004, p. 18195.

Kim et al., "Lack of the Burst Firing of Thalamocortical Relay Neurons and Resistance to Absence Seizures in Mice Lacking α1G T-type Ca2+ Channels",Neuron, vol. 31, 2001, p. 35.

Chen et al., "Association between Genetic Variation of CACNA1H and Childhood Absence Epilepsy",Annals of Neurology, vol. 54, 2003, p. 239.

Cataldi et al., "Zn2+ Slows Down CaV3.3 Gating Kinetics: Implications for Thalamocortical Activity", Journal of Neurophysiology, vol. 98, 2007, p. 2274.

Todorovic et al., "Regulation of T-Type Calcium Channels in the Peripheral Pain Pathway", Channels, vol. 1, 2007, p. 238.

Bourinet et al., "Silencing of the Cav3.2 t-type calcium channel gene in sensory neurons demonstrates its major role in nociception",EMBO Journal, vol. 24, 2005, p. 315.

Na et al., "Attenuated Neuropathic Pain in Cav3.1 Null Mice", Molecular Cells, vol. 25, 2008, p. 242.

Wen et al., "Intrathecal administration of Cav3.2 and Cav3.3 antisense oligonucleotide reverses tactile allodynia and thermal hyperalgesia in rats following chronic compression of dorsal root of ganglion", Acta Pharmacologica Sinica, vol. 27, 2006, p. 1547.

Choi et al., "Attenuated pain responses in mice lacking Cav3.2 T-type channels",Genes, Brain and behavior, vol. 6, 2007, p. 425.

Dogrul et al., "Reversal of experimental neuropathic pain by T-type calcium channel blockers",Pain, vol. 105, 2003, p. 159-168.

Flatters et al., "Ethosuximide reverses paclitaxel- and vincristine-induced painful peripheral neuropathy", Pain, vol. 109, 2004, p. 150-161.

Messinger et al., "In vivo silencing of the Cav3.2 T-type calcium channels in sensory neurons alleviates hyperalgesia in rats with streptozocin-induced diabetic neuropathy",Pain, vol. 145, 2009, p. 184-195.

Ono et al., "Pathophysiological Significance of T-type Ca2 Channels: Properties and Functional Roles of T-type Ca2+ Channels in Cardiac Pacemaking", Journal of Pharmacological Sciences, vol. 99, 2005, p. 197-204.

Kuwahara et al., "Pathophysiological Significance of T-type Ca2+ Channels: Transcriptional Regulation of T-type Ca2+ Channel—Regulation of CACNA1H by Neuron-Restrictive Silencer Factor", Journal of Pharmacological Sciences, vol. 99, 2005, p. 211-213.

Tanaka et al., "Pathophysiological Significance of T-type Ca2+ Channels: T-type Ca2+ Channels and Drug Development", Journal of Pharmacological Sciences, vol. 99, 2005, p. 214-220.

Baylis et al., "Comparison of L-Type and Mixed L- and T-Type Calcium Channel Blockers on Kidney Injury Caused by Deoxycorticosterone-Salt Hypertension in Rats", American Journal of Kidney Disease, vol. 38, 2001, p. 1292-1297.

Hayashi et al., "Pathophysiological Significance of T-type Ca2+ Channels: Role of T-type Ca2+ Channels in Renal Microcirculation" Journal of Pharmacological Science, Journal of Pharmacological Science, vol. 99, 2005, p. 221-227.

Hayashi et al., "Ca2+ Cannel Subtypes and Pharmacology in the Kidney",Circulation Research, vol. 100, 2007, p. 342.

Bilici et al., "Protective Effect of T-Tpe Calcium Channel Blocker in Histamine-Induced Paw Inflammation in Rat", Pharmacological Research, vol. 44, 2001, p. 527.

Noll et al., "Comparative Pharmacological Properties among Calcium Channel Blockers: T-Channel versus L-Channel Blockade", Cardiology, vol. 89, 1998, p. 10-15.

Rossier et al., "Inhibitory Action of Mibefradil on Calcium Signaling and Aldosterone Synthesis in Bovine Adrenal Glomerulosa Cells1", The Journal of Pharmacology and Experimental Therapeutics, vol. 287, 1998, p. 824-831.

Gray et al., "The role of voltage gated T-type Ca2+ channel isoforms in mediating "capacitative" Ca2+ entry in cancer cells",Cell Calcium, vol. 36, 2004, p. 489-497.

(56) References Cited

OTHER PUBLICATIONS

Bertolesi et al., "The Ca2+ Channel Antagonists Mibefradil and Pimozide Inhibit Cell Growth via Different Cytotoxic Mechanisms", Molecular Phaarmacology, vol. 62, 2002, p. 210.

Shen et al., "Prophylactic and therapeutic functions of T-type calcium blockers against noise-induced hearing loss", Hearing Research, vol. 226, 2007, p. 52-60.

Harada et al., "Clinical Efficacy of Efonidipine Hydrochloride, a T-type Calcium Channel Inhibitor, on Sympathetic Activities—Examination Using Spectral Analysis of Heart Rate/Blood Pressure Variabilities and 123I-Metaiodobenzylguanidine Myocardinal Scintigraphy-", Circulation Journal, vol. 67, 2003, pp. 139-145.

Levine et al., "Effect of Mibefradil, a T-Type Calcium Channel Blocker, on Morbidity and Mortality in Moderate to Severe Congestive Heart Failure: The MACH-1 Study", Circulation, vol. 101, 2001, p. 758-764.

Ishimitsu et al., "Efonidipine Reduces Proteinuria and Plasma Aldosterone in Patients with Chronic Glomerulonephritis", Hypertension Research, vol. 30, 2007, p. 621.

Shin et al., "T-type Ca2+ channels as therapeutic targets in the nervous system", Current Opinion in Pharmacology, vol. 8, 2008, p. 33-41.

Bezprozvanny et al., "Voltage-Dependent Blockade of Diverse Types of Voltage-Gated Ca2+ Channels Expressed in *Xenopus* Oocytes by the Ca2+ Channel Antagonist Mibefradil (Ro 40-5967)", Molecular PHarmacology, vol. 48, 1995, pp. 540-549.

RING-FUSED HETEROCYCLIC DERIVATIVE

CROSS-REFERENCE TO RELATED APPLICATIONS

This application is the U.S. national phase application pursuant to 35 U.S.C. §371 of PCT International Patent Application No. PCT/JP2012/052224, filed Feb. 1, 2012, which claims priority to Japanese Patent Application No. 2011-019742, filed Feb. 1, 2011. The contents of these applications are incorporated herein by reference in their entirety.

TECHNICAL FIELD

The present invention relates to a novel ring-fused heterocyclic derivative or a pharmaceutically acceptable salt thereof having a T-type calcium channel regulatory effect and useful as a therapeutic and/or preventive agent for pruritus, and the like, and to a T-type calcium channel inhibitor and the like that contain a ring-fused heterocyclic derivative or a pharmaceutically acceptable salt thereof as an active ingredient.

BACKGROUND ART

Voltage-dependent calcium channels are ion channels that cause influx of calcium ions into cells under the potential difference between the interior and the exterior of a cell, and are known to have important biological functions, including neuronal excitation, synaptic transmission, muscle contraction, cardiac automaticity, secretion of neurotransmitters and hormones, cell proliferation and differentiation, and the like. Voltage-dependent calcium channels have been classified into any of the five categories T, L, P/Q, N, and R by their electrophysiological and pharmacological properties [Physiological Review, Vol. 83, p. 117 (2003)]. Of these five channels, only the T-type channels are activated by high membrane potentials, and are called low-voltage-activated channels. The other four channels are called high-voltage-activated (hereinafter, "HVA") channels, because of their activation at low membrane potentials. As the name suggests, the T (transient)-type calcium channels are characterized by transient activation and quick inactivation. On the other hand, the HVA channels require a long time for inactivation.

It is known that the HVA channels basically function as a heterotetramer having $\alpha 1$, $\alpha 2/8$, $\beta$, and $\gamma$ subunits. The $\alpha 1$ subunit is the subunit that forms a channel pore, whereas the other subunits function as regulatory or accessory subunits. On the other hand, it is believed that the T-type calcium channels function with the $\alpha 1$ subunit alone. To date, ten $\alpha 1$ subunits are known in voltage-dependent calcium channels, and three of these $\alpha 1$ subunits, $\alpha 1G$ (Cav3.1), $\alpha 1H$ (Cav3.2), and $\alpha 1I$ (Cav3.3) are known to form the T-type calcium channels.

The expression of T-type calcium channels has been confirmed in various regions, including the peripheral and central nervous systems, heart, kidneys, smooth muscle, skeletal muscle, endocrine cells, bone, sperm, and the like. As physiological functions of the T-type calcium channels, neuronal firing, sleeping, pain transmission, heart's pacemaker function, renovascular tonus, hormone secretion, fertilization, and the like are reported [Physiological Review, Vol. 83, p. 117 (2003); Trends in Pharmacological Science, Vol. 30, p. 32 (2008); Proceedings of the National Academy of Science of the United States of America, Vol. 102, p 1743 (2005); Proceedings of the National Academy of Science of the United States of America, Vol. 101, p. 18195 (2004)].

As a disease associated with enhancement of the T-type calcium channels, epilepsy [Neuron, Vol. 31, p. 35 (2001); Annals of Neurology, Vol. 54, p. 239 (2003); Journal of Neurophysiology, Vol. 98, p. 2274 (2007)], pain [Channels, Vol. 1, p. 238 (2007); EMBO Journal, Vol. 24, p. 315 (2005); Journal of Neuroscience, Vol. 27, p. 3305 (2007); Molecular Cells, Vol. 25, p. 242 (2008); Acta Pharamacologica Sinica, Vol. 27, p. 1547 (2006); Genes, Brain and Behavior, Vol. 6, p. 425 (2007); Pain, Vol. 105, p. 159 (2003); Pain, Vol. 109, p. 150 (2004); Pain, Vol. 145, p. 184 (2009)], heart disease [Journal of Pharmacological Sciences, Vol. 99, p. 197 (2005); Journal of Pharmacological Sciences, Vol. 99, p. 205 (2005); Journal of Pharmacological Sciences, Vol. 99, p. 211 (2005); Journal of Pharmacological Sciences, Vol. 99, p. 214 (2005)], kidney disease [American Journal of Kidney Disease, Vol. 38, p. 1241 (2001); Journal of Pharmacological Science, Vol. 99, p. 221 (2005); Circulation Research, Vol. 100, p. 342 (2007)], inflammation and edema [Pharmacological Research, Vol. 44, p. 527 (2001)], arteriosclerosis [Cardiology, Vol. 89, p. 10 (1998)], aldosteronism [The Journal of Pharmacology and Experimental Therapeutics, Vol. 287, p. 824 (1998)], cancer [Cell Calcium, Vol. 36, p. 489 (2004); Molecular Pharmacology, Vol. 62, p. 210 (2002)], hearing impairment [Hearing Research, Vol. 226, p. 52 (2007)], and the like have been reported. T-type calcium channel antagonists are thus considered effective for the treatment or prevention of these diseases. In fact, the cardioprotective effect [Circulation Journal, Vol. 67, 139-145 (2003); Circulation, Vol. 101, p. 758 (2000)] and the renoprotective effect [Hypertension Research, Vol. 30, p. 621 (2007)] of T-type calcium channel antagonists are reported in the clinic. Further, involvement of T-type calcium channels in sleeping [Proceedings of the National Academy of Science of the United States of America, Vol. 102, p. 1743 (2005); Proceedings of the National Academy of Science of the United States of America, Vol. 101, p. 18195 (2004)] is reported, and their antagonists are potentially effective for the treatment and/or prevention of sleep disorder [Current Opinion in Pharmacology, Vol. 8, p. 33 (2008)]. Further, in recent years, it was reported that T-type calcium channel antagonists may be effective for the treatment and/or prevention of pruritus (WO2010/110428).

From among the compounds that act on the T-type calcium channels, many compounds are known as, for example, T-type calcium channel inhibitors. Examples include efonidipine (see, Non-Patent Documents 1 and 2), mibefradil (see, Non-Patent Document 3), diphenylmethane derivatives (see, Patent Document 1), dihydroquinazoline derivatives (see, Patent Documents 2 and 3), piperidine derivatives (see, Patent Document 4), piperazine derivatives (see, Patent Document 5), azetidine and azetidone derivatives (see, Patent Document 6), thiazole derivatives (see, Patent Document 7), pyridine derivatives (see, Patent Document 8), and the like.

On the other hand, as the known imidazopyridine derivatives, imidazo[1,2-a]pyridine derivatives (A) having arylamino at the 7-position (see Patent Document 9), imidazo[1,2-a]pyridine derivatives (B) having aryl at the 2- or 3-position (see Patent Document 10), and the like are known. Also, imidazo[1,2-a]pyridine derivatives (C) having aminoalkyl at the 3-position (see Patent Document 11), imidazo[1,2-a]pyridine derivatives (D) having aralkyl at the 3-position (see Patent Document 12), imidazo[1,2-a]pyridine derivatives (E) having cycloalkyl at also the 3-position (see Patent Document 13), and the like are known. Yet imidazo[1,2-a]pyridine derivatives (F) having cycloalkylamino and the like at the 3-position (see Patent Document 14), imidazo[1,2-a]pyridine derivatives (G) having aroyl and the like at the 3-position (see Patent Document 15), imidazo[1,2-a]pyridine derivatives (H)

having a hydroxamic acid side chain at the 7-position (see Patent Document 16), imidazo[1,2-a]pyridine derivatives (I) (see Patent Document 17) and (J) (see Patent Document 18) having a carbamoyl group at the 7-position, and the like are known. Compounds described in Patent Documents 20 to 35 are known yet as other examples of the imidazo[1,2-a]pyridine derivatives.

Furthermore, the imidazopyrimidine derivatives include imidazo[1,2-c]pyrimidine derivatives (K) having a carbamoyl group at the 7-position (see Patent Document 18), imidazo[1,2-a]pyrimidine derivatives (L) having aralkyl at the 3-position (see Patent Document 19), and the like are known.

[Chemical Formula 1]

(A)
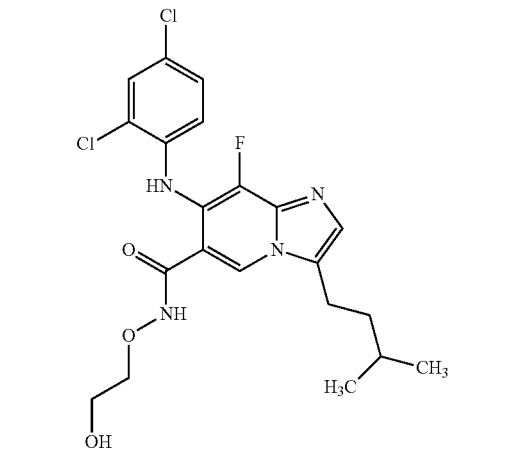

(B)
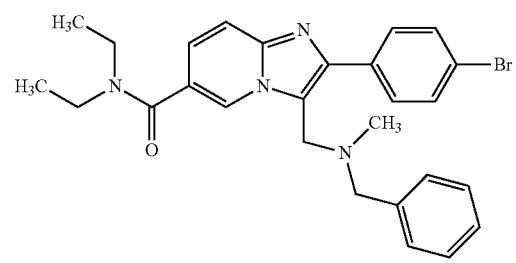

(C)
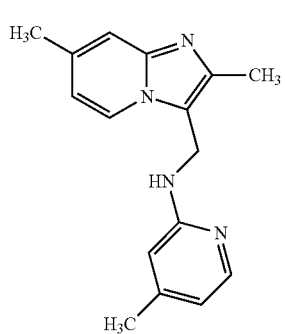

(D)
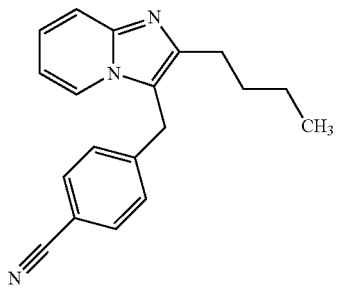

(E)
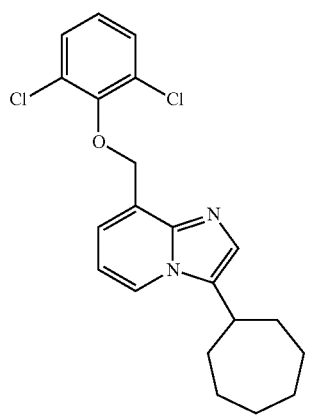

(F)
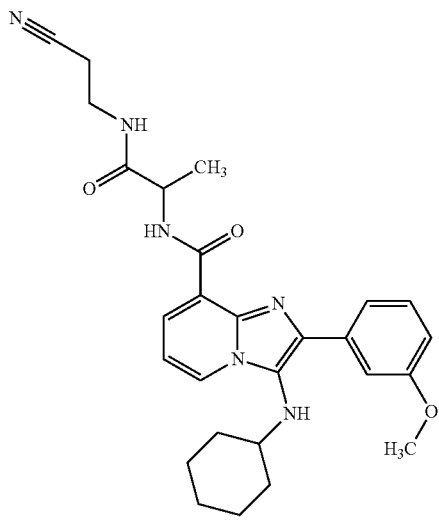

(G)
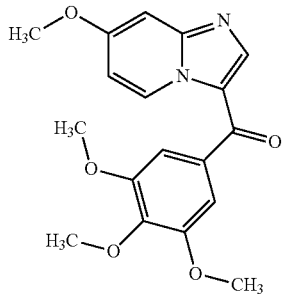

-continued (H)
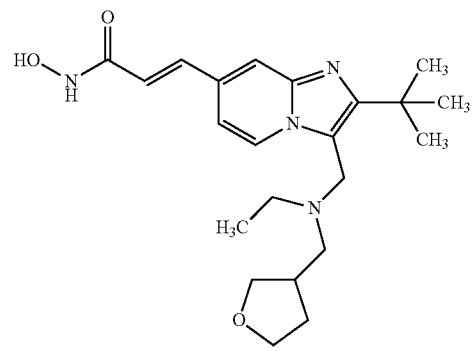

(I)
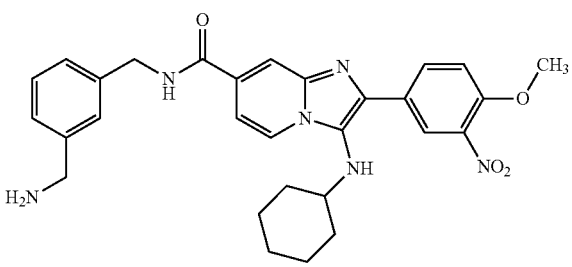

(J)
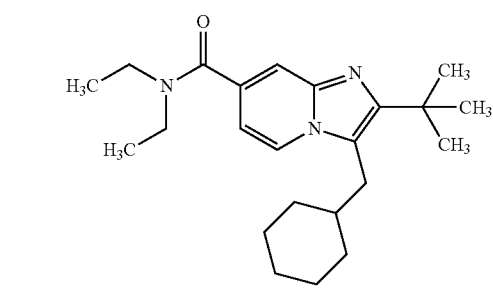

(K)
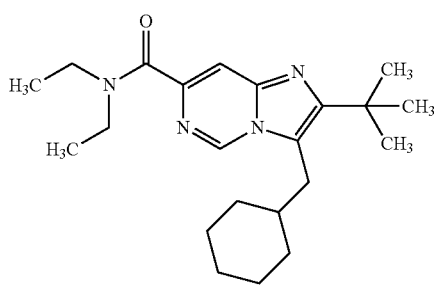

(L)
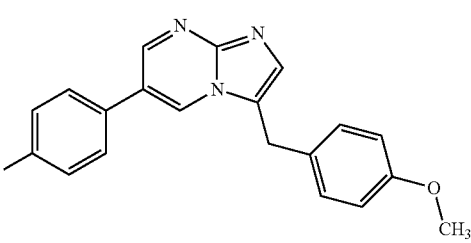

PRIOR ART DOCUMENTS

Patent Documents

Patent Document 1: WO2006/023883
Patent Document 2: WO2004/035000
Patent Document 3: Publication of European Patent Application 01568695
Patent Document 4: WO2007/002361
Patent Document 5: Publication of European Patent Application 01757590
Patent Document 6: WO2008/033447
Patent Document 7: WO2007/075852
Patent Document 8: WO2007/120729
Patent Document 9: Publication of US Patent Application 2006/030610
Patent Document 10: WO2002/066478
Patent Document 11: Publication of US Patent Application 2005/0239822
Patent Document 12: U.S. Pat. No. 5,420,138
Patent Document 13: Publication of US Patent Application 2006/0281750
Patent Document 14: WO2006/094235
Patent Document 15: Publication of US Patent Application 2006/0148801
Patent Document 16: Publication of US Patent Application 2008/0085896
Patent Document 17: WO2006/094235
Patent Document 18: WO2008/032764
Patent Document 19: WO2008/064157
Patent Document 20: WO2002/066477
Patent Document 21: WO1999/00372
Patent Document 22: WO2008/008539
Patent Document 23: WO2006/101455
Patent Document 24: WO2003/070732
Patent Document 25: Japanese Published Unexamined Patent Application No. 324688/1998
Patent Document 26: WO1991/08211
Patent Document 27: Publication of US Patent Application 2010/0168084
Patent Document 28: WO2011/097607
Patent Document 29: Japanese Published Unexamined Patent Application No. 2011-140452
Patent Document 30: WO2011/057145
Patent Document 31: Publication of US Patent Application 2010/0184800
Patent Document 32: WO1998/37075
Patent Document 33: Publication of European Patent Application 356234
Patent Document 34: WO2001/083481
Patent Document 35: Publication of European Patent Application 404190

Non-Patent Documents

Non-Patent Document 1: Circulation Journal, 2003, Vol. 67, pp. 139-145
Non-Patent Document 2: Hypertension Research, 2007, Vol. 30, pp. 621-626
Non-Patent Document 3: Molecular Pharmacology, 1995, Vol. 48, pp. 540-549

DISCLOSURE OF THE INVENTION

Problems that the Invention is to Solve

It is an object of the present invention to provide a novel ring-fused heterocyclic derivative or a pharmaceutically acceptable salt thereof and the like having a T-type calcium channel regulatory effect and useful as, for example, a T-type calcium channel inhibitor, a therapeutic and/or preventive agent for pruritus, and the like. Another object is to provide a T-type calcium channel inhibitor and the like that contain a ring-fused heterocyclic derivative or a pharmaceutically acceptable salt thereof as an active ingredient.

Means for Solving the Problems

The present invention relates to the following (1) to (35).

(1) A T-type calcium channel inhibitor which comprises, as an active ingredient, a ring-fused heterocyclic derivative represented by the general formula (I) or a pharmaceutically acceptable salt thereof,

[Chemical Formula 2]

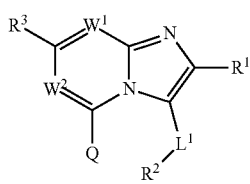

(I)

[wherein $R^1$ represents optionally substituted lower alkyl, optionally substituted lower alkenyl, optionally substituted cycloalkyl, optionally substituted lower alkoxy, an optionally substituted aromatic heterocyclic group, an optionally substituted aliphatic heterocyclic group, optionally substituted aralkyl, —C(=O)$R^4$ (wherein $R^4$ represents optionally substituted lower alkyl, optionally substituted aralkyl, optionally substituted cycloalkyl, or an optionally substituted aliphatic heterocyclic group), —C(=O)O$R^4$ (wherein $R^4$ has the same definition as described above), —C(=O)N$R^5R^6$ (wherein $R^5$ and $R^6$ may be the same or different, and each represents a hydrogen atom, optionally substituted lower alkyl, or optionally substituted aralkyl), —N$R^7$C(=O)O$R^4$ (wherein $R^4$ has the same definition as described above, and $R^7$ represents a hydrogen atom, or optionally substituted lower alkyl), or —S(O)$_n R^4$ (wherein $R^4$ has the same definition as described above, and n represents an integer of 0 to 2), $R^2$ represents optionally substituted cycloalkyl, optionally substituted aryl, an optionally substituted aromatic heterocyclic group, an optionally substituted aliphatic heterocyclic group, optionally substituted lower alkyl, optionally substituted lower alkenyl, or optionally substituted lower alkynyl, Q represents a hydrogen atom, halogen, optionally substituted lower alkyl, optionally substituted cycloalkyl, or optionally substituted lower alkoxy, $R^3$ represents (i) —C(=O)N$R^8R^9$ {wherein $R^8$ and $R^9$ may be the same or different, and each represents a hydrogen atom, optionally substituted lower alkyl, optionally substituted lower alkenyl, optionally substituted cycloalkyl, optionally substituted cycloalkenyl, optionally substituted aralkyl, optionally substituted aryl, an optionally substituted aromatic heterocyclic group, an optionally substituted aliphatic heterocyclic group, or —O$R^{10}$ (wherein $R^{10}$ represents optionally substituted lower alkyl, optionally substituted lower alkenyl, optionally substituted cycloalkyl, optionally substituted aralkyl, optionally substituted aryl, an optionally substituted aromatic heterocyclic group, or an optionally substituted aliphatic heterocyclic group), or $R^8$ and $R^9$ are combined together with the adjacent nitrogen atom thereto to form an optionally substituted nitrogen-containing heterocyclic group}, (ii) —C(=O)N$R^{7A}$—N$R^{7B}$C(=O)$R^{10}$ (wherein $R^{7A}$ and $R^{7B}$ may be the same or different, and each has the same definition as the above $R^7$, and $R^{10}$ has the same definition as described above), (iii) —N$R^{7A}$C(=O)$R^{10}$ (wherein $R^{7A}$ and $R^{10}$ have the same definitions as described above, respectively), (iv) —N$R^{7A}$C(=O)N$R^8R^9$ (wherein $R^{7A}$ has the same definition as described above, and $R^8$ and $R^9$ may be the same or different, and have the same definitions as described above, respectively), (v) —N$R^{7A}$C(=O)O$R^{19}$ (wherein $R^{7A}$ and $R^{10}$ have the same definitions as described above, respectively), (vi) —SO$_2$N$R^8R^9$ (wherein $R^8$ and $R^9$ may be the same or different, and have the same definitions as described above, respectively), (vii) —N$R^{7A}$SO$_2R^{10}$ (wherein $R^{7A}$ and $R^{10}$ have the same definitions as described above, respectively), (viii) —N$R^{7A}$SO$_2$N$R^8R^9$ (wherein $R^{7A}$ has the same definition as described above, and $R^8$ and $R^9$ may be the same or different, and have the same definitions as described above, respectively), or (ix) optionally substituted benzimidazol-2-yl, $L^1$ represents —C$R^{11A}R^{11B}$— (wherein $R^{11A}$ and $R^{11B}$ may be the same or different, and each represents a hydrogen atom, optionally substituted lower alkyl, halogen, optionally substituted lower alkoxy, or hydroxy), or (C$R^{11A}R^{11B}$)$n^1$-$L^2$-{wherein $R^{11A}$ and $R^{11B}$ may be the same or different, and have the same definitions as described above, respectively, $n^1$ represents an integer of 0 to 1, and $L^2$ represents —C(=O)—, —O—, —S(O)$n^2$- (wherein $n^2$ has the same definition as the above n), or —SO$_2$N$R^{7C}$— (wherein $R^{7C}$ represents a hydrogen atom, optionally substituted lower alkyl, or optionally substituted cycloalkyl)}, or -$L^1$-$R^2$ represents —C$R^{7C}$=C$R^AR^B$ (wherein $R^{7C}$ has the same definition as described above, and $R^A$ and $R^B$ are combined together with the carbon atom attached thereto to form optionally substituted cycloalkyl or an optionally substituted aliphatic heterocyclic group), and $W^1$ and $W^2$ may be the same or different, and each represents a nitrogen atom, or C—$R^{12}$ (wherein $R^{12}$ represents a hydrogen atom, halogen, optionally substituted lower alkyl, optionally substituted cycloalkyl, optionally substituted lower alkoxy, or optionally substituted lower alkenyl)].

(2) A ring-fused heterocyclic derivative represented by the general formula (IA) or a pharmaceutically acceptable salt thereof,

[Chemical Formula 3]

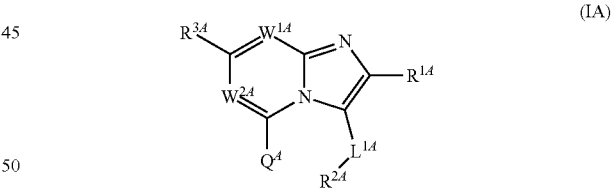

(IA)

[wherein $R^{1A}$ has the same definition as the above $R^1$, $R^{2A}$ has the same definition as the above $R^2$, and $Q^A$ has the same definition as the above Q, $R^{3A}$ represents (i) —C(=O)NH$R^{9A}$ {wherein $R^{9A}$ represents a hydrogen atom, optionally substituted lower alkyl, optionally substituted lower alkenyl, optionally substituted cycloalkyl, optionally substituted cycloalkenyl, optionally substituted aralkyl, optionally substituted aryl, an optionally substituted aromatic heterocyclic group, an optionally substituted aliphatic heterocyclic group, or —O$R^{10}$ (wherein $R^{10}$ has the same definition as described above)}, (ii) —C(=O)N$R^{7A}$—N$R^{7B}$C(=O)$R^{10}$ (wherein $R^{7A}$ and $R^{7B}$ may be the same or different, and each has the same definition as the above $R^7$, and $R^{10}$ has the same definition as described above), (iii) —NHC(=O) $R^{10}$ (wherein $R^{10}$ has the same definition as described above), (iv) —NHC(=O)NR$^{8A}$R$^{9A}$ (wherein R$^{8A}$ and R$^{9A}$ may be the same or different, and have the same definition as the above R$^{9A}$), (v) —NR$^{7A}$C(=O)OR$^{10}$ (wherein R$^{7A}$ and R$^{10}$ have the same definitions as described above, respectively), (vi) —SO$_2$NR$^{8A}$R$^{9A}$ (wherein R$^{8A}$ and R$^{9A}$ may be the same or different, and each has the same definition as the above R$^{9A}$), (vii) —NHSO$_2$R$^{10}$ (wherein R$^{10}$ has the same definition as described above), (viii) —NHSO$_2$NR$^{8A}$R$^{9A}$ (wherein R$^{8A}$ and R$^{9A}$ may be the same or different, and each has the same definition as the above R$^{9A}$), or (ix) optionally substituted benzimidazol-2-yl, L$^{1A}$ represents —CR$^{11A}$R$^{11B}$— (wherein R$^{11A}$ and R$^{11B}$ may be the same or different, and have the same definitions as described above, respectively), or —(CR$^{11A}$R$^{11B}$)n$^1$-L$^2$- (wherein R$^{11A}$, R$^{11B}$, n$^1$, and L$^2$ have the same definitions as described above, respectively), or -L$^{1A}$-R$^{2A}$ represents —CR$^{7C}$=CR$^A$R$^B$ (wherein R$^{7C}$, R$^A$, and R$^B$ have the same definitions as described above, respectively), and W$^{1A}$ and W$^{2A}$ may be the same or different, and each represents a nitrogen atom, or C—R$^{12}$ (wherein R$^{12}$ has the same definition as described above)].

(3) The ring-fused heterocyclic derivative or a pharmaceutically acceptable salt thereof according to (2), wherein R$^{1A}$ is optionally substituted lower alkyl or optionally substituted cycloalkyl.

(4) The ring-fused heterocyclic derivative or a pharmaceutically acceptable salt thereof according to (2), wherein R$^{1A}$ is optionally substituted lower alkyl.

(5) The ring-fused heterocyclic derivative or a pharmaceutically acceptable salt thereof according to (2), wherein R$^{1A}$ is halogen-substituted lower alkyl.

(6) The ring-fused heterocyclic derivative or a pharmaceutically acceptable salt thereof according to (2), wherein R$^{1A}$ is optionally substituted cycloalkyl.

(7) The ring-fused heterocyclic derivative or a pharmaceutically acceptable salt thereof according to any one of (2) to (6), wherein R$^{2A}$ is optionally substituted cycloalkyl.

(8) The ring-fused heterocyclic derivative or a pharmaceutically acceptable salt thereof according to any one of (2) to (6), wherein R$^{2A}$ is an optionally substituted aliphatic heterocyclic group.

(9) The ring-fused heterocyclic derivative or a pharmaceutically acceptable salt thereof according to any one of (2) to (8), wherein L$^{1A}$ is —CR$^{11A}$R$^{11B}$— (wherein R$^{11A}$ and R$^{11B}$ may be the same or different, and have the same definitions as described above, respectively).

(10) The ring-fused heterocyclic derivative or a pharmaceutically acceptable salt thereof according to (9), wherein R$^{11A}$ and R$^{11B}$ are hydrogen atoms.

(11) The ring-fused heterocyclic derivative or a pharmaceutically acceptable salt thereof according to any one of (2) to (8), wherein L$^{1A}$ is —(CR$^{11A}$R$^{11B}$)n$^1$-L$^2$- (wherein R$^{11A}$, R$^{11B}$, n$^1$, and L$^2$ have the same definitions as described above, respectively).

(12) The ring-fused heterocyclic derivative or a pharmaceutically acceptable salt thereof according to (11), wherein n$^1$ is 0.

(13) The ring-fused heterocyclic derivative or a pharmaceutically acceptable salt thereof according to (11), wherein n$^1$ is 1.

(14) The ring-fused heterocyclic derivative or a pharmaceutically acceptable salt thereof according to any one of (11) to (13), wherein L$^2$ is —O—.

(15) The ring-fused heterocyclic derivative or a pharmaceutically acceptable salt thereof according to any one of (11) to (13), wherein L$^2$ is —S(O)n$^2$- (wherein n$^2$ has the same definition as described above).

(16) The ring-fused heterocyclic derivative or a pharmaceutically acceptable salt thereof according to (15), wherein n$^2$ is 2.

(17) The ring-fused heterocyclic derivative or a pharmaceutically acceptable salt thereof according to any one of (11) to (13), wherein L$^2$ is —SO$_2$NR$^{7C}$— (wherein R$^{7C}$ has the same definition as described above).

(18) The ring-fused heterocyclic derivative or a pharmaceutically acceptable salt thereof according to any one of (2) to (17), wherein Q$^A$ is a hydrogen atom, halogen, or optionally substituted lower alkyl.

(19) The ring-fused heterocyclic derivative or a pharmaceutically acceptable salt thereof according to any one of (2) to (17), wherein Q$^A$ is a hydrogen atom.

(20) The ring-fused heterocyclic derivative or a pharmaceutically acceptable salt thereof according to any one of (2) to (17), wherein Q$^A$ is halogen.

(21) The ring-fused heterocyclic derivative or a pharmaceutically acceptable salt thereof according to any one of (2) to (17), wherein Q$^A$ is optionally substituted lower alkyl.

(22) The ring-fused heterocyclic derivative or a pharmaceutically acceptable salt thereof according to any one of (2) to (21), wherein R$^{3A}$ is —NHC(=O)R$^{10}$ (wherein R$^{10}$ has the same definition as described above).

(23) The ring-fused heterocyclic derivative or a pharmaceutically acceptable salt thereof according to any one of (2) to (21), wherein R$^{3A}$ is —C(=O)NHR$^{9A}$ (wherein R$^{9A}$ has the same definition as described above).

(24) The ring-fused heterocyclic derivative or a pharmaceutically acceptable salt thereof according to (23), wherein R$^{9A}$ is optionally substituted lower alkyl, optionally substituted aryl, an optionally substituted aromatic heterocyclic group, or an optionally substituted aliphatic heterocyclic group.

(25) The ring-fused heterocyclic derivative or a pharmaceutically acceptable salt thereof according to (23), wherein R$^{9A}$ is optionally substituted lower alkyl.

(26) The ring-fused heterocyclic derivative or a pharmaceutically acceptable salt thereof according to (23), wherein R$^{9A}$ is optionally substituted aryl.

(27) The ring-fused heterocyclic derivative or a pharmaceutically acceptable salt thereof according to (23), wherein R$^{9A}$ is an optionally substituted aromatic heterocyclic group.

(28) The ring-fused heterocyclic derivative or a pharmaceutically acceptable salt thereof according to (23), wherein R$^{9A}$ is an optionally substituted aliphatic heterocyclic group.

(29) The ring-fused heterocyclic derivative or a pharmaceutically acceptable salt thereof according to any one of (2) to (28), wherein W$^{1A}$ and W$^{2A}$, may be the same or different, and each is C—R$^{12}$ (wherein R$^{12}$ has the same definition as described above).

(30) The ring-fused heterocyclic derivative or a pharmaceutically acceptable salt thereof according to (2) to (29), wherein W$^{1A}$ is C—R$^{12A}$ (wherein R$^{12A}$ represents a hydrogen atom).

(31) The ring-fused heterocyclic derivative or a pharmaceutically acceptable salt thereof according to (2) to (30), wherein W$^{2A}$ is C—R$^{12B}$ (wherein R$^{12B}$ represents a hydrogen atom).

(32) The ring-fused heterocyclic derivative or a pharmaceutically acceptable salt thereof according to (2) to (30), wherein W$^{2A}$ is C—R$^{12C}$ (wherein R$^{12C}$ represents halogen).

(33) A T-type calcium channel inhibitor which comprises, as an active ingredient, the ring-fused heterocyclic derivative or a pharmaceutically acceptable salt thereof described in any one of (2) to (32).

(34) A therapeutic and/or preventive agent for a disease associated with a T-type calcium channel, which comprises, as an active ingredient, the ring-fused heterocyclic derivative or a pharmaceutically acceptable salt thereof described in any one of (2) to (32).

(35) A therapeutic and/or preventive agent for pruritus, which comprises, as an active ingredient, the ring-fused heterocyclic derivative or a pharmaceutically acceptable salt thereof described in any one of (2) to (32).

Effect of the Invention

The present invention provides a novel ring-fused heterocyclic derivative or a pharmaceutically acceptable salt thereof and the like having a T-type calcium channel inhibitory effect and useful as a therapeutic and/or preventive agent for pruritus and the like. The invention also provides a T-type calcium channel inhibitor and the like that contains such a ring-fused heterocyclic derivative or a pharmaceutically acceptable salt thereof as an active ingredient.

MODE FOR CARRYING OUT THE INVENTION

In the following, a compound represented by general formula (I) will be referred to as compound (I). The compounds having the other formula numbers are referred to in the same manner.

In the definition of each group in the general formula (I) and (IA),

Examples of the lower alkyl and the lower alkyl moiety of the lower alkoxy include linear or branched alkyl having 1 to 10 carbon atoms, more specifically, methyl, ethyl, propyl, isopropyl, butyl, isobutyl, sec-butyl, tert-butyl, pentyl, isopentyl, neopentyl, hexyl, heptyl, octyl, nonyl, decyl, and the like.

Examples of the lower alkenyl include linear or branched alkenyl having 2 to 10 carbon atoms, more specifically, vinyl, allyl, 1-propenyl, butenyl, pentenyl, hexenyl, heptenyl, octenyl, nonenyl, decenyl, and the like.

Examples of the lower alkynyl include linear or branched alkynyl having 2 to 10 carbon atoms, more specifically, ethynyl, propynyl, butynyl, pentynyl, hexynyl, heptynyl, octynyl, nonynyl, decynyl, and the like.

Examples of the cycloalkyl include cycloalkyl having to 8 carbon atoms, more specifically, cyclopropyl, cyclobutyl, cyclopentyl, cyclohexyl, cycloheptyl, cyclooctyl, and the like.

Examples of the cycloalkenyl include cycloalkenyl having 3 to 8 carbon atoms, more specifically, cyclopropenyl, cyclobutenyl, cyclopentenyl, cyclohexenyl, cycloheptenyl, cyclooctenyl, and the like.

Examples of the aralkyl include aralkyl having 7 to 16 carbon atoms, more specifically, benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl, and the like.

Examples of the aryl include aryl having 6 to 14 carbon atoms, more specifically, phenyl, naphthyl, azulenyl, anthryl, and the like.

Examples of the aliphatic heterocyclic group include 5- to 7-membered monocyclic aliphatic heterocyclic groups containing at least one atom selected from a nitrogen atom, an oxygen atom, and a sulfur atom, and bicyclic or tricyclic fused-ring aliphatic heterocyclic groups of 3- to 8-membered rings fused to one another containing at least one atom selected from a nitrogen atom, an oxygen atom, and a sulfur atom. Specific examples include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, 4,5-dihydro-1,3-thiazolyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzoimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, dioxanyl, oxetanyl, 1,4-dioxepanyl, tetrahydro-2H-thiopyranyl, 2-oxa-6-azaspiro[3.3]heptanyl, 1,4-oxazepanyl, and the like.

Examples of the aromatic heterocyclic group include 5- or 6-membered monocyclic aromatic heterocyclic groups containing at least one atom selected from a nitrogen atom, an oxygen atom, and a sulfur atom, bicyclic or tricyclic fused-ring aromatic heterocyclic groups of 3- to 8-membered rings fused to one another containing at least one atom selected from a nitrogen atom, an oxygen atom, and a sulfur atom, and the like. Specific examples include furyl, thienyl, pyrrolyl, imidazolyl, pyrazolyl, oxazolyl, isooxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzooxazolyl, benzothiazolyl, isoindolyl, indolyl, indazolyl, benzoimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, pyridonyl, and the like.

Examples of the nitrogen-containing heterocyclic group formed with the adjacent nitrogen atom include 5- or 6-membered monocyclic heterocyclic groups containing at least one nitrogen atom (the monocyclic heterocyclic groups may contain other atoms selected from a nitrogen atom, an oxygen atom, and a sulfur atom), bicyclic or tricyclic fused-ring heterocyclic groups of 3- to 8-membered rings fused to one another containing at least one nitrogen atom (the fused-ring heterocyclic groups may contain other atoms selected from a nitrogen atom, an oxygen atom, and a sulfur atom), and the like. Specific examples include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzoimidazolidinyl, benzoimidazolyl, dihydroindazolyl, indazolyl, benzotriazolyl, pyrrolopyridinyl, pyrrolopyrimidinyl, imidazopyridinyl, purinyl9H-carbazolyl, 3-azaspiro[5.5]undecane, 2H-spirobenzofuran-3,4'-piperidinyl, 2,3-dihydro-1H-pyrrolo[2,3-b]pyridyl, and the like.

The halogen means each atom of fluorine, chlorine, bromine, or iodine.

The cycloalkyl formed by $R^A$ and $R^B$ combined together with the carbon atom attached thereto has the same meaning as the cycloalkyl above. The aliphatic heterocyclic group formed by $R^A$ and $R^B$ combined together with the carbon atom attached thereto has the same meaning as the aliphatic heterocyclic group above.

Examples of the substituents of the optionally substituted lower alkyl, the optionally substituted lower alkoxy, the optionally substituted lower alkenyl, and the optionally substituted lower alkynyl, which may be the same or different and in number of 1 to 3, include substituents selected from the group comprising halogen, hydroxy, sulfanyl, nitro, cyano, carboxy, carbamoyl, $C_{3-8}$cycloalkyl, an optionally substituted aliphatic heterocyclic group {examples of the substituents of the substituted aliphatic heterocyclic group, which may be in number of 1 to 3, include halogen, hydroxy, cyano, $C_{1-10}$alkylsulfonyl, $C_{1-10}$alkoxy, $diC_{1-10}$alkylamino, optionally substituted $C_{1-10}$alkyl (examples of the substituents of the substituted $C_{1-10}$alkyl, which may be in number of 1 to 3, include hydroxy, $C_{1-10}$alkoxy, and the like), and the like}, an aromatic heterocyclic group, $C_{1-10}$alkoxy, $C_{3-8}$cycloalkoxy, $C_{6-14}$aryloxy, $C_{7-16}$aralkyloxy, $C_{2-11}$alkanoyloxy, $C_{7-15}$aroyloxy, $C_{1-10}$alkylsulfanyl, $C_{1-10}$alkylsulfonyl, $-NR^{13}R^{14}$ (wherein $R^{13}$ and $R^{14}$ may be the same or different, and each represents a hydrogen atom, $C_{1-10}$alkyl, $C_{3-8}$cycloalkyl, $C_{6-14}$aryl, an aromatic heterocyclic group, $C_{7-16}$aralkyl, $C_{2-11}$alkanoyl, $C_{7-15}$aroyl, $C_{1-10}$alkoxycarbonyl, or $C_{7-16}$aralkyloxycarbonyl), $C_{2-11}$alkanoyl, $C_{7-15}$aroyl, $C_{1-10}$alkoxycarbonyl, $C_{6-14}$aryloxycarbonyl, $C_{1-10}$alkylcarbamoyl, and $diC_{1-10}$alkylcarbamoyl.

Examples of the substituents of the optionally substituted aryl, the optionally substituted aromatic heterocyclic group, the optionally substituted aralkyl, and the optionally substituted benzimidazol-2-yl, which may be the same or different and in number of 1 to 3, include substituents selected from the group comprising halogen, hydroxy, sulfanyl, nitro, cyano, carboxy, carbamoyl, $C_{1-10}$alkyl, trifluoromethyl, $C_{3-8}$cycloalkyl, $C_{6-14}$aryl, an aliphatic heterocyclic group, an aromatic heterocyclic group, $C_{1-10}$alkoxy, $C_{3-8}$cycloalkoxy, $C_{6-14}$aryloxy, $C_{7-16}$aralkyloxy, $C_{2-11}$alkanoyloxy, $C_{7-15}$aroyloxy, $C_{1-10}$alkylsulfanyl, $C_{1-10}$alkylsulfonyl, $-NR^{13A}R^{14A}$ (wherein $R^{13}A$ and $R^{14A}$ may be the same or different, and have the same meaning as the above $R^{13}$), $C_{2-11}$alkanoyl, $C_{7-15}$aroyl, $C_{1-10}$alkoxycarbonyl, $C_{6-14}$aryloxycarbonyl, $C_{1-10}$alkylcarbamoyl, and $diC_{1-10}$alkylcarbamoyl.

Examples of the substituents of the optionally substituted cycloalkyl, the optionally substituted cycloalkenyl, the optionally substituted aliphatic heterocyclic group, the optionally substituted cycloalkyl formed by $R^A$ and $R^B$ combined together with the carbon atom attached thereto, the optionally substituted aliphatic heterocyclic group formed by $R^A$ and $R^B$ combined together with the carbon atom attached thereto, and the optionally substituted nitrogen-containing heterocyclic group formed with the adjacent nitrogen atom, which may be the same or different and in number of 1 to 3, include substituents selected from the group comprising oxo, halogen, hydroxy, sulfanyl, nitro, cyano, carboxy, carbamoyl, optionally substituted $C_{1-10}$alkyl (examples of the substituents of the substituted $C_{1-10}$alkyl, which may be in number of 1 to 3, include halogen, hydroxy, $C_{1-10}$alkoxy, $C_{3-8}$cycloalkyl, an aromatic heterocyclic group, and the like), trifluoromethyl, $C_{3-8}$cycloalkyl, $C_{6-14}$aryl, an aliphatic heterocyclic group, an aromatic heterocyclic group, $C_{1-10}$alkoxy, $C_{3-8}$cycloalkoxy, $C_{6-14}$aryloxy, $C_{7-16}$aralkyloxy, $C_{2-11}$alkanoyloxy, $C_{7-15}$aroyloxy, $C_{1-10}$alkylsulfanyl, $C_{1-10}$alkylsulfonyl, $-NR^{13B}R^{14B}$ (wherein $R^{13B}$ and $R^{14B}$ may be the same or different, and have the same meaning as the above $R^{13}$), $C_{2-11}$alkanoyl, $C_{7-15}$aroyl, $C_{1-10}$alkoxycarbonyl, $C_{6-14}$aryloxycarbonyl, $C_{1-10}$alkylcarbamoyl, and $diC_{1-10}$alkylcarbamoyl.

Examples of the $C_{1-10}$alkyl, and the alkyl moieties of the $C_{1-10}$alkoxy, the $C_{1-10}$alkoxycarbonyl, the $C_{1-10}$alkylsulfanyl, the $C_{1-10}$alkylsulfonyl, the $C_{1-10}$alkylcarbamoyl, the $diC_{1-10}$alkylcarbamoyl, the $C_{2-11}$alkanoyl, and the $C_{2-11}$alkanoyloxy include the groups exemplified above for the lower alkyl.

Examples of the $C_{3-8}$cycloalkyl and the cycloalkyl moieties of the $C_{3-8}$cycloalkoxy include the groups exemplified above for the cycloalkyl.

Examples of the $C_{6-14}$aryl, and the aryl moieties of the $C_{6-14}$aryloxy, the $C_{7-15}$aroyl, the $C_{7-15}$aroyloxy, and the $C_{6-14}$aryloxycarbonyl include the groups exemplified above for the aryl.

Examples of the $C_{7-16}$aralkyl, and the aralkyl moieties of the $C_{7-16}$aralkyloxy and the $C_{7-16}$aralkyloxycarbonyl include the groups exemplified above for the aralkyl.

Examples of the aliphatic heterocyclic group, the aromatic heterocyclic group, and the halogen include the groups exemplified above for the aliphatic heterocyclic group, the aromatic heterocyclic group, and the halogen, respectively.

In the groups of the compound (I) or (IA), Preferred as $R^1$ or $R^{1A}$ are lower alkyl optionally substituted with halogen, and the like.

Preferred as $R^2$ or $R^{2A}$ are optionally substituted cyclohexyl and the like.

Preferred as Q are a hydrogen atom, methyl, a chlorine atom, and the like.

Preferred as $L^1$ or $L^{1A}$ are $CH_2$, $SO_2$, $SO_2NH$, and the like.

Preferred as $W^1$ or $W^{1A}$, which may be the same or different, are CH, $C(CH_3)$, and the like.

Preferred as $W^2$ or $W^{2A}$, which may be the same or different, are CH, $C(CH_3)$, $C(Cl)$, and the like.

Examples of the pharmaceutically acceptable salts of the compounds (I) and (IA) include pharmaceutically acceptable acid addition salts, metal salts, ammonium salts, organic amine addition salts, amino acid addition salts, and the like. Examples of the pharmaceutically acceptable acid addition salts of the compounds (I) and (IA) include inorganic acid salts such as hydrochloride, hydrobromate, nitrate, sulfate, phosphate and the like, and organic acid salts such as acetate, oxalate, maleate, fumarate, citrate, benzoate, methane sulfonate and the like. Examples of the pharmaceutically acceptable metal salts include alkali metal salts (such as sodium salts, potassium salts and the like), alkali-earth metal salts (such as magnesium salts, calcium salts and the like), aluminum salts, zinc salts, and the like. Examples of the pharmaceutically acceptable ammonium salts include salts of ammonium, tetramethylammonium, and the like. Examples of the pharmaceutically acceptable organic amine addition salts include addition salts of morpholine, piperidine, and the like. Examples of the pharmaceutically acceptable amino acid addition salts include addition salts of lysine, glycine, phenylalanine, aspartic acid, glutamic acid, and the like.

Producing processes of the compounds (I) are explained below.

In the producing processes below, when the defined groups undergo changes under the conditions of the producing processes, or are inappropriate for carrying out the producing processes, the desired products can be produced by using a method of introducing and removing protective groups commonly used in organic synthetic chemistry [for example, such as the method described in Protective Groups in Organic Synthesis, Third Edition; T. W. Greene; John Wiley & Sons Inc. (1999)], and the like. Further, the order of the reaction steps such as the introduction of substituents may be changed, if necessary.

Compounds (I) can be produced according to the following steps.

Producing Process 1

Among compound (I), compound (I-a) in which $R^3$ is —C(=O)NR$^8$R$^9$ (wherein $R^8$ and $R^9$ have the same meanings as described above, respectively), compound (I-b) in which $R^3$ is —C(=O)NH$_2$, compound (I-c) in which $R^3$ is —C(=O)NHR$^{9E}$ (wherein $R^{9E}$ represents optionally substituted aryl or an optionally substituted aromatic heterocyclic group), and compound (I-d) in which $R^3$ is —C(=O)NR$^{9E}$R$^{9F}$ (wherein $R^{9E}$ has the same meaning as described above, and $R^{9F}$ represents optionally substituted lower alkyl) can be produced by the following steps.

[Chemical Formula 4]

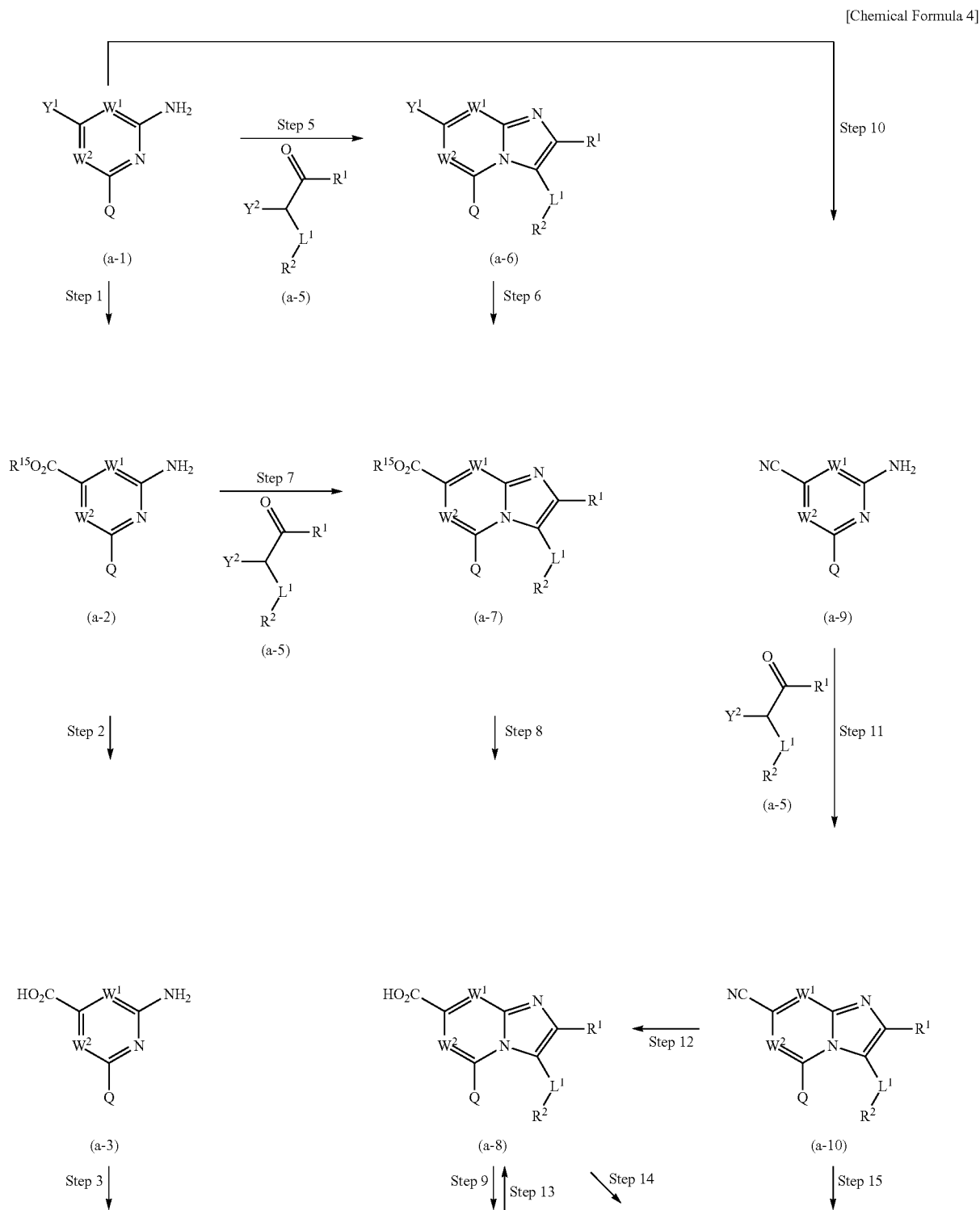

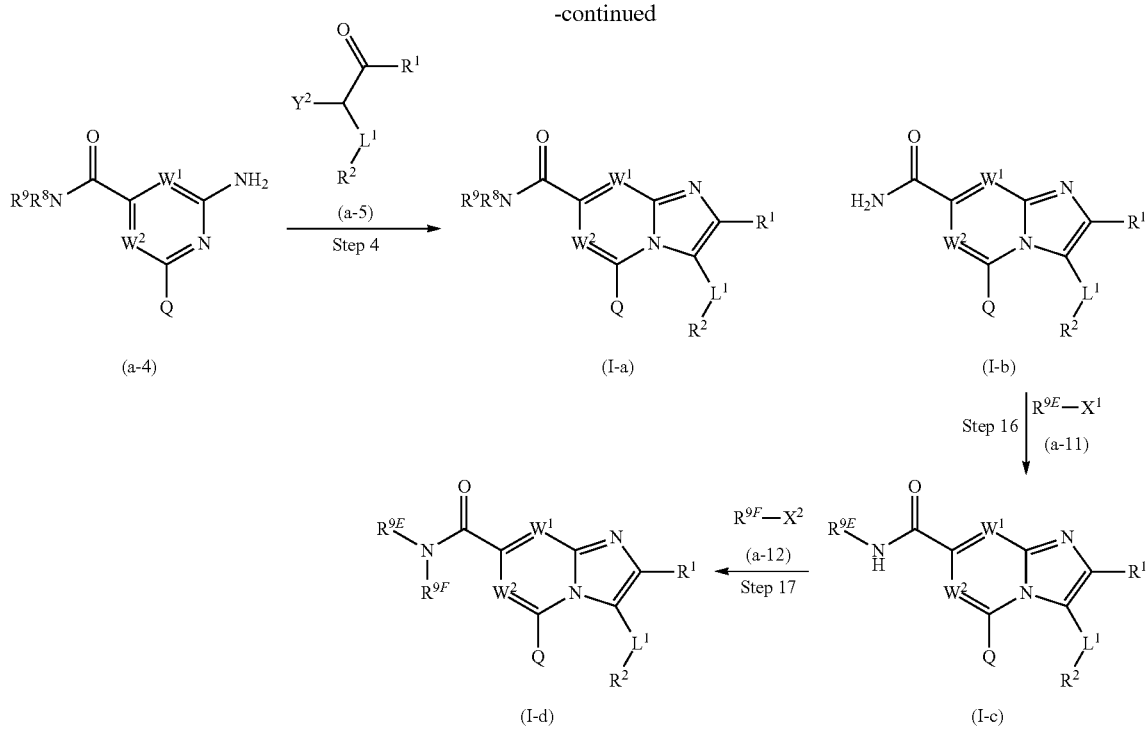

(wherein, $Y^1$ and $Y^2$ may be the same or different, and each represents a chlorine atom, a bromine atom, or an iodine atom, $X^1$ and $X^2$ may be the same or different, and each represents a chlorine atom, a bromine atom, an iodine atom, methanesulfonyloxy, trifluoromethanesulfonyloxy, or the like, $R^{15}$ represents $C_{1-10}$alkyl or $C_{7-16}$aralkyl, and $R^1$, $R^2$, Q, $R^8$, $R^9$, $R^{9E}$, $R^{9F}$, $L^1$, $W^1$ and $W^2$ have the same meanings as described above, respectively)

Step 1

Compound (a-2) can be produced by reacting compound (a-1) in a solvent at a temperature between −20° C. and the boiling point of the solvent used under ordinary pressure or increased pressure for 5 minutes to 72 hours in a carbon monoxide atmosphere in the presence of 1 equivalent to a large excess amount of $R^{15}OH$ (wherein $R^{15}$ has the same meaning as described above) and 1 to 100 mol % of a palladium catalyst, and, if necessary, 1 to 100 mol % of a catalyst ligand and/or 1 to 10 equivalents of a base.

Examples of the base include potassium carbonate, potassium phosphate, potassium hydroxide, triethylamine, diisopropylethylamine, N-methylmorpholine, pyridine, 1,8-diazabicyclo[5.4.0]-7-undecene (DBU), potassium acetate, sodium acetate, and the like. Examples of the palladium catalyst include palladium acetate, tetrakis(triphenylphosphine)palladium, and the like. Examples of the catalyst ligand include triphenylphosphine, 1,1'-bis(diphenylphosphino)ferrocene, 1,3-bis(diphenylphosphino)propane, and the like. Examples of the solvent include dichloromethane, chloroform, 1,2-dichloroethane, toluene, ethyl acetate, acetonitrile, diethyl ether, tetrahydrofuran (THF), 1,2-dimethoxyethane (DME), 1,4-dioxane, N,N-dimethylformamide (DMF), N,N-dimethylacetoamide (DMA), N-methylpyrrolidone (NMP), water, and the like. These may be used either alone or as a mixture.

Compound (a-1) and $R^{15}OH$ can be obtained as commercially available products.

Step 2

Compound (a-3) can be produced using compound (a-2), by a method according to the removing method of the protective group described in, for example, Protective Groups in Organic Synthesis; T. W. Greene; John Wiley & Sons Inc. (1981), and the like.

For example, when $R^{15}$ is $C_{1-10}$alkyl, compound (a-3) can be produced by treating compound (a-2) in a water-containing solvent with 1 equivalent to a large excess amount of a base at a temperature between 0° C. and the boiling point of the solvent used for 5 minutes to 72 hours.

Examples of the base include sodium hydroxide, potassium hydroxide, lithium hydroxide, and the like. Examples of the solvent include methanol, ethanol, propanol, THF, 1,4-dioxane, DME, toluene, dichloromethane, DMF, and the like. Mixed solvents of these with water also can be used.

As another example, when $R^{15}$ is tert-butyl, compound (a-3) can be produced by treating compound (a-2) in a solvent or without solvent with 1 equivalent to a large excess amount of an acid at a temperature between −30° C. and 100° C. for 5 minutes to 72 hours.

Examples of the acid include hydrochloric acid, sulfuric acid, trifluoroacetic acid, methanesulfonic acid, and the like. Examples of the solvent include methanol, ethanol, propanol, THF, 1,4-dioxane, DME, toluene, ethyl acetate, dichloromethane, DMF, water, and the like. These may be used either alone or as a mixture.

Step 3

Compound (a-4) can be produced by reacting compound (a-3) in a solvent or without solvent with 1 to 30 equivalents of $HNR^8R^9$ (wherein $R^8$ and $R^9$ have the same meanings as described above, respectively) at a temperature between −30° C. and 150° C. for 5 minutes to 72 hours in the presence of 1 to 30 equivalents of a condensing agent, and, if necessary, in the presence of 0.1 to 30 equivalents of an additive.

Examples of the condensing agent include dicyclohexylcarbodiimide (DCC), diisopropylcarbodiimide, N-(3-dimethylaminopropyl)-N'-ethylcarbodiimide (EDC), EDC hydrochloride, 4-(4,6-dimethoxy-1,3,5-triazin-2-yl)-4-methylmorpholonium chloride (DMT-MM), and the like. Examples of the additive include 1-hydroxybenzotriazole hydrate, triethylamine, 4-dimethylaminopyridine (DMAP), potassium carbonate, sodium carbonate, sodium hydrogen carbonate, tetramethylethylenediamine (TMEDA), pyridine, tdiisopropylethylamine, DBU, and the like. These may be used either alone or as a mixture. Examples of the solvent include acetonitrile, dichloromethane, 1,2-dichloroethane, chloroform, DME, DMF, DMA, 1,4-dioxane, THF, diethyl ether, diisopropylether, benzene, toluene, xylene, pyridine, NMP, water, and the like. These may be used either alone or as a mixture.

Step 4

Compound (I-a) can be produced by reacting compound (a-4) with 0.1 to 10 equivalents of compound (a-5) in a solvent or without solvent at a temperature between 0° C. and 300° C. for 5 minutes to 72 hours, if necessary, in the presence of 1 to 10 equivalents of a suitable base, and, if necessary, in the presence of 0.1 to 1,000 weight % of a suitable additive.

Examples of the base include potassium carbonate, sodium carbonate, potassium hydrogen carbonate, sodium hydrogen carbonate, potassium hydroxide, potassium hydroxide, triethylamine, diisopropylethylamine, N-methylmorpholine, pyridine, DBU, and the like. Examples of the additive include a molecular sieve 4A, and the like. Examples of the solvent include methanol, ethanol, propanol, butanol, DMF, DMA, NMP, acetonitrile, diethyl ether, THF, DME, 1,4-dioxane, dimethylsulfoxide (DMSO), and the like. These may be used either alone or as a mixture.

Compound (a-5) can be obtained as a commercially available product. Alternatively, compound (a-5) may be synthesized by using a known method, or may be produced by using, for example, the method described in the producing process 12 below.

Step 5

Compound (a-6) can be produced in the same manner as in the above step 4, using compound (a-1) and compound (a-5).

Step 6

Compound (a-7) can be produced in the same manner as in the above step 1, using compound (a-6).

Step 7

Compound (a-7) can be produced in the same manner as in the above step 4, using compound (a-2).

Step 8

Compound (a-8) can be produced in the same manner as in the above step 2, using compound (a-7).

Step 9

Compound (I-a) can be produced in the same manner as in the above step 3, using compound (a-8).

Step 10

Compound (a-9) can be produced by reacting compound (a-1) in a solvent with 1 to 10 equivalents of a cyanylating agent at a temperature between 0° C. and the boiling point of the solvent used for 5 minutes to 72 hours in the presence of 1 to 100 mol % of a catalyst and 1 to 100 mol % of a catalyst ligand with optionally added 1 to 10 equivalents of a base and an additive.

Examples of the catalyst include palladium acetate, tris (dibenzylideneacetone)dipalladium and chloroform adducts thereof, tetrakis(triphenylphosphine)palladium, and the like. Examples of the catalyst ligand include tributylphosphine, 1,1'-bis(diphenylphosphino)ferrocene (DPPF), and the like. Examples of the base include potassium carbonate, sodium carbonate, sodium hydrogen carbonate, tetramethylethylenediamine (TMEDA), pyridine, triethylamine, diisopropylethylamine, DBU, DMAP, and the like. Examples of the additive include copper(I) iodide, potassium iodide, zinc powder, iron (III) chloride, and the like. Examples of the cyanylating agent include copper(I) cyanide, sodium cyanide, potassium cyanide, tetrabutylammonium cyanide, zinc cyanide, potassium copper(I) cyanide, trimethylsilyl cyanide, and the like. Examples of the solvent include THF, DME, 1,4-dioxane, DMF, DMA, NMP, DMSO, toluene, and the like. These may be used either alone or as a mixture.

Step 11

Compound (a-10) can be produced in the same manner as in the above step 4, using compound (a-9).

Step 12

Compound (a-8) can be produced by reacting compound (a-10) in a solvent at a temperature between 0° C. and the boiling point of the solvent used for 5 minutes to 72 hours in the presence of 1 equivalent to a large excess amount of a base, or in the presence of a catalytic amount to a large excess amount of an acid.

Examples of the base include sodium hydroxide, potassium hydroxide, lithium hydroxide, and the like. Examples of the acid include hydrochloric acid, sulfuric acid, acetic acid, trifluoroacetic acid, methanesulfonic acid, and the like. Examples of the solvent include methanol, ethanol, propanol, isobutyl alcohol, THF, 1,4-dioxane, DME, toluene, dichloromethane, DMF, water, and the like. These may be used either alone or as a mixture.

Step 13

Compound (a-8) can be produced in the same manner as in the above step 12, using compound (I-a).

Step 14

Compound (I-b) can be produced in the same manner as in the above step 3, using compound (a-8) and aqueous ammonia.

Step 15

Compound (I-b) can be produced in the same manner as in the above step 12, using compound (a-10).

Step 16

Compound (I-c) can be produced by reacting compound (I-b) in a solvent with 1 to 10 equivalents of compound (a-11) at a temperature between room temperature and 150° C. for 5 minutes to 72 hours in the presence of a catalytic amount to 10 equivalents of a copper reagent or a palladium reagent. The reaction may be performed in the presence of a catalytic amount to 10 equivalents of a base, as well as in the presence of a catalytic amount to 10 equivalents of an organophosphorus compound.

Examples of the copper reagent include copper(0), copper (I) iodide, copper(II) iodide, copper(II) acetate, copper(II) oxide, copper(I) chloride, and the like. Preferred examples include copper(I) iodide, copper(II) acetate, and the like. Examples of the palladium reagent include palladium (II) acetate, bis(triphenylphosphine)palladium(II) chloride, tetrakis(triphenylphosphine)palladium(0), [1,2-bis(diphenylphosphino)ethane]palladium(II) chloride, (1,1'-bis (diphenylphosphino)ferrocene)palladium(II) chloride, bis (dibenzylideneacetone)palladium(0), tris (dibenzylideneacetone)dipalladium(0), and the like. Preferred examples include palladium(II) acetate, bis(triphenylphosphine)palladium(II) chloride, tetrakis(triphenylphosphine)palladium(0), and the like. Examples of the base include potassium carbonate, cesium carbonate, lithium chloride, potassium chloride, potassium tert-butoxide, sodium tert-butoxide, triethylamine, potassium acetate, sodium ethoxide, sodium carbonate, sodium hydroxide, potassium phosphate, ethylenediamine, glycine, N-methylpyrrolidine, pyridine, 1,2-diaminocyclohexane, and the like. Preferred examples include potassium carbonate, cesium carbonate, potassium tert-butoxide, potassium phosphate, ethylenediamine, 1,2-diaminocyclohexane, and the like. Examples of the organophosphorus compound include triphenylphosphine, tri(2-furyl)phosphine, 2-dicyclohexylphosphino-2'-(N,N-dimethylamino)biphenyl, diphenylphosphinoferrocene, 4,5'-bis(diphenylphosphino)-9,9'-dimethyl xanthene, and the like. Preferred examples include 2-dicyclohexylphosphino-2'-(N,N-dimethylamino) biphenyl, and the like. Examples of the solvent include diethyl ether, THF, 1,4-dioxane, DMF, DMA, DMSO, benzene, toluene, xylene, dichloromethane, chloroform, carbon tetrachloride, 1,2-dichloroethane, acetonitrile, ethyl acetate, methyl acetate, methyl ethyl ketone, methanol, ethanol, propanol, 2-propanol, butanol, hexane, and the like. Preferred examples include THF, 1,4-dioxane, DMF, and the like.

Compound (a-11) can be obtained as a commercially available product, or by using known methods [for example, *Jikken Kagaku Kouza*, 4th Ed., Vol. 19, p. 416, Maruzen Co., Ltd. (1992), and the like] or modified methods thereof.

Step 17

Compound (I-d) can be produced by reacting compound (I-c) with 1 to 20 equivalents of compound (a-12) in a solvent at a temperature between −10° C. and the boiling point of the solvent used for 5 minutes to 72 hours, if necessary, in the presence of 1 to 20 equivalents of a base, and, if necessary, in the presence of 1 to 20 equivalents of an additive.

Compound (a-12) can be obtained as a commercially available product, or by using known methods [for example, *Jikken Kagaku Kouza*, 4th Ed., Vol. 19, p. 416, Maruzen Co., Ltd. (1992), and the like] or modified methods thereof.

Examples of the base include potassium carbonate, potassium hydroxide, sodium hydroxide, sodium methoxide, potassium tert-butoxide, sodium hydride, triethylamine, diisopropylethylamine, N-methylmorpholine, pyridine, DBU, DMAP, and the like. Examples of the additive include potassium iodide, and the like. Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, DMSO, pyridine, water, and the like. These may be used either alone or as a mixture.

Producing Process 2

Among compound (I), compound (I-e) in which $R^3$ is $-NR^{7A}R^{16}$ {wherein $R^{7A}$ has the same meaning as described above, and $R^{16}$ represents $-C(=O)R^{10}$ (wherein $R^{10}$ has the same meaning as described above), $-C(=O)NR^8R^9$ (wherein $R^8$ and $R^9$ have the same meanings as described above, respectively), $-C(=O)OR^{10}$ (wherein $R^{10}$ has the same meaning as described above), $-SO_2R^{10}$ (wherein $R^{10}$ has the same meaning as described above), or $-SO_2NR^8R^9$ (wherein $R^8$ and $R^9$ have the same meanings as described above, respectively)} can be produced according to the following steps.

[Chemical Formula 5]

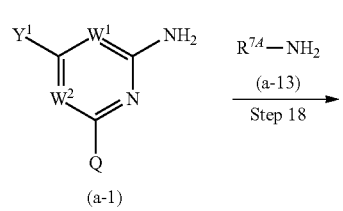

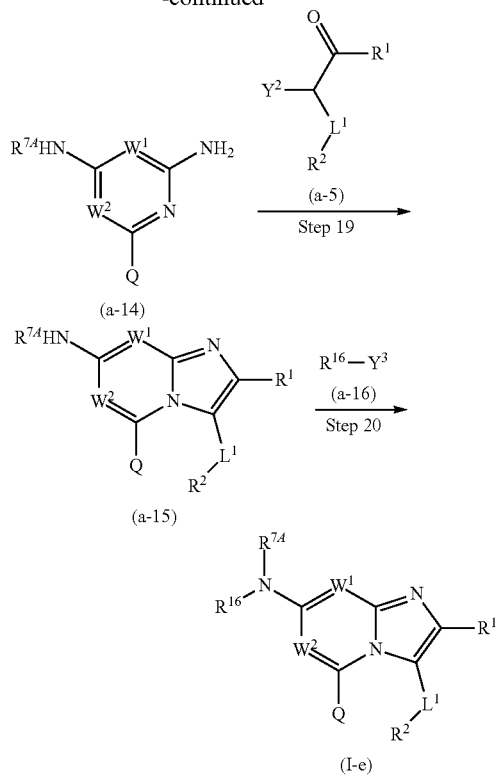

(wherein, $Y^1, Y^2, R^1, R^2, Q, R^{7A}, R^{16}, L^1, W^1$, and $W^2$ have the same meanings as described above, respectively, and $Y^3$ has the same meaning as $Y^1$ and $Y^2$)

Step 18

Compound (a-14) can be produced according to the method described in, for example, WO2006/040520, and the like, using compound (a-1).

For example, compound (a-14) can be produced by reacting compound (a-1) with 1 equivalent to a large excess amount of compound (a-13) in a solvent or without solvent at a temperature between room temperature and 250° C. for 5 minutes to 72 hours, if necessary, in the presence of 1 to 20 equivalents of a base, and, if necessary, using a sealed container such as a seal tube, if necessary, with a microwave reactor.

Compound (a-13) can be obtained as a commercially available product, or by using known methods [for example, *Jikken Kagaku Kouza*, 4th Ed., Vol. 20, p. 279, Maruzen Co., Ltd. (1992), and the like] or modified methods thereof.

Examples of the base include potassium carbonate, sodium carbonate, potassium hydrogen carbonate, sodium hydrogen carbonate, triethylamine, diisopropylethylamine, N-methylmorpholine, pyridine, DBU, and the like. Examples of the solvent include THF, DME, benzene, toluene, xylene, 1,4-dioxane, DMF, DMA, NMP, water, and the like. These may be used either alone or as a mixture.

Step 19

Compound (a-15) can be produced in the same manner as in the above step 4, using compound (a-14) and compound (a-5).

Step 20

Compound (I-e) can be produced by reacting compound (a-15) with 1 to 20 equivalents of compound (a-16) in a solvent at a temperature between −10° C. and the boiling point of the solvent used for 5 minutes to 72 hours, if necessary, in the presence of 1 to 20 equivalents of a base.

Compound (a-16) can be obtained as a commercially available product, or by using known methods [for example, Shin *Jikken Kagaku Kouza*, 4th Ed., Vol. 14, p. 1106, 1120, Maruzen Co., Ltd. (1977) and the like] or modified methods thereof.

Examples of the base include potassium carbonate, sodium carbonate, lithium hydroxide, potassium hydroxide, sodium hydroxide, sodium hydride, sodium methoxide, potassium tert-butoxide, triethylamine, diisopropylethylamine, N-methylmorpholine, N-methylpiperidine, pyridine, DBU, 4-dimethylaminopyridine, and the like. These may be used either Examples of the solvent include methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These may be used either alone or as a mixture.

Producing Process 3

Among compound (I), compound (I-f) in which $R^3$ is —NHR$^{16}$ (wherein $R^{16}$ has the same meaning as described above), compound (I-g) in which $R^3$ is —NR$^{7A-1}$R$^{16}$ (wherein $R^{7A-1}$ represents optionally substituted lower alkyl, and $R^{16}$ has the same meaning as described above), and compound (I-h) in which $R^3$ is —SO$_2$NR$^8$R$^9$ (wherein $R^8$ and $R^9$ have the same meanings as described above, respectively).

[Chemical Formula 6]

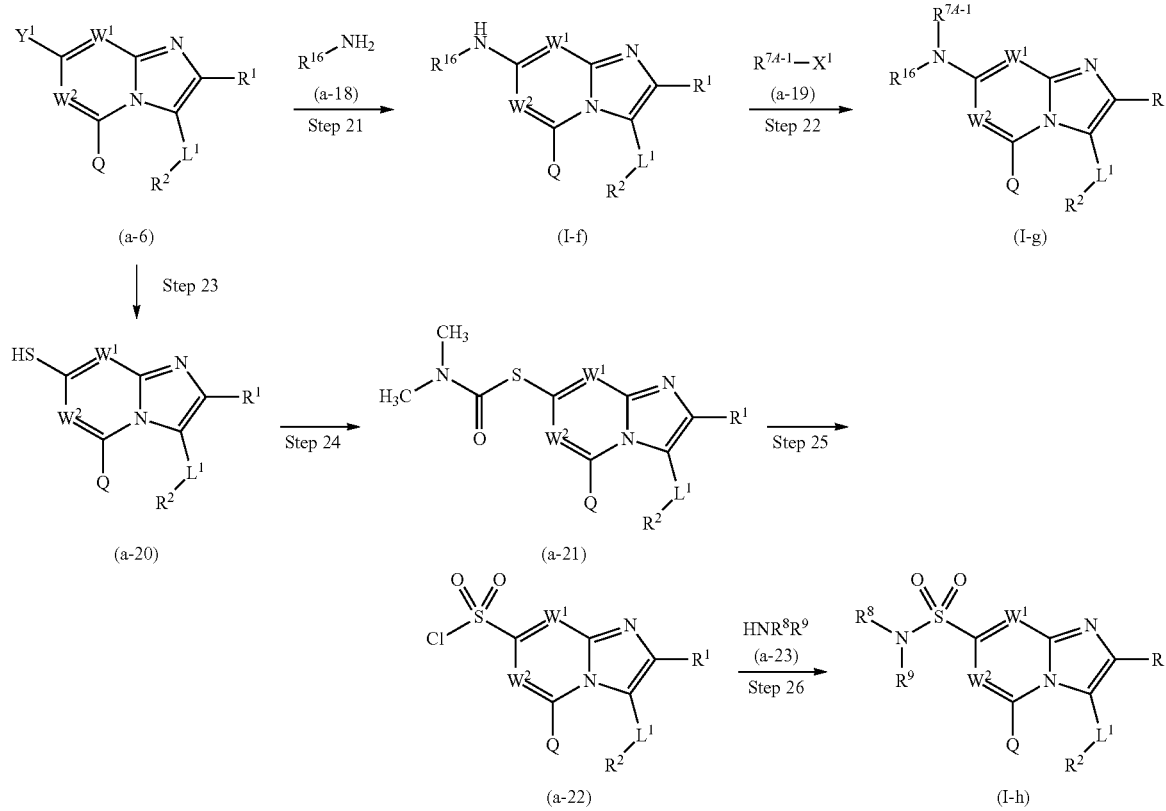

(wherein, $Y^1$, $X^1$, $L^1$, $R^1$, $R^2$, Q, $R^{7A-1}$, $R^8$, $R^9$, $R^{16}$, $W^1$ and $W^2$ have the same meanings as described above, respectively)

Step 21

Compound (I-f) can be produced in the same manner as in the above step 18, using compound (a-6) obtained in producing process 1, and compound (a-18).

Compound (a-18) can be obtained as a commercially available product, or by using known methods [for example, *Jikken Kagaku Kouza*, 4th Ed., Vol. 22, p. 137, Maruzen Co., Ltd. (1992)] or modified methods thereof.

Step 22

Compound (I-g) can be produced in the same manner as in the above step 17, using compound (I-f) and compound (a-19).

Compound (a-19) can be obtained as a commercially available product, or by using known methods [for example, *Jikken Kagaku Kouza*, 4th Ed., Vol. 19, p. 416, Maruzen Co., Ltd. (1992), and the like] or modified methods thereof.

alone or as a mixture. Examples of the solvent include methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These may be used either alone or as a mixture.

Also, among compound (I-e), the compound in which $R^{16}$ is —CONHR$^8$ (wherein $R^8$ has the same meaning as described above), can be produced by reacting compound (a-15) with 1 to 10 equivalents of $R^8$—NCO (wherein $R^8$ has the same meaning as described above) in a solvent or without solvent at a temperature between −30° C. and the boiling point of the solvent used for 5 minutes to 72 hours.

$R^8$—NCO (wherein $R^8$ has the same meaning as described above) can be obtained as a commercially available product, or by using known methods [for example, *Jikken Kagaku Kouza*, 4th Ed., Vol. 20, p. 304, p. 360, Maruzen Co., Ltd. (1992)] or modified methods thereof.

Step 23

Compound (a-20) can be produced by reacting compound (a-6) with 1 to 20 equivalents of sodium thiomethoxide in a solvent at a temperature between 0° C. and the boiling point of the solvent used for 5 minutes to 72 hours.

Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, DMSO, pyridine, and the like. These may be used either alone or as a mixture.

Step 24

Compound (a-21) can be produced by reacting compound (a-20) with 1 to 20 equivalents of N,N-dimethylcarbamoyl chloride in a solvent at a temperature between −10° C. and the boiling point of the solvent used for 5 minutes to 72 hours, if necessary, in the presence of 1 to 20 equivalents of a base.

Examples of the base include potassium carbonate, sodium carbonate, potassium hydrogen carbonate, sodium hydrogen carbonate, triethylamine, diisopropylethylamine, N-methyl-

*Jikken Kagaku Kouza,* 4th Ed., Vol. 20, p. 279, Maruzen Co., Ltd. (1992), and the like] or modified methods thereof.

Examples of the base include potassium carbonate, potassium hydroxide, sodium hydroxide, sodium methoxide, potassium tert-butoxide, triethylamine, diisopropylethylamine, N-methylmorpholine, pyridine, DBU, DMAP, and the like. Examples of the additive include potassium iodide, and the like. Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, DMSO, pyridine, water, and the like. These may be used either alone or as a mixture.

Producing Process 4

Among compound (I), compound (I-i) in which $R^3$ is —C(=O)NH—NHC(=O)—$R^{10}$ (wherein $R^{10}$ has the same meaning as described above), and compound (I-j) in which $R^3$ is —NHC(=O)O$R^{10}$ (wherein $R^{10}$ has the same meaning as described above) also can be produced according to the following steps.

[Chemical Formula 7]

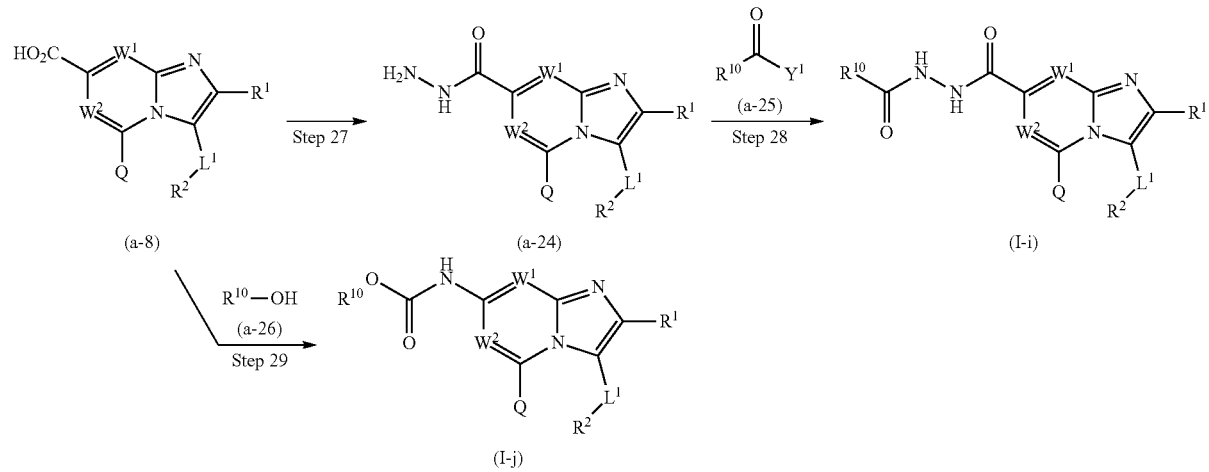

(wherein, $Y^1$, $R^1$, $R^2$, Q, $R^{10}$, $L^1$, $W^1$ and $W^2$ have the same meanings as described above, respectively)

Step 27

Compound (a-24) can be produced by reacting compound (a-8) obtained in the same manner as in producing process 1 with 1 to 20 equivalents of hydrazine hydrate in a solvent at a temperature between −10° C. and the boiling point of the solvent used for 5 minutes to 72 hours, if necessary, in the presence of 1 to 20 equivalents of a condensing agent, if necessary, in the presence of 1 to equivalents of a base, and if necessary, in the presence of 1 to 20 equivalents of an additive.

Examples of the base include potassium carbonate, potassium hydroxide, sodium hydroxide, sodium methoxide, potassium tert-butoxide, triethylamine, diisopropylethylamine, N-methylmorpholine, pyridine, DBU, DMAP, and the like. Examples of the condensing agent include 1,3-dicyclohexanecarbodiimide (DCC), 1,3-diisopropylcarbodiimide, 1-(3-dimethylaminopropyl)-3-ethylcarbodiimide (EDC), EDC hydrochloride, and the like. Examples of the additive include potassium iodide, and the like. Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, morpholine, pyridine, DBU, and the like. Examples of the solvent include acetonitrile, dichloromethane, 1,2-dichloroethane, chloroform, DME, DMF, DMA, 1,4-dioxane, THF, diethyl ether, diisopropylether, benzene, toluene, xylene, pyridine, NMP, and the like. These may be used either alone or as a mixture.

Step 25

Compound (a-22) can be produced by reacting compound (a-21) with 1 to 20 equivalents of N-chlorosuccinimide and 1 to 10 equivalents of hydrochloric acid in a solvent at a temperature between −10° C. and the boiling point of the solvent used for 5 minutes to 72 hours. Examples of the solvent include acetonitrile, water, and the like. These may be used either alone or as a mixture.

Step 26

Compound (I-h) can be produced by reacting compound (a-22) with 1 to 20 equivalents of compound (a-23) in a solvent at a temperature between −10° C. and the boiling point of the solvent used for 5 minutes to 72 hours, if necessary, in the presence of 1 to 20 equivalents of a base, and, if necessary, in the presence of 1 to 20 equivalents of an additive.

Compound (a-23) can be obtained as a commercially available product, or by using known methods [for example, NMP, DMSO, pyridine, water, and the like. These may be used either alone or as a mixture.

Step 28

Compound (I-i) can be obtained by reacting compound (a-24) with 1 to 20 equivalents of compound (a-25) in a solvent at a temperature between −10° C. and the boiling point of the solvent used for 5 minutes to 72 hours, preferably in the presence of 1 to 20 equivalents of a base, if necessary.

Compound (a-25) can be obtained as a commercially available product, or by using known methods [for example, *Jikken Kagaku Kouza,* 4th Ed., Vol. 22, p. 115, Maruzen Co., Ltd. (1992), and the like] or modified methods thereof.

Examples of the base include potassium carbonate, sodium carbonate, lithium hydroxide, potassium hydroxide, sodium hydroxide, sodium hydride, sodium methoxide, potassium tert-butoxide, triethylamine, diisopropylethylamine, N-methylmorpholine, N-methylpiperidine, pyridine, DBU, and the like. Examples of the solvent include methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These may be used either alone or as a mixture.

Step 29

Compound (I-j) can be produced by reacting compound (a-8) with 1 equivalent to a large excess amount of compound (a-26) in a solvent at a temperature between 0° C. and 150° C. for 5 minutes to 72 hours in the presence of 1 to a large excess amount of an azidizing agent, and, if necessary, 1 to a large excess amount of a base.

Compound (a-26) can be obtained as a commercially available product, or by using known methods [for example, *Jikken Kagaku Kouza,* 4th Ed., Vol. 20, p. 1, Maruzen Co., Ltd. (1992), and the like] or modified methods thereof.

Examples of the azidizing agent include sodium azide, potassium azide, diphenylphosphoryl azide, and the like. Examples of the base include potassium carbonate, sodium carbonate, potassium hydrogen carbonate, sodium hydrogen carbonate, triethylamine, diisopropylethylamine, N-methylmorpholine, pyridine, DBU, and the like. Examples of the solvent include THF, DME, benzene, toluene, xylene, 1,4-dioxane, DMF, DMA, NMP, and the like. These may be used either alone or as a mixture.

Producing Process 5

Among compound (I), compound (I-l) in which $R^3$ is an optionally substituted benzimidazol-2-yl group) also can be produced according to the following step.

[Chemical Formula 8]

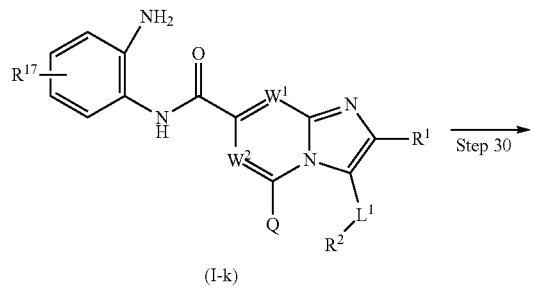

(I-k)

Step 30

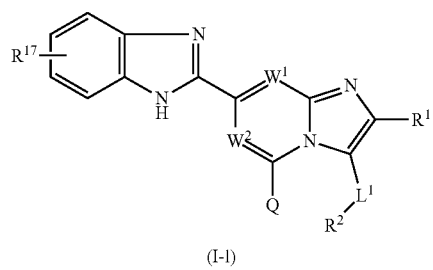

(I-l)

(wherein, $R^1$, $R^2$, Q, $L^1$, $W^1$ and $W^2$ have the same meanings as described above, respectively, and $R^{17}$ represents any of the substituents exemplified above for the substituents of the optionally substituted benzimidazol-2-yl)

Step 30

Compound (I-l) can be produced by reacting compound (I-k) obtained in the producing process 1 in a solvent or without solvent at a temperature between −10° C. and the boiling point of the solvent used for 5 minutes to 72 hours in the presence of 1 to 20 equivalents of an acid.

Examples of the acid include acetic acid, hydrochloric acid, sulfuric acid, trifluoroacetic acid, methanesulfonic acid, and the like. Examples of the solvent include methanol, ethanol, propanol, THF, 1,4-dioxane, DME, toluene, ethyl acetate, dichloromethane, DMF, water, and the like. These may be used either alone or as a mixture.

Alternatively, compound (I-l) also can be produced by reacting compound (I-k) obtained in the producing process 1 in a solvent or without solvent at a temperature between −10° C. and the boiling point of the solvent used for 5 minutes to 72 hours in the presence of 1 to 20 equivalents of a base.

Examples of the base include potassium carbonate, potassium hydroxide, sodium hydroxide, sodium methoxide, potassium tert-butoxide, triethylamine, diisopropylethylamine, N-methylmorpholine, pyridine, DBU, DMAP, and the like. Examples of the additive include potassium iodide, and the like. Examples of the solvent include methanol, ethanol, propanol, THF, 1,4-dioxane, DME, toluene, ethyl acetate, dichloromethane, DMF, water, and the like. These may be used either alone or as a mixture.

Producing Process 6

Among compound (I), compound (I-n) in which $R^4$ is —C(=O)$NR^5R^6$ (wherein $R^5$ and $R^6$ have the same meanings as described above), compound (I-o) in which $R^4$ is —NHC(=O)$OR^{4A}$ (wherein $R^{4A}$ has the same meaning as above $R^4$), compound (I-p) in which $R^4$ is —C(=O)$R^{4A}$ (wherein $R^{4A}$ has the same meaning as above $R^4$), and compound (I-q) in which $R^1$ is —$CF_2R^{4A}$ (wherein $R^{4A}$ has the same meaning as above $R^4$) also can be produced according to the following steps.

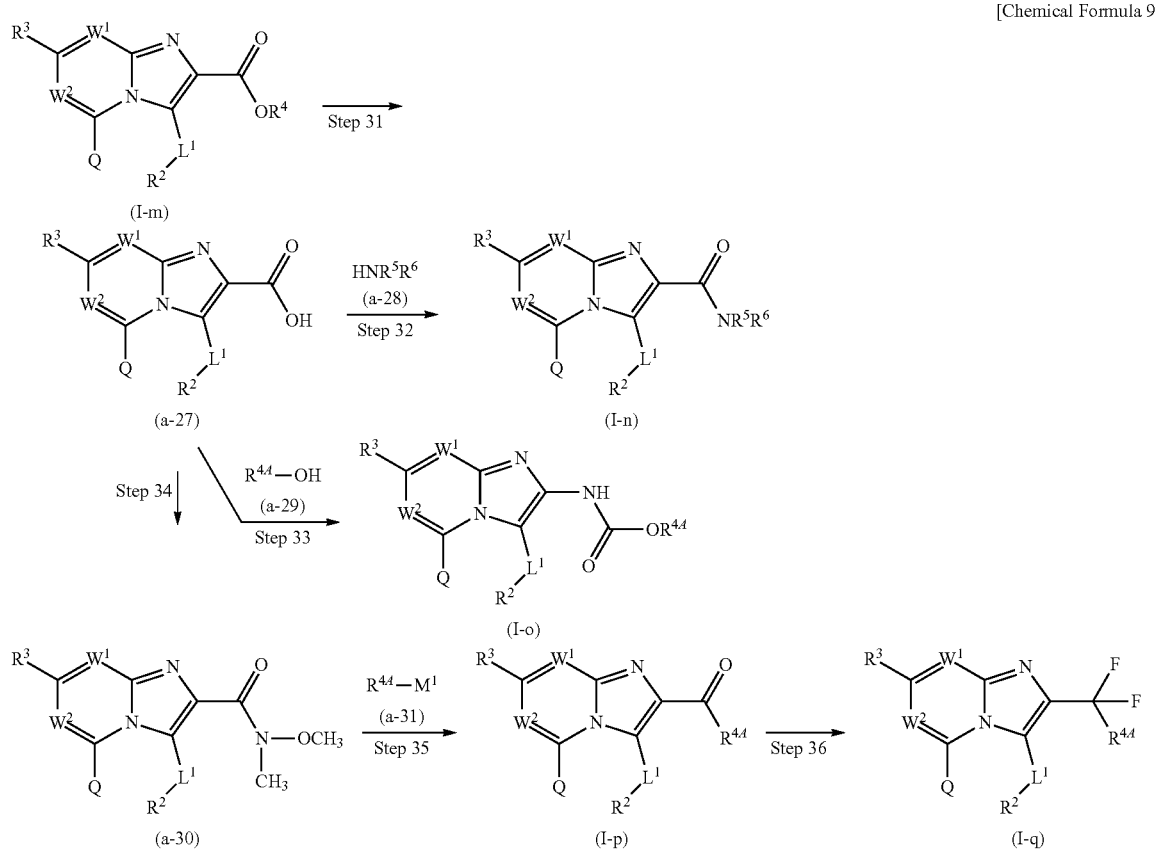

(wherein, $R^2$, $R^3$, Q, $R^4$, $R^{4A}$, $R^5$, $R^6$, $L^1$, $W^1$ and $W^2$ have the same meanings as described above, respectively, and $M^1$ represents a metallic group such as MgBr, MgCl, Li and the like)

Step 31

Compound (a-27) can be produced in the same manner as in the above step 2, using compound (I-m) obtained in the producing processes 1 to 5.

Step 32

Compound (I-n) can be produced in the same manner as in the above step 3, using compound (a-27) and compound (a-28).

Compound (a-28) can be obtained as a commercially available product, or by using known methods [for example, Jikken Kagaku Kouza, 4th Ed., Vol. 20, p. 279, Maruzen Co., Ltd. (1992), and the like] or modified methods thereof.

Step 33

Compound (I-o) can be obtained in the same manner as in the above step 29, using compound (a-27) and compound (a-29).

Compound (a-29) can be obtained as a commercially available product, or by using known methods [for example, Jikken Kagaku Kouza, 4th Ed., Vol. 20, p. 1, Maruzen Co., Ltd. (1992), and the like] or modified methods thereof.

Step 34

Compound (a-30) can be produced in the same manner as in the above step 3, using compound (a-27), and commercially available N,O-dimethylhydroxylamine, and the like.

Step 35

Compound (I-p) can be produced by reacting compound (a-30) with 1 to 10 equivalents of compound (a-31) in a solvent at a temperature between −78° C. and the boiling point of the solvent used for 5 minutes to 72 hours.

Compound (a-31) can be obtained as a commercially available product, or by using known methods [for example, Jikken Kagaku Kouza 18, Organic Compound Syntheses VI, Organic Syntheses using Metals, 5th Ed., p. 59, Maruzen (2005)] or modified methods thereof.

Examples of the solvent include toluene, diethyl ether, THF, DME, dioxane, hexane, and the like. These may be used either alone or as a mixture.

Step 36

Compound (I-q) can be produced by reacting compound (I-p) with 1 equivalent to a large excess amount of a fluorinating agent in a solvent at a temperature between −78° C. and the boiling point of the solvent used for 5 minutes to 72 hours.

Examples of the fluorinating agent include diethylaminosulfate trifluoride (DAST), bis(2-methoxyethyl)aminosulfur trifluoride, and the like. Examples of the solvent include dichloromethane, 1,2-dichloroethane, and the like. These may be used either alone or as a mixture.

Producing Process 7

Among compound (I), compound (I-r) in which $L^1$ is —CH(OH)—, compound (I-s) in which $-L^1-R^2$ is —CH=$CR^AR^B$ (wherein $R^A$ and $R^B$ have the same meanings as described above, respectively), compound (I-t) in which $L^1$ is C(F)H—, compound (I-u) in which $L^1$ is —C(=O)—, and compound (I-v) in which $L^1$ is —CH($OR^{114-1}$)— (wherein $R^{114-1}$ represents optionally substituted lower alkyl) also can be produced according to the following steps.

[Chemical Formula 10]

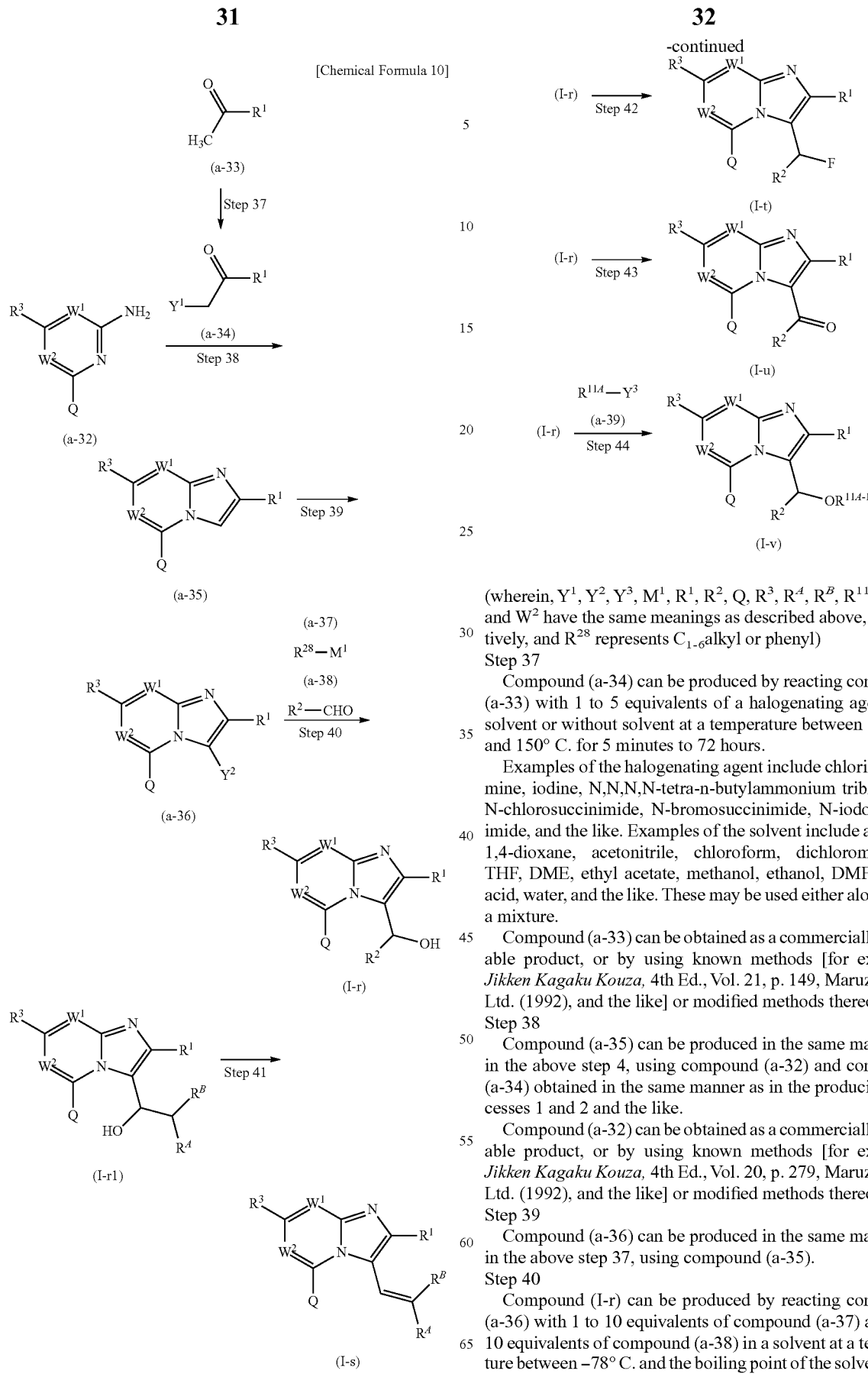

(wherein, $Y^1$, $Y^2$, $Y^3$, $M^1$, $R^1$, $R^2$, Q, $R^3$, $R^A$, $R^B$, $R^{11A-1}$, $W^1$ and $W^2$ have the same meanings as described above, respectively, and $R^{28}$ represents $C_{1-6}$alkyl or phenyl)

Step 37

Compound (a-34) can be produced by reacting compound (a-33) with 1 to 5 equivalents of a halogenating agent in a solvent or without solvent at a temperature between −30° C. and 150° C. for 5 minutes to 72 hours.

Examples of the halogenating agent include chlorine, bromine, iodine, N,N,N,N-tetra-n-butylammonium tribromide, N-chlorosuccinimide, N-bromosuccinimide, N-iodosuccinimide, and the like. Examples of the solvent include acetone, 1,4-dioxane, acetonitrile, chloroform, dichloromethane, THF, DME, ethyl acetate, methanol, ethanol, DMF, acetic acid, water, and the like. These may be used either alone or as a mixture.

Compound (a-33) can be obtained as a commercially available product, or by using known methods [for example, *Jikken Kagaku Kouza,* 4th Ed., Vol. 21, p. 149, Maruzen Co., Ltd. (1992), and the like] or modified methods thereof.

Step 38

Compound (a-35) can be produced in the same manner as in the above step 4, using compound (a-32) and compound (a-34) obtained in the same manner as in the producing processes 1 and 2 and the like.

Compound (a-32) can be obtained as a commercially available product, or by using known methods [for example, *Jikken Kagaku Kouza,* 4th Ed., Vol. 20, p. 279, Maruzen Co., Ltd. (1992), and the like] or modified methods thereof.

Step 39

Compound (a-36) can be produced in the same manner as in the above step 37, using compound (a-35).

Step 40

Compound (I-r) can be produced by reacting compound (a-36) with 1 to 10 equivalents of compound (a-37) and 1 to 10 equivalents of compound (a-38) in a solvent at a temperature between −78° C. and the boiling point of the solvent used for 5 minutes to 72 hours. Examples of the solvent include toluene, diethyl ether, THF, DME, dioxane, hexane, and the like. These may be used either alone or as a mixture.

Compound (a-37) can be obtained as a commercially available product, or by using known methods [for example, *Jikken Kagaku Kouza* 18, Organic Compound Syntheses VI, Organic Syntheses using Metals, 5th Ed., p. 59, Maruzen (2005)] or modified methods thereof.

Compound (a-38) can be obtained as a commercially available product, or by using known methods [for example, *Jikken Kagaku Kouza*, 4th Ed., Vol. 21, p. 1, Maruzen Co., Ltd. (1992), and the like] or modified methods thereof.

Step 41

Compound (I-s) can be produced by treating compound (I-r1) in which —$R^2$ of compound (I-r) is —$CHR^AR^B$ (wherein $R^A$ and $R^B$ have the same meanings as described above, respectively) with 1 to 10 equivalents of a sulfonylating agent in a solvent or without solvent at a temperature between −20° C. and 150° C. for 5 minutes to 72 hours, if necessary, in the presence of a catalytic amount to 10 equivalents of a base.

Examples of the sulfonylating agent include anhydrous trifluoromethanesulfonic acid, anhydrous methanesulfonic acid, methanesulfonyl chloride, p-toluenesulfonyl chloride, and the like. Examples of the base include triethylamine, diisopropylethylamine, pyridine, sodium hydride, and the like. Examples of the solvent include dichloromethane, chloroform, 1,2-dichloroethane, toluene, ethyl acetate, acetonitrile, diethyl ether, THF, DME, dioxane, DMF, DMA, NMP, pyridine, and the like. These may be used either alone or as a mixture.

Step 42

Compound (I-t) can be produced in the same manner as in the above step 36, using compound (I-r).

Step 43

Compound (I-u) can be produced by treating compound (I-r) with 1 to 10 equivalents of an oxidizing agent in a solvent at a temperature between −20° C. and the boiling point of the solvent used for 5 minutes to 72 hours.

Examples of the oxidizing agent include manganese dioxide, chromic acid, pyridinium chlorochromate, pyridinium dichromate, potassium permanganate, sulfur trioxide-pyridine, oxone, DMSO/oxalyl chloride, Dess-Martin periodinate, and the like. Examples of the solvent include dichloromethane, chloroform, 1,2-dichloroethane, toluene, ethyl acetate, acetonitrile, diethyl ether, THF, DME, dioxane, DMF, DMA, NMP, DMSO, pyridine, hydrochloric acid, acetic acid, propionic acid, acetic anhydride, sulfuric acid, water, and the like. These may be used either alone or as a mixture.

Step 44

Compound (I-v) can be produced in the same manner as in the above step 17, using compound (I-r) and compound (a-39).

Compound (a-39) can be obtained as a commercially available product, or by using known methods [for example, *Jikken Kagaku Kouza*, 4th Ed., Vol. 19, p. 416, Maruzen Co., Ltd. (1992), and the like] or modified methods thereof.

Producing Process 8

Among compound (I), compound (I-w) in which $L^1$ is —$CH_2O$— also can be produced according to the following steps.

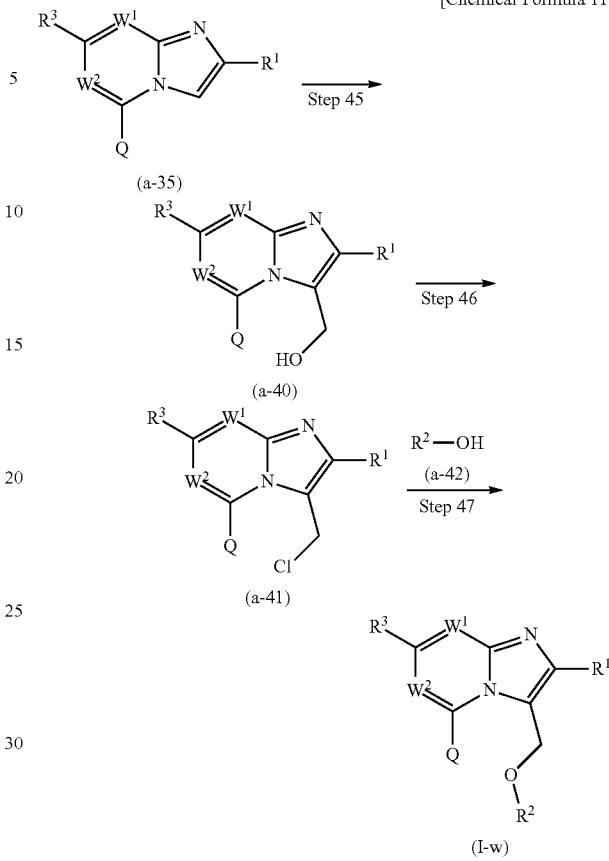

[Chemical Formula 11]

(wherein, $R^1$, $R^2$, Q, $R^3$, $W^1$ and $W^2$ have the same meanings as described above, respectively)

Step 45

Compound (a-40) can be produced by reacting compound (a-35) in formalin at a temperature between −10° C. and 100° C. for 5 minutes to 72 hours, if necessary, in the presence of 1 to 20 equivalents of an acid. Examples of the acid include acetic acid, hydrochloric acid, and the like.

Step 46

Compound (a-41) can be produced by treating compound (a-40) with 1 equivalent to a large excess amount of a chlorinating agent in a solvent or without solvent at a temperature between −20° C. and 150° C. for 5 minutes to 72 hours, if necessary, in the presence of a catalytic amount to 1 equivalent of an additive.

Examples of the chlorinating agent include phosphorus oxychloride, phosphorus pentachloride, phosphorus trichloride, thionyl chloride, and the like. Examples of the additive include DMF, pyridine, diisopropylethylamine, and the like. Examples of the solvent include dichloromethane, chloroform, 1,2-dichloroethane, toluene, diethyl ether, THF, DME, dioxane, DMF, DMA, NMP, pyridine, and the like. These may be used either alone or as a mixture.

Step 47

Compound (I-w) can be produced in the same manner as in the above step 17, using compound (a-41) and compound (a-42).

Compound (a-42) can be obtained as a commercially available product, or by using known methods [for example, *Jikken Kagaku Kouza*, 4th Ed., Vol. 20, p. 1, Maruzen Co., Ltd. (1992), and the like] or modified methods thereof.

Producing Process 9

Among compound (I), compound (I-x) in which $L^1$ is —S—, and compound (I-y) in which $L^1$ is —S(O)$n^3$- (wherein $n^3$ represents an integer of 1 to 2) also can be produced according to the following steps.

[Chemical Formula 12]

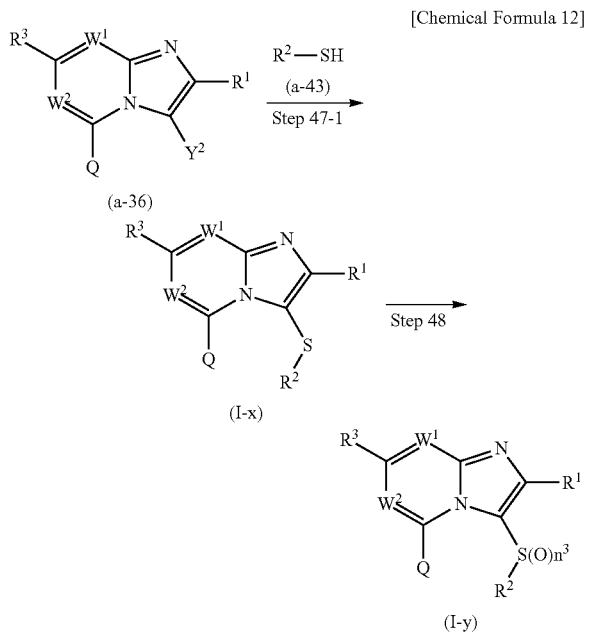

(wherein, $Y^2$, $R^1$, $R^2$, Q, $R^3$, $n^3$, $W^1$ and $W^2$ have the same meanings as described above, respectively)

Step 47-1

Compound (I-x) can be produced by reacting compound (a-36) with 1 to 10 equivalents of compound (a-43) in a solvent at a temperature between room temperature and 140° C. for 5 minutes to 72 hours in the presence of a catalytic amount to 10 equivalents of a copper reagent or a palladium reagent. The reaction also may be performed in the presence of a catalytic amount to 10 equivalents of a base in the presence of a catalytic amount to 10 equivalents of an additive. Further, the reaction can be performed in the presence of a catalytic amount to 10 equivalents of an organophosphorus compound.

Compound (a-43) can be obtained as a commercially available product, or by using known methods [for example, *Shin Jikken Kagaku Kouza*, Vol. 14, p. 1699, Maruzen Co., Ltd. (1978), and the like] or modified methods thereof.

Examples of the copper reagent include copper(0), copper (I) iodide, copper(II) iodide, copper(II) acetate, copper(II) oxide, copper(I) chloride, and the like. Preferred examples include copper(I) iodide, copper(II) acetate, and the like. Examples of the palladium reagent include palladium (II) acetate, bis(triphenylphosphine)palladium(II) chloride, tetrakis(triphenylphosphine)palladium(0), [1,2-bis(diphenylphosphino)ethane]palladium(II) chloride, (1,1'-bis (diphenylphosphino)ferrocene)palladium(II) chloride, and the like. Preferred examples include palladium(II) acetate, bis(triphenylphosphine)palladium(II) chloride, tetrakis (triphenylphosphine)palladium(0), and the like. Examples of the additive include α-pipecolic acid, and the like. Examples of the base include potassium carbonate, cesium carbonate, lithium chloride, potassium chloride, potassium tert-butoxide, sodium tert-butoxide, triethylamine, potassium acetate, sodium ethoxide, sodium carbonate, sodium hydroxide, potassium phosphate, ethylenediamine, glycine, N-methylpyrrolidine, pyridine, 1,2-diaminocyclohexane, and the like. Preferred examples include potassium carbonate, cesium carbonate, potassium tert-butoxide, potassium phosphate, ethylenediamine, 1,2-diaminocyclohexane, and the like. Examples of the organophosphorus compound include triphenylphosphine, tri(2-furyl)phosphine, 2-dicyclohexylphosphino-2'-(N,N-dimethylamino) biphenyl, diphenylphosphinoferrocene, and the like. Preferred examples include 2-dicyclohexylphosphino-2'-(N,N-dimethylamino) biphenyl, and the like. Examples of the solvent include diethyl ether, THF, 1,4-dioxane, DMF, DMA, DMSO, benzene, toluene, xylene, dichloromethane, chloroform, carbon tetrachloride, 1,2-dichloroethane, acetonitrile, ethyl acetate, methyl acetate, methyl ethyl ketone, methanol, ethanol, propanol, 2-propanol, butanol, hexane, and the like. Preferred examples include THF, 1,4-dioxane, DMF, DMSO, and the like.

Step 48

Compound (I-y) can be produced by treating compound (I-x) with 1 to 10 equivalents of an oxidizing agent in a solvent at a temperature between −20° C. and the boiling point of the solvent used for 5 minutes to 72 hours.

Examples of the oxidizing agent include m-chloroperbenzoic acid (m-CPBA), benzoyl peroxide, peracetic acid, hydrogen peroxide water, sodium periodate, and the like. Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, water, and the like. These may be used either alone or as a mixture.

Producing Process 10

Among compound (I), compound (I-z) in which $L^1$ is —SO$_2$—, and $R^2$ is —NR$^{18}$R$^{19}$ (wherein R$^{18}$ has the same meaning as the above R$^7$, and R$^{19}$ has the same meaning as the above R$^2$, or R$^{18}$ and R$^{19}$ are combined together with the adjacent nitrogen atom thereto to form an optionally substituted nitrogen-containing heterocyclic group) also can be produced according to the following steps.

[Chemical Formula 13]

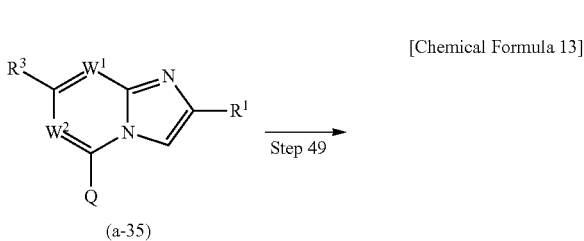

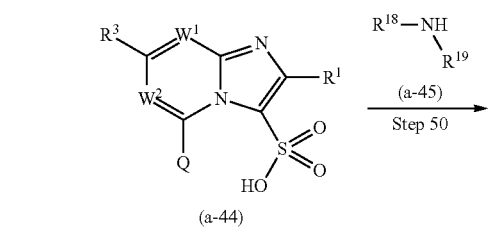

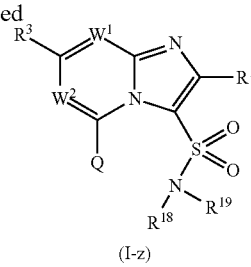

(I-z)

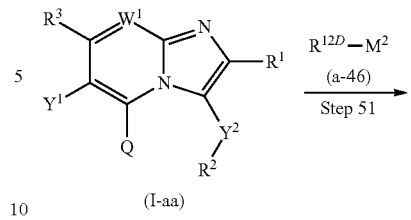

(I-aa)

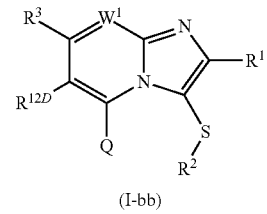

(I-bb)

(wherein, $R^1$, Q, $R^3$, $R^{18}$, $R^{19}$, $W^1$ and $W^2$ have the same meanings as described above, respectively)

Step 49

Compound (a-44) can be produced by reacting compound (a-35) with 0.5 to 10 equivalents of a sulfonylating agent in a solvent or without solvent at a temperature between −30° C. and the boiling point of the solvent used for 5 minutes to 72 hours.

Examples of the solvent include 1,2-dichloroethane, chloroform, methylene chloride, sulfolane, ethyl acetate, and the like. These may be used either alone or as a mixture. Of these, 1,2-dichloroethane or methylene chloride is preferred. Examples of the sulfonylating agent include chlorosulfonic acid, trimethylsilyl chlorosulfonate, fuming sulfuric acid, sulfur trioxide, sulfur dioxide, and the like.

Step 50

Compound (a-44) is treated with 1 to 20 equivalents of an acid halogenating agent in a solvent or without solvent at a temperature between −20° C. and the boiling point of the solvent used for 5 minutes to 72 hours to obtain a sulfonic acid halide of compound (a-44). Here, 0.01 to 0.5 equivalents of DMF, pyridine, and the like may be added, if necessary. The resulting sulfonic acid halide is reacted with 0.5 to 5 equivalents of compound (a-45) in a solvent at a temperature between −20° C. and the boiling point of the solvent used for 5 minutes to 72 hours in the presence of 1 to 10 equivalents of a base to produce compound (I-z).

Compound (a-45) can be obtained by as a commercially available product, or by using known methods [for example, *Jikken Kagaku Kouza*, 4th Ed., Vol. 20, p. 279, Maruzen Co., Ltd. (1992), and the like] or modified methods thereof.

Examples of the solvent used for the reaction to obtain the sulfonic acid halide include 1,2-dichloroethane, chloroform, methylene chloride, pyridine, THF, DME, toluene, DMF, dioxane, ethyl acetate, and the like. These may be used either alone or as a mixture. Of these, 1,2-dichloroethane, methylene chloride, and toluene are preferred. Examples of the acid halogenating agent include thionyl chloride, oxalyl chloride, phosphorus oxychloride, and the like. Examples of the solvent used for the reaction with the sulfonic acid halide and compound (a-45) include 1,2-dichloroethane, chloroform, methylene chloride, pyridine, acetonitrile, THF, DME, toluene, DMF, dioxane, ethyl acetate, and the like. These may be used either alone or as a mixture. Examples of the base include pyridine, triethylamine, 4-(dimethylamino)pyridine, N,N-diisopropylethylamine, sodium hydrogen carbonate aqueous solution, sodium hydroxide aqueous solution, and the like. Of these, triethylamine is preferred.

Producing Process 11

Among compound (I), compound (I-bb) in which $W^2$ is C—$R^{12D}$ (wherein $R^{12D}$ represents optionally substituted lower alkyl, or optionally substituted cycloalkyl) also can be produced according to the following step.

{wherein, $Y^1$, $R^1$, $R^2$, Q, $R^3$, $R^{12D}$, $L^1$, and $W^1$ have the same meanings as described above, respectively, and $M^2$ represents $B(OR^{20})(OR^{21})$ (wherein $R^{20}$ and $R^{21}$ may be the same or different, and each represents a hydrogen atom or $C_{1-6}$alkyl, or $R^{20}$ and $R^{21}$ together represent $C_{1-6}$ alkylene), or $SnR^{22}R^{23}R^{24}$ (wherein $R^{22}$, $R^{23}$, and $R^{24}$ may be the same or different, and each represents $C_{1-6}$alkyl or phenyl)}

Step 51

Compound (I-bb) can be produced by reacting compound (I-aa) obtained in the same manner as in the producing process 1 with 1 to 10 equivalents of compound (a-46) in a solvent at a temperature between −10° C. and the boiling point of the solvent used for 5 minutes to 72 hours in the presence of 0.001 to 1 equivalent of a palladium catalyst, and, if necessary, 0.1 to 10 equivalents of a base.

Compound (a-46) can be obtained as a commercially available product, or by using known methods [for example, *Jikken Kagaku Kouza*, 5th Ed., Vol. 18, p. 95, 183, Maruzen Co., Ltd. (2004), and the like] or modified methods thereof.

Examples of the base include potassium acetate, sodium acetate, potassium carbonate, cesium carbonate, sodium carbonate, sodium hydrogen carbonate, sodium hydroxide, lithium hydroxide, potassium hydroxide, potassium phosphate, pyridine, triethylamine, N-methylmorpholine, N-methylpiperidine, diisopropylethylamine, DBU, and the like. Examples of the palladium catalyst include a compound in which a phosphine ligand is coordinated to the palladium atom. Example of the palladium source include palladium acetate, trifluoropalladium acetate, trisdibenzylideneacetone dipalladium, and chloroform adducts thereof, and the like. Examples of the phosphine ligand include triphenylphosphine, 1,1'-bisdiphenylphosphinoferrocene, o-tolylphosphine, and the like. Preferably, these are used in 1 to 10 equivalents with respect to above the palladium source. It is also possible to use commercially available reagents, for example, such as tetrakistriphenylphosphinepalladium, [1,1'-bis(diphenylphosphino)-ferrocene]dichloropalladium(II), and the like. Examples of the solvent include methanol, ethanol, dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, water, and the like. These may be used either alone or as a mixture.

Producing Process 12

Among compound (a-5), compound (a-53) in which $L^1$ is —$CH_2$—, and $R^1$ is trifluoromethyl, and compound (a-58) in which $L^1$ is —$CH_2$—, and $R^1$ is $R^{14-1}$ (wherein $R^{14-1}$ represents optionally substituted lower alkyl, or optionally substituted cycloalkyl) also can be produced according to the following steps.

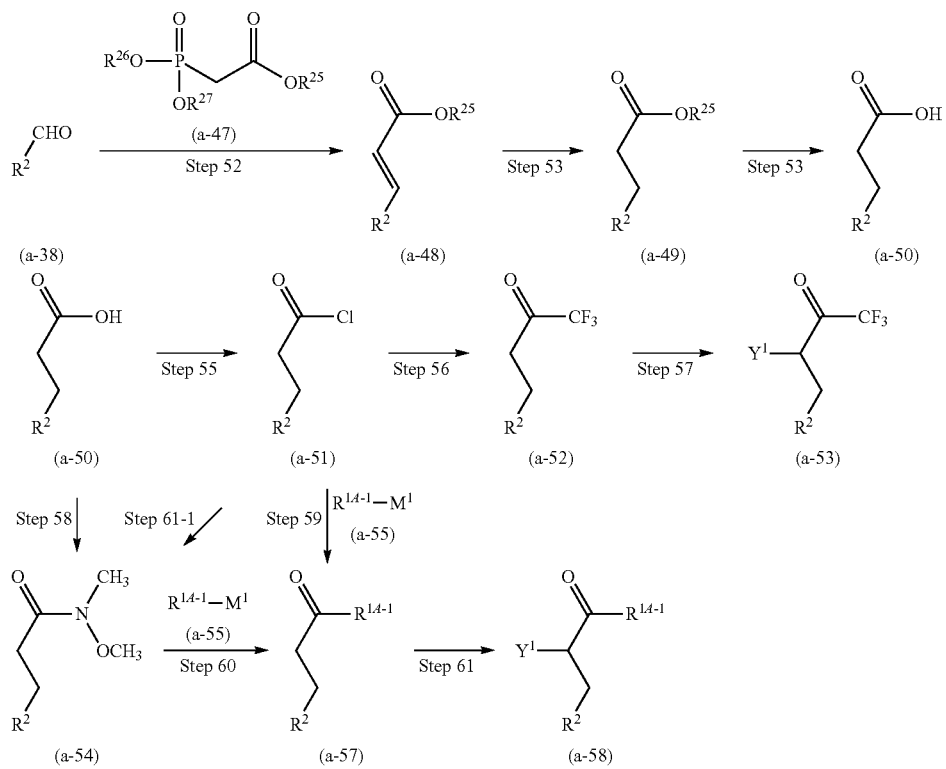

[Chemical Formula 15]

(wherein, $M^1$, $Y^1$, $R^{14-1}$, and $R^2$ have the same meanings as described above, respectively and $R^{25}$, $R^{26}$, and $R^{27}$ may be the same or different, and each represents $C_{1-6}$alkyl or phenyl)

Step 52

Compound (a-48) can be produced by reacting compound (a-38) with 1 to 10 equivalents of compound (a-47) in a solvent at a temperature between −78° C. and the boiling point of the solvent used for 5 minutes to 72 hours in the presence of 1 to 10 equivalents of a base.

Examples of the base include sodium hydride, potassium acetate, sodium hydrogen carbonate, potassium carbonate, potassium hydroxide, sodium hydroxide, sodium methoxide, potassium tert-butoxide, triethylamine, diisopropylethylamine, N-methylmorpholine, pyridine, DBU, and the like. Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, and the like. These may be used either alone or as a mixture.

Compound (a-47) can be obtained as a commercially available product, or by using known methods [for example, *Jikken Kagaku Kouza*, 4th Ed., Vol. 24, p. 229, Maruzen Co., Ltd. (1992), and the like] or modified methods thereof.

Step 53

Compound (a-49) can be produced by treating compound (a-48) in a solvent under a hydrogen atmosphere or in the presence of a suitable hydrogen source at a temperature between −20° C. and the boiling point of the solvent used under ordinary pressure or increased pressure for 5 minutes to 72 hours in the presence of a suitable catalyst.

Examples of the catalyst include palladium carbon, palladium, palladium hydroxide, palladium acetate, palladium black, and the like. These are used in 0.01 to 100 weight % with respect to compound (a-48). Examples of the hydrogen source include formic acid, ammonium formate, sodium formate, cyclohexadiene, hydrazine, and the like. These are used in 2 equivalents to a large excess amount. Examples of the solvent include methanol, ethanol, toluene, ethyl acetate, acetonitrile, diethyl ether, THF, DME, dioxane, DMF, DMA, NMP, water, and the like. These may be used either alone or as a mixture.

Step 54

Compound (a-50) can be produced in the same manner as in the above step 2, using compound (a-49).

Step 55

Compound (a-51) can be produced by treating compound (a-50) in a solvent or without solvent at a temperature between −20° C. and the boiling point of the solvent used for 5 minutes to 72 hours, using 1 to 20 equivalents of an acid halogenating agent. Here, 0.01 to 0.5 equivalents of DMF, pyridine, and the like may be added, if necessary.

Examples of the solvent include 1,2-dichloroethane, chloroform, methylene chloride, pyridine, THF, DME, toluene, DMF, dioxane, ethyl acetate, and the like. These may be used either alone or as a mixture. Of these, 1,2-dichloroethane, methylene chloride, and toluene are preferred. Examples of the acid halogenating agent include thionyl chloride, oxalyl chloride, phosphorus oxychloride, and the like.

Step 56

Compound (a-52) can be produced by reacting compound (a-51) with 1 to 20 equivalents of anhydrous trifluoroacetic acid in a solvent at a temperature between −20° C. and the boiling point of the solvent used for 5 minutes to 72 hours in the presence of 1 to 20 equivalents of a base.

Examples of the base include pyridine, and the like. Examples of the solvent include dichloromethane, diethyl ether, THF, DME, dioxane, and the like. These may be used either alone or as a mixture.

Step 57

Compound (a-53) can be produced in the same manner as in the above step 37, using a silyl enol ether of compound (a-52) obtained by the reaction of compound (a-52) with 1 to 10 equivalents of trimethylsilyl chloride in a solvent at a temperature between −10° C. and the boiling point of the solvent used for 5 minutes to 78 hours in the presence of 1 to 10 equivalents of a base.

Examples of the base include triethylamine, diisopropylethylamine, N-methylmorpholine, pyridine, DBU, and the like. Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, and the like. These may be used either alone or as a mixture.

Step 58

Compound (a-54) can be produced in the same manner as in the above step 34, using compound (a-50).

Step 59

Compound (a-57) can be produced by reacting compound (a-51) with 1 to 20 equivalents of compound (a-55) in a solvent at a temperature between −20° C. and the boiling point of the solvent used for 5 minutes to 72 hours in the presence of a catalytic amount to 1 equivalent of a copper catalyst.

Examples of the copper catalyst include copper chloride, and the like. Examples of the solvent include diethyl ether, THF, DME, dioxane, and the like. These may be used either alone or as a mixture.

Compound (a-55) can be obtained as a commercially available product, or by using known methods [for example, *Jikken Kagaku Kouza* 18, Organic Compound Syntheses VI, Organic Syntheses using Metals, 5th Ed., p. 59, Maruzen (2005)] or modified methods thereof.

Step 60

Compound (a-57) can be produced in the same manner as in the above step 35, using compound (a-54) and compound (a-55).

Step 61

Compound (a-58) can be produced in the same manner as in the above step 37, using compound (a-57).

Step 61-1

Compound (a-54) can be obtained by reacting compound (a-51) with 1 to 20 equivalents of commercially available N,O-dimethylhydroxylamine in a solvent at a temperature between −10° C. and the boiling point of the solvent used for 5 minutes to 72 hours, preferably in the presence of 1 to 20 equivalents of a base, if necessary.

Examples of the base include potassium carbonate, sodium carbonate, lithium hydroxide, potassium hydroxide, sodium hydroxide, sodium hydride, sodium methoxide, potassium tert-butoxide, triethylamine, diisopropylethylamine, N-methylmorpholine, N-methylpiperidine, pyridine, DBU, and the like. Examples of the solvent include dichloromethane, chloroform, 1,2-dichloroethane, toluene, xylene, ethyl acetate, acetonitrile, diethyl ether, THF, DME, 1,4-dioxane, DMF, DMA, NMP, DMSO, pyridine, and the like. These may be used either alone or as a mixture.

Producing Process 13

In compound (a-35), compound (a-61) in which $R^3$ is —$CONR^8R^9$ (wherein $R^8$ and $R^9$ may be the same or different, and have the same meanings as described above, respectively) also can be produced according to the following steps.

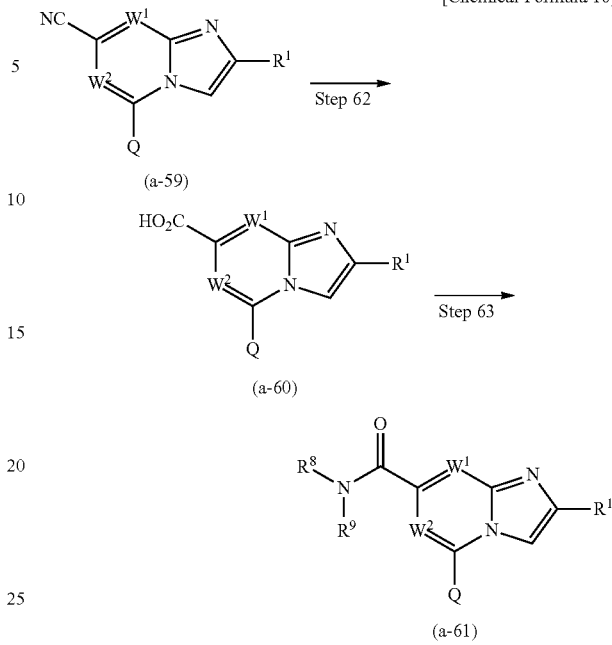

[Chemical Formula 16]

(wherein, $R^1$, Q, $W^1$, $W^2$, $R^8$, and $R^9$ have the same meanings as described above, respectively)

Step 62

Compound (a-60) can be produced in the same manner as in the step 12 of the producing process 1, using compound (a-59).

Compound (a-59) can be produced according to the method described in step 38 of the producing process 7.

Step 63

Compound (a-61) can be produced in the same manner as in the step 3 of the producing process 1, using compound (a-60).

Producing Process 14

In compound (a-10), compound (a-64) in which $L^1$ is —$CH_2O$— also can be produced according to the following steps.

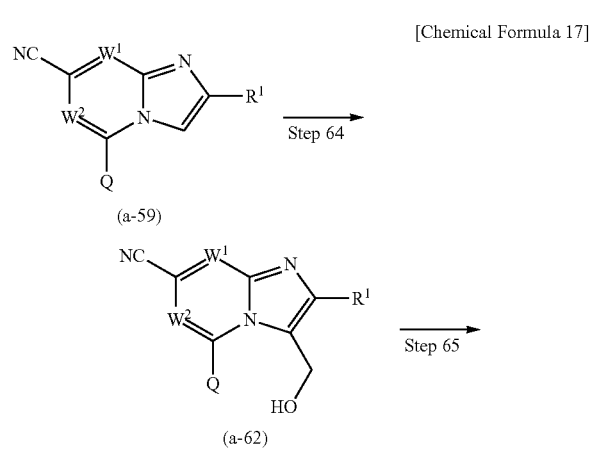

[Chemical Formula 17]

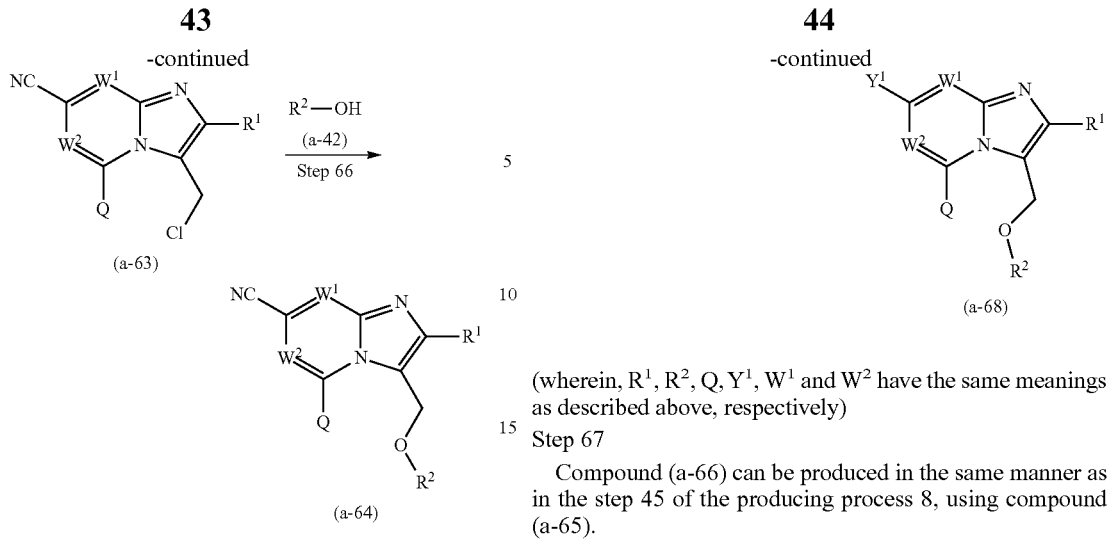

(wherein, $R^1$, $R^2$, Q, $W^1$ and $W^2$ have the same meanings as described above, respectively)

Step 64

Compound (a-62) can be produced in the same manner as in the step 45 of the producing process 8, using compound (a-59).

Step 65

Compound (a-63) can be produced in the same manner as in the step 46 of the producing process 8, using compound (a-62).

Step 66

Compound (a-64) can be produced in the same manner as in the step 47 of the producing process 8, using compound (a-63) and compound (a-42).

Producing Process 15

In compound (a-6), compound (a-68) in which $L^1$ is —$CH_2O$— also can be produced according to the following steps.

[Chemical Formula 18]

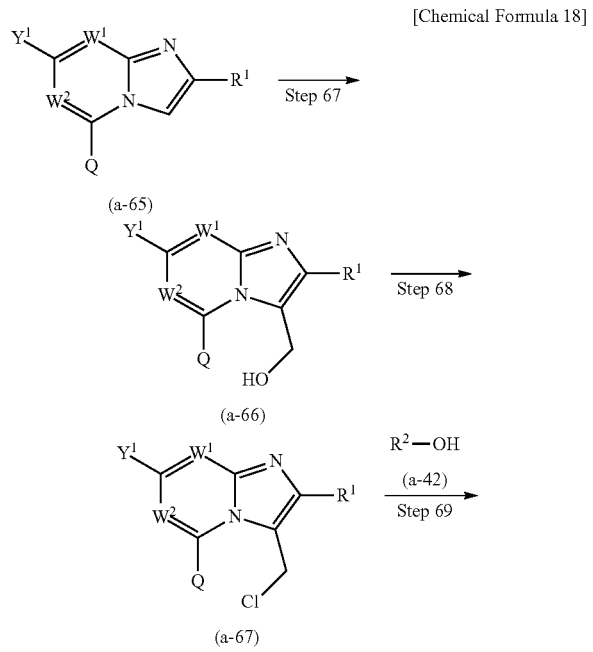

(wherein, $R^1$, $R^2$, Q, $Y^1$, $W^1$ and $W^2$ have the same meanings as described above, respectively)

Step 67

Compound (a-66) can be produced in the same manner as in the step 45 of the producing process 8, using compound (a-65).

Compound (a-65) can be produced according to the method described in step 38 of the producing process 7.

Step 68

Compound (a-67) can be produced in the same manner as in the step 46 of the producing process 8, using compound (a-66).

Step 69

Compound (a-68) can be produced in the same manner as in the step 47 of the producing process 8, using compound (a-67) and compound (a-42).

Producing Process 16

In compound (a-59), compound (a-70) in which $W^2$ is C—$R^{12D}$ (wherein $R^{12D}$ has the same meaning as described above) also can be produced according to the following step.

[Chemical Formula 19]

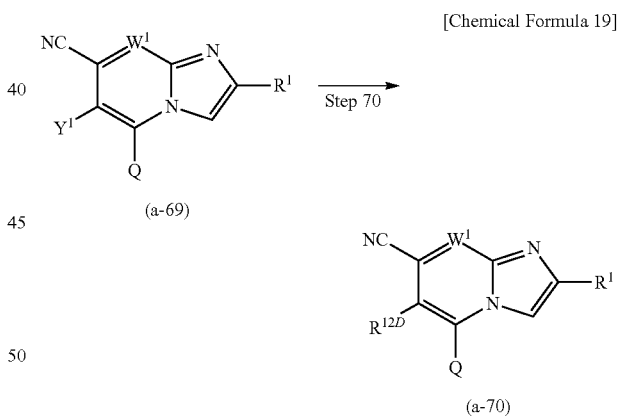

(wherein, $R^1$, Q, $R^{12D}$, $Y^1$ and $W^1$ have the same meanings as described above, respectively)

Step 70

Compound (a-70) can be produced in the same manner as in the step 51 of the producing process 11, using compound (a-69).

Compound (a-69) can be produced according to the method described in step 38 of the producing process 7.

Producing Process 17

In compound (a-10), compound (a-73) in which $L^1$ is —$S(O)_{n_3}$- (wherein $n^3$ has the same meaning as described above) also can be produced according to the following steps.

[Chemical Formula 20]

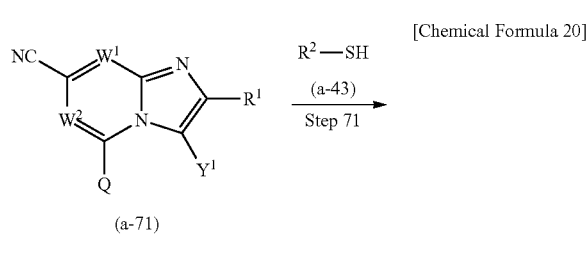

(a-71)

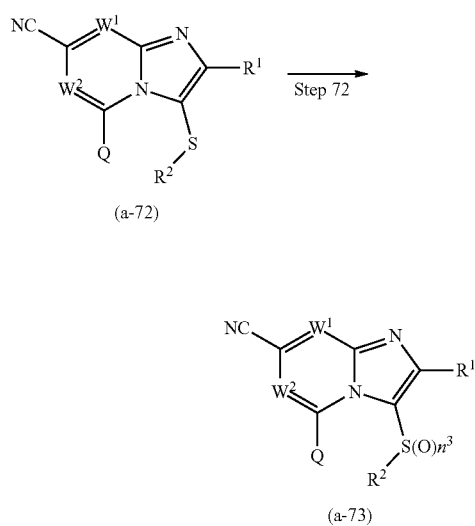

(wherein, $R^1$, $R^2$, Q, $Y^1$, $W^1$, $W^2$ and $n^3$ have the same meanings as described above, respectively)

Step 71

Compound (a-72) can be produced in the same manner as in the step 47-1 of the producing process 9, using compound (a-71).

Compound (a-71) can be produced according to the method described in step 39 of the producing process 7.

Step 72

Compound (a-73) can be produced in the same manner as in the step 48 of the producing process 9, using compound (a-72).

Producing Process 18

In compound (a-10), compound (a-75) in which $L^1$ is —$CH_2O$—, and $W^2$ is C—$R^{12D}$ (wherein $R^{12D}$ has the same meaning as described above) also can be produced according to the following step.

[Chemical Formula 21]

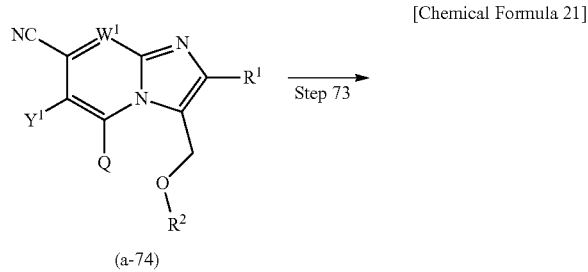

(a-74)

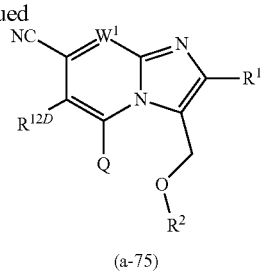

(a-75)

(wherein, $R^1$, $R^2$, Q, $R^{12D}$, $Y^1$ and $W^1$ have the same meanings as described above, respectively)

Step 73

Compound (a-75) can be produced in the same manner as in the step 51 of the producing process 11, using compound (a-74).

Compound (a-74) can be produced according to the method described in the producing process 14.

Producing Process 19

Among compound (a-2) and compound (a-9), compound (a-78) in which $W^2$ is C—$Y^1$ (wherein $Y^1$ has the same meaning as described above), and compound (a-79) in which $W^1$ is C—$Y^2$ (wherein $Y^2$ has the same meaning as described above) also can be produced according to the following steps.

[Chemical Formula 22]

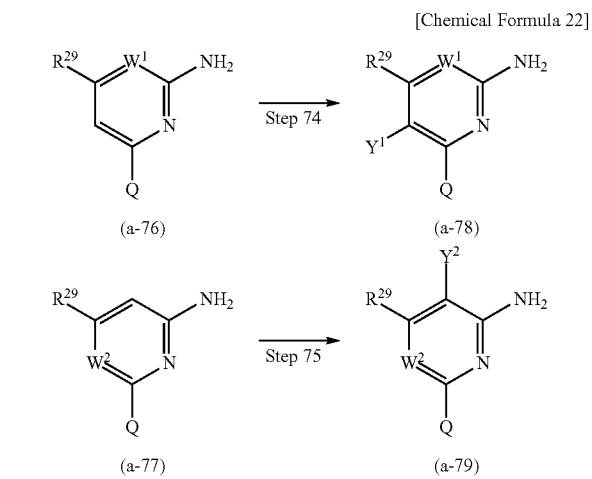

[wherein, $W^1$, $W^2$, $Y^1$, $Y^2$, and Q have the same meanings as described above, respectively, and $R^{29}$ represents —CN or —$CO_2R^{15}$ (wherein $R^{15}$ has the same meaning as described above)]

Step 74

Compound (a-78) can be produced in the same manner as in the above step 37, using the compound (a-76).

Compound (a-76) can be obtained as a commercially available product, or by using known methods [for example, WO2008/009750, and the like] or modified methods thereof.

Step 75

Compound (a-79) can be produced in the same manner as in the above step 37, using the compound (a-77).

Compound (a-77) can be obtained as a commercially available product, or by using known methods [for example, WO2008/009750, and the like] or modified methods thereof.

Producing Process 20

Among compound (a-2), compound (a-84) in which $W^2$ is C—$OR^{30}$ (wherein $R^{30}$ represents optionally substituted lower alkyl) also can be produced according to the following steps.

[Chemical Formula 23]

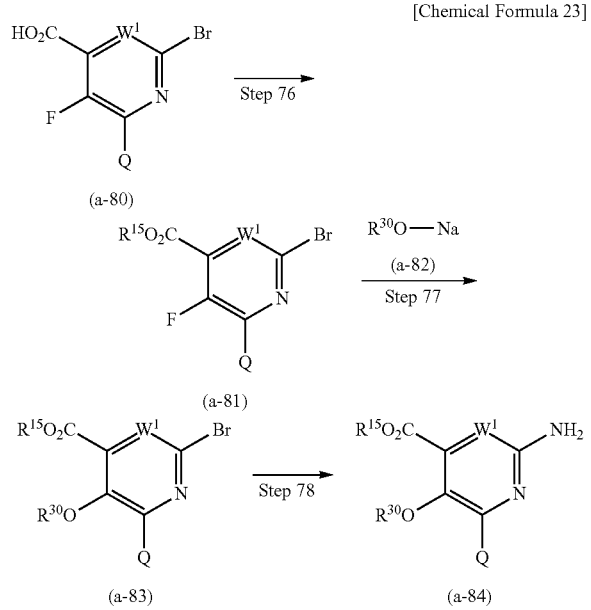

(wherein, Q, $R^{15}$, $R^{30}$, and $W^1$ have the same meanings as described above, respectively)

Step 76

Compound (a-81) can be produced in the same manner as in the above step 3, using the compound (a-80) and $R^{15}$—OH.

Compound (a-80) can be obtained as a commercially available product, or by using known methods [for example, *Jikken Kagaku Kouza,* 4th Ed., Vol. 22, p. 1, Maruzen Co., Ltd. (1992), and the like] or modified methods thereof.

Step 77

Compound (a-83) can be produced by reacting compound (a-81) with 1 to 20 equivalents of compound (a-82) in a solvent or without solvent at a temperature between −10° C. and the boiling point of the solvent used for 5 minutes to 72 hours.

Examples of the solvent include methanol, ethanol, and the like. These may be used either alone or as a mixture.

Compound (a-82) can be obtained as a commercially available product.

Step 78

Compound (a-84) can be produced by reacting compound (a-83) with 1 to 20 equivalents of a nitrogen source in a solvent in the presence of 1 to 100 mol % of a palladium catalyst at a temperature between −20° C. and the boiling point of the solvent used, if necessary, in the presence of 1 to 100 mol % of a catalyst ligand, and, if necessary, in the presence of 1 to a large excess amount of an acid under ordinary pressure or increased pressure for 5 minutes to 72 hours.

Examples of the nitrogen source include lithium bis(trimethylsilyl)amide, benzophenoneimine, and the like. Examples of the palladium catalyst include palladium acetate, tetrakis(triphenylphosphine)palladium, tris(dibenzylideneacetone)dipalladium(0), and the like. Examples of the catalyst ligand include triphenylphosphine, 1,1′-bis(diphenylphosphino)ferrocene, 1,3-bis(diphenylphosphino)propane, 2-(dicyclohexylphosphino)biphenyl, and the like. Examples of the acid include hydrochloric acid, and the like. Examples of the solvent include dichloromethane, chloroform, 1,2-dichloroethane, toluene, ethyl acetate, acetonitrile, diethyl ether, THF, DME, 1,4-dioxane, DMF, DMA, NMP, water, and the like. These may be used either alone or as a mixture.

Producing Process 21

Among compound (a-5), compound (a-58) in which $L^1$ is —$CH_2$—, and $R^1$ is $R^{1A-1}$ (wherein $R^{1A-1}$ has the same meaning as described above) also can be produced according to the following steps.

[Chemical Formula 24]

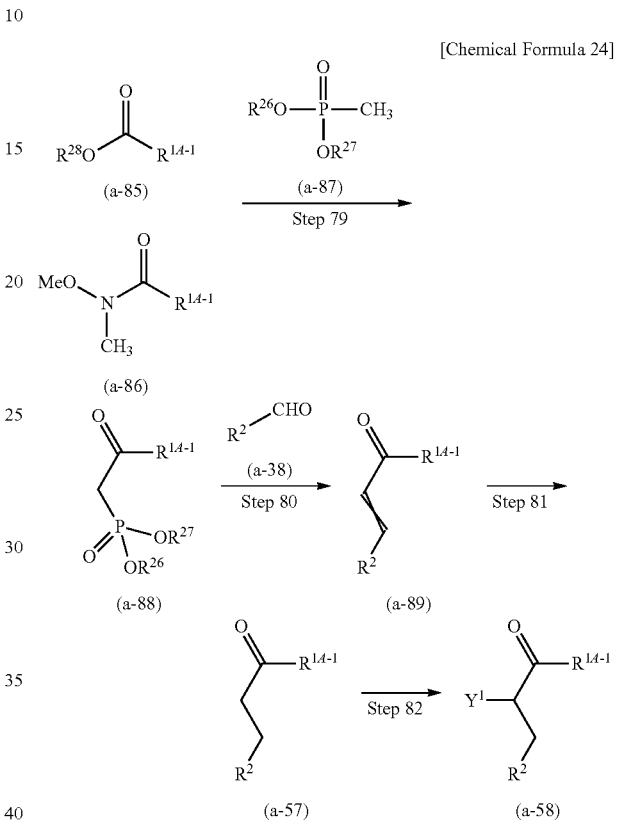

(wherein, $Y^1$, $R^{1A-1}$, $R^2$, $R^{26}$, $R^{27}$ and $R^{28}$ have the same meanings as described above, respectively)

Step 79

Compound (a-88) can be produced by reacting compound (a-85) or compound (a-86) with 1 to 20 equivalents of compound (a-87) in a solvent or without solvent at a temperature between −78° C. and the boiling point of the solvent used for 5 minutes to 72 hours in the presence of 1 to 20 equivalents of a base.

Examples of the base include n-butyllithium, and the like. Examples of the solvent include toluene, diethyl ether, THF, DME, dioxane, hexane, and the like. These may be used either alone or as a mixture.

Compound (a-85) can be obtained as a commercially available product, or by using known methods [for example, *Jikken Kagaku Kouza,* 4th Ed., Vol. 22, p. 43, Maruzen Co., Ltd. (1992), and the like] or modified methods thereof.

Compound (a-86) can be obtained as a commercially available product, or by using known methods [for example, *Jikken Kagaku Kouza,* 4th Ed., Vol. 22, p. 137, Maruzen Co., Ltd. (1992), and the like] or modified methods thereof.

Compound (a-87) can be obtained as a commercially available product, or by using known methods [for example, *Jikken Kagaku Kouza,* 4th Ed., Vol. 24, p. 229, Maruzen Co., Ltd. (1992), and the like] or modified methods thereof.

Step 80

Compound (a-89) can be produced in the same manner as in the above step 52, using compound (a-88) and compound (a-38).

Step 81

Compound (a-57) can be produced in the same manner as in the above step 53, using compound (a-89).

Step 82

Compound (a-58) can be produced in the same manner as in the above step 37 or step 57, using compound (a-57).

Producing Process 22

Among compounds (a-10), compound (a-96) in which $L^1$ is —$CH_2$— and $R^4$ is —C(=O)$OR^4$ (wherein $R^4$ has the same meaning as described above), compound (a-98) in which $R^1$ is —C($R^{30}$)$_2$OH (wherein $R^{30}$ has the same meaning as described above), and compound (a-100) in which $R^4$ is —C($R^{30}$)$_2$$OR^{31}$ (wherein $R^{30}$ has the same meaning as described above, and $R^{34}$ represents lower alkyl) also can be produced according to the following steps.

[Chemical Formula 25]

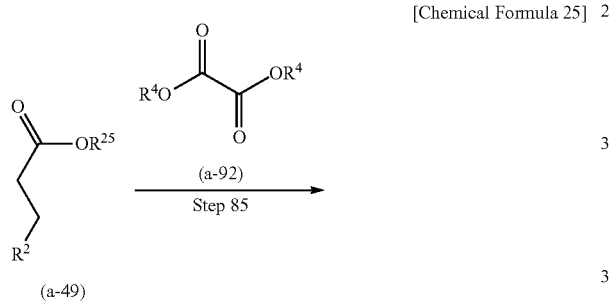

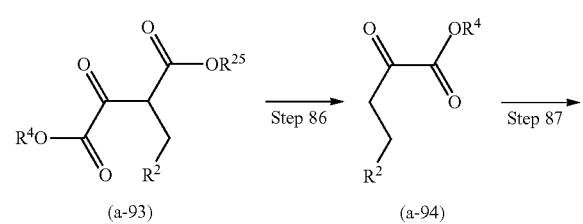

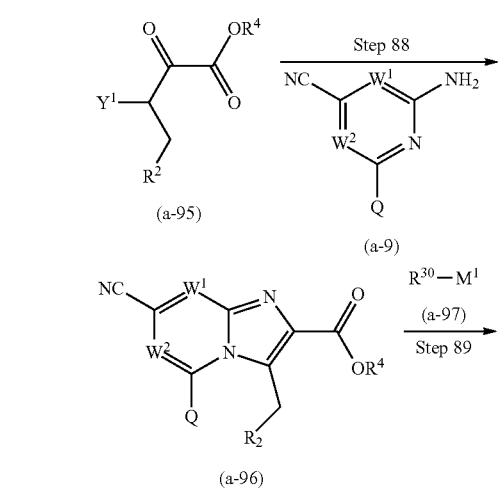

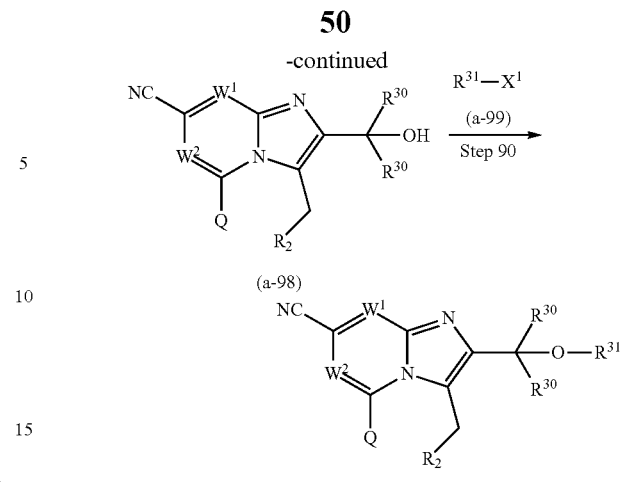

(wherein, $X^1$, $Y^1$, Q, $R^2$, $R^4$, $R^{25}$, $R^{30}$, $R^{31}$, $W^1$, $W^2$, and $M^1$ have the same meanings as described above, respectively)

Step 85

Compound (a-93) can be produced by reacting compound (a-49) with 1 to 20 equivalents of compound (a-92) in a solvent or without solvent at a temperature between −10° C. and the boiling point of the solvent used for 5 minutes to 72 hours in the presence of 1 to 20 equivalents of a base.

Examples of the base include sodium methoxide, sodium ethoxide, sodium tert-butoxide, and the like. Examples of the solvent include methanol, ethanol, tert-butanol, and the like. These may be used either alone or as a mixture.

Compound (a-92) can be obtained as a commercially available product, or by using known methods [for example, *Jikken Kagaku Kouza,* 4th Ed., Vol. 22, p. 43, Maruzen Co., Ltd. (1992), and the like] or modified methods thereof.

Step 86

Compound (a-94) can be produced by reacting compound (a-93) in a solvent at a temperature between −10° C. and the boiling point of the solvent used for 5 minutes to 72 hours in the presence of 1 to 20 equivalents of an inorganic salt.

Examples of the inorganic salt include sodium cyanide, potassium cyanide, sodium chloride, lithium chloride, and the like. Examples of the solvent include DMSO, and water. These are used as a mixture.

Step 87

Compound (a-95) can be produced in the same manner as in the above step 37, using compound (a-94).

Step 88

Compound (a-96) can be produced in the same manner as in the above step 4, using compound (a-95) and compound (a-9).

Step 89

Compound (a-98) can be produced in the same manner as in the above step 35, using compound (a-96) and compound (a-97).

Compound (a-97) can be obtained as a commercially available product, or by using known methods [for example, *Jikken Kagaku Kouza* 18, Organic Compound Syntheses VI, Organic Syntheses using Metals, 5th Ed., p. 59, Maruzen (2005)] or modified methods thereof.

Step 90

Compound (a-100) can be produced in the same manner as in the above step 17, using compound (a-98) and compound (a-99).

Compound (a-99) can be obtained as a commercially available product, or by using known methods [for example,

*Jikken Kagaku Kouza,* 4th Ed., Vol. 19, p. 416, Maruzen Co., Ltd. (1992), and the like] or modified methods thereof.

Producing Process 23

Among compound (a-7) and compound (a-10), compound (a-103) in which $L^1$ is —CH(OH)—, and compound (a-104) in which $L^1$ is —CH$_2$— also can be produced according to the following steps.

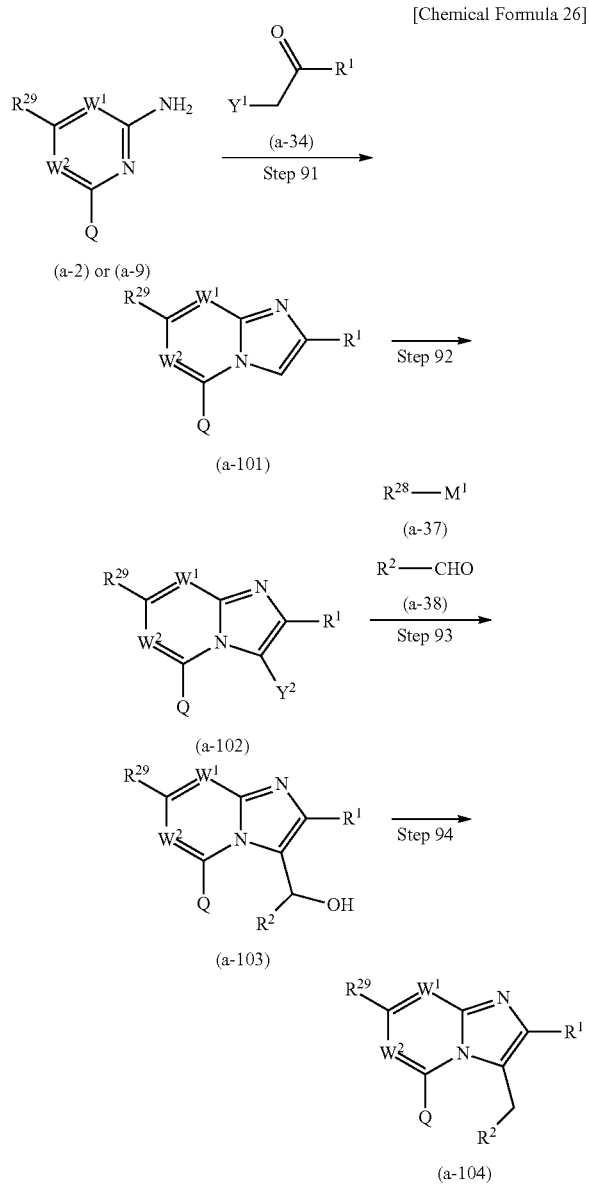

[Chemical Formula 26]

(wherein, $Y^1$, $R^1$, $R^2$, $R^{28}$, $R^{29}$, $M^1$, Q, $W^1$ and $W^2$ have the same meanings as described above, respectively)

Step 91

Compound (a-101) can be produced in the same manner as in the above step 4, using compound (a-2) or (a-9) and compound (a-34).

Step 92

Compound (a-102) can be produced in the same manner as in the above step 37, using compound (a-101).

Step 93

Compound (a-103) can be produced in the same manner as in the above step 40, using compound (a-102), compound (a-37), and compound (a-38).

Step 94

Compound (a-104) can be produced by reacting compound (a-103) with 1 equivalent to a large excess amount of alkylchlorosilane and 1 equivalent to a large excess amount of sodium iodide in a solvent at a temperature between −20° C. and the boiling point of the solvent used for 5 minutes to 72 hours.

Examples of the alkylchlorosilane include trimethylchlorosilane, triethylchlorosilane, dimethyldichlorosilane, and the like. Examples of the solvent include dichloromethane, hexane, acenitrile. These may be used either alone or as a mixture.

Compound (a-104) can be produced by reacting compound (a-103) in a solvent at a temperature between −78° C. and the boiling point of the solvent used for 5 minutes to 72 hours preferably in the presence of 1 to 10 equivalents of a reducing agent, and preferably 1 to 10 equivalents of Brønsted acid.

Examples of the reducing agent include sodium borohydride, lithium borohydride, triethylsilane, and the like. Examples of the Brønsted acid include hydrochloric acid, sulfuric acid, trifluoroacetic acid, acetic acid, methanesulfonic acid, and the like. Examples of the solvent include toluene, THF, DME, 1,4-dioxane, DMF, and the like. These may be used either alone or as a mixture.

Producing Process 24

Among compound (a-7) and compound (a-10), compound (a-106) in which $L^1$ is —SO$_2$—, and $R^2$ is —NR$^{18}$R$^{19}$ (wherein $R^{18}$ and $R^{19}$ have the same meanings as described above, respectively) also can be produced according to the following steps.

[Chemical Formula 27]

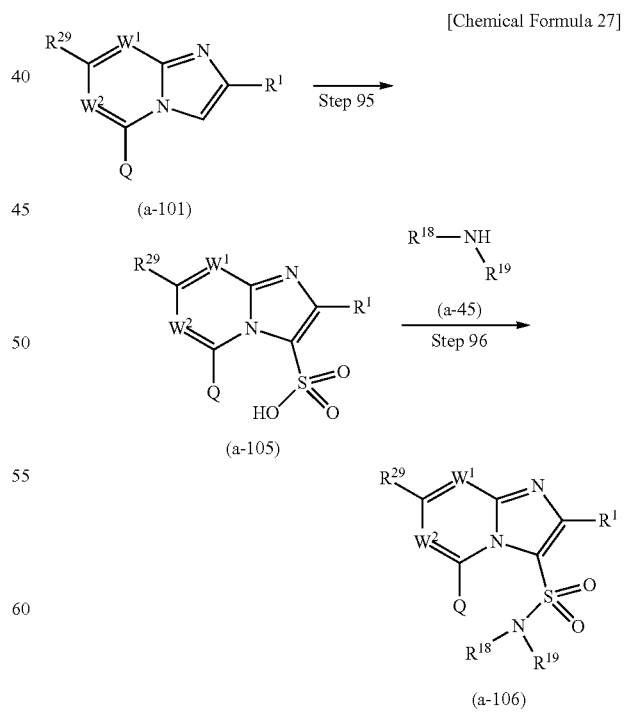

(wherein, $R^1$, $R^{18}$, $R^{19}$, $R^{29}$, Q, $W^1$ and $W^2$ have the same meanings as described above, respectively)

Step 95

Compound (a-105) can be produced in the same manner as in the above step 49, using compound (a-101) obtained in the above step 91.

Step 96

Compound (a-106) can be produced in the same manner as in the above step 50, using compound (a-105) and compound (a-45).

Producing Process 25

Among compound (a-7) and compound (a-10), compound (a-108) in which $L^1$ is —$CH_2$—, and $R^1$ is —$C(=CH_2)CH_3$) also can be produced according to the following step.

[Chemical Formula 28]

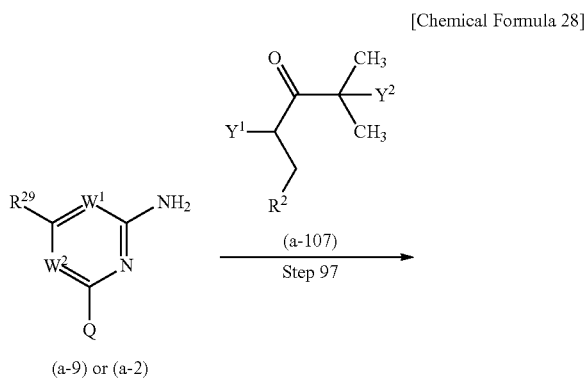

(wherein, $Y^1$, $Y^2$, $R^2$, $R^{29}$, Q, $W^1$ and $W^2$ have the same meanings as described above, respectively)

Step 97

Compound (a-108) can be produced in the same manner as in the above step 4, using compound (a-2) or (a-9), and compound (a-107) obtained according to the method of the above producing process 21.

Producing Process 26

Among compound (a-7) and compound (a-10), compound (a-110) in which $W^2$ is C—$R^{12D}$ (wherein $R^{12D}$ has the same meaning as described above), and compound (a-112) in which $W^2$ is C—$CR^{32}=CR^{33}R^{34}$ (wherein $R^{32}$, $R^{33}$, and $R^{34}$ may be the same or different, and each represents a hydrogen atom, or lower alkyl) also can be produced according to the following steps.

[Chemical Formula 29]

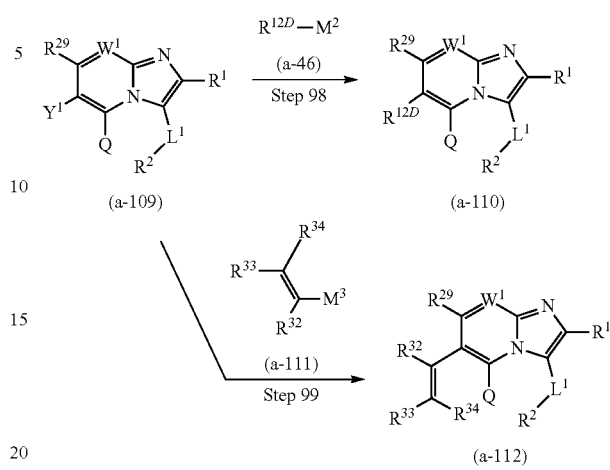

(wherein, $Y^1$, $L^1$, $R^1$, $R^2$, $R^{12D}$, $R^{29}$, $R^{32}$, $R^{33}$, $R^{34}$, $M^2$, Q, and $W^1$ have the same meanings as described above, respectively, and $M^3$ has the same meaning as the above $M^2$)

Step 98

Compound (a-110) can be produced in the same manner as in the above step 51, using compound (a-109) obtained according to the method of the above producing process 1, and compound (a-46).

Step 99

Compound (a-112) can be produced in the same manner as in above step 51, using compound (a-109) and compound (a-111).

Compound (a-111) can be obtained as a commercially available product, or by using known methods [for example, *Jikken Kagaku Kouza,* 5th Ed., Vol. 18, p. 95, 183, Maruzen Co., Ltd. (2004), and the like] or modified methods thereof.

Producing Process 27

Among compound (I-a), compound (I-dd) in which $R^8$ and $R^9$ are combined together with the adjacent nitrogen atom thereto to form an optionally substituted nitrogen-containing heterocyclic (aziridine ring) group) also can be produced according to the following step.

[Chemical Formula 30]

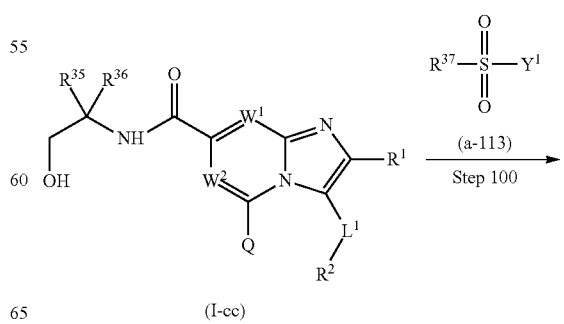

Producing Process 29

Compound (a-119) also can be produced according to the following steps.

[Chemical Formula 32]

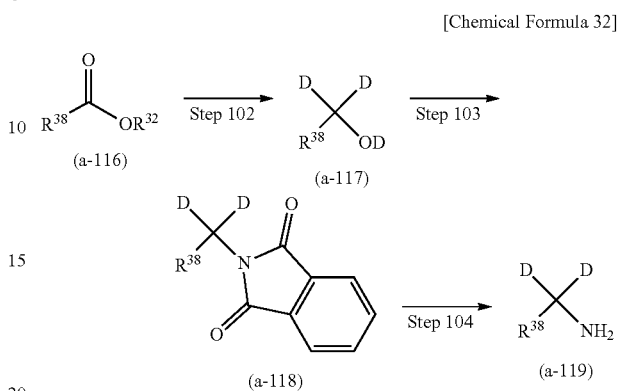

(wherein, R$^{32}$ has the same meaning as described above, R$^{38}$ represents optionally substituted lower alkyl, optionally substituted cycloalkyl, an optionally substituted aliphatic heterocyclic group, or an optionally substituted aromatic heterocyclic group)

Step 102

Compound (a-117) can be produced by reacting compound (a-116) in a solvent at a temperature between −10° C. and the boiling point of the solvent used for 5 minutes to 72 hours in the presence of 1 to 20 equivalents of a deuterating reducing agent.

Examples of the deuterating reducing agent include sodium borodeuteride, lithium borodeuteride, lithium aluminum deuteride, and the like. Examples of the solvent include acetonitrile, dichloromethane, 1,2-dichloroethane, chloroform, DME, DMF, DMA, 1,4-dioxane, THF, diethyl ether, diisopropylether, benzene, toluene, xylene, pyridine, NMP, methanol, ethanol, water, and deuterated solvents thereof, and the like. These may be used either alone or as a mixture.

Compound (a-116) can be obtained as a commercially available product, or by using known methods [for example, *Jikken Kagaku Kouza,* 4th Ed., Vol. 22, p. 43, Maruzen Co., Ltd. (1992), and the like] or modified methods thereof.

Step 103

Compound (a-118) can be produced by reacting compound (a-117) with 1 to 20 equivalents of phthalimide in a solvent at a temperature between −78° C. and the boiling point of the solvent used for 5 minutes to 72 hours in the presence of preferably 1 to 20 equivalents of a phosphine compound, and preferably 1 to 20 equivalents of an azo compound.

Examples of the phosphine compound include triphenylphosphine, tributylphosphine, and the like. Examples of the azo compound include diethylazodicarboxylate (DEAD), di-tert-butyl azadicarboxylate (DBAD), diisopropyl azadicarboxylate, N,N,N',N'-tetramethyl azadicarboxamide, 1,1'-(azadicarbonyl)dipiperazine, N,N,N',N'-tetraisopropyl azadicarboxamide, and the like. Examples of the preferable combination of the phosphine compound used and the azo compound used include a combination of triphenylphosphine, and DEAD or DBAD. Examples of the solvent include dichloromethane, chloroform, 1,2-dichloroethane, toluene, ethyl acetate, acetonitrile, diethyl ether, THF, DME, 1,4-dioxane, DMF, DMA, NMP, and the like. These may be used either alone or as a mixture.

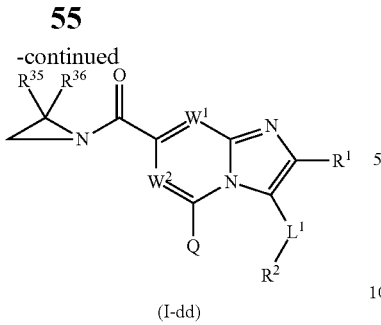

(I-dd)

(wherein, R$^{35}$ and R$^{36}$ may be the same or different, and each represents a hydrogen atom, or optionally substituted lower alkyl, R$^{37}$ represents a methyl group or a p-tolyl group, and Y$^{1}$, L$^{1}$, R$^{1}$, R$^{2}$, Q, W$^{1}$ and W$^{2}$ have the same meanings as described above, respectively)

Step 100

Compound (I-dd) can be produced by reacting compound (I-cc) obtained in the producing process 1 in a solvent at a temperature between −10° C. and the boiling point of the solvent used for 5 minutes to 72 hours with 1 to 20 equivalents of compound (a-113), if necessary, in the presence of 1 to 20 equivalents of a base.

Examples of the base include potassium carbonate, sodium carbonate, sodium hydrogen carbonate, TMEDA, pyridine, triethylamine, diisopropylethylamine, DBU, DMAP, and the like. Examples of the solvent include acetonitrile, dichloromethane, 1,2-dichloroethane, chloroform, DME, DMF, DMA, 1,4-dioxane, THF, diethyl ether, diisopropylether, benzene, toluene, xylene, pyridine, NMP, water, and the like. These may be used either alone or as a mixture.

Compound (a-113) can be obtained as a commercially available product.

Producing Process 28

Compound (a-115) also can be produced according to the following step.

[Chemical Formula 31]

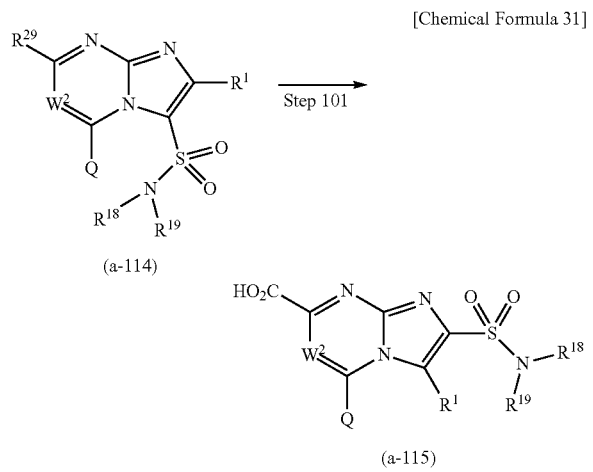

(wherein, R$^{1}$, R$^{12}$, R$^{19}$, R$^{29}$, Q, and W$^{2}$ have the same meanings as described above, respectively)

Step 101

Compound (a-115) can be produced in the same manner as in the above step 2 or the step 12, using compound (a-114) that can be synthesized according to the method of the above step 96.

Step 104

Compound (a-119) can be produced by treating compound (a-118) with 1 equivalent to a large excess amount of a base in a water-containing solvent at a temperature between 0° C. and the boiling point of the solvent used for 5 minutes to 72 hours.

Examples of the base include sodium hydroxide, potassium hydroxide, lithium hydroxide, hydrazine monohydrate, and the like. Examples of the solvent include methanol, ethanol, propanol, THF, 1,4-dioxane, DME, toluene, dichloromethane, DMF, water, and the like. These may be used either alone or as a mixture.

Producing Process 30

Compound (a-122) can be produced according to the following steps.

[Chemical Formula 33]

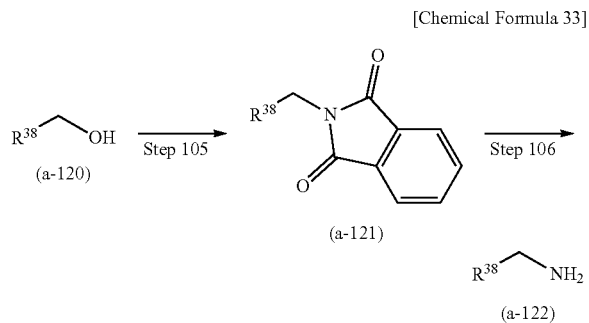

(wherein, $R^{38}$ has the same meaning as described above)

Step 105

Compound (a-121) can be produced in the same manner as in the above step 103, using compound (a-120).

Compound (a-120) can be obtained as a commercially available product, or by using known methods [for example, *Jikken Kagaku Kouza,* 4th Ed., Vol. 20, p. 1, Maruzen Co., Ltd. (1992), and the like] or modified methods thereof.

Step 106

Compound (a-122) can be produced in the same manner as in the above step 104, using compound (a-121).

Producing Process 31

Among compound (I), compound (I-ee) in which $L^1$ is —$SO_2$—, $R^2$ is —$NR^{18}R^{19}$ (wherein $R^{18}$ and $R^{19}$ have the same meanings as described above, respectively), and $R^1$ is —$NR^{39}R^{40}$ (wherein $R^{39}$ and $R^{40}$ are combined together with the adjacent nitrogen atom thereto to form an optionally substituted nitrogen-containing heterocyclic group), compound (I-ff) in which $R^1$ is —$OR^{33}$ (wherein $R^{30}$ has the same meaning as described above), compound (I-gg) in which $R^1$ is —$SR^{33}$ (wherein $R^{30}$ has the same meaning as described above), and compound (I-hh) in which $R^1$ is —$S(O)n^4R^{30}$ (wherein $n^4$ has the same meaning as $n^3$, and $R^{30}$ has the same meaning as described above) also can be produced according to the following steps.

[Chemical Formula 34]

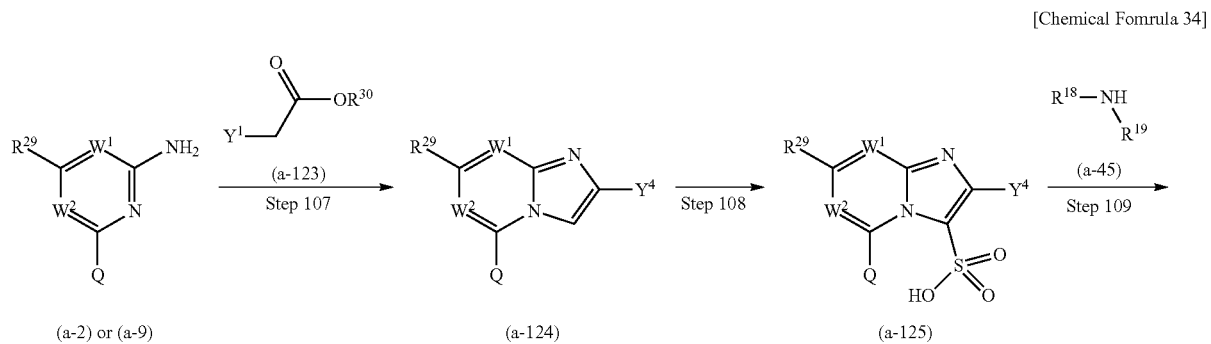

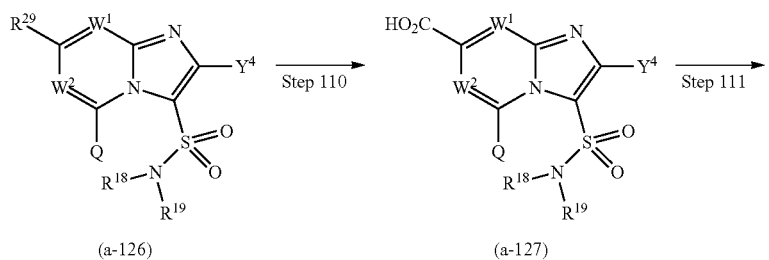

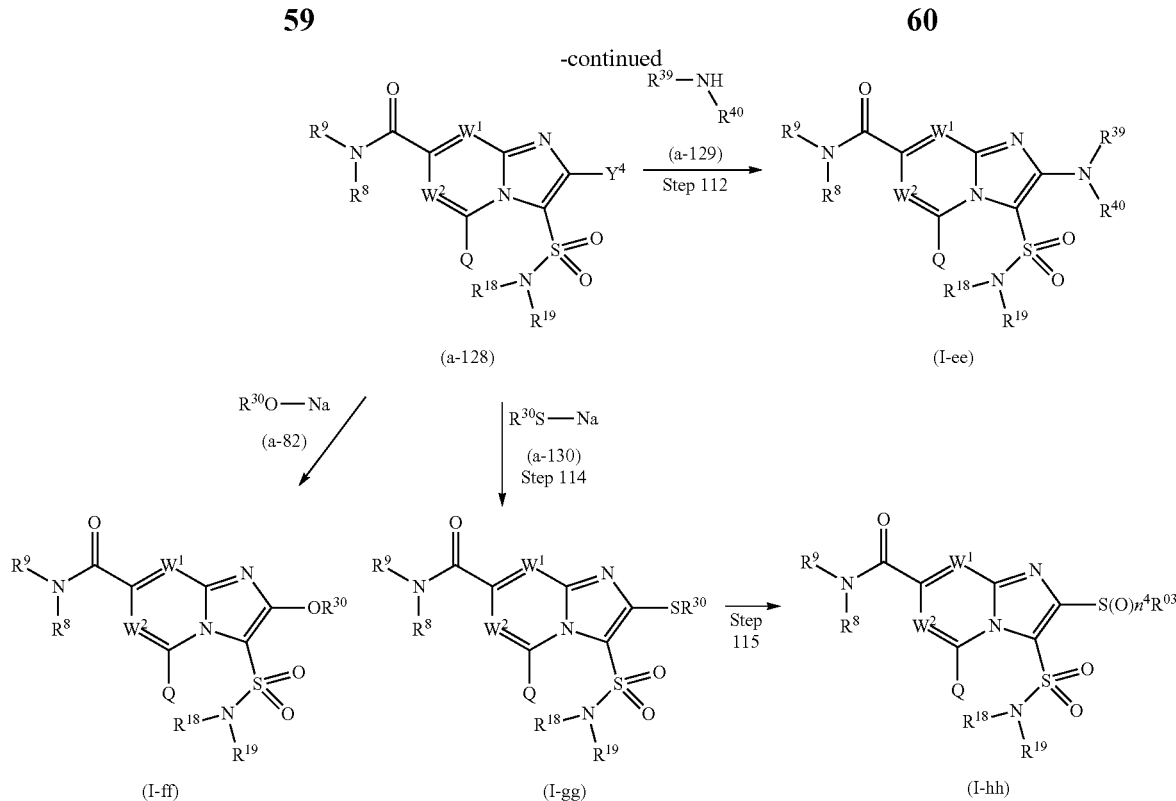

(wherein, Q, $R^8$, $R^9$, $R^{18}$, $R^{19}$, $R^{29}$, $R^{30}$, $R^{39}$, $R^{40}$, $Y^1$, $n^4$, $W^1$ and $W^2$ have the same meanings as described above, respectively, and $Y^4$ represents chlorine or bromine)

Step 107

Compound (a-124) can be produced by reacting the compound (a-2) or compound (a-9) with 1 to 20 equivalents of compound (a-123) in a solvent or without solvent at a temperature between 0° C. and the boiling point of the solvent used for 5 minutes to 72 hours, if necessary, in the presence of 1 to 10 equivalents of a suitable base, and, if necessary, in the presence of 0.1 to 1,000 weight % of a suitable additive, and then treating with 1 equivalent to a large excess amount of a chlorinating agent or a brominating agent at a temperature between −20° C. and 150° C. for 5 minutes to 72 hours, if necessary, in the presence of a catalytic amount to 1 equivalent of an additive.

Examples of the base include potassium carbonate, sodium carbonate, potassium hydrogen carbonate, sodium hydrogen carbonate, potassium hydroxide, potassium hydroxide, triethylamine, diisopropylethylamine, N-methylmorpholine, pyridine, DBU, and the like. Examples of the additive include molecular sieve 4A, and the like. Examples of the solvent include methanol, ethanol, propanol, butanol, DMF, DMA, NMP, acetonitrile, diethyl ether, THF, DME, 1,4-dioxane, DMSO, and the like. These may be used either alone or as a mixture.

Examples of the chlorinating agent include phosphorus oxychloride, phosphorus pentachloride, phosphorus trichloride, thionyl chloride, and the like. Examples of the brominating agent include phosphorus oxybromide, phosphorus tribromide, and the like. Examples of the additive include DMF, pyridine, diisopropylethylamine, and the like.

Compound (a-123) can be obtained as a commercially available product.

Step 108

Compound (a-125) can be produced in the same manner as in the above step 49, using compound (a-124).

Step 109

Compound (a-126) can be produced in the same manner as in the above step 50, using compound (a-125) and compound (a-45).

Step 110

Compound (a-127) can be produced in the same manner as in the above step 2 or step 12, using compound (a-126).

Step 111

Compound (a-128) can be produced in the same manner as in the above step 3, using compound (a-127).

Step 112

Compound (I-ee) can be produced by reacting compound (a-128) with 1 to 20 equivalents of compound (a-129) in a solvent or without solvent at a temperature between −78° C. and the boiling point of the solvent used for 5 minutes to 72 hours in the presence of 1 to 20 equivalents of a base.

Examples of the base include sodium hydride, potassium acetate, sodium hydrogen carbonate, potassium carbonate, potassium hydroxide, sodium hydroxide, sodium methoxide, potassium tert-butoxide, triethylamine, diisopropylethylamine, N-methylmorpholine, pyridine, DBU, and the like. Examples of the solvent include dichloromethane, chloroform, 1,2-dichloroethane, toluene, ethyl acetate, acetonitrile, diethyl ether, THF, DME, dioxane, DMF, DMA, NMP, and the like. These may be used either alone or as a mixture.

Compound (a-129) can be obtained as a commercially available product.

Step 113

Compound (I-ff) can be produced in the same manner as in the above step 77, using compound (a-128) and compound (a-82).

Step 114

Compound (I-gg) can be produced in the same manner as in the above step 77, using compound (a-128) and compound (a-130).

Compound (a-130) can be obtained as a commercially available product.

Step 115

Compound (I-hh) can be produced in the same manner as in the above step 48, using compound (I-gg).

Producing Process 32

Among compound (I-a), compound (I-jj) in which $R^8$ is H, and $R^9$ is a cyclohexenyl group) also can be produced according to the following step.

[Chemical Formula 35]

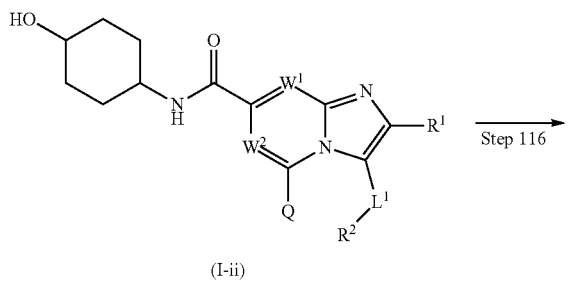

(I-ii)

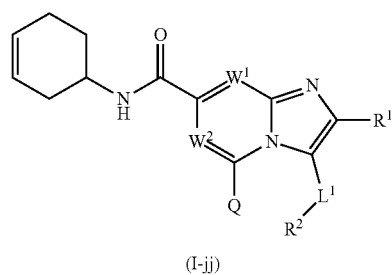

(I-jj)

(wherein, $L^1$, $R^1$, $R^2$, Q, $W^1$ and $W^2$ have the same meanings as described above, respectively)

Step 116

Compound (I-jj) can be produced by reacting compound (I-ii) obtained according to the producing process 1 in a solvent at a temperature between −78° C. and the boiling point of the solvent used for 5 minutes to 72 hours in the presence of 1 equivalent to a large excess amount of a fluorinating agent.

Examples of the fluorinating agent include diethylaminosulfate trifluoride (DAST), bis(2-methoxyethyl)aminosulfur trifluoride, and the like. Examples of the solvent include dichloromethane, 1,2-dichloroethane, and the like. These may be used either alone or as a mixture.

The transformation of the functional groups contained in $R^1$, $R^2$, $R^3$, $L^1$, Q, $W^1$, or $W^2$ of compounds (I) may be performed by using known methods [for example, methods described in Comprehensive Organic Transformations, 2nd edition, R. C. Larock, Vch Verlagsgesellschaft Mbh (1999), and the like] or modified methods thereof.

The intermediates and the target compounds in each above producing process can be isolated and purified by being subjected to separation and purification methods commonly used in organic synthesis chemistry, including, for example, filtration, extraction, washing, drying, evaporation, recrystallization, various chromatography techniques, and the like. The intermediates can also be used in to the next reaction without being purified.

Where compound (I) and compound (IA) contain stereoisomers such as geometric isomers and optical isomers, tautomers and the like, it is to be understood that all such isomers and other possible isomers and mixtures thereof are encompassed within the scope of the present invention.

Further, some of or all of the atoms in compound (I) or compound (IA) may be replaced with corresponding isotope atoms, and the present invention includes all compounds in which such replacements with isotope atoms occur. For example, some of or all of the hydrogen atoms in compound (I) or compound (IA) may be hydrogen atoms with an atomic weight of 2 (deuterium atoms).

Where some of or all of the atoms in compound (I) or compound (IA) are replaced with corresponding isotope atoms, such compound can be produced in the same manner as in the above producing processes, using commercially available building blocks. Further, where some of or all of the atoms in compound (I) or compound (IA) are replaced with deuterium atoms, such compound can be synthesized by using, for example, 1) a method in which carboxylic acid and the like are deuterated under basic conditions using deuterium peroxide (see U.S. Pat. No. 3,849,458), 2) a method in which alcohol, carboxylic acid, and the like are deuterated by using an iridium complex as a catalyst, and deuterated water as a deuterium source [see J. Am. Chem. Soc., Vol. 124, No. 10, 2092 (2002)], 3) a method in which fatty acid is deuterated by using a palladium carbon as a catalyst, and only deuterium gas as a deuterium source [see LIPIDS, Vol. 9, No. 11, 913 (1974)], 4) a method in which acrylic acid, methyl acrylate, methacrylic acid, methyl methacrylate, and the like are deuterated by using platinum, palladium, rhodium, ruthenium, iridium metal and the like as a catalyst, and, deuterated water, or deuterated water and deuterium gas as a deuterium source (see JP-B-1993-19536, Japanese Published Unexamined Patent Application No. 1986-277648, and Japanese Published Unexamined Patent Application No. 1986-275241), 5) a method in which acrylic acid, methyl methacrylate, and the like are deuterated with a catalyst such as palladium, nickel, copper, and copper chromite, using deuterated water as a deuterium source (see Japanese Published Unexamined Patent Application No. 1988-198638), and the like.

To obtain a salt of compound (I) or compound (IA), when compound (I) or compound (IA) is obtained in the form of a salt, it may be purified as it is. Further, when compound (I) or compound (IA) is obtained in a free form, compound (I) or compound (IA) may be dissolved or suspended in a suitable solvent, followed by addition of an acid or a base to form a salt. Then, the resulting salt may be isolated and purified.

Compound (I) and compound (IA), and pharmaceutically acceptable salts thereof may exist in the form of adducts with water or various solvents. Such adducts are also encompassed within the scope of the present invention.

Specific examples of compound (I) or compound (IA) of the present invention are presented in Table 1 to Table 19. However, it should be noted that the compounds of the present invention are not limited to the following.

TABLE 1

[Structure: N,N-diethyl imidazo[1,2-a]pyridine-7-carboxamide with 3-(cyclohexylmethyl) and 2-R¹ substituents]

| Compound No. | —R¹ |
|---|---|
| 1 | —C(=O)—O—CH₂CH₃ (ethyl ester) |
| 2 | —C(=O)—NH—CH₂CH₂CH₂CH₃ (n-butyl amide) |
| 3 | —NH—C(=O)—O—CH₂—C₆H₅ (benzyl carbamate) |
| 4 | —C(=O)—CH₃ (acetyl) |
| 5 | —CF₂—CH₃ (1,1-difluoroethyl) |
| 6 | cyclopropyl |

TABLE 2

[Structure: N,N-diethyl imidazo[1,2-a]pyridine-7-carboxamide with 2-isopropyl and 3-L¹-R² substituents]

| Compound No. | —L¹—R² |
|---|---|
| 7 | —CH(OH)—cyclohexyl |
| 8 | —CHF—cyclohexyl |
| 9 | —CH(OCH₃)—cyclohexyl |
| 10 | —CH= cyclohexylidene |
| 11 | —C(=O)—cyclohexyl |
| 12 | —S—cyclohexyl |
| 13 | —S(=O)₂—cyclohexyl |

TABLE 3

[Structure: imidazo[1,2-a]pyridine with 2-tert-butyl, 3-(cyclohexylmethyl), and 7-R³ substituents]

| Compound No. | R³— |
|---|---|
| 14 | 3-methylpiperidin-1-yl carbonyl |

TABLE 3-continued
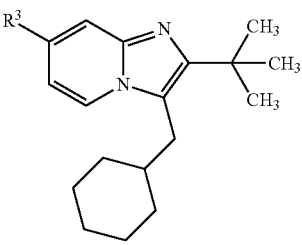
| Compound No. | R³— |
|---|---|
| 15 | 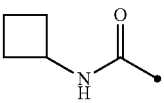 |
| 16 | 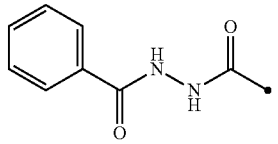 |
| 17 | 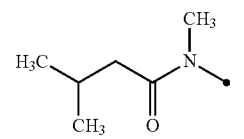 |
| 18 | 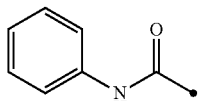 |
| 19 | 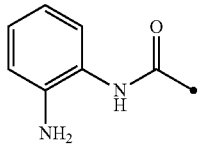 |
| 20 | 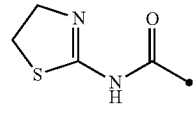 |
TABLE 4
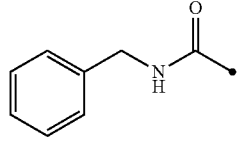
| Compound No. | R³— |
|---|---|
| 21 | 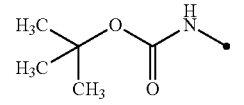 |
| 22 | 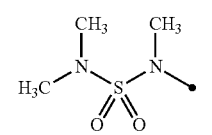 |
| 23 | 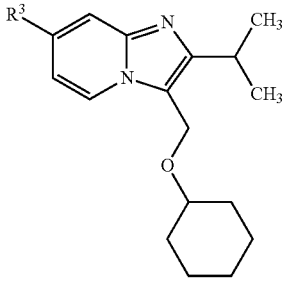 |
| 24 | 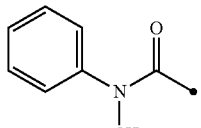 |
| 25 | 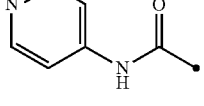 |
| 26 | 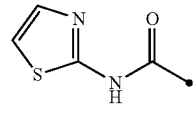 |
| 27 | 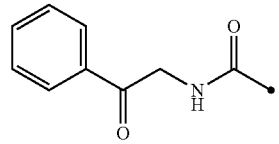 |
| 28 | 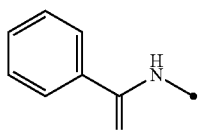 |
| 29 | 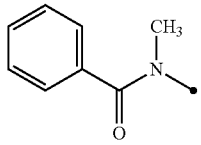 |

TABLE 4-continued
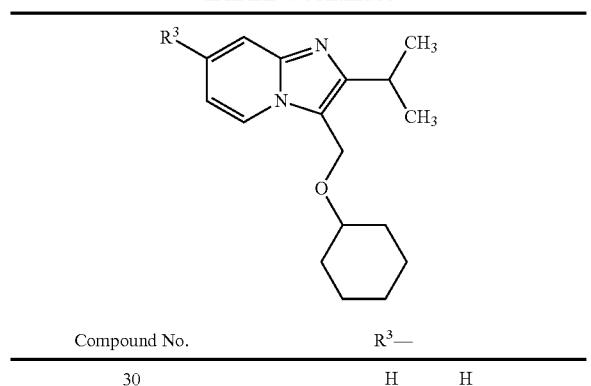
| Compound No. | R³— |
|---|---|
| 30 | (phenyl-NH-C(O)-NH-) |
| 31 | (phenyl-S(O)₂-NH-) |
| 32 | (phenyl-NH-S(O)₂-) |
| 33 | (benzimidazol-2-yl) |
TABLE 5
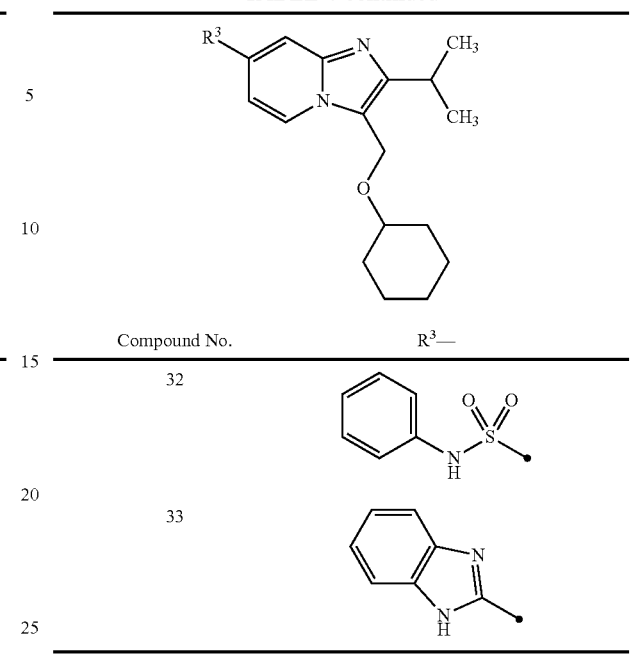
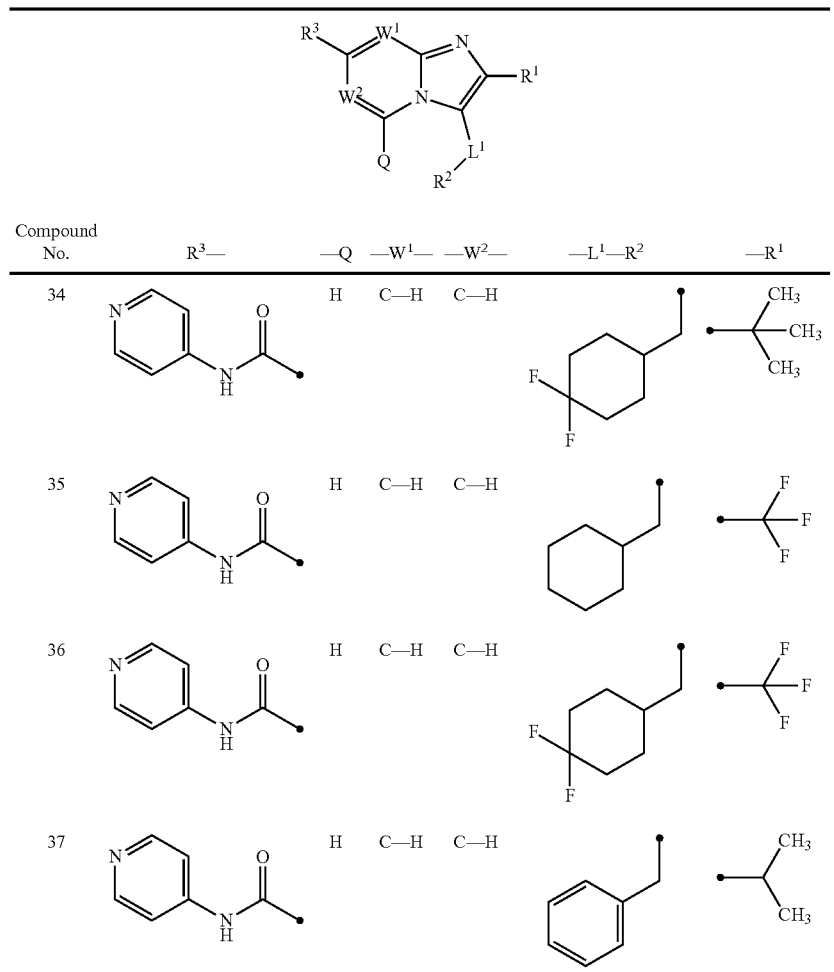
| Compound No. | R³— | —Q | —W¹— | —W²— | —L¹—R² | —R¹ |
|---|---|---|---|---|---|---|
| 34 | (pyridin-4-yl-NH-C(O)-) | H | C—H | C—H | (4,4-difluorocyclohexylmethyl) | $C(CH_3)_3$ |
| 35 | (pyridin-4-yl-NH-C(O)-) | H | C—H | C—H | (cyclohexylmethyl) | $CF_3$ |
| 36 | (pyridin-4-yl-NH-C(O)-) | H | C—H | C—H | (4,4-difluorocyclohexylmethyl) | $CF_3$ |
| 37 | (pyridin-4-yl-NH-C(O)-) | H | C—H | C—H | (benzyl) | $CH(CH_3)_2$ |

TABLE 5-continued

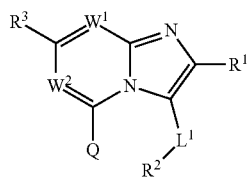

| Compound No. | R³— | —Q | —W¹— | —W²— | —L¹—R² | —R¹ |
|---|---|---|---|---|---|---|
| 38 | 4-pyridyl-NHC(O)- | H | C—H | C—H | cyclohexyl-SO₂- | isobutyl |
| 39 | 4-pyridyl-NHC(O)- | H | C—H | C—CH₃ | cyclohexyl-SO₂- | isobutyl |
| 40 | phenyl-NHC(O)- | H | C—H | C—H | cyclohexyl-S- | isobutyl |
| 41 | phenyl-NHC(O)- | H | C—H | C—H | cyclohexyl-SO₂- | isobutyl |
| 42 | 4-pyridyl-NHC(O)- | H | C—CH₃ | C—H | cyclohexyl-CH₂- | neopentyl |
| 43 | 4-pyridyl-NHC(O)- | H | C—H | C—CH₃ | cyclohexyl-O-CH₂- | isobutyl |
| 44 | tetrahydropyran-4-yl-NHC(O)- | CH₃ | C—H | C—H | 4,4-difluorocyclohexyl-CH₂- | CF₃ |

TABLE 6

[Structure: imidazo-pyrazine core with R³, W¹, W² positions, tert-butyl and cyclohexylmethyl substituents]

| Compound No. | R³— | —W¹— | —W²— |
|---|---|---|---|
| 45 | H₃C-CH₂-N(CH₂-CH₃)-C(=O)- | N | C—H |
| 46 | Ph-NH-C(=O)- | N | C—H |
| 47 | Ph-NH-C(=O)- | C—H | N |

TABLE 7

[Structure: 7-R³-2-(trifluoromethyl)imidazo[1,2-a]pyridine with 3-((4,4-difluorocyclohexyl)methyl) substituent]

| Compound No. | R³— |
|---|---|
| 48 | 3-(methylsulfonyl)phenyl-NH-C(=O)- |
| 49 | 3-cyclopropylisoxazol-5-yl-NH-C(=O)- |
| 50 | cyclobutyl-NH-C(=O)- |

TABLE 7-continued

| Compound No. | R³— |
|---|---|
| 51 | 3,3-difluorocyclobutyl-NH-C(=O)- |
| 52 | 4-methyltetrahydropyran-4-yl-NH-C(=O)- |
| 53 | 3,3-dimethyltetrahydropyran-4-yl-NH-C(=O)- |
| 54 | 2,2-dimethyltetrahydropyran-4-yl-NH-C(=O)- |
| 55 | cyclopropylmethyl-NH-C(=O)- |
| 56 | (3-ethyloxetan-3-yl)methyl-NH-C(=O)- |
| 57 | (2-methyltetrahydrofuran-2-yl)methyl-NH-C(=O)- |
| 58 | (4-cyanotetrahydropyran-4-yl)methyl-NH-C(=O)- |
| 59 | (4-(methoxymethyl)tetrahydropyran-4-yl)methyl-NH-C(=O)- |

TABLE 7-continued
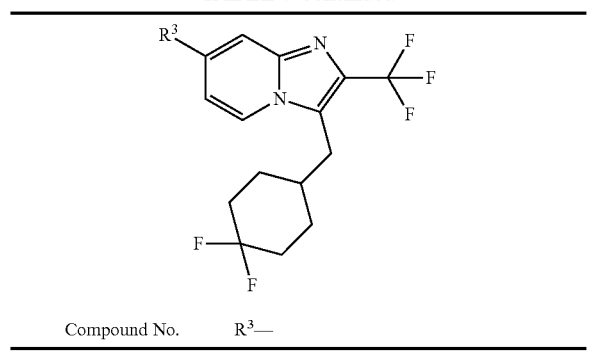
| Compound No. | R³— |
|---|---|
| 60 | 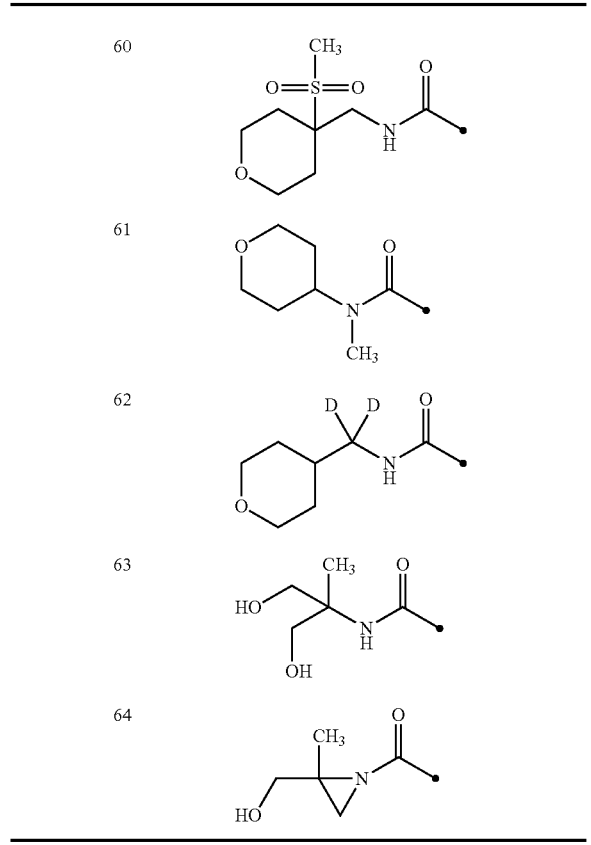 |
| 61 | |
| 62 | |
| 63 | |
| 64 | |
TABLE 8
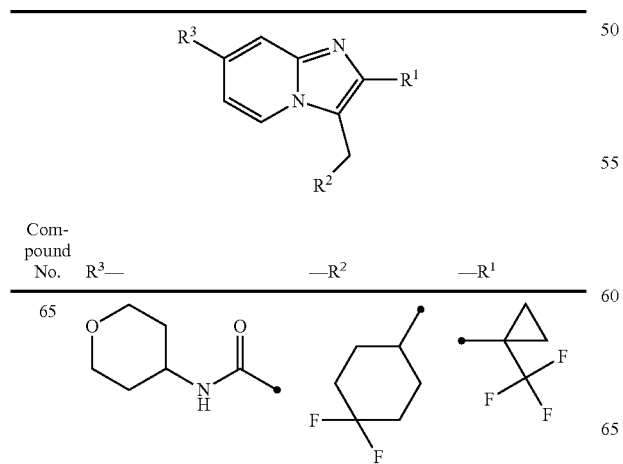
| Compound No. | R³— | —R² | —R¹ |
|---|---|---|---|
| 65 | | | |
TABLE 8-continued
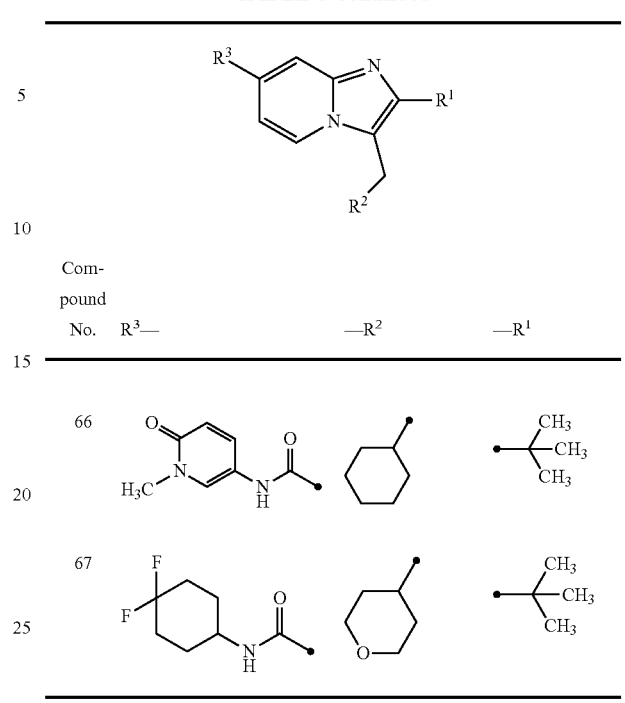
| Compound No. | R³— | —R² | —R¹ |
|---|---|---|---|
| 66 | | | |
| 67 | | | |
TABLE 9
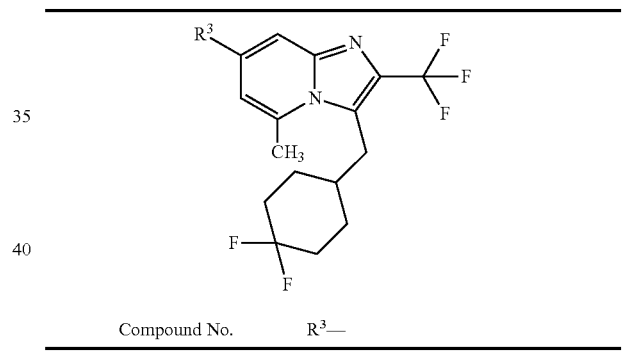
| Compound No. | R³— |
|---|---|
| 68 | 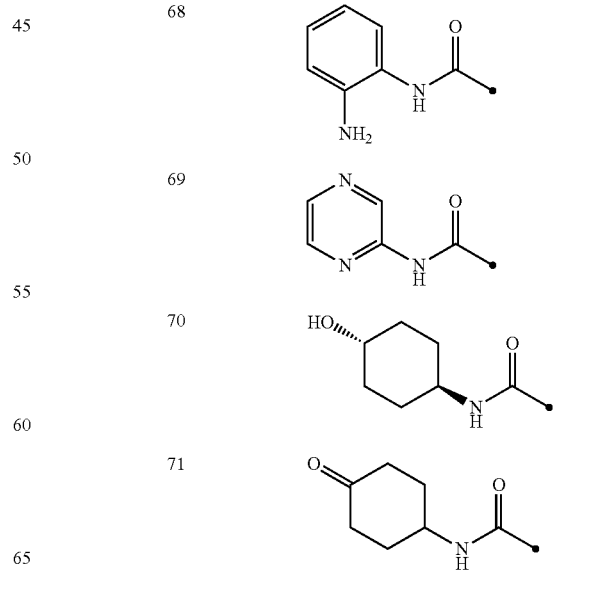 |
| 69 | |
| 70 | |
| 71 | |

TABLE 9-continued
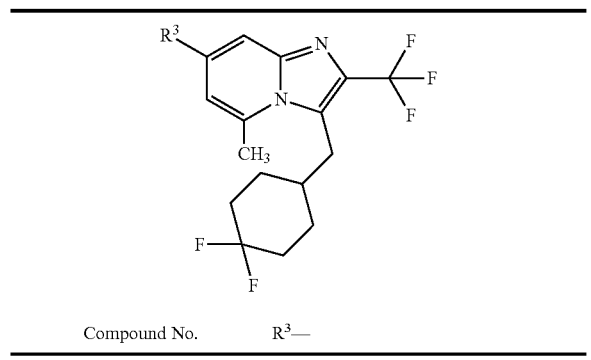
| Compound No. | R³— |
|---|---|
| 72 | 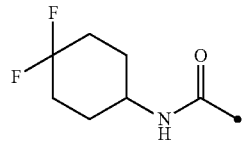 |
| 73 | 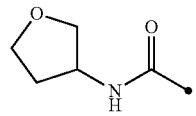 |
| 74 | 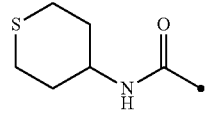 |
| 75 | 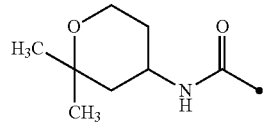 |
| 76 | 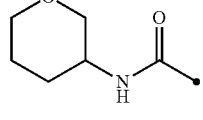 |
| 77 | 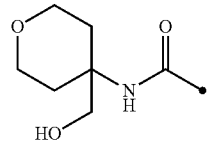 |
| 78 | 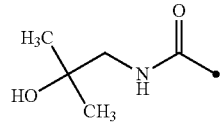 |
| 79 | 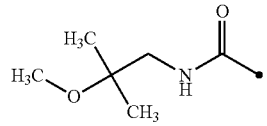 |
| 80 | 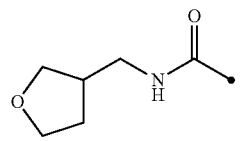 |
TABLE 9-continued
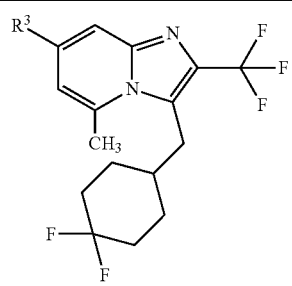
| Compound No. | R³— |
|---|---|
| 81 | 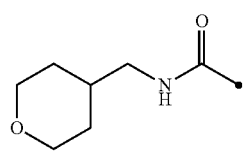 |
| 82 | 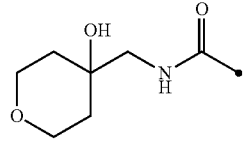 |
| 83 | 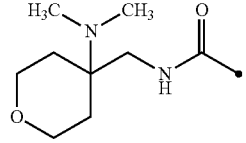 |
| 84 | 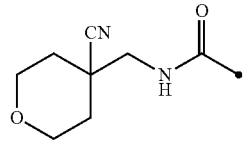 |
| 85 | 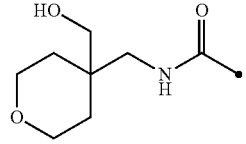 |
| 86 | 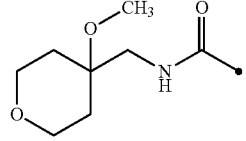 |
| 87 | 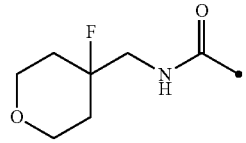 |
| 88 | 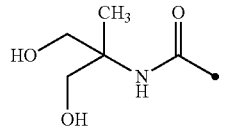 |

TABLE 9-continued
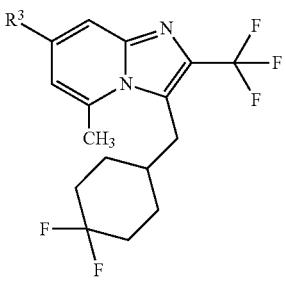
| Compound No. | R³— |
|---|---|
| 89 | 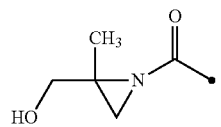 |
| 90 | 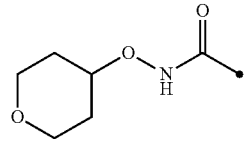 |
| 91 | 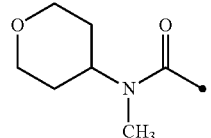 |
| 92 | 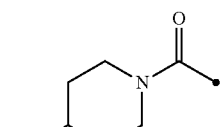 |
| 93 | 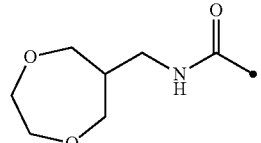 |
| 94 | 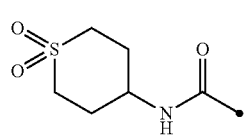 |
| 95 | 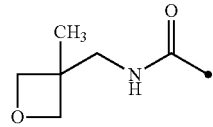 |
TABLE 10
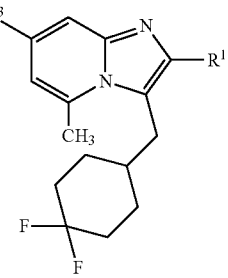
| Compound No. | R³— | —R¹ |
|---|---|---|
| 96 | 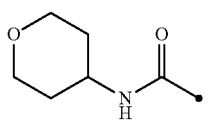 | 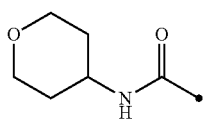 |
| 97 | 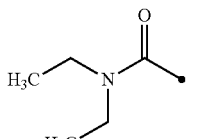 | 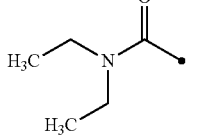 |
| 98 | 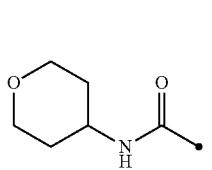 | 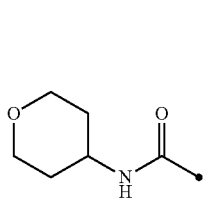 |
| 99 | | |
| 100 | | |
| 101 | | |

TABLE 11
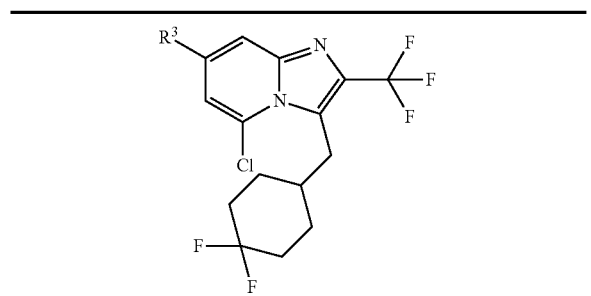
| Compound No. | R³— |
|---|---|
| 102 | 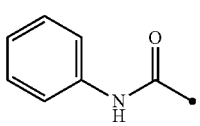 |
| 103 | 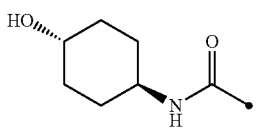 |
| 104 | 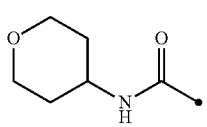 |
| 105 | 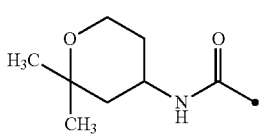 |
| 106 | 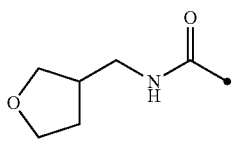 |
TABLE 12
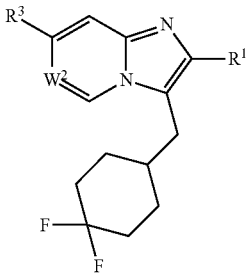
| Compound No. | R³— | —W²— | —R¹ |
|---|---|---|---|
| 107 | 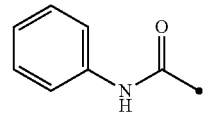 | C—Cl |  |
TABLE 12-continued
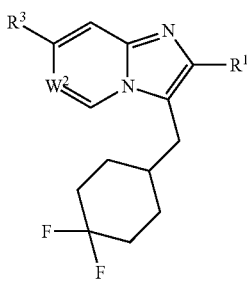
| Compound No. | R³— | —W²— | —R¹ |
|---|---|---|---|
| 108 | 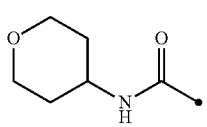 | C—Cl |  |
| 109 | 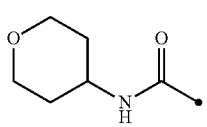 | C—Cl |  |
| 110 | 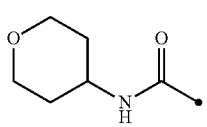 | C—Cl | 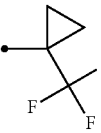 |
| 111 | 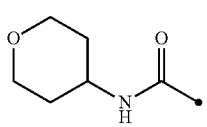 | C—Cl | 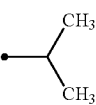 |
| 112 | 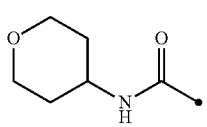 | C—Cl |  |
| 113 | 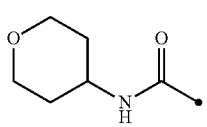 | C—Cl | 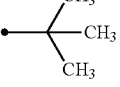 |
| 114 | 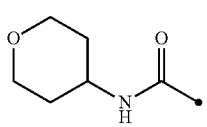 | C—Cl | 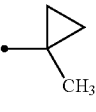 |
| 115 | 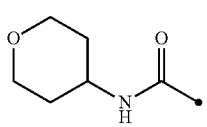 | C—Cl | 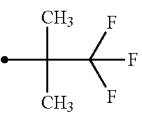 |
| 116 | 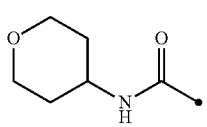 | C—Cl | 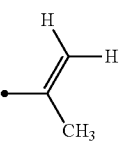 |

TABLE 12-continued

[Structure: imidazopyridine core with R³, W², R¹ substituents and 4,4-difluorocyclohexylmethyl group]

| Compound No. | R³— | —W²— | —R¹ |
|---|---|---|---|
| 117 | phenyl-NH-C(=O)- | C—Br | CF₃ |
| 118 | tetrahydropyran-4-yl-NH-C(=O)- | C—CH₃ | CF₃ |
| 119 | tetrahydropyran-4-yl-NH-C(=O)- | C—OCH₃ | CF₃ |

TABLE 13

[Structure with R³, W¹, W², Q substituents, trifluoromethyl group and 4,4-difluorocyclohexylmethyl group]

| Compound No. | R³— | —Q | —W¹— | —W²— |
|---|---|---|---|---|
| 120 | phenyl-NH-C(=O)- | H | C—H | C=CH₂ (vinyl) |
| 121 | tetrahydropyran-4-yl-NH-C(=O)- | H | C—H | C=CH₂ (vinyl) |
| 122 | tetrahydropyran-4-yl-NH-C(=O)- | H | C—CH₃ | C—H |

TABLE 13-continued

| Compound No. | R³— | —Q | —W¹— | —W²— |
|---|---|---|---|---|
| 123 | tetrahydropyran-4-yl-NH-C(=O)- | H | C—Cl | C—H |
| 124 | tetrahydropyran-4-yl-NH-C(=O)- | CH₃ | C—H | C—Cl |
| 125 | phenyl-NH-C(=O)- | CH₃ | C—H | C—I |
| 126 | phenyl-C(=O)-NH- | H | C—H | C—H |
| 127 | 1H-benzimidazol-2-yl | CH₃ | C—H | C—H |

TABLE 14

[Structure: imidazopyridine with R³, isopropyl, and L¹-R² substituents]

| Compound No. | R³— | —L¹—R² |
|---|---|---|
| 128 | phenyl-NH-C(=O)- | -S(=O)₂-NH-cyclohexyl |

TABLE 14-continued

| Compound No. | R³— | —L¹—R²— |
|---|---|---|
| 129 | phenyl-NH-C(O)- | -S(O)₂-NH-CH(cyclopropyl)(cyclopropyl) |
| 130 | phenyl-NH-C(O)- | -S(O)₂-N(CH(CH₃)₂)(cyclopropyl) |
| 131 | phenyl-NH-C(O)- | -S(O)₂-N(cyclopropyl)₂ |
| 132 | phenyl-NH-C(O)- | -S(O)₂-N(phenyl)(CH₃) |
| 133 | phenyl-NH-C(O)- | -S(O)₂-N(azetidine-3,3-diF) |
| 134 | (2,2-dimethyltetrahydropyran-4-yl)-NH-C(O)- | -S(O)₂-N(azetidine-3,3-diF) |
| 135 | benzyl-O-NH-C(O)- | -S(O)₂-N(azetidine-3,3-diF) |
| 136 | indolin-1-yl-C(O)- | -S(O)₂-N(piperidin-1-yl) |
| 137 | (4-methyltetrahydropyran-4-yl)CH₂-NH-C(O)- | -S(O)₂-NH-C(CH₃)₃ |

TABLE 15

| Compound No. | —L¹—R² | —R¹ |
|---|---|---|
| 138 | -S(O)₂-N(azetidine-3,3-diF) | cyclopropyl |
| 139 | -S(O)₂-N(4,4-difluoropiperidin-1-yl) | -N(azetidine-3,3-diF) |
| 140 | -S(O)₂-N(4,4-difluoropiperidin-1-yl) | -N(pyrrol-1-yl) |
| 141 | -S(O)₂-N(4,4-difluoropiperidin-1-yl) | -S-CH₃ |

TABLE 15-continued
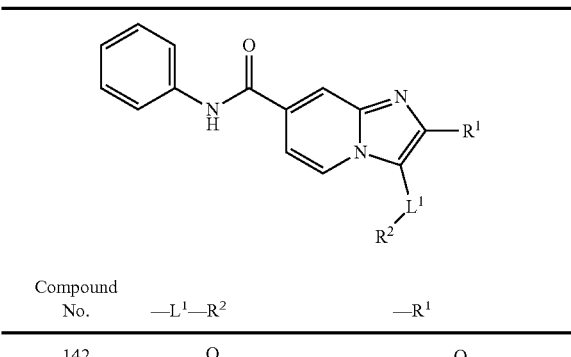
| Compound No. | —L¹—R² | —R¹ |
|---|---|---|
| 142 | 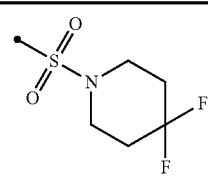 | 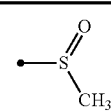 |
| 143 | 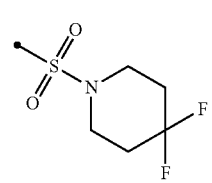 | 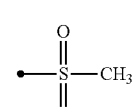 |
| 144 | 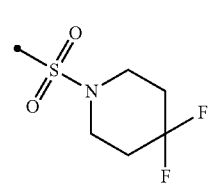 | 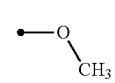 |
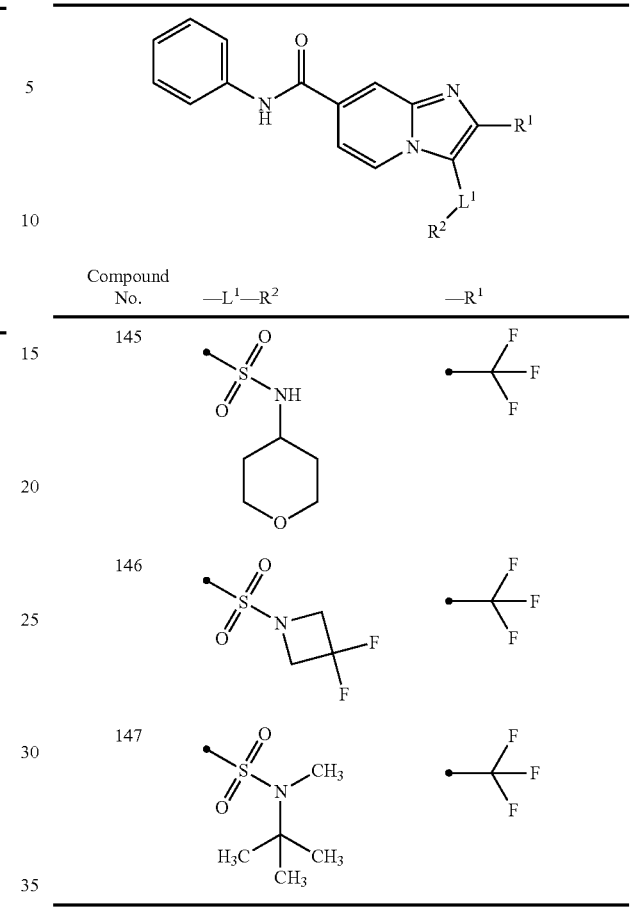
TABLE 16
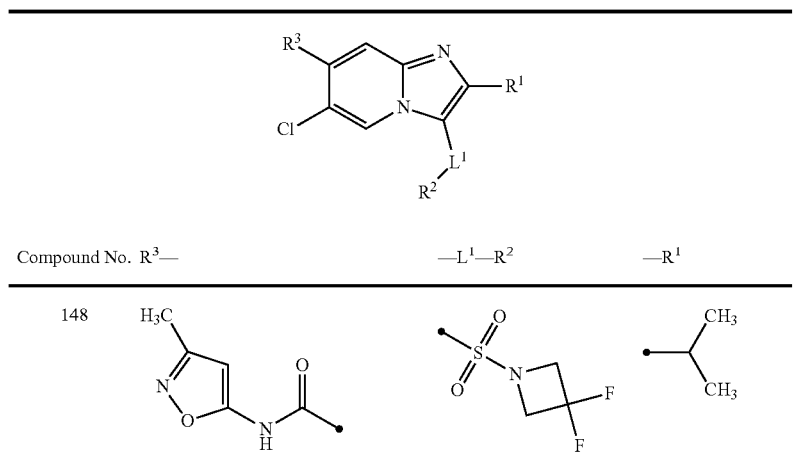
| Compound No. | R³— | —L¹—R² | —R¹ |
|---|---|---|---|
| 148 | | | |
| 149 | 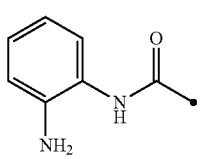 | 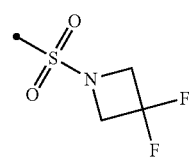 | 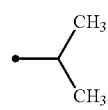 |

TABLE 16-continued

| Compound No. | R³— | —L¹—R² | —R¹ |
|---|---|---|---|
| 150 | cyclopropylmethyl-NH-C(O)- | -S(O)₂-N(azetidine-3,3-diF) | isopropyl |
| 151 | 3,3-difluorocyclobutyl-NH-C(O)- | -S(O)₂-N(azetidine-3,3-diF) | isopropyl |
| 152 | benzyl-O-NH-C(O)- | -S(O)₂-N(azetidine-3,3-diF) | isopropyl |
| 153 | 2,2-dimethyltetrahydropyran-4-yl-NH-C(O)- | -S(O)₂-N(azetidine-3,3-diF) | isopropyl |
| 154 | phenyl-NH-C(O)- | -S(O)₂-NH-(3,3-difluorocyclobutyl) | isopropyl |
| 155 | phenyl-NH-C(O)- | -S(O)₂-NH-phenyl | isopropyl |
| 156 | phenyl-NH-C(O)- | -S(O)₂-NH-C(CH₃)₃ | isopropyl |

TABLE 16-continued

| Compound No. | R³— | —L¹—R² | —R¹ |
|---|---|---|---|
| 157 | 3-methylisoxazol-5-yl-NH-C(O)-CH₂- | -S(O)₂-NH-C(CH₃)₃ | isopropyl |
| 158 | 3,3-difluorocyclobutyl-NH-C(O)-CH₂- | -S(O)₂-NH-C(CH₃)₃ | isopropyl |
| 159 | benzyloxy-NH-C(O)-CH₂- | -S(O)₂-NH-C(CH₃)₃ | isopropyl |
| 160 | indolin-1-yl-C(O)-CH₂- | -S(O)₂-NH-C(CH₃)₃ | CF₃ |
| 161 | (tetrahydropyran-4-yl)(methyl)N-C(O)-CH₂- | -S(O)₂-NH-C(CH₃)₃ | CF₃ |
| 162 | (tetrahydropyran-4-yl)-NH-C(O)-CH₂- | -S(O)₂-NH-C(CH₃)₃ | t-butyl |

TABLE 17

| Compound No. | R³— | —W²—L¹—R² |
|---|---|---|
| 163 | phenyl-NH-C(=O)-CH₂- | C—CH₃; —SO₂-cyclohexyl |
| 164 | H₃C-O-N(CH₃)-C(=O)-CH₂- | C—CH₃; —SO₂-(4,4-difluoropiperidin-1-yl) |
| 165 | pyridin-4-yl-NH-C(=O)-CH₂- | C—CH₃; —SO₂-(4,4-difluoropiperidin-1-yl) |
| 166 | phenyl-NH-C(=O)-CH₂- | C—CH₃; —SO₂-(2-oxa-6-azaspiro[3.3]heptan-6-yl) |
| 167 | (4,4-difluorocyclohexyl)-NH-C(=O)-CH₂- | C—CH₃; —SO₂-(2-oxa-6-azaspiro[3.3]heptan-6-yl) |
| 168 | phenyl-NH-C(=O)-CH₂- | C—CH₃; —SO₂-NH-C(CH₃)₃ |
| 169 | phenyl-C(=O)-NH-CH₂- | C—H; —SO₂-(3-fluoroazetidin-1-yl... 3-F) |
| 170 | 1H-benzimidazol-2-yl-CH₂- | C—Cl; —SO₂-(3-fluoroazetidin-1-yl... 3-F) |

TABLE 18

| Compound No. | R³— | —W¹— | —W²—L¹—R² | —R¹ |
|---|---|---|---|---|
| 171 | phenyl-NH-C(=O)-CH₂- | N | C—H; —SO₂-(4,4-difluoropiperidin-1-yl) | isopropyl |
| 172 | cyclohexyl-NH-C(=O)-CH₂- | N | C—H; —SO₂-(4,4-difluoropiperidin-1-yl) | isopropyl |

TABLE 18-continued

| Compound No. | R³— | —W¹— | —W²— | —L¹—R² | —R¹ |
|---|---|---|---|---|---|
| 173 | tetrahydropyran-4-yl-NH-C(=O)-CH₂- | N | C—H | -S(=O)₂-N(4,4-difluoropiperidinyl) | -CH(CH₃)₂ |
| 174 | phenyl-NH-C(=O)-CH₂- | C—H | N | -S(=O)₂-N(4,4-difluoropiperidinyl) | -CH(CH₃)₂ |
| 175 | cyclohexyl-NH-C(=O)-CH₂- | C—H | N | -S(=O)₂-N(4,4-difluoropiperidinyl) | -CH(CH₃)₂ |
| 176 | phenyl-NH-C(=O)-CH₂- | N | C—H | -CH(CH₃)₂ | -S(=O)₂-N(4,4-difluoropiperidinyl) |
| 177 | tetrahydropyran-4-yl-NH-C(=O)-CH₂- | N | C—H | -CH(CH₃)₂ | -S(=O)₂-N(4,4-difluoropiperidinyl) |

TABLE 19

| Compound No. | R³— | —Q | —W²— | —L¹—R² | —R¹ |
|---|---|---|---|---|---|
| 178 | phenyl-O-NH-C(=O)-CH₂- | H | C—Cl | -S(=O)₂-N(3,3-difluoroazetidinyl) | -CH(CH₃)₂ |

TABLE 19-continued

| Compound No. | R³— | —Q | —W²— | —L¹—R² | —R¹ |
|---|---|---|---|---|---|
| 179 | phenyl-NH-C(O)-* | H | C—Cl | *-S(O)₂-NH-C(CH₃)₂-C≡CH | isopropyl (CH(CH₃)₂) |
| 180 | cyclohexenyl-NH-C(O)-* | H | C—H | *-CH₂-(4,4-difluorocyclohexyl) | *-CF₃ |
| 181 | (tetrahydropyran-4-yl)-O-NH-C(O)-* | H | C—Cl | *-CH₂-(4,4-difluorocyclohexyl) | *-CF₃ |
| 182 | (2-hydroxy-2-methylpropyl)-NH-C(O)-* | Cl | C—H | *-CH₂-(4,4-difluorocyclohexyl) | *-CF₃ |
| 183 | (tetrahydropyran-4-yl)-NH-C(O)-* | CH₃ | C—H | *-CH₂-(4,4-difluorocyclohexyl) | *-C(O)-CH₃ |

Next, the pharmacological effects of the representative compounds (I) are described in detail using Test Examples.

Test Example 1

The Inhibitory Effect for Intracellular Calcium Response Via Cav3.2 T-Type $Ca^{2+}$ Channels Intracellular calcium response was measured with an FLIPR Calcium 3 Assay Kit (Molecular Devices). To prepare an indicator solution, the fluorescence indicator attached to the kit was dissolved in an assay buffer containing 20 mmol/L HEPES-NaOH (pH 7.4), 0.5 mmol/L $CaCl_2$, 0.75 mg/mL amaranth, Hanks' Balanced Salt Solutions (calcium and magnesium free).

A human Cav3.2 T-type $Ca^{2+}$ channel-expressing cell line was produced according to a known method [Analytical Biochemistry, Vol. 400, p. 163 (2010)], using KJMGER8 cells (Namalwa cell-derived cell line) as a host. The cells were suspended in the indicator solution in $1 \times 10^6$ cells/mL density, and plated in a 384-well clear-bottom black plate (Nunc) in 40 μL/well portions, then incubated in a $CO_2$ incubator (95% air, 5% $CO_2$) at 37° C. for 30 minutes. By using an FDSS 6000 (Hamamatsu Photonics K.K.), a solution (5 μL/well) containing the test compound in 10-fold concentration of the final concentration (prepared using an assay buffer containing 1 vol % DMSO and 0.2 vol % bovine serum albumin) was added and incubated for 5 minutes. Then, 5 μL/well of an assay buffer containing 50 mmol/L $CaCl_2$ (final concentration 5 mmol/L) was added to induce reaction, and the fluorescence (excitation wavelength 480 nm, fluorescence wavelength 540 nm) was measured every two seconds for 2 minutes and 40 seconds.

The difference between the minimum value and the maximum value of the fluorescence values after the $CaCl_2$ addition was used as the index of calcium response. The calcium response in the absence of the test compound was taken as 100% with respect to the calcium response in the presence of 3 μmol/L mibefradil (T-type $Ca^{2+}$ channel inhibitor; Sigma-Aldrich), and the test compound concentration that shows a 50% inhibitory effect ($IC_{50}$ value) was calculated.

The IC$_{50}$ of compounds 12, 14, 15, 16, 17, 19, 20, 21, 24, 25, 28, 33, 34, 35, 37, 38, 39, 40, 41, 42, 43, 48, 50, 51, 52, 53, 56, 57, 59, 65, 68, 70, 71, 72, 73, 74, 75, 76, 78, 79, 80, 81, 84, 85, 86, 87, 90, 91, 93, 95, 96, 97, 100, 101, 102, 103, 104, 105, 106, 107, 108, 109, 110, 111, 113, 114, 115, 117, 120, 124, 125, 126, 127, 129, 130, 131, 132, 133, 135, 136, 138, 143, 146, 147, 148, 149, 150, 151, 152, 153, 154, 155, 156, 157, 158, 159, 162, 163, 165, 166, 168, 170, 171, 172, 175, 179, 180, 181, and 182 for the human Cav3.2 T-type Ca$^{2+}$ current was <100 nmol/L. It was confirmed that compound (I) or (IA) and pharmaceutically acceptable salts thereof inhibit the human Cav3.2 T-type Ca$^{2+}$ current. Therefore, compound (I) or (IA) and pharmaceutically acceptable salts thereof were considered useful as therapeutic and/or preventive agents for diseases associated with the T-type Ca$^{2+}$ channels.

Thus, compound (I) or pharmaceutically acceptable salt thereof was considered useful as therapeutic and/or preventive agent for epilepsy (for example, absence epilepsy), sleep disorder (for example, insomnia), pain (for example, neuropathic pain, trigeminal neuralgia, diabetic pain, postherpetic neuralgia, neuropathic low back pain, HIV-related pain, fibromyalgia syndrome, cancer pain, inflammatory pain, acute pain, chronic pain, postoperative pain, acute pain after tooth extraction, chronic musculoskeletal pain, nociceptive pain, psychogenic pain, menstrual pain and the like), migraine, pruritus [for example, diseases accompanied by skin lesion, including, for example, atopic dermatitis, neurodermatitis, senile cutaneous pruritus, seborrheic dermatitis, caterpillar dermatitis, urticaria, eczema•dermatitis, photosensitivity, autosensitive dermatitis, prurigo, insect bites and stings, scabies, mycosis, cutaneous pruritus, hypertrophic scar, psoriasis such as plaque psoriasis, hydroa, xeroderma, lichen, ringworm, burn, and the like; as well as forms of pruritus that are not necessarily accompanied by skin lesion, including, for example, those caused by visceral diseases such as hepatic and biliary tract diseases (cirrhosis such as primary biliary cirrhosis, cholestasis, hepatitis, and the like), kidney diseases (kidney failure such as chronic kidney failure, kidney dialysis, and the like), and endocrine and metabolic diseases (thyroid disease such as thyroid dysfunction, diabetes, and the like), cancers (such as malignant lymphoma, and digestive cancer), hematological disorders (such as polycythemia vera, and hypoferric anemia), neurological disorders (such as multiple sclerosis, and neurosis), AIDS, pregnancy, and drug side effects; and pruritus accompanied by ophthalmic or otorhinolaryngological diseases], heart diseases (for example, cardiac hypertrophy, heart failure, myocardial infarction, cardiac arrhythmia, atrial fibrillation, hypertension), kidney diseases (for example, nephritis, nephropathy, kidney failure), endocrine diseases (for example, aldosteronism, Cushing's syndrome, hyperthyroidism, hyperinsulinemia and the like), cancers (for example, prostate cancer, breast cancer, leukemia, neuroblastoma, retinoblastoma and the like), hearing impairment (for example, noise-induced hearing impairment), and the like.

Test Example 2

Inhibitory Effect for Pruritus in Morphine-Induced Pruritus Mice

Morphine (1 nmol/5 µL, dissolved in physiological saline) or physiological saline was intrathecally administered between the fifth and sixth lumbar vertebrae of male ddY mice using a microsyringe fitted with a 30-gauge injection needle. Mice administered with only morphine were used as a control group, and mice administered with only physiological saline as a physiological saline-administered group.

After the morphine administration, the number of scratching behavior with the hind legs which observed immediately in the mice was measured for 30 minutes. Because mice show a rapid, continuous scratching behavior in each scratching behavior, a series of such behavior was counted as a single scratching behavior.

The test compounds were administered 30 minutes before the morphine administration. Each test compound was suspended in a 0.5% methylcellulose solution, and orally administered in 10 mL/kg volume.

As a result, the increase of the scratching behavior observed in the morphine-induced pruritus mice was inhibited by the administration at a dose of 30 mg/kg or less of the compounds 14, 15, 21, 24, 34, 35, 36, 38, 41, 43, 44, 50, 51, 52, 54, 70, 72, 73, 75, 76, 78, 79, 80, 81, 84, 96, 100, 101, 103, 104, 105, 108, 109, 110, 111, 113, 114, 118, 126, 133, 148, or 182.

Therefore, it was confirmed that compound (I) or (IA) and pharmaceutically acceptable salts thereof were useful as therapeutic and/or preventive agents for pruritus, for example, diseases accompanied by skin lesion such as atopic dermatitis, neurodermatitis, senile cutaneous pruritus, seborrheic dermatitis, caterpillar dermatitis, urticaria, eczema•dermatitis, photosensitivity, autosensitive dermatitis, prurigo, insect bites and stings, scabies, mycosis, cutaneous pruritus, hypertrophic scar, psoriasis such as plaque psoriasis, hydroa, xeroderma, lichen, ringworm, burn; as well as pruritus that are not necessarily accompanied by skin lesion, for example, those caused by visceral diseases such as hepatic and biliary diseases (cirrhosis such as primary biliary cirrhosis, cholestasis, hepatitis, and the like), kidney diseases (kidney failure such as chronic kidney failure, kidney dialysis, and the like), endocrine and metabolic diseases (thyroid disease such as thyroid dysfunction, diabetes, and the like) and the like, cancers (malignant lymphoma, digestive system cancer, and the like), hematological disorders (such as polycythemia vera, and hypoferric anemia), neurological disorders (such as multiple sclerosis, and hematological disorders), AIDS, pregnancy, or drug side effects; and pruritus accompanied by ophthalmic and otorhinolaryngological diseases, and the like.

Compound (I) or compound (IA) and a pharmaceutically acceptable salt thereof can be administered alone. However, usually, compound (I) or (IA) and a pharmaceutically acceptable salt thereof are preferably provided in various pharmaceutical preparations. The pharmaceutical preparations are used for animals or humans.

The pharmaceutical preparations according to the present invention may contain compound (I) or (IA) and a pharmaceutically acceptable salt thereof as an active ingredient, either alone or as a mixture with any other active ingredient for other treatments. Further, the pharmaceutical preparations are prepared by mixing the active ingredient with one or more pharmaceutically acceptable carriers (for example, diluent, solvent, excipient, and the like) and then subjecting the mixture to any method well known in the technical field of pharmaceutics.

As for the administration route, it is preferred to select the most effective route of administration. Examples of the administration route include oral administration, and parenteral administration such as intravenous administration and the like.

Examples of the dosage form include a tablet, injection, and the like.

Suitable dosage forms for the oral administration, for example, tablets, can be prepared by using excipients such as lactose, disintegrators such as starch, lubricants such as magnesium stearate, binders such as hydroxypropyl cellulose, and the like.

Suitable dosage forms for the parenteral administration, for example, injections, can be prepared by using diluents, or solvents, for example, a salt solution, a glucose solution, a mixture of brine with a glucose solution, and the like.

The doses and the frequencies of administration of compound (I) or (IA) and a pharmaceutically acceptable salt thereof may vary depending upon dosage form, age and body weight of a patient, nature or seriousness of the symptom to be treated, and the like. In the oral administration, in general, a dose of 0.01 to 1,000 mg, preferably, 0.05 to 100 mg, is administered to an adult patient once or several times a day. In parenteral administration such as intravenous administration, a dose of 0.001 to 1,000 mg, preferably, 0.01 to 100 mg, is administered to an adult patient once or several times a day. However, these doses and frequencies of administration vary by the various conditions described above.

The present invention is described below more specifically using Examples. However, it should be noted that the scope of the present invention is not limited by the these Examples.

Note that the proton nuclear magnetic resonance spectra ($^1$H NMR) used in Examples were measured at 270 MHz, 300 MHz, or 400 MHz, and exchangeable protons may not be clearly observed depending on the compound and measurement conditions. Common notation is used to represent signal multiplicity. The symbol br denotes apparently wide signal.

Example 1

Ethyl 3-cyclohexylmethyl-7-(N,N-diethylcarbamoyl) imidazo[1,2-a]pyridine-2-carboxylate (Compound 1)

Step 1

Ethyl 4-cyclohexyl-2-oxobutanoate (200 mg, 0.943 mmol) obtained according to the method described in Chem. Pharm. Bull., Vol. 34, p. 1128 (1986) was dissolved in ethanol (2.0 mL), and the solution was stirred under heat and reflux for 1 hour after adding tetra-n-butylammonium tribromide (460 mg, 0.954 mmol). The reaction mixture was allowed to cool to room temperature, and extracted with ethyl acetate after adding a sodium hydrogen carbonate aqueous solution. The organic layer was washed with saturated brine, and dried over anhydrous sodium sulfate. The solvent was then evaporated under reduced pressure. The residue was purified by silica gel column chromatography (hexane/ethyl acetate=90/10) to give ethyl 3-bromo-4-cyclohexyl-2-oxobutanoate (198 mg, yield 72%).

$^1$H NMR (270 MHz, CDCl$_3$, δ): 5.14 (t, J=7.4 Hz, 1H), 4.39 (q, J=7.0 Hz, 2H), 1.94 (dd, J=7.3, 7.3 Hz, 2H), 1.85-1.65 (m, 7H), 1.40 (t, J=7.0 Hz, 3H), 1.33-1.12 (m, 4H).

Step 2

Ethyl 3-bromo-4-cyclohexyl-2-oxobutanoate (1.20 g, 4.12 mmol) obtained in step 1 was dissolved in n-butanol (12 mL), and the solution was stirred under heat and reflux for 1 hour after adding 2-amino-N,N-diethylpyridine-4-carboxamide (800 mg, 4.12 mmol) obtained according to the method described in WO2008/032764. The reaction mixture was allowed to cool to room temperature, and extracted with ethyl acetate after adding a sodium hydrogen carbonate aqueous solution. The organic layer was washed with saturated brine, and dried over anhydrous magnesium sulfate. The solvent was then evaporated under reduced pressure. The residue was purified by silica gel column chromatography (chloroform/methanol=95/5) to give compound 1 (948 mg, yield 60%).

$^1$H NMR (270 MHz, CDCl$_3$, δ): 8.01 (dd, J=7.1, 0.8 Hz, 1H), 7.63 (dd, J=1.7, 0.8 Hz, 1H), 6.96 (dd, J=7.3, 1.7 Hz, 1H), 4.47 (q, J=7.2 Hz, 2H), 3.63-3.30 (br m, 4H), 3.19 (d, J=7.3 Hz, 2H), 1.75-1.60 (m, 6H), 1.46 (t, J=7.3 Hz, 3H), 1.29-1.08 (m, 11H); ESIMS m/z: [M+H]$^+$ 386.

Example 2

N-Butyl-3-cyclohexylmethyl-7-(N,N-diethylcarbamoyl)imidazo[1,2-a]pyridine-2-carboxamide (Compound 2)

Step 1

Compound 1 (947 mg, 2.46 mmol) was suspended in a 50% ethanol aqueous solution (10 mL), and the suspension was stirred at 50° C. for 1 hour after adding lithium hydroxide.1 hydrate (130 mg, 3.10 mmol). Under ice-cooled condition, 3 mol/L hydrochloric acid was added to the reaction mixture. The precipitated solid was collected by filteration, and dried under reduced pressure to give 3-cyclohexylmethyl-7-(N,N-diethylcarbamoyl)imidazo[1,2-a]pyridine-2-carboxylic acid (579 mg, yield 66%).

$^1$H NMR (300 MHz, CDCl$_3$, δ): 8.04 (dd, J=7.3, 1.1 Hz, 1H), 7.81-7.76 (br m, 1H), 7.00 (dd, J=7.3, 1.5 Hz, 1H), 3.64-3.33 (br m, 4H), 3.23 (d, J=7.3 Hz, 2H), 1.75-1.59 (m, 6H), 1.32-1.13 (m, 11H); ESIMS m/z: [M+H]$^+$ 358.

Step 2

3-Cyclohexylmethyl-7-(N,N-diethylcarbamoyl) imidazo[1,2-a]pyridine-2-carboxylic acid (30.0 mg, 0.0839 mmol) obtained in step 1 was dissolved in THF (1.0 mL), and the solution was stirred at room temperature for 1 hour after adding butylamine (0.0120 mL, 0.122 mmol), 1-(3-dimethylaminopropyl)-3-ethylcarbodiimidehydrochloride (EDC.HCl) (24.0 mg, 0.125 mmol), and 1-hydroxybenzotriazole-hydrate (HOBt.H$_2$O) (20.0 mg, 0.131 mmol). The reaction mixture was extracted with ethyl acetate after adding a saturated sodium hydrogen carbonate aqueous solution. The organic layer was washed with saturated brine, and dried over anhydrous magnesium sulfate. The solvent was then evaporated under reduced pressure. The residue was purified by silica gel column chromatography (chloroform/methanol=99/1→95/5) to give compound 2 (30.1 mg, yield 87%).

$^1$H NMR (300 MHz, CDCl$_3$, δ): 7.99 (dd, J=7.1, 0.7 Hz, 1H), 7.51 (dd, J=1.6, 0.7 Hz, 1H), 7.48-7.41 (br m, 1H), 6.88 (dd, J=7.1, 1.6 Hz, 1H), 3.53-3.40 (m, 6H), 3.26 (d, J=7.3 Hz, 2H), 1.72-1.57 (m, 6H), 1.48-1.38 (m, 2H), 1.29-1.12 (m, 13H), 0.96 (t, J=7.3 Hz, 3H); ESIMS m/z: [M+H]$^+$ 413.

Example 3

Benzyl 3-cyclohexylmethyl-7-(diethylcarbamoyl) imidazo[1,2-a]pyridin-2-ylcarbamate (Compound 3)

3-Cyclohexylmethyl-7-(N,N-diethylcarbamoyl) imidazo[1,2-a]pyridine-2-carboxylic acid (50.0 mg, 0.140 mmol) obtained in step 1 of Example 2 was dissolved in toluene (1.0 mL), and the solution was heated and refluxed for 3 hours after adding triethylamine (0.0400 mL, 0.278 mmol), diphenylphosphoryl azide (0.121 mL, 0.560 mmol), and benzyl alcohol (0.072 mL, 0.700 mmol). The reaction mixture was filtered through a Presep (registered trademark; diatomaceous earth, granular type M, 4.5 g/25 mL) after adding a saturated sodium hydrogen carbonate aqueous solution. The solvent was then evaporated under reduced pressure. The residue was purified by silica gel column chromatography (chloroform/methanol=98/2→94/6) to give compound 3 (42.5 mg, yield 66%).

$^1$H NMR (300 MHz, CDCl$_3$, δ): 7.92 (d, J=7.0 Hz, 1H), 7.49 (s, 1H), 7.37-7.31 (m, 6H), 6.88 (d, J=7.0 Hz, 1H), 5.23 (s, 2H), 3.63-3.27 (m, 4H), 2.84 (d, J=6.6 Hz, 2H), 1.60-1.56 (m, 5H), 1.28-0.98 (m, 12H); ESIMS m/z: [M+H]$^+$ 463.

Example 4

2-Acetyl-3-cyclohexylmethyl-N,N-diethylimidazo[1,2-a]pyridine-7-carboxamide (Compound 4)

Step 1

3-Cyclohexylmethyl-7-(N,N-diethylcarbamoyl)imidazo[1,2-a]pyridine-2-carboxylic acid (181 mg, 0.506 mmol) obtained in step 1 of Example 2 was dissolved in DMF (1.8 mL), and the solution was stirred at room temperature for 2 hours after adding EDC.HCl (146 mg, 0.760 mmol), HOBt.H$_2$O (116 mg, 0.760 mmol), N,O-dimethylhydroxylamine hydrochloride (74.0 mg, 0.760 mmol), and pyridine (0.0610 mL, 0.760 mmol). Under ice-cooled condition, a saturated sodium hydrogen carbonate aqueous solution was added, and the reaction mixture was extracted with ethyl acetate. The organic layer was washed with saturated brine, and dried over anhydrous magnesium sulfate. The solvent was then evaporated under reduced pressure. The residue was purified by silica gel column chromatography (chloroform/methanol=100/0→95/5) to give 3-cyclohexylmethyl-7-(N,N-diethylcarbamoyl)-N-methoxy-N-methylimidazo[1,2-a]pyridine-2-carboxamide (200 mg, yield 99%).

$^1$H-NMR (270 MHz CDCl$_3$, δ): 8.01 (dd, J=7.0, 0.8 Hz, 1H), 7.60-7.56 (m, 1H), 6.92 (dd, J=7.0, 1.7 Hz, 1H), 3.86 (s, 3H), 3.60-3.42 (m, 4H), 3.52 (s, 3H), 3.08 (d, J=7.3 Hz, 2H), 1.80-1.55 (m, 5H), 1.35-0.99 (m, 12H); ESIMS m/z: [M+H]$^+$ 401.

Step 2

3-Cyclohexylmethyl-7-(N,N-diethylcarbamoyl)-N-methoxy-N-methylimidazo[1,2-a]pyridine-2-carboxamide (112 mg, 0.280 mmol) obtained in step 1 was dissolved in THF (1.0 mL). Under ice-cooled condition, methylmagnesium bromide (1 mol/L-THF solution) (0.420 mL, 0.420 mmol) was added, and the mixture was stirred at room temperature for 3 hours. Under ice-cooled condition, a saturated ammonium chloride aqueous solution was added, and the reaction mixture was extracted with ethyl acetate. The organic layer was washed with saturated brine, and dried over anhydrous magnesium sulfate. The solvent was then evaporated under reduced pressure. The residue was purified by silica gel column chromatography (chloroform/methanol=98/2→95/5) to give compound 4 (26.7 mg, yield 27%).

$^1$H-NMR (270 MHz CDCl$_3$, δ): 8.01 (d, J=7.0 Hz, 1H), 7.61 (s, 1H), 6.93 (d, J=7.0 Hz, 1H), 3.69-3.30 (m, 4H), 3.18 (d, J=7.3 Hz, 2H), 2.74 (s, 3H), 1.68-1.56 (m, 6H), 1.24-1.15 (m, 11H); ESIMS m/z: [M+H]$^+$ 356.

Example 5

3-Cyclohexylmethyl-2-(1,1-difluoroethyl)-N,N-diethylimidazo[1,2-a]pyridine-7-carboxamide (Compound 5)

Compound 4 (10.0 mg, 0.0281 mmol) was dissolved in dichloromethane (1.0 mL). Under ice-cooled condition, bis(2-methoxyethyl)aminosulfur trifluoride (0.130 mL, 0.703 mmol) was added, and the mixture was stirred overnight at room temperature. Under ice-cooled condition, a saturated sodium hydrogen carbonate aqueous solution was added, and the reaction mixture was extracted with ethyl acetate. The organic layer was washed with saturated brine, and dried over anhydrous magnesium sulfate. The solvent was then evaporated under reduced pressure. The residue was purified by preparative thin-layer chromatography (hexane/ethyl acetate=25/75) to give compound 5 (3.3 mg, yield 31%).

$^1$H NMR (300 MHz, CDCl$_3$, δ): 7.99 (d, J=7.2 Hz, 1H), 7.59 (s, 1H), 6.94 (d, J=7.2 Hz, 1H), 3.65-3.29 (m, 4H), 2.96 (d, J=7.0 Hz, 2H), 2.14 (t, J=18.7 Hz, 3H), 1.68-1.64 (m, 5H), 1.22-1.10 (m, 12H); ESIMS m/z: [M+H]$^+$ 378.

Example 6

3-Cyclohexylmethyl-2-cyclopropyl-N,N-diethylimidazo[1,2-a]pyridine-7-carboxamide (Compound 6)

Step 1

3-Cyclohexylpropionic chloride (1.00 g, 5.71 mmol) was dissolved in dichloromethane (10 mL). Under ice-cooled condition, pyridine (0.910 mL, 11.3 mmol) and N,O-dimethylhydroxylamine hydrochloride (840 mg, 8.57 mmol) were added, and the mixture was stirred at room temperature for 2 hours. The reaction mixture was extracted with ethyl acetate after adding a saturated sodium hydrogen carbonate aqueous solution. The organic layer was washed with saturated brine, and dried over anhydrous magnesium sulfate. The solvent was then evaporated under reduced pressure. The residue was purified by silica gel column chromatography (hexane/ethyl acetate=90/10→80/20) to give 3-cyclohexyl-N-methoxy-N-methylpropaneamide (1.13 g, yield 99%).

$^1$H NMR (270 MHz, CDCl$_3$, δ): 3.69 (d, J=2.9 Hz, 3H), 3.18 (s, 3H), 2.46-2.38 (m, 2H), 1.78-0.83 (m, 13H).

Step 2

3-Cyclohexyl-N-methoxy-N-methylpropaneamide (100 mg, 0.502 mmol) obtained in step 1 was dissolved in THF (1.0 mL). Under ice-cooled condition, cyclopropylmagnesium bromide (0.5 mol/L THF solution) (1.20 mL, 0.600 mmol) was added, and the mixture was stirred at room temperature for 3 hours. The reaction mixture was extracted with ethyl acetate after adding a saturated ammonium chloride aqueous solution. The organic layer was washed with saturated brine, and dried over anhydrous magnesium sulfate. The solvent was then evaporated under reduced pressure. The residue was purified by silica gel column chromatography (hexane/ethyl acetate=90/10→80/20) to give 3-cyclohexyl-1-cyclopropylpropan-1-one (61.7 mg, yield 68%).

$^1$H NMR (270 MHz, CDCl$_3$, δ): 2.55 (t, J=6.7 Hz, 2H), 1.94-1.91 (m, 1H), 1.70-1.65 (m, 6H), 1.51-1.47 (m, 2H), 1.22-1.15 (m, 3H), 1.03-0.81 (m, 6H).

Step 3

3-Cyclohexyl-1-cyclopropylpropan-1-one (61.0 mg, 0.338 mmol) obtained in step 2 was dissolved in methanol (1.0 mL), and the mixture was cooled to −5° C., and a dilute solution of bromine (0.0200 mL, 0.372 mmol) in methanol (1.0 mL) was slowly dropped to the mixture. After the dropping, the mixture was stirred at room temperature for hours. Under ice-cooled condition, a sodium thiosulfate aqueous solution was added, and the reaction mixture was extracted with ethyl acetate. The organic layer was washed with saturated brine, and dried over anhydrous magnesium sulfate. The solvent was then evaporated under reduced pressure. The residue was purified by silica gel column chromatography (ethyl acetate/hexane=5/95) to give 2-bromo-3-cyclohexyl-1-cyclopropylpropan-1-one (87.6 mg, quantitative).

¹H NMR (300 MHz, CDCl₃, δ): 4.47 (t, J=7.5 Hz, 1H), 2.26-2.17 (m, 1H), 1.91 (dd, J=6.8, 6.7 Hz, 2H), 1.70-1.65 (m, 4H), 1.51-1.44 (m, 1H), 1.26-0.86 (m, 10H).

Step 4

2-Bromo-3-cyclohexyl-1-cyclopropylpropan-1-one (82.0 mg, 0.318 mmol) obtained in step 3 was dissolved in n-butanol (1.0 mL), and the solution was stirred overnight at 130° C. after adding 2-amino-N,N-diethylpyridine-4-carboxamide (64.0 mg, 0.366 mmol). The reaction mixture was extracted with ethyl acetate after adding a saturated sodium hydrogen carbonate aqueous solution. The organic layer was washed with saturated brine, and dried over anhydrous magnesium sulfate. The solvent was then evaporated under reduced pressure. The residue was purified by silica gel column chromatography (chloroform/methanol=98/2→94/6) to give compound 6 (69.5 mg, yield 62%).

¹H NMR (270 MHz, CDCl₃, δ): 7.87 (d, J=7.1 Hz, 1H), 7.47 (s, 1H), 6.83 (d, J=7.1 Hz, 1H), 3.57-3.34 (m, 4H), 2.83 (d, J=6.9 Hz, 2H), 1.97-1.94 (m, 1H), 1.74-1.70 (m, 5H), 1.27-0.96 (m, 16H); ESIMS m/z: [M+H]⁺ 354.

Example 7

3-{Cyclohexyl(hydroxy)methyl}-N,N-diethyl-2-isopropylimidazo[1,2-a]pyridine-7-carboxamide (Compound 7)

Step 1

2-Isopropylimidazo[1,2-a]pyridine-7-carbonitrile (2.27 g, yield 58%) was obtained in the same manner as in step 2 of Example 1, using 1-bromo-3-methylbutan-2-one obtained according to the method described in Org. Synth., Vol. 55, p. 24, and 4-cyano-2-aminopyridine.

¹H NMR (270 MHz, CDCl₃, δ): 8.13 (dd, J=6.9, 1.0 Hz, 1H), 7.96-7.94 (m, 1H), 7.50 (s, 1H), 6.89 (dd, J=6.9, 1.7 Hz, 1H), 3.16 (sep, J=6.9 Hz, 1H), 1.38 (d, J=6.9 Hz, 6H); ESIMS m/z: [M+H]⁺ 186.

Step 2

2-Isopropylimidazo[1,2-a]pyridine-7-carbonitrile (15.9 g, 85.8 mmol) obtained in step 1 was dissolved in a 50% ethanol aqueous solution (80 mL). Under water-cooled condition, lithium hydroxide.1 hydrate (7.20 g, 172 mmol) was added, and the mixture was stirred under heat and reflux for 3 hours. Under ice-cooled condition, 3 mol/L hydrochloric acid (62 mL) was added to the reaction mixture. The precipitated crystals were collected by filteration, washed with water, and dried to give 2 isopropylimidazo[1,2-a]pyridine-7-carboxylic acid (14.6 g, yield 83%).

¹H NMR (300 MHz, DMSO-d⁶, δ): 8.52 (d, J=7.0 Hz, 1H), 8.02 (d, J=1.1 Hz, 1H), 7.88 (s, 1H), 7.25 (dd, J=7.0, 1.1 Hz, 1H), 3.09-3.00 (m, 1H), 1.30 (d, J=7.0 Hz, 6H); ESIMS m/z: [M+H]⁺ 205.

Step 3

2-Isopropylimidazo[1,2-a]pyridine-7-carboxylic acid (3.00 g, 14.7 mmol) obtained in step 2 was dissolved in DMF (15 mL), and the solution was stirred at 60° C. for 2 hours after adding EDC.HCl (4.20 g, 22.0 mmol), HOBt.H₂O (3.00 g, 22.0 mmol), and diethylamine (2.70 mL, 29.4 mmol). The reaction mixture was extracted with ethyl acetate after adding a saturated sodium hydrogen carbonate aqueous solution. The organic layer was washed with a saturated ammonium chloride aqueous solution and saturated brine, and dried over anhydrous magnesium sulfate. The solvent was then evaporated under reduced pressure. The resulting residue was dissolved in DMF (20 mL), and stirred under light shielding at room temperature for 1 hour after adding N-iodosuccinimide (4.20 g, 18.5 mmol). The reaction mixture was extracted with ethyl acetate after adding a saturated sodium hydrogen carbonate aqueous solution. The organic layer was washed with saturated brine, and dried over anhydrous magnesium sulfate. The solvent was then evaporated under reduced pressure. The residue was slurried with heptane. The resulting crystals were collected by filteration, and dried to give N,N-diethyl-3-iodo-2-isopropylimidazo[1,2-a]pyridine-7-carboxamide (6.40 g, yield 99%).

¹H NMR (300 MHz, CDCl₃, δ): 8.13 (d, J=7.0 Hz, 1H), 7.54 (s, 1H), 6.95 (d, J=7.0 Hz, 1H), 3.53-3.46 (m, 4H), 3.24-3.15 (m, 1H), 1.38 (d, J=7.0 Hz, 6H), 1.31-0.99 (m, 6H); ESIMS m/z: [M+H]⁺ 386.

Step 4

N,N-Diethyl-3-iodo-2-isopropylimidazo[1,2-a]pyridine-7-carboxamide (300 mg, 0.779 mmol) obtained in step 3 was dissolved in THF (3.0 mL), and the solution was stirred at −5° C. for 5 minutes after adding isopropylmagnesium bromide (2 mol/L THF solution) (0.428 mL, 0.857 mmol) at −78° C., and then at room temperature for 2 hours after adding cyclohexanecarboxyaldehyde (0.141 mL, 1.17 mmol). The reaction mixture was extracted with ethyl acetate after adding a saturated ammonium chloride aqueous solution. The organic layer was washed with saturated brine, and dried over anhydrous magnesium sulfate. The solvent was then evaporated under reduced pressure. The residue was purified by silica gel column chromatography (chloroform/methanol=98/2→94/6) to give compound 7 (134 mg, yield 46%).

¹H NMR (270 MHz, CDCl₃, δ): 8.46 (d, J=7.3 Hz, 1H), 7.51 (s, 1H), 6.72 (d, J=7.3 Hz, 1H), 4.83 (d, J=9.5 Hz, 1H), 3.59-3.30 (m, 4H), 3.13-3.04 (m, 1H), 2.56-2.53 (m, 1H), 2.30-2.25 (m, 1H), 2.04-2.00 (m, 1H), 1.81-1.70 (m, 2H), 1.33 (dd, J=6.4, 3.2 Hz, 6H), 1.25-1.11 (m, 12H), 0.88-0.84 (m, 1H); ESIMS m/z: [M+H]⁺ 372.

Example 8

3-Cyclohexylfluoromethyl-N,N-diethyl-2-isopropylimidazo[1,2-a]pyridine-7-carboxamide (Compound 8)

Compound 8 (10.5 mg, yield 21%) was obtained in the same manner as in Example 5, using compound 7.

¹H NMR (300 MHz, CDCl₃, δ): 7.55 (s, 1H), 7.44 (s, 1H), 6.78 (s, 1H), 5.33 (dd, J=45.5, 7.7 Hz, 1H), 3.59-3.31 (m, 4H), 3.19-3.10 (m, 1H), 2.17-1.58 (m, 5H), 1.39 (d, J=5.4 Hz, 6H), 1.19-1.15 (m, 12H); ESIMS m/z: [M+H]⁺ 374.

Example 9

3-{Cyclohexyl(methoxy)methyl}-N,N-diethyl-2-isopropylimidazo[1,2-a]pyridine-7-carboxamide (Compound 9)

Compound 7 (22.0 mg, 0.0590 mmol) was dissolved in DMF (0.5 mL). Under ice-cooled condition, 60% sodium hydride (4.0 mg, 0.089 mmol) and methane iodide (0.0060 mL, 0.089 mmol) were added, and the mixture was stirred at room temperature for 2 hours. The reaction mixture was filtered through a Presep (registered trademark; diatomaceous earth, granular type M, 4.5 g/25 mL) after adding a saturated ammonium chloride aqueous solution. The solvent was then evaporated under reduced pressure. The residue was purified by silica gel column chromatography (chloroform/methanol=100/0→96/4) to give compound 9 (16.3 mg, yield 71%).

¹H NMR (300 MHz, CDCl₃, δ): 8.39 (dd, J=7.0, 0.8 Hz, 1H), 7.55 (dd, J=1.5, 0.8 Hz, 1H), 6.77 (dd, J=7.0, 1.5 Hz,

1H), 4.28 (d, J=9.5 Hz, 1H), 3.57-3.39 (m, 4H), 3.19 (s, 3H), 3.11-3.07 (m, 1H), 2.28-2.24 (m, 1H), 2.01-1.97 (m, 1H), 1.82-1.78 (m, 1H), 1.65-1.62 (m, 2H), 1.39 (d, J=7.3 Hz, 3H), 1.36 (d, J=7.3 Hz, 3H), 1.24-1.19 (m, 12H); ESIMS m/z: [M+H]$^+$ 386.

Example 10

3-Cyclohexylidenemethyl-N,N-diethyl-2-isopropylimidazo[1,2-a]pyridine-7-carboxamide (Compound 10)

Compound 7 (130 mg, 0.350 mmol) was dissolved in DMF (2.0 mL). Under ice-cooled condition, 60% sodium hydride (21.0 mg, 0.525 mmol) and methanesulfonylchloride (0.0410 mL, 0.525 mmol) were added, and the mixture was stirred at 80° C. for 2 hours. Under ice-cooled condition, a saturated ammonium chloride aqueous solution and a saturated sodium hydrogen carbonate aqueous solution were added, and the reaction mixture was filtered through a Presep (registered trademark; diatomaceous earth, granular type M, 4.5 g/25 mL). The solvent was then evaporated under reduced pressure. The residue was purified by silica gel column chromatography (chloroform/methanol=100/0→94/6) to give compound 10 (123 mg, quantitative).
$^1$H NMR (300 MHz, CDCl$_3$, δ): 8.09 (brs, 1H), 7.98 (d, J=7.0 Hz, 1H), 7.16 (brs, 1H), 5.93 (s, 1H), 3.72-3.59 (m, 4H), 3.20-3.13 (m, 1H), 2.43 (t, J=5.9 Hz, 2H), 1.99 (t, J=5.9 Hz, 2H), 1.74-1.53 (m, 6H), 1.45 (d, J=7.0 Hz, 6H), 1.25-1.24 (m, 6H); ESIMS m/z: [M+H]$^+$ 354.

Example 11

3-Cyclohexanecarbonyl-N,N-diethyl-2-isopropylimidazo[1,2-a]pyridine-7-carboxamide (Compound 11)

Compound 7 (340 mg, 0.915 mmol) was dissolved in dichloromethane (3.4 mL). Under ice-cooled condition, Dess-Martin periodinate (427 mg, 1.01 mmol) was added, and the mixture was stirred for 3 hours. The reaction mixture was extracted with ethyl acetate after adding a saturated sodium hydrogen carbonate aqueous solution. The organic layer was washed with saturated brine, and dried over anhydrous magnesium sulfate. The solvent was then evaporated under reduced pressure. The residue was purified by silica gel column chromatography (hexane/ethyl acetate=50/50→0/100) to give compound 11 (206 mg, yield 61%).
$^1$H NMR (270 MHz, CDCl$_3$, δ): 9.75 (dd, J=7.1, 0.9 Hz, 1H), 7.65 (dd, J=1.6, 0.9 Hz, 1H), 6.99 (dd, J=7.1, 1.6 Hz, 1H), 3.69-3.46 (m, 3H), 3.47-3.24 (m, 2H), 3.15-3.10 (m, 1H), 1.93-1.89 (m, 4H), 1.75-1.62 (m, 3H), 1.48 (d, J=6.6 Hz, 6H), 1.42-1.33 (m, 3H), 1.27-1.25 (m, 6H); ESIMS m/z: [M+H]$^+$ 370.

Example 12

3-Cyclohexylthio-N,N-diethyl-2-isopropylimidazo[1,2-a]pyridine-7-carboxamide (Compound 12)

N,N-Diethyl-3-iodo-2-isopropylimidazo[1,2-a]pyridine-7-carboxamide (100 mg, 0.260 mmol) obtained in step 3 of Example 7, copper iodide (I) (25.0 mg, 0.130 mmol), tripotassium phosphate (110 mg, 0.519 mmol), and α-pipecolic acid (16.0 mg, 0.130 mmol) were dissolved in DMSO (1.0 mL), and the mixture was stirred at 80° C. The reaction mixture was stirred for 4 hours after adding cyclohexanethiol (0.0960 mL, 0.389 mmol). After adding water, the reaction mixture was filtered through Celite (registered trademark), and extracted with ethyl acetate. The organic layer was washed with saturated brine, and dried over anhydrous magnesium sulfate. The solvent was then evaporated under reduced pressure. The residue was purified by silica gel column chromatography (chloroform/methanol=100/0→96/4) to give compound 12 (50.0 mg, yield 52%).
$^1$H NMR (270 MHz, CDCl$_3$, δ): 8.45 (d, J=7.2 Hz, 1H), 7.56 (s, 1H), 6.91 (d, J=7.2 Hz, 1H), 3.42-3.33 (m, 5H), 2.84-2.80 (m, 1H), 1.94-1.79 (m, 2H), 1.80-1.67 (m, 2H), 1.59 (m, 1H), 1.43-1.34 (m, 6H), 1.33-1.02 (m, 11H); ESIMS m/z: [M+H]$^+$ 374.

Example 13

3-Cyclohexylsulfonyl-N,N-diethyl-2-isopropylimidazo[1,2-a]pyridine-7-carboxamide (Compound 13)

Compound 12 (334 mg, 0.894 mmol) was dissolved in dichloromethane (3.3 mL). Under ice-cooled condition, m-chloroperbenzoic acid (339 mg, 1.97 mmol) was added, and the mixture was stirred at room temperature for 4 hours. Under ice-cooled condition, a saturated sodium hydrogen carbonate aqueous solution was added, and the reaction mixture was filtered through a Presep (registered trademark; diatomaceous earth, granular type M, 4.5 g/25 mL). The solvent was then evaporated under reduced pressure. The residue was purified by silica gel column chromatography (chloroform/methanol=100/0→96/4) to give compound 13 (238 mg, yield 66%).
$^1$H NMR (270 MHz, CDCl$_3$, δ): 8.92 (d, J=7.8 Hz, 1H), 7.65-7.64 (m, 1H), 6.99 (d, J=7.8 Hz, 1H), 3.76-3.66 (m, 1H), 3.56-3.36 (m, 4H), 3.00-2.90 (m, 1H), 2.08-2.06 (m, 2H), 1.91-1.87 (m, 2H), 1.72-1.69 (m, 1H), 1.52-1.48 (m, 1H), 1.39 (d, J=6.8 Hz, 6H), 1.23-1.19 (m, 10H); ESIMS m/z: [M+H]$^+$ 406.

Example 14

(2-tert-Butyl-3-cyclohexylmethylimidazo[1,2-a]pyridin-7-yl)(3-methylpiperidin-1-yl)methanone (Compound 14)

Compound 14 (36.1 mg, yield 92%) was obtained in the same manner as in step 2 of Example 2, using 2-tert-butyl-3-cyclohexylmethylimidazo[1,2-a]pyridine-7-carboxylic acid obtained according to the method described in WO2008/032764, and 3-methylpiperidine.
$^1$H NMR (270 MHz, CDCl$_3$, δ): 7.89 (dd, J=7.3, 1.0 Hz, 1H), 7.54 (dd, J=1.7, 1.0 Hz, 1H), 6.84 (dd, J=7.3, 1.7 Hz, 1H), 4.31-4.06 (br m, 1H), 3.01-2.92 (br m, 1H), 2.91 (d, J=6.9 Hz, 2H), 2.66-2.54 (m, 1H), 1.92-1.83 (m, 1H), 1.77-1.62 (m, 9H), 1.48 (s, 9H), 1.04-1.28 (m, 7H), 0.90 (d, J=6.6 Hz, 3H); ESIMS m/z: [M+H]$^+$ 396.

Example 15

2-tert-Butyl-N-cyclobutyl-3-cyclohexylmethylimidazo[1,2-a]pyridine-7-carboxamide (Compound 15)

Compound 15 (58.3 mg, yield 99%) was obtained in the same manner as in step 2 of Example 2, using 2-tert-butyl-3-cyclohexylmethylimidazo[1,2-a]pyridine-7-carboxylic acid and cyclobutylamine.
$^1$H NMR (300 MHz, CDCl$_3$, δ): 7.91 (d, J=7.3 Hz, 1H), 7.86 (d, J=1.8 Hz, 1H), 7.23 (dd, J=7.3, 1.8 Hz, 1H), 6.21 (d, J=7.3 Hz, 1H), 4.65-4.49 (m, 1H), 2.92 (d, J=7.3 Hz, 2H), 2.51-2.39 (m, 2H), 2.01-1.85 (m, 2H), 1.84-1.56 (m, 8H), 1.48 (s, 9H), 1.28-1.03 (m, 5H); ESIMS m/z: [M+H]$^+$ 368.

Example 16

N-Benzyl-2-tert-butyl-3-cyclohexylmethylimidazo[1,2-a]pyridine-7-carboxamide (Compound 16)

Compound 16 (55.7 mg, yield 87%) was obtained in the same manner as in step 2 of Example 2, using 2-tert-butyl-3-cyclohexylmethylimidazo[1,2-a]pyridine-7-carboxylic acid and benzylamine.
$^1$H NMR (300 MHz, CDCl$_3$, δ): 7.94-7.89 (m, 2H), 7.39-7.28 (m, 6H), 6.42 (t, J=5.5 Hz, 1H), 4.65 (d, J=5.5 Hz, 2H), 2.92 (d, J=7.3 Hz, 2H), 1.73-1.59 (m, 6H), 1.47 (s, 9H), 1.27-1.03 (m, 5H); ESIMS m/z: [M+H]$^+$ 404.

Example 17

N'-Benzoyl-2-tert-butyl-3-cyclohexylmethylimidazo[1,2-a]pyridine-7-carbohydrazide (Compound 17)

Step 1
2-tert-Butyl-3-cyclohexylmethylimidazo[1,2-a]pyridine-7-carboxylic acid (500 mg, 1.59 mmol) was suspended in THF (5.0 mL), and the suspension was stirred at room temperature for 1 hour after adding carbonyldiimidazole (CDI) (280 mg, 1.73 mmol). The reaction mixture was stirred at room temperature for 1 hour after adding hydrazine monohydrate (0.240 mL, 4.80 mmol). Water was added to the reaction mixture. The precipitated solid was collected by filteration, and dried under reduced pressure to give 2-tert-butyl-3-cyclohexylmethylimidazo[1,2-a]pyridine-7-carbohydrazide (331 mg, yield 79%).
$^1$H NMR (270 MHz, CDCl$_3$, δ): 7.93 (d, J=7.3 Hz, 1H), 7.90 (s, 1H), 7.55-7.38 (br m, 1H), 7.20 (d, J=7.3 Hz, 1H), 2.93 (d, J=7.3 Hz, 2H), 1.77-1.57 (m, 8H), 1.47 (s, 9H), 1.26-1.05 (m, 5H).
Step 2
2-tert-Butyl-3-cyclohexylmethylimidazo[1,2-a]pyridine-7-carbohydrazide (100 mg, 0.304 mmol) obtained in step 1 was dissolved in dichloromethane (1.0 mL), and the solution was stirred at room temperature for 1 hour after adding pyridine (0.0370 mL, 0.459 mmol) and benzoyl chloride (0.0390 mL, 0.336 mmol). The reaction mixture was extracted with ethyl acetate after adding a saturated sodium hydrogen carbonate aqueous solution. The organic layer was washed with saturated brine, and dried over anhydrous magnesium sulfate. The solvent was then evaporated under reduced pressure. The residue was purified by silica gel column chromatography (chloroform/methanol=99/1→95/5) to give compound 17 (109 mg, yield 83%).
$^1$H NMR (270 MHz, CDCl$_3$, δ): 8.18 (d, J=1.1 Hz, 1H), 7.94 (d, J=7.0 Hz, 1H), 7.90-7.86 (m, 2H), 7.62-7.42 (m, 3H), 7.27-7.24 (m, 2H), 2.94 (d, J=7.3 Hz, 2H), 1.77-1.61 (m, 6H), 1.49 (s, 9H), 1.27-1.03 (m, 6H); ESIMS m/z: [M+H]$^+$ 433.

Example 18 tert-Butyl 2-tert-butyl-3-cyclohexylmethylimidazo[1,2-a]pyridine-7-ylcarbamate (Compound 18)

2-tert-Butyl-3-cyclohexylmethylimidazo[1,2-a]pyridine-7-carboxylic acid (45.0 mg, 0.143 mmol) was dissolved in toluene (1.0 mL), and the solution was stirred under heat and reflux for 1 hour after adding diphenylphosphoryl azide (0.0620 mL, 0.289 mmol) and triethylamine (0.0400 mL, 0.287 mmol). The reaction mixture was stirred under heat and reflux for 1 hour after adding tert-butanol (0.0280 mL, 0.284 mmol). After adding water to the reaction mixture, the reaction mixture was filtered through a Presep (registered trademark; diatomaceous earth, granular type M, 4.5 g/25 mL). The solvent was then evaporated under reduced pressure. The residue was purified by silica gel column chromatography (chloroform/methanol=95/5) to give compound 18 (11.3 mg, yield 20%).
$^1$H NMR (270 MHz, CDCl$_3$, δ): 7.75 (d, J=7.9 Hz, 1H), 7.27-7.18 (m, 2H), 6.55 (s, 1H), 2.85 (d, J=6.9 Hz, 2H), 1.74-1.61 (m, 5H), 1.52 (s, 9H), 1.45 (s, 9H), 1.24-0.95 (m, 6H); ESIMS m/z: [M+H]$^+$ 386.

Example 19

N-(2-tert-Butyl-3-cyclohexylmethylimidazo[1,2-a]pyridin-7-yl)-N,3-dimethylbutanamide (Compound 19)

Step 1
2-Bromo-1-cyclohexyl-4,4-dimethylpentan-3-one (310 mg, 1.13 mmol) obtained according to the method described in WO2008/032764 was dissolved in n-butanol (1.5 mL), and the solution was stirred overnight under heat and reflux after adding 2-amino-4-methylaminopyridine (230 mg, 1.87 mmol) obtained according to the method described in WO2006/040520 and potassium carbonate (270 mg, 1.96 mmol). The reaction mixture was allowed to cool to room temperature, and extracted with ethyl acetate after adding a sodium hydrogen carbonate aqueous solution. The organic layer was washed with saturated brine, and dried over anhydrous magnesium sulfate. The solvent was then evaporated under reduced pressure. The residue was purified by silica gel column chromatography (hexane/ethyl acetate=80/20→0/100) to give 2-tert-butyl-3-cyclohexylmethyl-N-methylimidazo[1,2-a]pyridine-7-amine (197 mg, yield 58%).
$^1$H NMR (270 MHz, CDCl$_3$, δ): 7.56 (d, J=7.6 Hz, 1H), 6.50 (d, J=2.3 Hz, 1H), 6.16 (dd, J=7.6, 2.3 Hz, 1H), 3.79 (q, J=5.3 Hz, 1H), 2.84 (d, J=5.3 Hz, 3H), 2.80 (d, J=6.9 Hz, 2H), 1.69-1.53 (m, 6H), 1.44 (s, 9H), 1.22-0.97 (m, 5H); ESIMS m/z: [M+H]$^+$ 300.
Step 2
2-tert-Butyl-3-cyclohexylmethyl-N-methylimidazo[1,2-a]pyridine-7-amine (0.0400 g, 0.134 mmol) obtained in step 1 was dissolved in dichloromethane (1.0 mL), and the solution was stirred at room temperature for 2 hours after adding isovaleryl chloride (0.0240 mL, 0.186 mmol) and triethylamine (0.0360 mL, 0.258 mmol). The reaction mixture was filtered through a Presep (registered trademark; diatomaceous earth, granular type M, 4.5 g/25 mL) after adding a saturated sodium hydrogen carbonate aqueous solution. The solvent was then evaporated under reduced pressure. The residue was purified by silica gel chromatography (chloroform/methanol=95/5) to give compound 19 (34.5 mg, yield 67%).
$^1$H NMR (300 MHz, CDCl$_3$, δ): 7.89 (d, J=7.3 Hz, 1H), 7.35 (d, J=1.8 Hz, 1H), 6.57 (dd, J=7.3, 1.8 Hz, 1H), 3.27 (s, 3H), 2.92 (d, J=7.0 Hz, 2H), 2.24-2.08 (m, 3H), 1.79-1.65 (m, 6H), 1.48 (s, 9H), 1.27-1.09 (m, 5H), 0.87 (d, J=6.2 Hz, 6H); ESIMS m/z: [M+H]$^+$ 384.

Example 20

N-(2-tert-Butyl-3-cyclohexylmethylimidazo[1,2-a]pyridin-7-yl)-N,N',N'-trimethylsulfamide (Compound 20)

2-tert-Butyl-3-cyclohexylmethyl-N-methylimidazo[1,2-a]pyridine-7-amine (40.0 mg, 0.134 mmol) obtained in step 1 of Example 19 was dissolved in 1,2-dichloroethane (1.0 mL), and the solution was stirred at 100° C. for 30 minutes after adding dimethylsulfamoyl chloride (0.0290 mL, 0.270 mmol) and N,N-dimethylaminopyridine (8.20 mg, 0.067 mmol). The reaction mixture was extracted with ethyl acetate after adding a saturated sodium hydrogen carbonate aqueous solution. The organic layer was washed with saturated brine, and dried over anhydrous magnesium sulfate. The solvent was then evaporated under reduced pressure. The residue was purified by silica gel chromatography (chloroform/methanol=95/5) to give compound 20 (19.8 mg, yield 36%).

$^1$H NMR (270 MHz, CDCl$_3$, δ): 7.80 (d, J=7.5 Hz, 1H), 7.44 (d, J=2.2 Hz, 1H), 7.00 (dd, J=7.5, 2.2 Hz, 1H), 3.30 (s, 3H), 2.90-2.84 (m, 2H), 2.85 (s, 6H), 1.77-1.63 (m, 6H), 1.46 (s, 9H), 1.25-1.06 (m, 5H); ESIMS m/z: [M+H]$^+$ 407.

Example 21

3-Cyclohexyloxymethyl-2-isopropyl-N-phenylimidazo[1,2-a]pyridine-7-carboxamide (Compound 21)

Step 1

2-Isopropylimidazo[1,2-a]pyridine-7-carbonitrile (500 mg, 2.70 mmol) obtained in step 1 of Example 7 was suspended in a 38% formaldehyde aqueous solution (5.0 mL), and the suspension was stirred at 50° C. for 7 hours after adding acetic acid (0.50 mL). Under ice-cooled condition, a saturated sodium hydrogen carbonate aqueous solution was added, and the reaction mixture was extracted with chloroform-isopropanol mixed solvent (6/1). The organic layer was washed with saturated brine, and dried over anhydrous magnesium sulfate. The solvent was then evaporated under reduced pressure. The residue was purified by silica gel column chromatography (hexane/ethyl acetate=1/1) to give 3-hydroxymethyl-2-isopropyl[1,2-a]pyridine-7-carbonitrile (478 mg, yield 82%).

$^1$H NMR (300 MHz, CDCl$_3$, δ): 8.32 (d, J=7.0 Hz, 1H), 7.97 (d, J=1.5 Hz, 1H), 6.97 (dd, J=7.0, 1.5 Hz, 1H), 5.03 (d, J=5.1 Hz, 2H), 3.22 (sep, J=7.0 Hz, 1H), 1.75 (t, J=5.1 Hz, 1H), 1.37 (d, J=7.0 Hz, 6H); ESIMS m/z: [M+H]$^+$ 216.

Step 2

Under ice-cooled condition, 60% sodium hydride (100 mg, 2.50 mmol) was suspended in DMF (2.0 mL), and the suspension was stirred at room temperature for 10 minutes while slowly dropping cyclohexanol (0.240 mL, 2.28 mmol) (solution A). Concurrently, 3-hydroxymethyl-2-isopropyl[1,2-a] pyridine-7-carbonitrile (245 mg, 1.14 mmol) obtained in step 1 was dissolved in thionyl chloride (2.0 mL), and the solution was stirred under heat and reflux for 2 hours. The solvent was evaporated from the reaction mixture under reduced pressure, and the residue was dissolved in DMF (2.0 mL). Then, the solution A prepared above was added under ice-cooled condition, and the mixture was stirred at 70° C. for 2 hours. The reaction mixture was extracted with ethyl acetate after adding a sodium hydrogen carbonate aqueous solution. The organic layer was washed with saturated brine, and dried over anhydrous sodium sulfate. The solvent was then evaporated under reduced pressure. The residue was purified by silica gel chromatography (chloroform/methanol=95/5) to give 3-cyclohexyloxymethyl-2-isopropyl[1,2-a]pyridine-7-carbonitrile (336 mg, yield 99%).

$^1$H NMR (270 MHz, CDCl$_3$, δ): 8.24 (dd, J=7.1, 0.8 Hz, 1H), 7.98 (dd, J=1.7, 0.8 Hz, 1H), 6.94 (dd, J=7.1, 1.7 Hz, 1H), 4.85 (s, 2H), 3.39-3.27 (m, 1H), 3.21 (sep, J=6.9 Hz, 1H), 1.97-1.67 (m, 4H), 1.38 (d, J=6.9 Hz, 6H), 1.35-1.18 (m, 6H); ESIMS m/z: [M+H]$^+$ 298.

Step 3

3-Cyclohexyloxymethyl-2-isopropyl[1,2-a]pyridine-7-carboxylic acid (282 mg, yield 59%) was obtained in the same manner as in step 2 of Example 7, using 3-cyclohexyloxymethyl-2-isopropyl[1,2-a]pyridine-7-carbonitrile obtained in step 2.

$^1$H NMR (270 MHz, CDCl$_3$, δ): 8.75 (s, 1H), 8.33 (d, J=6.9 Hz, 1H), 7.77 (d, J=6.9 Hz, 1H), 4.89 (s, 2H), 3.97 (br s, 1H), 3.41-3.25 (m, 2H), 1.97-1.86 (m, 2H), 1.79-1.70 (m, 2H), 1.52 (d, J=6.9 Hz, 6H), 1.18-1.40 (m, 6H); ESIMS m/z: [M+H]$^+$ 317.

Step 4

3-Cyclohexyloxymethyl-2-isopropyl[1,2-a]pyridine-7-carboxylic acid (50.0 mg, 0.158 mmol) obtained in step 2 was dissolved in THF (1.0 mL), and the solution was stirred at 50° C. for 1 hour after adding aniline (0.0300 mL, 0.329 mmol), EDC.HCl (46.0 mg, 0.240 mmol), and HOBt.H$_2$O (36.0 mg, 0.235 mmol). The reaction mixture was extracted with ethyl acetate after adding a saturated sodium hydrogen carbonate aqueous solution. The organic layer was washed with saturated brine, and dried over anhydrous magnesium sulfate. The solvent was then evaporated under reduced pressure. The residue was purified by silica gel column chromatography (chloroform/methanol=99/1→95/5) to give compound 21 (24.2 mg, yield 38%).

$^1$H NMR (300 MHz, CDCl$_3$, δ): 8.25 (dd, J=7.3, 0.7 Hz, 1H), 8.10 (dd, J=1.1, 0.7 Hz, 1H), 8.02 (s, 1H), 7.68-7.63 (m, 2H), 7.43-7.35 (m, 3H), 7.21-7.14 (m, 1H), 4.87 (s, 2H), 3.38-3.28 (m, 1H), 3.22 (sep, J=6.9 Hz, 1H), 1.97-1.88 (m, 2H), 1.77-1.70 (m, 2H), 1.60-1.50 (m, 1H), 1.39 (d, J=6.9 Hz, 6H), 1.38-1.16 (m, 5H); ESIMS m/z: [M+H]$^+$ 392.

Example 22

3-Cyclohexyloxymethyl-2-isopropyl-N-methyl-N-phenylimidazo[1,2-a]pyridine-7-carboxamide (Compound 22)

Compound 21 (68.0 mg, 0.173 mmol) was dissolved in DMF (0.5 mL). Under ice-cooled condition, potassium carbonate (48.0 mg, 0.348 mmol) and methane iodide (0.0160 mL, 0.257 mmol) were added, and the mixture was stirred overnight at room temperature. After adding water to the reaction mixture, the reaction mixture was filtered through a Presep (registered trademark; diatomaceous earth, granular type M, 4.5 g/25 mL). The solvent was then evaporated under reduced pressure. The residue was purified by silica gel column chromatography (chloroform/methanol=97/3) to give compound 22 (201 mg, yield 29%).

$^1$H NMR (270 MHz, CDCl$_3$, δ): 7.93 (dd, J=7.1, 0.8 Hz, 1H), 7.55 (dd, J=1.8, 0.8 Hz, 1H), 7.29-7.22 (m, 2H), 7.20-7.06 (m, 3H), 6.74 (dd, J=7.1, 1.8 Hz, 1H), 4.75 (s, 2H), 3.51 (s, 3H), 3.30-3.20 (m, 1H), 3.13 (sep, J=6.9 Hz, 1H), 1.94-1.79 (m, 2H), 1.75-1.63 (m, 2H), 1.32 (d, J=6.9 Hz, 6H), 1.30-1.17 (m, 6H); ESIMS m/z: [M+H]$^+$ 406.

Example 23

N-(2-Aminophenyl)-3-cyclohexyloxymethyl-2-isopropylimidazo[1,2-a]pyridine-7-carboxamide (Compound 23)

Compound 23 (155 mg, yield 68%) was obtained in the same manner as in step 4 of Example 21, using 3-cyclohexyloxymethyl-2-isopropyl[1,2-a]pyridine-7-carboxylic acid obtained in step 3 of Example 21, and 1,2-diaminobenzene.

¹H NMR (270 MHz, CDCl₃, δ): 8.24 (dd, J=7.3, 0.7 Hz, 1H), 8.16-8.08 (m, 2H), 7.44 (d, J=7.3 Hz, 1H), 7.39 (dd, J=7.1, 1.8 Hz, 1H), 7.27-7.23 (m, 1H), 7.14-7.05 (m, 1H), 6.92-6.83 (m, 2H), 4.86 (s, 2H), 3.84 (br s, 1H), 3.36-3.17 (m, 2H), 1.96-1.86 (m, 2H), 1.78-1.61 (m, 2H), 1.39 (d, J=6.9 Hz, 6H), 1.35-1.17 (m, 6H); ESIMS m/z: [M+H]⁺ 407.

Example 24

3-Cyclohexyloxymethyl-2-isopropyl-N-(pyridin-4-yl)imidazo[1,2-a]pyridine-7-carboxamide (Compound 24)

Compound 24 (79.0 mg, yield 64%) was obtained in the same manner as in step 4 of Example 21, using 3-cyclohexyloxymethyl-2-isopropyl[1,2-a]pyridine-7-carboxylic acid obtained in step 3 of Example 21, and 4-aminopyridine.

¹H NMR (270 MHz, CDCl₃, δ): 8.57 (dd, J=4.8, 1.5 Hz, 2H), 8.35 (s, 1H), 8.26 (dd, J=7.3, 1.5 Hz, 1H), 8.09 (dd, J=1.8, 1.5 Hz, 1H), 7.62 (dd, J=4.8, 1.5 Hz, 2H), 7.36 (dd, J=7.3, 1.8 Hz, 1H), 4.86 (s, 2H), 3.39-3.30 (m, 1H), 3.21 (sep, J=6.9 Hz, 1H), 1.98-1.88 (m, 2H), 1.77-1.75 (m, 2H), 1.38 (d, J=6.9 Hz, 6H), 1.37-1.17 (m, 6H); ESIMS m/z: [M+H]⁺ 393.

Example 25

3-Cyclohexyloxymethyl-2-isopropyl-N-(thiazol-2-yl)imidazo[1,2-a]pyridine-7-carboxamide (Compound 25)

Compound 25 (40.6 mg, yield 65%) was obtained in the same manner as in step 4 of Example 21, using 3-cyclohexyloxymethyl-2-isopropyl[1,2-a]pyridine-7-carboxylic acid obtained in step 3 of Example 21, and 2-aminothiazole.

¹H NMR (270 MHz, CDCl₃, δ): 11.72 (s, 1H), 8.30-8.25 (m, 2H), 7.40 (dd, J=7.3, 1.7 Hz, 1H), 7.29 (d, J=3.6 Hz, 1H), 6.98 (d, J=3.6 Hz, 1H), 4.88 (s, 2H), 3.42-3.31 (m, 1H), 3.23 (sep, J=6.9 Hz, 1H), 2.01-1.87 (m, 2H), 1.82-1.70 (m, 2H), 1.40 (d, J=6.9 Hz, 6H), 1.38-1.19 (m, 6H); ESIMS m/z: [M+H]⁺ 399.

Example 26

3-Cyclohexyloxymethyl-N-(4,5-dihydrothiazol-2-yl)-2-isopropylimidazo[1,2-a]pyridine-7-carboxamide (Compound 26)

Compound 25 (8.9 mg, yield 14%) was obtained in the same manner as in step 4 of Example 21, using 3-cyclohexyloxymethyl-2-isopropyl[1,2-a]pyridine-7-carboxylic acid obtained in step 3 of Example 21, and 2-amino-4,5-dihydrothiazole.

¹H NMR (300 MHz, CDCl₃, δ): 8.53 (d, J=1.6 Hz, 1H), 8.14 (d, J=7.1 Hz, 1H), 7.58 (dd, J=7.1, 1.6 Hz, 1H), 4.84 (s, 2H), 3.81 (t, J=7.9 Hz, 2H), 3.37-3.28 (m, 3H), 3.20 (sep, J=7.0 Hz, 1H), 1.96-1.86 (m, 2H), 1.79-1.70 (m, 2H), 1.39 (d, J=7.0 Hz, 6H), 1.37-1.17 (m, 6H); ESIMS m/z: [M+H]⁺ 401.

Example 27

3-Cyclohexyloxymethyl-2-isopropyl-N-(2-oxo-2-phenylethyl)imidazo[1,2-a]pyridine-7-carboxamide (Compound 27)

The 3-cyclohexyloxymethyl-2-isopropyl[1,2-a]pyridine-7-carboxylic acid (50.0 mg, 0.158 mmol) obtained in step 3 of Example 21 was dissolved in DMF (0.5 mL), and the solution was stirred at room temperature for 2 hours after adding EDC.HCl (61.0 mg, 0.318 mmol), HOBt.H₂O (12.0 mg, 0.0784 mmol), 2-amino-1-phenylethanonehydrochloride (55.0 mg, 0.320 mmol), and triethylamine (0.0440 mL, 0.315 mmol). A sodium hydrogen carbonate aqueous solution was added to the reaction mixture. The precipitated crystals were collected by filteration, washed with water, and reslurried in tert-butyl methyl ether to give compound 27 (47.1 mg, yield 69%).

¹H NMR (270 MHz, CDCl₃, δ): 8.24 (d, J=7.3 Hz, 1H), 8.15 (s, 1H), 8.07-8.02 (m, 2H), 7.69-7.62 (m, 1H), 7.58-7.50 (m, 2H), 7.39 (t, J=4.3 Hz, 1H), 7.34 (dd, J=6.9, 1.7 Hz, 1H), 4.97 (d, J=4.3 Hz, 2H), 4.87 (s, 2H), 3.38-3.28 (m, 1H), 3.21 (sep, J=7.0 Hz, 1H), 1.97-1.86 (m, 2H), 1.77-1.60 (m, 2H), 1.40 (d, J=6.9 Hz, 6H), 1.37-1.18 (m, 6H); ESIMS m/z: [M+H]⁺ 434.

Example 28

N-(3-Cyclohexyloxymethyl-2-isopropylimidazo[1,2-a]pyridin-7-yl)benzamide (Compound 28)

Step 1

7-Bromo-2-isopropylimidazo[1,2-a]pyridine (594 mg, yield 41%) was obtained in the same manner as in step 2 of Example 1, using 1-bromo-3-methylbutan-2-one, and 4-bromo-2-aminopyridine.

¹H NMR (270 MHz, CDCl₃, δ): 7.91 (d, J=6.9 Hz, 1H), 7.72 (d, J=2.0 Hz, 1H), 7.31 (s, 1H), 6.82 (dd, J=6.9, 2.0 Hz, 1H), 3.09 (sep, J=6.9 Hz, 1H), 1.35 (d, J=6.9 Hz, 6H); ESIMS m/z: [M+H]⁺ 239, 241.

Step 2

(7-Bromo-2-isopropylimidazo[1,2-a]pyridin-3-yl)methanol (562 mg, yield 84%) was obtained in the same manner as in step 1 of Example 21, using 7-bromo-2-isopropylimidazo[1,2-a]pyridine obtained in step 1.

¹H NMR (270 MHz, CDCl₃, δ): 8.08 (dd, J=7.1, 0.8 Hz, 1H), 7.76 (dd, J=2.0, 0.8 Hz, 1H), 6.92 (dd, J=7.1, 2.0 Hz, 1H), 4.96 (d, J=5.3 Hz, 2H), 3.17 (sep, J=6.9 Hz, 1H), 1.54 (t, J=5.3 Hz, 1H) 1.36 (d, J=6.9 Hz, 6H); ESIMS m/z: [M+H]⁺ 269, 271.

Step 3

7-Bromo-3-cyclohexyloxymethyl-2-isopropylimidazo[1,2-a]pyridine (649 mg, quantitative) was obtained in the same manner as in step 2 of Example 21, using (7-bromo-2-isopropylimidazo[1,2-a]pyridin-3-yl)methanol obtained in step 2.

¹H NMR (270 MHz, CDCl₃, δ): 8.02 (d, J=7.3 Hz, 1H), 7.76 (d, J=2.0 Hz, 1H), 6.88 (dd, J=7.3, 2.0 Hz, 1H), 4.80 (s, 2H), 3.34-3.24 (m, 1H), 3.15 (sep, J=6.9 Hz, 1H), 1.93-1.83 (m, 2H), 1.78-1.69 (m, 2H), 1.57-1.50 (m, 1H), 1.36 (d, J=6.9 Hz, 6H), 1.34-1.15 (m, 5H); ESIMS m/z: [M+H]⁺ 351, 353.

Step 4

7-Bromo-3-cyclohexyloxymethyl-2-isopropylimidazo[1,2-a]pyridine (50.0 mg, 0.142 mmol) obtained in step 3 was dissolved in 1,4-dioxane (1.0 mL), and the solution was stirred at 90° C. for 2 hours after adding benzamide (34.4 mg, 0.284 mmol), palladium acetate (6.40 mg, 0.0252 mmol), 4,5'-bis(diphenylphosphino)-9,9'-dimethylxanthene (50.0 mg, 0.0863 mmol), and cesium carbonate (93.0 mg, 0.285 mmol). After adding a saturated sodium hydrogen carbonate aqueous solution to the reaction mixture, the reaction mixture was filtered through a Presep (registered trademark; diatomaceous earth, granular type M, 4.5 g/25 mL). The solvent was then evaporated under reduced pressure. The residue was purified by silica gel column chromatography (chloroform/methanol=98/2) to give compound 28 (46.3 mg, yield 83%).

¹H NMR (270 MHz, CDCl₃, δ): 8.12 (d, J=7.6 Hz, 1H), 8.03 (br s, 1H), 7.92-7.87 (m, 2H), 7.71 (d, J=2.0 Hz, 1H), 7.60-7.46 (m, 3H), 7.40 (dd, J=7.6, 2.0 Hz, 1H), 4.82 (s, 2H), 3.37-3.25 (m, 1H), 3.15 (sep, J=6.6 Hz, 1H), 1.96-1.87 (m, 2H), 1.80-1.71 (m, 2H), 1.58-1.52 (m, 1H), 1.36 (d, J=6.6 Hz, 6H), 1.34-1.18 (m, 5H); ESIMS m/z: [M+H]⁺ 392.

Example 29

N-(3-Cyclohexyloxymethyl-2-isopropylimidazo[1,2-a]pyridin-7-yl)-N-methylbenzamide (Compound 29)

Compound 29 (3.70 mg, yield 19%) was obtained in the same manner as in Example 9, using compound 28.
¹H NMR (270 MHz, CDCl₃, δ): 7.94 (d, J=7.3 Hz, 1H), 7.44-7.38 (m, 2H), 7.33-7.18 (m, 4H), 6.45 (dd, J=7.3, 2.0 Hz, 1H), 4.76 (s, 2H), 3.51 (s, 3H), 3.33-3.22 (m, 1H), 3.13 (sep, J=6.9 Hz, 1H), 1.92-1.83 (m, 2H), 1.78-1.69 (m, 2H), 1.59-1.53 (m, 1H), 1.34 (d, J=6.9 Hz, 6H), 1.29-1.17 (m, 5H); ESIMS m/z: [M+H]⁺ 406.

Example 30

1-(3-Cyclohexyloxymethyl-2-isopropylimidazo[1,2-a]pyridin-7-yl)-3-phenylurea (Compound 30)

7-Bromo-3-cyclohexyloxymethyl-2-isopropylimidazo[1,2-a]pyridine (50.0 mg, 0.142 mmol) obtained in step 3 of Example 28 was dissolved in 1,4-dioxane (1.0 mL), and the solution was stirred at 100° C. for 2 hours after adding phenylurea (30.0 mg, 0.221 mmol), tris(dibenzylideneacetone)dipalladium(0)chloroform complex (15.0 mg, 0.0144 mmol), 4,5'-bis(diphenylphosphino)-9,9'-dimethylxanthene (25.0 mg, 0.0432 mmol), and cesium carbonate (70.0 mg, 0.215 mmol). After adding water to the reaction mixture, the reaction mixture was filtered through a Presep (registered trademark; diatomaceous earth, granular type M, 4.5 g/25 mL). The solvent was then evaporated under reduced pressure. The residue was purified by silica gel column chromatography (chloroform/methanol=98/2) to give compound 30 (17.7 mg, yield 31%).
¹H NMR (300 MHz, DMSO-d⁶, δ): 8.93 (s, 1H), 8.76 (s, 1H), 8.12 (d, J=7.3 Hz, 1H), 7.62 (d, J=1.8 Hz, 1H), 7.49-7.44 (m, 2H), 7.34-7.26 (m, 2H), 7.03-6.93 (m, 2H), 4.76 (s, 2H), 3.34-3.29 (m, 1H), 3.11 (sep, J=6.9 Hz, 1H), 1.88-1.79 (m, 2H), 1.69-1.61 (m, 2H), 1.51-1.41 (m, 1H), 1.29-1.19 (m, 6H), 1.24 (d, J=6.9 Hz, 5H); ESIMS m/z: [M+H]⁺ 407.

Example 31

N-(3-Cyclohexyloxymethyl-2-isopropylimidazo[1,2-a]pyridin-7-yl)benzenesulfoneamide (Compound 31)

Bis(dibenzylideneacetone)palladium(0) (16.0 mg, 0.0278 mmol), 2-dicyclohexylphosphino-2'-(dimethylamino)biphenyl (34.0 mg, 0.0862 mmol), and cesium carbonate (93.0 mg, 0.285 mmol) were dissolved in 1,4-dioxane (1.0 mL), and the solution was stirred at room temperature for 5 minutes. The mixture was stirred at 150° C. for 30 minutes after adding 7-bromo-3-cyclohexyloxymethyl-2-isopropylimidazo[1,2-a]pyridine (50.0 mg, 0.142 mmol) obtained in step 3 of Example 28, and benzenesulfoneamide (45.0 mg, 0.287 mmol), using a microwave chemical synthesizer (CEM Discover). After adding water to the reaction mixture, the reaction mixture was filtered through a Presep (registered trademark; diatomaceous earth, granular type M, 4.5 g/25 mL). The solvent was then evaporated under reduced pressure. The residue was purified by silica gel column chromatography (chloroform/methanol=98/2) to give compound 31 (28.8 mg, yield 47%).
¹H NMR (300 MHz, CDCl₃, δ): 7.96 (dd, J=8.1, 1.5 Hz, 2H), 7.90 (d, J=7.3 Hz, 1H), 7.53-7.40 (m, 3H), 7.35 (d, J=1.5 Hz, 1H), 6.84 (dd, J=7.3, 2.2 Hz, 1H), 4.68 (s, 2H), 3.34-3.24 (m, 1H), 3.08 (sep, J=7.0 Hz, 1H), 1.93-1.84 (m, 2H), 1.77-1.68 (m, 2H), 1.57-1.49 (m, 1H), 1.33 (d, J=7.0 Hz, 6H), 1.31-1.18 (m, 5H); ESIMS m/z: [M+H]⁺ 428.

Example 32

3-Cyclohexyloxymethyl-2-isopropyl-N-phenylimidazo[1,2-a]pyridine-7-sulfoneamide (Compound 32)

Step 1
7-Bromo-3-cyclohexyloxymethyl-2-isopropylimidazo[1,2-a]pyridine (50.0 mg, 0.142 mmol) obtained in step 3 of Example 28 was dissolved in DMA (1.0 mL), and the solution was stirred at 160° C. for 30 minutes after adding sodium thiomethoxide (80.0 mg, 1.14 mmol). After adding water to the reaction mixture, the reaction mixture was extracted with ethyl acetate. The organic layer was washed with saturated brine, and dried over anhydrous sodium sulfate. The solvent was then evaporated under reduced pressure. The residue was purified by silica gel chromatography (chloroform/methanol=95/5) to give 3-cyclohexyloxymethyl-2-isopropylimidazo[1,2-a]pyridine-7-thiol (35.3 mg, yield 82%).
¹H NMR (270 MHz, CDCl₃, δ): 7.73 (br s, 1H), 7.48 (br s, 1H), 7.08 (br s, 1H), 4.72 (s, 2H), 3.91 (s, 1H), 3.36-3.26 (m, 1H), 3.10 (sep, J=6.9 Hz, 1H), 1.94-1.82 (m, 2H), 1.78-1.67 (m, 2H), 1.57-1.51 (m, 1H), 1.37 (d, J=6.9 Hz, 6H), 1.33-1.18 (m, 5H); ESIMS m/z: [M+H]⁺ 305.
Step 2
3-Cyclohexyloxymethyl-2-isopropylimidazo[1,2-a]pyridine-7-thiol (210 mg, 0.691 mmol) obtained in step 1 was dissolved in 1,2-dichloroethane (2.0 mL). Under ice-cooled condition, triethylamine (0.140 mL, 1.00 mmol) and dimethylcarbamoyl chloride (0.0770 mL, 0.834 mmol) were added, and the mixture was stirred at room temperature for 30 minutes. After adding a saturated sodium hydrogen carbonate aqueous solution to the reaction mixture, the reaction mixture was filtered through a Presep (registered trademark; diatomaceous earth, granular type M, 4.5 g/25 mL). The solvent was then evaporated under reduced pressure. The residue was purified by silica gel column chromatography (hexane/ethyl acetate=70/30) to give S-3-(cyclohexyloxymethyl)-2-isopropylimidazo[1,2-a]pyridin-7-yl dimethylthiocarbamate (121 mg, yield 47%).
¹H NMR (270 MHz, CDCl₃, δ): 8.13 (dd, J=7.1, 0.8 Hz, 1H), 7.72 (dd, J=1.7, 0.8 Hz, 1H), 6.89 (dd, J=7.1, 1.7 Hz, 1H), 4.81 (s, 2H), 3.34-2.94 (m, 8H), 1.94-1.85 (m, 2H), 1.78-1.68 (m, 2H), 1.59-1.45 (m, 1H), 1.36 (d, J=6.9 Hz, 6H), 1.34-1.09 (m, 5H); ESIMS m/z: [M+H]⁺ 376.
Step 3
N-Chlorosuccinimide (50.0 mg, 0.373 mmol) was added to a mixed solvent of acetonitrile (0.50 mL), water (0.10 mL), and concentrated hydrochloric acid (0.0160 mL), and the mixture was stirred at room temperature for 5 minutes. Under ice-cooled condition, an acetonitrile solution (0.5 mL) of S-3-(cyclohexyloxymethyl)-2-isopropylimidazo[1,2-a]pyridin-7-yl dimethylthiocarbamate (35.3 mg, 0.0940 mmol) obtained in step 2 was gently added, and the mixture was stirred at room temperature for 30 minutes. The mixture was further stirred at 50° C. for 1 hour after adding aniline (90 mL, 0.987 mmol). Then, a saturated sodium hydrogen carbonate aqueous solution was added to the reaction mixture, the reaction mixture was filtered through a Presep (registered trademark; diatomaceous earth, granular type M, 4.5 g/25 mL). The solvent was then evaporated under reduced pressure. The residue was purified by silica gel column chromatography (chloroform/methanol=95/5) to give compound 32 (3.00 mg, yield 7%).

$^1$H NMR (270 MHz, CDCl$_3$, δ): 8.17 (dd, J=7.3, 0.7 Hz, 1H), 8.10 (dd, J=2.0, 0.7 Hz, 1H), 7.30-7.21 (m, 4H), 7.16-7.03 (m, 3H), 4.81 (s, 2H), 3.36-3.24 (m, 1H), 3.18 (sep, J=6.9 Hz, 1H), 1.95-1.69 (m, 4H), 1.36 (d, J=6.9 Hz, 6H), 1.18-1.35 (m, 6H); ESIMS m/z: [M+H]$^+$ 428.

Example 33

2-(3-Cyclohexyloxymethyl-2-isopropylimidazo[1,2-a]pyridin-7-yl)-1H-benzimidazole (Compound 33)

Compound 23 (40.0 mg, 0.0985 mmol) was dissolved in acetic acid (1.0 mL), and the solution was stirred for 30 minutes under heat and reflux. After adding a saturated sodium hydrogen carbonate aqueous solution to the reaction mixture, the reaction mixture was filtered through a Presep (registered trademark; diatomaceous earth, granular type M, 4.5 g/25 mL). The solvent was then evaporated under reduced pressure. The residue was purified by silica gel column chromatography (chloroform/methanol=95/5) to give compound 33 (21.8 mg, yield 57%).

$^1$H NMR (270 MHz, DMSO-d$^6$, δ): 8.39 (dd, J=7.3, 1.0 Hz, 1H), 8.25 (dd, J=1.7, 1.0 Hz, 1H), 7.71 (dd, J=7.3, 1.7 Hz, 1H), 7.66-7.57 (m, 2H), 7.27-7.19 (m, 2H), 4.86 (s, 2H), 3.45-3.14 (m, 2H), 1.91-1.80 (m, 2H), 1.72-1.60 (m, 2H), 1.53-1.41 (m, 1H), 1.31 (d, J=6.6 Hz, 6H), 1.31-1.12 (m, 5H); ESIMS m/z: [M+H]$^+$ 389.

Example 34

2-tert-Butyl-3-(4,4-difluorocyclohexylmethyl)-N-(pyridin-4-yl)imidazo[1,2-a]pyridine-7-carboxamide (Compound 34)

Step 1

60% sodium hydride (1.40 g, 35.0 mmol) was suspended in THF (50 mL), and Triethyl phosphonoacetate (7.00 mL, 35.3 mmol) was dropped under ice-cooled condition to the mixture. After the dropping, the mixture was stirred at room temperature for 10 minutes, and a mixture of 4,4-difluorocyclohexanecarbaldehyde (3.50 g, 23.6 mmol) and THF (10 mL) was dropped under ice-cooled condition in a manner that keeps the internal temperature at or below 10° C. After the dropping, the mixture was stirred at room temperature for 1 hour. Then, a saturated ammonium chloride aqueous solution was added to the reaction mixture, and the reaction mixture was extracted with ethyl acetate. The organic layer was washed with saturated brine, and dried over magnesium sulfate. The solvent was then evaporated under reduced pressure. The residue was purified by silica gel column chromatography (hexane/ethyl acetate=90/10) to give ethyl(E)-3-(4,4-difluorocyclohexyl)acrylate (4.78 g, yield 93%).

$^1$H NMR (270 MHz, CDCl$_3$, δ): 6.90 (dd, J=15.9, 6.9 Hz, 1H), 5.83 (dd, J=15.9, 1.5 Hz, 1H), 4.20 (q, J=7.2 Hz, 2H), 2.36-1.43 (m, 9H), 1.29 (t, J=7.1 Hz, 3H).

Step 2

Ethyl(E)-3-(4,4-difluorocyclohexyl)acrylate (520 mg, 2.39 mmol) obtained in step 1 was dissolved in ethanol (8.0 mL), and 10% palladium/carbon (containing water) (200 mg) was added. After displacing inside of the reaction vessel with hydrogen gas, the reaction mixture was stirred overnight at room temperature. The reaction mixture was filtered through Celite (registered trademark), and the solvent was evaporated under reduced pressure to give ethyl 3-(4,4-difluorocyclohexyl)propionate (522 mg, yield 99%).

$^1$H NMR (270 MHz, CDCl$_3$, δ): 4.13 (q, J=7.1 Hz, 2H), 2.32 (t, J=7.7 Hz, 2H), 2.15-1.99 (m, 2H), 2.14-2.00 (m, 2H), 1.83-1.17 (m, 7H), 1.26 (t, J=7.1 Hz, 3H).

Step 3

3-(4,4-Difluorocyclohexyl)propionic acid (3.84 g, quantitative) was obtained in the same manner as in step 1 of Example 2, using ethyl 3-(4,4-difluorocyclohexyl)propionate obtained in step 2.

$^1$H NMR (270 MHz, CDCl$_3$, δ): 2.39 (t, J=7.7 Hz, 2H), 2.18-2.01 (m, 2H), 1.85-1.21 (m, 9H).

Step 4

3-(4,4-Difluorocyclohexyl)propionic acid (330 mg, 1.72 mmol) obtained in step 3 was dissolved in thionyl chloride (3.0 mL), and the solution was stirred for 4 hours under heat and reflux. The solvent was then evaporated under reduced pressure. The residue was dissolved in THF (3.3 mL) under ice-cooled condition, and the mixture was stirred at room temperature for 30 minutes after adding copper chloride(I) (8.5 mg, 0.086 mmol) and tert-butyl magnesium chloride (2 mol/L-THF solution) (1.03 mL, 2.06 mmol). Under ice-cooled condition, a saturated ammonium chloride aqueous solution was added, and the reaction mixture was extracted with ethyl acetate. The organic layer was washed with saturated brine, and dried over anhydrous magnesium sulfate. The solvent was then evaporated under reduced pressure. The residue was dissolved in ethanol (4.0 mL), and the solution was stirred for 2 hours under heat and reflux after adding tetra-n-butylammonium tribromide (910 mg, 1.89 mmol). Under ice-cooled condition, a saturated sodium hydrogen carbonate aqueous solution was added, and the reaction mixture was extracted with ethyl acetate. The organic layer was washed with saturated brine, and dried over anhydrous magnesium sulfate. The solvent was then evaporated under reduced pressure. The residue was purified by silica gel column chromatography (hexane/ethyl acetate=97/3→90/10) to give 2-bromo-1-(4,4-difluorocyclohexyl)-4,4-dimethylpentan-3-one (433 mg, yield 81%).

$^1$H NMR (270 MHz, CDCl$_3$, δ): 4.71-4.68 (m, 1H), 2.15-1.16 (m, 11H), 1.23 (d, J=5.6 Hz, 9H).

Step 5

2-tert-Butyl-3-(4,4-difluorocyclohexylmethyl)imidazo[1,2-a]pyridine-7-carbonitrile (70.0 mg, yield 34%) was obtained in the same manner as in step 2 of Example 1, using 2-bromo-1-(4,4-difluorocyclohexyl)-4,4-dimethylpentan-3-one obtained in step 4, and 2-aminopyridine-4-carbonitrile.

$^1$H NMR (270 MHz, CDCl$_3$, δ): 7.95 (dd, J=1.8, 0.8 Hz, 1H), 7.93 (dd, J=7.1, 0.8 Hz, 1H), 6.92 (dd, J=7.1, 1.8 Hz, 1H), 3.02 (d, J=7.3 Hz, 2H), 2.18-2.04 (m, 2H), 1.87-1.46 (m, 7H), 1.48 (s, 9H); ESIMS m/z: [M+H]$^+$ 332.

Step 6

2-tert-Butyl-3-(4,4-difluorocyclohexylmethyl)imidazo[1,2-a]pyridine-7-carboxylic acid (40.0 mg, yield 54%) was obtained in the same manner as in step 2 of Example 7, using 2-tert-butyl-3-(4,4-difluorocyclohexylmethyl)imidazo[1,2-a]pyridine-7-carbonitrile obtained in step 5.

$^1$H NMR (300 MHz, CDCl$_3$, δ): 8.61 (s, 1H), 8.28 (d, J=7.0 Hz, 1H), 7.75 (d, J=7.0 Hz, 1H), 4.25 (br s, 1H), 3.12 (d, J=7.3 Hz, 2H), 2.16-2.01 (m, 2H), 1.94-1.40 (m, 7H), 1.58 (s, 9H); ESIMS m/z: [M+H]$^+$ 351.

Step 7

Compound 34 (31.0 mg, yield 75%) was obtained in the same manner as in step 4 of Example 21, using 2-tert-butyl- 3-(4,4-difluorocyclohexylmethyl)imidazo[1,2-a]pyridine-7-carboxylic acid obtained in step 6, and 4-aminopyridine.

$^1$H NMR (270 MHz, CDCl$_3$, δ): 8.58 (dd, J=4.8, 1.5 Hz, 2H), 8.04 (dd, J=2.0, 1.0 Hz, 1H), 7.98 (dd, J=7.3, 1.0 Hz, 1H), 7.93 (s, 1H), 7.58 (dd, J=4.8, 1.5 Hz, 2H), 7.36 (dd, J=7.3, 2.0 Hz, 1H), 3.05 (d, J=7.3 Hz, 2H), 2.19-2.04 (m, 2H), 1.83-1.38 (m, 7H), 1.49 (s, 9H); ESIMS m/z: [M+H]$^+$ 427.

Example 35

3-Cyclohexylmethyl-N-(pyridin-4-yl)-2-trifluoromethylimidazo[1,2-a]pyridine-7-carboxamide (Compound 35)

Step 1

3-Cyclohexylmethyl-2-trifluoromethylimidazo[1,2-a]pyridine-7-carbonitrile (157 mg, yield 54%) was obtained in the same manner as in step 2 of Example 1, using 3-bromo-4-cyclohexyl-1,1,1-trifluorobutan-2-one obtained according to the method described in J. Fluor. Chem., Vol. 39, p. 271 (1988), and 2-aminopyridine-4-carbonitrile.

$^1$H NMR (270 MHz, CDCl$_3$, δ): 8.09-8.05 (m, 2H), 7.06 (dd, J=7.3, 1.3 Hz, 1H), 2.96 (d, J=6.9 Hz, 2H), 1.78-1.59 (m, 6H), 1.01-1.29 (m, 5H); ESIMS m/z: [M+H]$^+$ 308.

Step 2

3-Cyclohexylmethyl-2-trifluoromethylimidazo[1,2-a]pyridine-7-carboxylic acid (157 mg, yield 95%) was obtained in the same manner as in step 2 of Example 7, using 3-cyclohexylmethyl-2-trifluoromethylimidazo[1,2-a]pyridine-7-carbonitrile obtained in step 1.

$^1$H NMR (270 MHz, CDCl$_3$, δ): 8.47 (s, 1H), 8.03 (d, J=7.9 Hz, 1H), 7.53 (d, J=7.9 Hz, 1H), 2.96 (d, J=6.9 Hz, 2H), 1.75-1.60 (m, 6H), 1.23-1.10 (m, 5H); ESIMS m/z: [M+H]$^+$ 327.

Step 3

Compound 35 (38.0 mg, yield 51%) was obtained in the same manner as in step 4 of Example 21, using 3-cyclohexylmethyl-2-trifluoromethylimidazo[1,2-a]pyridine-7-carboxylic acid obtained in step 2, and 4 aminopyridine.

$^1$H NMR (270 MHz, CDCl$_3$, δ): 8.59 (dd, J=4.8, 1.5 Hz, 2H), 8.19 (s, 1H), 8.11-8.07 (m, 2H), 7.61 (dd, J=4.8, 1.5 Hz, 2H), 7.47 (dd, J=6.9, 2.0 Hz, 1H), 2.97 (d, J=6.9 Hz, 2H), 1.78-1.65 (m, 6H), 1.24-1.06 (m, 5H); ESIMS m/z: [M+H]$^+$ 403.

Example 36

3-(4,4-Difluorocyclohexylmethyl)-N-(pyridin-4-yl)-2-trifluoromethylimidazo[1,2-a]pyridine-7-carboxamide (Compound 36)

Step 1

3-(4,4-Difluorocyclohexyl)propionic acid (500 mg, 2.60 mmol) obtained in step 3 of Example 34 was dissolved in dichloromethane (5.0 mL), and the solution was stirred at room temperature for 30 minutes after adding oxalyl chloride (0.430 mL, 5.12 mmol) and DMF (0.010 mL). The solvent was then evaporated under reduced pressure. The residue was dissolved in dichloromethane (10 mL), and the mixture was cooled to −10° C., and stirred at room temperature for 2 hours after adding anhydrous trifluoroacetic acid (2.20 mL, 15.8 mmol) and pyridine (1.70 mL, 21.3 mmol). Upon being cooled to −10° C., the mixture was extracted with dichloromethane after gently adding water in a manner that keeps the internal temperature at or below 0° C. The organic layer was washed with 3 mol/L hydrochloric acid and a saturated sodium hydrogen carbonate aqueous solution, and then with saturated brine, and dried over anhydrous sodium sulfate. The solvent was then evaporated under reduced pressure. The residue was purified by silica gel chromatography (hexane/ethyl acetate=70/30) to give 4-(4,4-difluorocyclohexyl)-1,1,1-trifluorobutan-2-one (204 mg, yield 35%).

$^1$H NMR (300 MHz, CDCl$_3$, δ): 2.75 (t, J=7.3 Hz, 2H), 2.16-2.02 (m, 2H), 1.84-1.60 (m, 6H), 1.43-1.22 (m, 3H).

Step 2

4-(4,4-Difluorocyclohexyl)-1,1,1-trifluorobutan-2-one (100 mg, 0.410 mmol) obtained in step 1 was dissolved in DMF (1.0 mL). Under ice-cooled condition, triethylamine (0.110 mL, 0.788 mmol) and chlorotrimethylsilane (0.0570 mL, 0.450 mmol) were added, and the mixture was stirred at 0° C. for 30 minutes. The reaction mixture was extracted with hexane after adding saturated sodium hydrogen carbonate. The organic layer was washed with saturated brine, and dried over anhydrous magnesium sulfate. The solvent was then evaporated under reduced pressure. The residue was dissolved in dichloromethane (1.0 mL). Under ice-cooled condition, bromine (73.0 mg, 0.456 mmol) was added, and the mixture was stirred at room temperature for 30 minutes. The reaction mixture was filtered through a Presep (registered trademark; diatomaceous earth, granular type M, 4.5 g/25 mL) after adding a saturated sodium hydrogen carbonate aqueous solution and sodium thiosulfate aqueous solution. The solvent was then evaporated under reduced pressure. The residue was purified by silica gel column chromatography (hexane/ethyl acetate=80/20) to give 3-bromo-4-(4,4-difluorocyclohexyl)-1,1,1-trifluorobutan-2-one (73.8 mg, yield 56%).

$^1$H NMR (270 MHz, CDCl$_3$, δ): 4.67 (dd, J=8.6, 6.6 Hz, 1H), 2.17-1.23 (m, 11H).

Step 3

3-(4,4-Difluorocyclohexylmethyl)-2-trifluoromethylimidazo[1,2-a]pyridine-7-carbonitrile (66.6 mg, yield 42%) was obtained in the same manner as in step 2 of Example 1, using 3-bromo-4-(4,4-difluorocyclohexyl)-1,1,1-trifluorobutan-2-one obtained in step 2, and 2-aminopyridine-4-carbonitrile.

$^1$H NMR (270 MHz, CDCl$_3$, δ): 8.11-8.05 (m, 2H), 7.12-7.07 (m, 1H), 3.05 (d, J=6.9 Hz, 2H), 2.17-2.04 (m, 2H), 1.84-1.39 (m, 7H).

Step 4

3-(4,4-Difluorocyclohexylmethyl)-2-trifluoromethylimidazo[1,2-a]pyridine-7-carboxylic acid (63.0 mg, yield 90%) was obtained in the same manner as in step 2 of Example 7, using 3-(4,4-difluorocyclohexylmethyl)-2-trifluoromethylimidazo[1,2-a]pyridine-7-carbonitrile obtained in step 3.

$^1$H NMR (270 MHz, CDCl$_3$, δ): 8.49 (dd, J=2.0, 1.2 Hz, 1H), 8.03 (dd, J=7.4, 1.2 Hz, 1H), 7.56 (dd, J=7.1, 2.0 Hz, 1H), 3.06 (d, J=7.6 Hz, 2H), 1.90-1.27 (m, 9H); ESIMS m/z: [M+H]$^+$ 363.

Step 5

Compound 36 (32.1 mg, yield 66%) was obtained in the same manner as in step 4 of Example 21, using 3-(4,4-difluorocyclohexylmethyl)-2-trifluoromethylimidazo[1,2-a]pyridine-7-carboxylic acid obtained in step 4, and 4-aminopyridine.

$^1$H NMR (300 MHz, CDCl$_3$, δ): 8.60 (dd, J=4.8, 1.5 Hz, 2H), 8.24 (s, 1H), 8.12 (dd, J=1.6, 1.1 Hz, 1H), 8.08 (dd, J=7.3, 1.1 Hz, 1H), 7.62 (dd, J=4.8, 1.5 Hz, 2H), 7.51 (dd, J=7.1, 1.6 Hz, 1H), 3.06 (d, J=7.0 Hz, 2H), 2.19-2.05 (m, 2H), 1.86-1.22 (m, 7H); ESIMS m/z: [M+H]$^+$ 439.

Example 37

3-Benzyl-2-isopropyl-N-(pyridin-4-yl)imidazo[1,2-a]pyridine-7-carboxamide (Compound 37)

Step 1

4-Methyl-1-phenylpentan-3-one (330 mg, 1.88 mmol) obtained according to the method described in Tetrahedron Lett., Vol. 23, p. 5059 (1982) was dissolved in methanol (6.0 mL). Under ice-cooled condition, bromine (330 mg, 2.06 mmol) was gently added to the solution, and the mixture was stirred at room temperature for 5 hours. The reaction mixture was extracted with ethyl acetate after adding a sodium hydrogen carbonate aqueous solution and a saturated sodium thiosulfate aqueous solution. The organic layer was washed with saturated brine, and dried over anhydrous magnesium sulfate. The solvent was then evaporated under reduced pressure. The residue was purified by silica gel column chromatography (hexane/ethyl acetate=90/10) to give 2-bromo-4-methyl-1-phenylpentan-3-one (401 mg, yield 84%).

$^1$H NMR (300 MHz, CDCl$_3$, δ): 7.34-7.15 (m, 5H), 4.58 (dd, J=8.4, 6.2 Hz, 1H), 3.49 (dd, J=13.9, 8.4 Hz, 1H), 3.15 (dd, J=13.9, 6.2 Hz, 1H), 2.82 (sep, J=7.0 Hz, 1H), 1.12 (d, J=7.0 Hz, 3H), 0.88 (d, J=7.0 Hz, 3H).

Step 2

3-Benzyl-2-isopropylimidazo[1,2-a]pyridine-7-carbonitrile (64.0 mg, yield 15%) was obtained in the same manner as in step 2 of Example 1, using 2-bromo-4-methyl-1-phenylpentan-3-one obtained in step 1, and 2-aminopyridine-4-carbonitrile.

$^1$H NMR (270 MHz, CDCl$_3$, δ): 7.98 (dd, J=1.7, 0.8 Hz, 1H), 7.70 (dd, J=7.3, 0.8 Hz, 1H), 7.33-7.21 (m, 3H), 7.08-7.03 (m, 2H), 6.79 (dd, J=7.3, 1.7 Hz, 1H), 4.32 (s, 2H), 3.27 (sep, J=6.9 Hz, 1H), 1.41 (d, J=6.9 Hz, 6H); ESIMS m/z: [M+H]$^+$ 276.

Step 3

3-Benzyl-2-isopropylimidazo[1,2-a]pyridine-7-carboxylic acid (61.5 mg, yield 90%) was obtained in the same manner as in step 2 of Example 7, using 3-benzyl-2-isopropylimidazo[1,2-a]pyridine-7-carbonitrile obtained in step 2.

$^1$H NMR (270 MHz, CDCl$_3$, δ): 8.77 (s, 1H), 7.85 (d, J=6.6 Hz, 1H), 7.65-7.60 (m, 1H), 7.35-7.21 (m, 3H), 7.11-7.06 (m, 2H), 4.37 (s, 2H), 3.44-3.10 (m, 2H), 1.55 (d, J=6.9 Hz, 6H); ESIMS m/z: [M+H]$^+$ 295.

Step 4

Compound 37 (23.1 mg, yield 53%) was obtained in the same manner as in step 4 of Example 21, using 3-benzyl-2-isopropylimidazo[1,2-a]pyridine-7-carboxylic acid obtained in step 3, and 4-aminopyridine.

$^1$H NMR (270 MHz, CDCl$_3$, δ): 8.56 (dd, J=4.8, 1.5 Hz, 2H), 8.08 (dd, J=1.8, 0.8 Hz, 1H), 8.00 (s, 1H), 7.74 (dd, J=7.1, 0.8 Hz, 1H), 7.56 (dd, J=4.8, 1.5 Hz, 2H), 7.33-7.18 (m, 4H), 7.10-7.05 (m, 2H), 4.34 (s, 2H), 3.28 (sep, J=6.9 Hz, 1H), 1.42 (d, J=6.9 Hz, 6H); ESIMS m/z: [M+H]$^+$ 371.

Example 38

3-Cyclohexylsulfonyl-2-isopropyl-N-(pyridin-4-yl)imidazo[1,2-a]pyridine-7-carboxamide (Compound 38)

Step 1

Compound 13 (237 mg, 0.584 mmol) was dissolved in isobutyl alcohol (1.2 mL), and the solution was stirred overnight under heat and reflux after adding a 5 mol/L sodium hydroxide aqueous solution (1.2 mL). The reaction mixture was stirred after adding diethyl ether, and the aqueous layer was removed. Then, 3 mol/L hydrochloric acid (2.0 mL) was added to the aqueous layer, and the mixture was stirred. The precipitated crystals were collected by filteration to give 3-cyclohexylsulfonyl-2-isopropylimidazo[1,2-a]pyridine-7-carboxylic acid (86.2 mg, yield 42%).

$^1$H NMR (270 MHz, DMSO-d$^6$, δ): 8.89 (d, J=6.9 Hz, 1H), 8.20 (s, 1H), 7.56 (d, J=6.9 Hz, 1H), 3.64-3.61 (m, 1H), 3.37-3.30 (m, 1H), 1.98-1.96 (m, 2H), 1.78-1.76 (m, 2H), 1.62-1.57 (m, 1H), 1.46-1.07 (m, 11H); ESIMS m/z: [M+H]$^+$ 351.

Step 2

Compound 38 (57.0 mg, yield 63%) was obtained in the same manner as in step 4 of Example 21, using 3-cyclohexylsulfonyl-2-isopropylimidazo[1,2-a]pyridine-7-carboxylic acid obtained in step 1, and 4-aminopyridine.

$^1$H NMR (270 MHz, CDCl$_3$, δ): 9.00 (dd, J=7.3, 1.2 Hz, 1H), 8.60 (dd, J=4.8, 1.6 Hz, 2H), 8.15 (s, 1H), 8.12 (s, 1H), 7.61 (dd, J=4.8, 1.6 Hz, 2H), 7.46 (dd, J=7.3, 1.2 Hz, 1H), 3.77-3.68 (m, 1H), 3.02-2.96 (m, 1H), 2.09-2.05 (m, 2H), 1.91-1.89 (m, 2H), 1.57-1.44 (m, 2H), 1.40 (d, J=6.0 Hz, 6H), 1.32-1.14 (m, 4H); ESIMS m/z: [M+H]$^+$ 427.

Example 39

3-Cyclohexylsulfonyl-2-isopropyl-6-methyl-N-(pyridin-4-yl)imidazo[1,2-a]pyridine-7-carboxamide (Compound 39)

Step 1

6-Bromo-2-isopropylimidazo[1,2-a]pyridine-7-carbonitrile (294 mg, yield 22%) was obtained in the same manner as in step 2 of Example 1, using 1-bromo-3-methylbutan-2-one obtained according to the method described in Org. Synth., Vol. 55, p. 24, and 2-amino-5-bromopyridine-4-carbonitrile obtained according to the method described in WO2007/113226.

$^1$H NMR (300 MHz, CDCl$_3$, δ): 8.34 (s, 1H), 7.96 (s, 1H), 7.47 (s, 1H), 3.15 (sep, J=6.9 Hz, 1H), 1.37 (d, J=6.9 Hz, 6H); ESIMS m/z: [M+H]$^+$ 264, 266.

Step 2

6-Bromo-2-isopropylimidazo[1,2-a]pyridine-7-carbonitrile (200 mg, 0.757 mmol) obtained in step 1 was dissolved in 1,4-dioxane-water (2/1) (1.5 mL), and the solution was stirred under heat and reflux for 3 hours after adding methylboronic acid (140 mg, 2.33 mmol), sodium carbonate (240 mg, 2.26 mmol), and [1,1'-bis(diphenylphosphino)-ferrocene]dichloropalladium(II) (62.0 mg, 0.0759 mmol). The reaction mixture was allowed to cool to room temperature, and, after adding water, the mixture was filtered through a Presep (registered trademark; diatomaceous earth, granular type M, 4.5 g/25 mL). The solvent was then evaporated under reduced pressure. The residue was purified by silica gel column chromatography (chloroform/methanol=98/2) to give 2-isopropyl-6-methyl-imidazo[1,2-a]pyridine-7-carbonitrile (58.0 mg, yield 38%).

$^1$H NMR (270 MHz, CDCl$_3$, δ): 7.96 (s, 1H), 7.91 (s, 1H), 7.40 (s, 1H), 3.13 (sep, J=6.9 Hz, 1H), 2.46 (s, 3H), 1.37 (d, J=6.9 Hz, 6H); ESIMS m/z: [M+H]$^+$ 200.

Step 3

2-Isopropyl-6-methylimidazo[1,2-a]pyridine-7-carbonitrile (500 mg, 2.51 mmol) obtained in step 2 was dissolved in DMF (3.0 mL), and the solution was stirred at room temperature for 6 hours under light shielding after adding N-iodosuccinimide (621 mg, 2.76 mmol). A sodium carbonate aqueous solution was added to the reaction mixture. The precipitated crystals were collected by filtration, and dried under reduced pressure to give 3-iodo-2-isopropyl-6-methylimidazo[1,2-a]pyridine-7-carbonitrile (752 mg, yield 92%).

$^1$H NMR (270 MHz, CDCl$_3$, δ): 7.99 (br s, 1H), 7.89 (br s, 1H), 3.21-3.18 (m, 1H), 2.54 (s, 3H), 1.37 (d, J=6.9 Hz, 6H).

Step 4

3-Cyclohexylthio-2-isopropyl-6-methylimidazo[1,2-a]pyridine-7-carbonitrile (241 mg, yield 50%) was obtained in the same manner as in Example 12, using 3-iodo-2-isopropyl-6-methylimidazo[1,2-a]pyridine-7-carbonitrile obtained in step 3.

$^1$H NMR (300 MHz, CDCl$_3$, δ): 8.31 (s, 1H), 7.92 (s, 1H), 3.51-3.42 (m, 1H), 2.88-2.83 (m, 1H), 2.53 (s, 3H), 1.85-1.77 (m, 4H), 1.60-1.58 (m, 1H), 1.37-1.34 (m, 5H), 1.36 (d, J=7.0 Hz, 6H).

Step 5

3-Cyclohexylsulfonyl-2-isopropyl-6-methylimidazo[1,2-a]pyridine-7-carbonitrile (237 mg, yield 90%) was obtained in the same manner as in Example 13, using 3-cyclohexylthio-2-isopropyl-6-methylimidazo[1,2-a]pyridine-7-carbonitrile obtained in step 4.

$^1$H NMR (300 MHz, CDCl$_3$, δ): 8.80 (s, 1H), 7.99 (s, 1H), 3.70-3.61 (m, 1H), 2.95-2.90 (m, 1H), 2.51 (s, 3H), 2.03-2.00 (m, 2H), 1.88-1.86 (m, 2H), 1.70-1.67 (m, 1H), 1.53-1.11 (m, 5H), 1.34 (d, J=6.6 Hz, 6H).

Step 6

3-Cyclohexylsulfonyl-2-isopropyl-6-methylimidazo[1,2-a]pyridine-7-carboxylic acid (179 mg, yield 72%) was obtained in the same manner as in step 2 of Example 7, using 3-cyclohexylsulfonyl-2-isopropyl-6-methylimidazo[1,2-a]pyridine-7-carbonitrile obtained in step 5.

$^1$H NMR (270 MHz, DMSO-d$^6$, δ): 8.63 (s, 1H), 8.11 (s, 1H), 3.65-3.55 (m, 1H), 3.47-3.43 (m, 1H), 2.50 (s, 3H), 1.97-1.93 (m, 2H), 1.78-1.76 (m, 2H), 1.61-1.58 (m, 1H), 1.46-1.06 (m, 5H), 1.28 (d, J=7.3 Hz, 6H); ESIMS m/z: [M+H]$^+$ 365.

Step 7

Compound 39 (93.0 mg, yield 96%) was obtained in the same manner as in step 4 of Example 21, using 3-cyclohexylsulfonyl-2-isopropyl-6-methylimidazo[1,2-a]pyridine-7-carboxylic acid obtained in step 6, and 4-aminopyridine.

$^1$H NMR (270 MHz, CDCl$_3$, δ): 8.76 (s, 1H), 8.59 (d, J=6.6 Hz, 2H), 7.86-7.82 (br m, 2H), 7.56 (d, J=6.6 Hz, 2H), 3.74-3.64 (m, 1H), 3.00-2.90 (m, 1H), 2.51 (s, 3H), 2.09-2.01 (m, 2H), 1.93-1.88 (m, 2H), 1.73-1.68 (m, 1H), 1.50-1.42 (m, 1H), 1.37 (d, J=7.6 Hz, 6H), 1.30-1.12 (m, 4H); ESIMS m/z: [M+H]$^+$ 441.

Example 40

3-Cyclohexylthio-2-isopropyl-N-phenylimidazo[1,2-a]pyridine-7-carboxamide (Compound 40)

Step 1

3-Iodo-2-isopropyl-N-phenylimidazo[1,2-a]pyridine-7-carboxamide (2.91 g, quantitative) was obtained in the same manner as in step 3 of Example 7, using 2-isopropylimidazo[1,2-a]pyridine-7-carboxylic acid obtained in step 2 of Example 7, and aniline.

$^1$H NMR (300 MHz, CDCl$_3$, δ): 8.17 (d, J=7.0 Hz, 1H), 8.02 (s, 1H), 7.99-7.88 (m, 1H), 7.64 (d, J=7.0 Hz, 2H), 7.43-7.38 (m, 3H), 7.18 (t, J=7.3 Hz, 1H), 3.26-3.17 (m, 1H), 1.39 (d, J=6.6 Hz, 6H).

Step 2

Compound 40 (98.0 mg, yield 20%) was obtained in the same manner as in Example 12, using 3-iodo-2-isopropyl-N-phenylimidazo[1,2-a]pyridine-7-carboxamide obtained in step 1.

$^1$H NMR (270 MHz, CDCl$_3$, δ): 8.48 (d, J=7.2 Hz, 1H), 8.11-7.94 (m, 2H), 7.63 (d, J=8.2 Hz, 2H), 7.39-7.37 (m, 3H), 7.19-7.15 (m, 1H), 3.54-3.44 (m, 1H), 2.88-2.84 (m, 1H), 1.93-1.75 (m, 4H), 1.37 (d, J=6.9 Hz, 6H), 1.26-1.16 (m, 6H); ESIMS m/z: [M+H]$^+$ 394.

Example 41

3-Cyclohexylsulfonyl-2-isopropyl-N-phenylimidazo[1,2-a]pyridine-7-carboxamide (Compound 41)

Compound 41 (60.0 mg, yield 92%) was obtained in the same manner as in Example 13, using compound 40.

$^1$H NMR (300 MHz, CDCl$_3$, δ): 8.97 (d, J=7.3 Hz, 1H), 8.20 (br s, 1H), 8.01-7.98 (m, 1H), 7.64 (d, J=7.9 Hz, 2H), 7.46-7.41 (m, 3H), 7.23-7.17 (m, 1H), 3.80-3.65 (m, 1H), 3.00-2.96 (m, 1H), 2.10-2.05 (m, 2H), 1.92-1.87 (m, 2H), 1.60-1.11 (m, 6H), 1.40 (d, J=6.9 Hz, 6H); ESIMS m/z: [M+H]$^+$ 426.

Example 42

2-tert-Butyl-3-cyclohexylmethyl-8-methyl-N-(pyridin-4-yl)imidazo[1,2-a]pyridine-7-carboxamide (Compound 42)

Step 1

Methyl 2-tert-butyl-3-cyclohexylmethyl-8-methylimidazo[1,2-a]pyridine-7-carboxylate (44.8 mg, yield 39%) was obtained in the same manner as in step 2 of Example 1, using 2-bromo-1-cyclohexyl-4,4-dimethylpentan-3-one, and methyl 2-amino-3-methylpyridine-4-carboxylate obtained according to the method described in European Patent 1790650.

$^1$H NMR (270 MHz, CDCl$_3$, δ): 7.71 (d, J=7.3 Hz, 1H), 7.25 (d, J=7.3 Hz, 1H), 3.91 (s, 3H), 2.96 (s, 3H), 2.89 (d, J=7.3 Hz, 2H), 1.77-1.57 (m, 6H), 1.48 (s, 9H), 1.25-1.00 (m, 5H); ESIMS m/z: [M+H]$^+$ 343.

Step 2

2-tert-Butyl-3-cyclohexylmethyl-8-methylimidazo[1,2-a]pyridine-7-carboxylic acid (38.5 mg, yield 90%) was obtained in the same manner as in step 1 of Example 2, using methyl 2-tert-butyl-3-cyclohexylmethyl-8-methylimidazo[1,2-a]pyridine-7-carboxylate obtained in step 1.

$^1$H NMR (270 MHz, CDCl$_3$, δ): 7.94 (d, J=6.9 Hz, 1H), 7.56 (d, J=6.9 Hz, 1H), 3.10 (s, 3H), 2.99 (d, J=7.6 Hz, 2H), 1.76-1.67 (m, 5H), 1.64 (s, 9H), 1.35-1.07 (m, 6H); ESIMS m/z: [M+H]$^+$ 329.

Step 3

Compound 42 (11.6 mg, yield 63%) was obtained in the same manner as in step 4 of Example 21, using 2-tert-butyl-3-cyclohexylmethyl-8-methylimidazo[1,2-a]pyridine-7-carboxylic acid obtained in step 2, and 4 aminopyridine.

$^1$H NMR (270 MHz, CDCl$_3$, δ): 8.55 (dd, J=5.0, 1.7 Hz, 2H), 8.03 (s, 1H), 7.71 (d, J=6.9 Hz, 1H), 7.61 (dd, J=5.0, 1.7 Hz, 2H), 6.77 (d, J=6.9 Hz, 1H), 2.91 (d, J=6.9 Hz, 2H), 2.79 (s, 3H), 1.76-1.58 (m, 6H), 1.49 (s, 9H), 1.21-1.05 (m, 5H); ESIMS m/z: [M+H]$^+$ 405.

Example 43

3-Cyclohexyloxymethyl-2-isopropyl-6-methyl-N-(pyridin-4-yl)imidazo[1,2-a]pyridine-7-carboxamide (Compound 43)

Step 1

6-Bromo-3-hydroxymethyl-2-isopropylimidazo[1,2-a]pyridine-7-carbonitrile (241 mg, yield 74%) was obtained in the same manner as in step 1 of Example 21, using 6-bromo-2-isopropylimidazo[1,2-a]pyridine-7-carbonitrile obtained in step 1 of Example 39.

$^1$H NMR (270 MHz, CDCl$_3$, δ): 8.52 (s, 1H), 7.98 (s, 1H), 5.02 (s, 2H), 3.20 (sep, J=6.9 Hz, 1H), 1.80 (s, 1H), 1.36 (d, J=6.9 Hz, 6H); ESIMS m/z: [M+H]$^+$ 294, 296.

Step 2

6-Bromo-3-cyclohexyloxymethyl-2-isopropylimidazo[1,2-a]pyridine-7-carbonitrile (1.42 g, yield 65%) was obtained in the same manner as in step 2 of Example 21, using 6-bromo-3-hydroxymethyl-2-isopropylimidazo[1,2-a]pyridine-7-carbonitrile obtained in step 1.

$^1$H NMR (270 MHz, CDCl$_3$, δ): 8.43 (s, 1H), 7.98 (s, 1H), 4.83 (s, 2H), 3.38-3.28 (m, 1H), 3.19 (sep, J=7.0 Hz, 1H), 1.96-1.86 (m, 2H), 1.80-1.71 (m, 2H), 1.62-1.51 (m, 1H), 1.36 (d, J=7.0 Hz, 6H), 1.34-1.18 (m, 5H); ESIMS m/z: [M+H]$^+$ 376, 378.

Step 3

6-Bromo-3-cyclohexyloxymethyl-2-isopropylimidazo[1,2-a]pyridine-7-carbonitrile (100 mg, 0.266 mmol) obtained in step 2 was dissolved in 1,4-dioxane-water (2/1) (1.5 mL), and the solution was stirred under heat and reflux for 3 hours after adding methylboronic acid (64.0 mg, 1.07 mmol), sodium carbonate (85.0 mg, 0.802 mmol), and [1,1'-bis(diphenylphosphino)-ferrocene]dichloropalladium(II) (44.0 mg, 0.0539 mmol). The reaction mixture was allowed to cool to room temperature, and, after adding water, the mixture was filtered through a Presep (registered trademark; diatomaceous earth, granular type M, 4.5 g/25 mL). The solvent was then evaporated under reduced pressure. The residue was purified by silica gel column chromatography (chloroform/methanol=98/2) to give 3-cyclohexyloxymethyl-2-isopropyl-6-methylimidazo[1,2-a]pyridine-7-carbonitrile (51.4 mg, yield 62%).

$^1$H NMR (270 MHz, CDCl$_3$, δ): 8.07-8.05 (m, 1H), 7.93 (s, 1H), 4.82 (s, 2H), 3.37-3.27 (m, 1H), 3.17 (sep, J=6.9 Hz, 1H), 2.50 (s, 3H), 1.97-1.87 (m, 2H), 1.83-1.70 (m, 2H), 1.60-1.50 (m, 1H), 1.37 (d, J=6.9 Hz, 6H), 1.36-1.18 (m, 5H); ESIMS m/z: [M+H]$^+$ 312.

Step 4

3-Cyclohexyloxymethyl-2-isopropyl-6-methylimidazo[1,2-a]pyridine-7-carboxylic acid (22.0 mg, yield 40%) was obtained in the same manner as in step 2 of Example 7, using 3-cyclohexyloxymethyl-2-isopropyl-6-methylimidazo[1,2-a]pyridine-7-carbonitrile obtained in step 3.

$^1$H NMR (270 MHz, CDCl$_3$, δ): 8.41 (br s, 1H), 7.87 (br s, 1H), 6.87 (br s, 1H), 4.75 (br s, 1H), 3.34-3.13 (m, 2H), 2.54 (s, 3H), 1.94-1.83 (m, 2H), 1.77-1.67 (m, 3H), 1.57-1.51 (m, 1H), 1.42 (d, J=6.6 Hz, 6H), 1.34-1.18 (m, 5H); ESIMS m/z: [M+H]$^+$ 331.

Step 5

Compound 43 (26.3 mg, yield 90%) was obtained in the same manner as in step 4 of Example 21, using 3-cyclohexyloxymethyl-2-isopropyl-6-methylimidazo[1,2-a]pyridine-7-carboxylic acid obtained in step 4, and 4-aminopyridine.

$^1$H NMR (270 MHz, CDCl$_3$, δ): 9.47 (s, 1H), 8.54 (dd, J=4.8, 1.5 Hz, 2H), 7.96 (s, 1H), 7.87 (s, 1H), 7.68 (dd, J=4.8, 1.5 Hz, 2H), 4.78 (s, 2H), 3.35-3.26 (m, 1H), 3.13 (sep, J=6.9 Hz, 1H), 2.47 (s, 3H), 1.96-1.86 (m, 2H), 1.80-1.71 (m, 2H), 1.60-1.51 (m, 1H), 1.35-1.21 (m, 11H); ESIMS m/z: [M+H]$^+$ 407.

Example 44

3-(4,4-Difluorocyclohexylmethyl)-5-methyl-N-(tetrahydro-2H-pyran-4-yl)-2-trifluoromethylimidazo[1,2-a]pyridine-7-carboxamide (Compound 44)

Step 1

Ethyl 3-(4,4-difluorocyclohexylmethyl)-5-methyl-2-trifluoromethylimidazo[1,2-a]pyridine-7-carboxylate (148 mg, yield 19%) was obtained in the same manner as in step 2 of Example 1, using 3-bromo-4-(4,4-difluorocyclohexyl)-1,1,1-trifluorobutan-2-one obtained in step 2 of Example 36, and ethyl 2-amino-6-methylpyridine-4-carboxylate obtained according to the method described in WO2008/009750.

$^1$H NMR (270 MHz, CDCl$_3$, δ): 8.26 (s, 1H), 7.22 (s, 1H), 4.41 (q, J=7.1 Hz, 2H), 3.23 (d, J=6.2 Hz, 2H), 2.89 (s, 3H), 2.15-2.03 (br m, 2H), 1.83-1.29 (m, 7H), 1.41 (t, J=7.1 Hz, 3H); ESIMS m/z: [M+H]$^+$ 405.

Step 2

3-(4,4-Difluorocyclohexylmethyl)-5-methyl-2-trifluoromethylimidazo[1,2-a]pyridine-7-carboxylic acid (114 mg, yield 84%) was obtained in the same manner as in step 2 of Example 7, using ethyl 3-(4,4-difluorocyclohexylmethyl)-5-methyl-2-trifluoromethylimidazo[1,2-a]pyridine-7-carboxylate obtained in step 1.

$^1$H NMR (300 MHz, DMSO-d$^6$, δ): 7.75 (s, 1H), 7.25 (s, 1H), 3.14 (d, J=7.0 Hz, 2H), 2.86 (s, 3H), 2.04-1.58 (m, 7H), 1.33-1.15 (m, 2H); ESIMS m/z: [M+H]$^+$ 376.

Step 3

Compound 44 (52.8 mg, yield 72%) was obtained in the same manner as in step 4 of Example 21, using 3-(4,4-difluorocyclohexylmethyl)-5-methyl-2-trifluoromethylimidazo[1,2-a]pyridine-7-carboxylic acid obtained in step 2, and 4-aminotetrahydropyran.

$^1$H NMR (300 MHz, CDCl$_3$, δ): 7.80 (d, J=1.5 Hz, 1H), 7.11 (d, J=1.5 Hz, 1H), 6.17 (d, J=7.7 Hz, 1H), 4.26-4.13 (m, 1H), 4.05-3.97 (m, 2H), 3.59-3.49 (m, 2H), 3.21 (d, J=5.5 Hz, 2H), 2.89 (s, 3H), 2.18-1.96 (m, 4H), 1.75-1.42 (m, 9H); ESIMS m/z: [M+H]$^+$ 460.

Example 45

2-tert-Butyl-3-cyclohexylmethyl-N,N-diethylimidazo[1,2-a]pyrimidine-7-carboxamide (Compound 45)

Step 1

2-Amino-N,N-diethylpyrimidine-4-carboxamide (701 mg, yield 63%) was obtained in the same manner as in step 2 of Example 2, using commercially available 2 aminopyrimidine-4-carboxylic acid, and diethylamine.

$^1$H NMR (270 MHz, CDCl$_3$, δ): 8.39 (d, J=5.1 Hz, 1H), 6.75 (d, J=5.1 Hz, 1H), 5.10 (s, 2H), 3.52 (q, J=7.1 Hz, 2H), 3.31 (q, J=7.1 Hz, 2H), 1.24 (t, J=7.1 Hz, 3H), 1.17 (t, J=7.1 Hz, 3H).

Step 2

Compound 45 (51.0 mg, yield 27%) was obtained in the same manner as in step 2 of Example 1, using 2-amino-N,N-diethylpyrimidine-4-carboxamide obtained in step 1, and 2-bromo-1-cyclohexyl-4,4-dimethylpentan-3-one obtained according to the method described in WO2008/032764.

$^1$H NMR (300 MHz, CDCl$_3$, δ): 8.24 (d, J=7.2 Hz, 1H), 7.20 (d, J=7.2 Hz, 1H), 3.74 (q, J=7.1 Hz, 2H), 3.58 (q, J=7.1

Hz, 2H), 2.91 (d, J=7.0 Hz, 2H), 1.69-1.65 (m, 5H), 1.50 (s, 9H), 1.28-1.07 (m, 12H); ESIMS m/z: [M+H]⁺ 371.

Example 46

2-tert-Butyl-3-cyclohexylmethyl-N-phenylimidazo [1,2-a]pyrimidine-7-carboxamide (Compound 46)

Step 1
2-tert-Butyl-3-cyclohexylmethylimidazo[1,2-a]pyrimidine-7-carboxylic acid (28.8 mg, yield 51%) was obtained in the same manner as in step 1 of Example 38, using compound 45.
¹H NMR (270 MHz, CDCl₃, δ): 8.41 (d, J=7.2 Hz, 1H), 7.72 (d, J=7.2 Hz, 1H), 2.98 (d, J=7.3 Hz, 2H), 1.71-1.64 (m, 5H), 1.53 (s, 9H), 1.23-1.15 (m, 6H); ESIMS m/z: [M+H]⁺ 316.

Step 2
Compound 46 (8.8 mg, yield 18%) was obtained in the same manner as in step 4 of Example 21, using 2-tert-butyl-3-cyclohexylmethylimidazo[1,2-a]pyrimidine-7-carboxylic acid obtained in step 1, and aniline.
¹H-NMR (300 MHz, CDCl₃, δ): 9.93 (s, 1H), 8.38 (d, J=7.0 Hz, 1H), 7.86-7.76 (m, 3H), 7.43-7.36 (m, 2H), 7.20-7.12 (m, 1H), 2.97 (d, J=7.3 Hz, 2H), 1.79-1.60 (m, 6H), 1.54 (s, 9H), 1.26-1.15 (m, 5H); ESIMS m/z: [M+H]⁺ 391.

Example 47

2-tert-Butyl-3-cyclohexylmethyl-N-phenylimidazo [1,2-c]pyrimidine-7-carboxamide (Compound 47)

Step 1
Propyl 6-aminopyrimidine-4-carboxylate (1.20 g, 6.62 mmol) obtained according to the method described in WO2008/032764, and 2-bromo-1-cyclohexyl-4,4-dimethylpentan-3-one (1.21 g, 4.42 mmol) obtained according to the method described in WO2008/032764 were stirred overnight at 130° C. Under ice-cooled condition, a saturated sodium hydrogen carbonate aqueous solution was added, and the reaction mixture was extracted with ethyl acetate. The organic layer was washed with saturated brine, and dried over anhydrous magnesium sulfate. The solvent was then evaporated under reduced pressure. The residue was purified by silica gel column chromatography (hexane/ethyl acetate=10/90→30/70) to give propyl 2-tert-butyl-3-cyclohexylmethylimidazo[1,2-c]pyrimidine-7-carboxylate (289 mg, yield 18%).
¹H NMR (270 MHz, CDCl₃, δ): 8.88 (d, J=1.3 Hz, 1H), 8.33 (d, J=1.3 Hz, 1H), 4.37 (t, J=6.6 Hz, 2H), 3.00 (d, J=7.0 Hz, 2H), 1.84-1.82 (m, 2H), 1.70-1.64 (m, 6H), 1.48 (s, 9H), 1.20-1.11 (m, 5H), 1.04 (t, J=7.3 Hz, 3H).

Step 2
Propyl 2-tert-butyl-3-cyclohexylmethylimidazo[1,2-c]pyrimidine-7-carboxylate (280 mg, 0.783 mmol) obtained in step 1 was dissolved in a 70% ethanol aqueous solution (3.0 mL), and the solution was stirred at room temperature for 1 hour after adding lithium hydroxide.1 hydrate (36.1 mg, 0.862 mmol). Under ice-cooled condition, 3 mol/L hydrochloric acid (0.287 mL) was added to the reaction mixture. The precipitated crystals were collected by filteration, and dried under reduced pressure to give 2-tert-butyl-3-cyclohexylmethylimidazo[1,2-c]pyrimidine-7-carboxylic acid (197 mg, yield 80%).
¹H NMR (270 MHz, DMSO-d⁶, δ): 9.12 (s, 1H), 7.79 (s, 1H), 3.03 (d, J=7.3 Hz, 2H), 1.60-1.53 (m, 6H), 1.40 (s, 9H), 1.20-1.10 (m, 5H).

Step 3
Compound 47 (55.7 mg, yield 90%) was obtained in the same manner as in step 4 of Example 21, using 2-tert-butyl-3-cyclohexylmethylimidazo[1,2-c]pyrimidine-7-carboxylic acid obtained in step 2, and aniline.
¹H NMR (270 MHz, CDCl₃, δ): 9.76 (br s, 1H), 8.82-8.78 (br m, 1H), 8.43-8.42 (br m, 1H), 7.78-7.75 (m, 2H), 7.39-7.37 (m, 2H), 7.17-7.12 (m, 1H), 3.03 (d, J=6.9 Hz, 2H), 1.73-1.71 (m, 5H), 1.55-1.48 (m, 2H), 1.50 (s, 9H), 1.20-1.16 (m, 4H); ESIMS m/z: [M+H]⁺ 391.

Example 48

3-(4,4-Difluorocyclohexylmethyl)-N-(3-methanesulfonylphenyl)-2-trifluoromethylimidazo[1,2-a] pyridine-7-carboxamide (Compound 48)

3-(4,4-Difluorocyclohexylmethyl)-2-trifluoromethylimidazo[1,2-a]pyridine-7-carboxylic acid (50.0 mg, 0.138 mmol) obtained in step 4 of Example 36 was dissolved in dichloromethane (1.0 mL). Under ice-cooled condition, oxalyl chloride (0.0180 mL, 0.207 mmol) and DMF (0.0010 mL, 0.014 mmol) were added, and the mixture was stirred at room temperature for 20 minutes. The solvent was then evaporated under reduced pressure, and dichloroethane (1.0 mL) was added. After adding N,N-diisopropylethylamine (0.0480 mL, 0.276 mmol) and 3-methanesulfonephenylamine (0.0470 mg, 0.276 mmol), the mixture was stirred at 50° C. for 2 hours. Then, a saturated sodium hydrogen carbonate aqueous solution was added to the reaction mixture, and the mixture was filtered through a Presep (registered trademark; diatomaceous earth, granular type M, 4.5 g/25 mL). The solvent was then evaporated under reduced pressure. The residue was purified by silica gel column chromatography (hexane/ethyl acetate=50/50→0/100) to give compound 48 (21.3 mg, yield 34%).
¹H NMR (270 MHz, CDCl₃, δ): 8.74 (s, 1H), 8.22-8.15 (m, 3H), 8.08 (dd, J=7.3, 0.7 Hz, 1H), 7.75-7.71 (m, 1H), 7.61 (dd, J=8.1, 8.1 Hz, 1H), 7.53 (dd, J=7.3, 1.8 Hz, 1H), 3.13 (s, 3H), 3.05 (d, J=7.7 Hz, 2H), 2.06 (s, 2H), 1.80-1.46 (m, 7H); ESIMS m/z: [M+H]⁺ 516.

Example 49

3-(4,4-Difluorocyclohexylmethyl)-N-{(tetrahydro-2H-pyran-4-yl)methyl-d₂}-2-trifluoromethylimidazo [1,2-a]pyridine-7-carboxamide (Compound 62)

Step 1
Methyl tetrahydro-2H-pyrancarboxylate (1.00 g, 6.94 mmol) was dissolved in a THF-CD₃OD-D₂O (10:2:1) mixed solvent (25 mL). Under ice-cooled condition, sodium borodeuteride (0.581 g, 13.9 mmol) was added, and the mixture was stirred at 50° C. for 2 hours. Under ice-cooled condition, acetone and a saturated sodium hydrogen carbonate aqueous solution were added, and the reaction mixture was extracted with ethyl acetate. The organic layer was washed with saturated brine, and dried over anhydrous magnesium sulfate. The solvent was then evaporated under reduced pressure. The residue was purified by silica gel column chromatography (hexane/ethyl acetate=80/20→50/50) to give (tetrahydro-2H-pyran-4-yl)methanol-d₃ (0.581 g, yield 70%).
¹H NMR (270 MHz, CDCl₃, δ): 4.04-3.95 (m, 2H), 3.47-3.33 (m, 2H), 1.80-1.28 (m, 5H).

Step 2
(Tetrahydro-2H-pyran-4-yl)methanol-d₃ (0.580 g, 4.87 mmol) obtained in step 1 was dissolved in toluene (6 mL), and the solution was stirred at 50° C. for 1 hour after adding phthalimide (0.788 g, 5.35 mmol), triphenylphosphine (1.53 g, 5.84 mmol), and a toluene solution of diethyl azodicarboxylate (2.2 mol/L) (3.32 mL, 7.30 mmol). The solvent was then evaporated under reduced pressure. The residue was purified by silica gel column chromatography (hexane/ethyl acetate=80/20→50/50) to give 2-{(tetrahydro-2H-pyran-4-yl)methyl-d$_2$}isoindoline-1,3-dione (0.686 g, yield 57%).

$^1$H NMR (270 MHz, CDCl$_3$, δ): 7.88-7.83 (m, 2H), 7.76-7.70 (m, 2H), 4.01-3.93 (m, 2H), 3.41-3.29 (m, 2H), 2.11-1.98 (m, 1H), 1.64-1.31 (m, 4H).

Step 3

2-{(Tetrahydro-2H-pyran-4-yl)methyl-d$_2$}isoindoline-1,3-dione (0.680 g, 2.75 mol) obtained in step 2 was suspended in ethanol (5.0 mL), and the suspension was stirred overnight under heat and reflux after adding hydrazine monohydrate (0.160 mL, 3.30 mmol). Under ice-cooled condition, hexane was added to the reaction mixture, and the precipitate was removed by filtration. Then, 2 mol/L hydrochloric acid (ethanol solution) (1.34 mL) was added to the filtrate under ice-cooled condition. The precipitated white crystals were collected by filteration, and dried under reduced pressure to give (tetrahydro-2H-pyran-4-yl)methaneamine-d$_3$ hydrochloride (0.179 g, yield 42%).

$^1$H NMR (270 MHz, CD$_3$OD, δ): 4.00-3.93 (m, 2H), 3.47-3.37 (m, 2H), 1.93-1.82 (m, 1H), 1.72-1.63 (m, 2H), 1.42-1.27 (m, 2H).

Step 4

3-(4,4-Difluorocyclohexylmethyl)-2-trifluoromethylimidazo[1,2-a]pyridine-7-carboxylic acid (70 mg, 0.193 mmol) obtained in step 4 of Example 36 was dissolved in THF (1.0 mL), and the solution was stirred at room temperature for 1 hour after adding (tetrahydro-2H-pyran-4-yl)methaneamine-d$_3$ hydrochloride (59 mg, 0.386 mmol), EDC.HCl (15 mg, 0.097 mmol), HOBt.H$_2$O (15 mg, 0.097 mmol), and potassium carbonate (53 mg, 0.386 mmol). After adding a saturated sodium hydrogen carbonate aqueous solution to the reaction mixture, the mixture was filtered through a Presep (registered trademark; diatomaceous earth, granular type M, 4.5 g/25 mL). The solvent was then evaporated under reduced pressure. The residue was purified by silica gel column chromatography (chloroform/methanol=98/2→95/5) to give compound 62 (29.5 mg, yield 21%).

$^1$H NMR (270 MHz, CDCl$_3$, δ): 8.02 (dd, J=7.2, 1.0 Hz, 1H), 7.94 (dd, J=2.0, 1.0 Hz, 1H), 7.44 (dd, J=7.2, 2.0 Hz, 1H), 6.25 (br s, 1H), 4.05-3.96 (m, 2H), 3.47-3.33 (m, 2H), 3.03 (d, J=7.2 Hz, 2H), 2.18-1.23 (m, 14H); ESIMS m/z: [M+H]$^+$ 462.

Example 50

3-(4,4-Difluorocyclohexylmethyl)-N-(1,3-dihydroxy-2-methylpropan-2-yl)-2-trifluoromethylimidazo[1,2-a]pyridine-7-carboxamide (Compound 63)

3-(4,4-Difluorocyclohexylmethyl)-2-trifluoromethylimidazo[1,2-a]pyridine-7-carboxylic acid (0.200 g, 0.552 mmol) obtained in step 4 of Example 36 was dissolved in DMF (2.0 mL), and the solution was stirred at room temperature for 1 hour after adding 2-amino-2-methyl-1,3-propanediol (0.116 g, 1.10 mmol), and 4-(4,6-dimethoxy-1,3,5-triazin-2-yl)-4-methylmorpholonium chloride (DMT-MM) (0.306 g, 1.10 mmol). Then, a saturated sodium hydrogen carbonate aqueous solution was added to the reaction mixture, and the mixture was filtered through a Presep (registered trademark; diatomaceous earth, granular type M, 4.5 g/25 mL). The solvent was then evaporated under reduced pressure. The residue was purified by silica gel column chromatography (chloroform/methanol=95/5→90/10). The resulting white solid was reslurried in tert-butyl methyl ether to give compound 63 (230 mg, yield 93%).

$^1$H NMR (270 MHz, DNSO-d$^6$, δ): 8.65 (d, J=7.3 Hz, 1H), 8.16 (s, 1H), 7.65 (br s, 1H), 7.40 (d, J=7.3 Hz, 1H), 4.76 (t, J=5.9 Hz, 2H), 3.69-3.54 (m, 4H), 3.08 (d, J=7.3 Hz, 2H), 2.05-1.18 (m, 9H), 1.30 (s, 3H); ESIMS m/z: [M+H]$^+$ 450.

Example 51

{3-(4,4-Difluorocyclohexylmethyl)-2-trifluoromethylimidazo[1,2-a]pyridin-7-yl}{(2-hydroxymethyl)-2-methylaziridin-1-yl}methanone (Compound 64)

Compound 63 (30.0 mg, 0.0670 mmol) was dissolved in pyridine (0.6 mL), and the solution was stirred at room temperature for 2 hours after adding p-toluenesulfonylchloride (14.0 mg, 0.0730 mmol). After adding a saturated sodium hydrogen carbonate aqueous solution to the reaction mixture, the mixture was filtered through a Presep (registered trademark; diatomaceous earth, granular type M, 4.5 g/25 mL), and the solvent was then evaporated under reduced pressure. The residue was purified by silica gel column chromatography (chloroform/methanol=95/5→90/10) to give compound 64 (11.3 mg, yield 39%).

$^1$H NMR (270 MHz, CDCl$_3$, δ): 8.11 (d, J=1.5 Hz, 1H), 7.91 (d, J=7.3 Hz, 1H), 7.51 (dd, J=7.3, 1.5 Hz, 1H), 4.53 (d, J=8.4 Hz, 1H), 4.16 (d, J=8.4 Hz, 1H), 3.83-3.74 (m, 1H), 3.59-3.48 (m, 1H), 3.02 (d, J=7.0 Hz, 2H), 2.30-2.22 (m, 1H), 2.18-2.05 (m, 2H), 1.82-1.38 (m, 7H), 1.36 (s, 3H); ESIMS m/z: [M+H]$^+$ 432.

Example 52

3-(4,4-Difluorocyclohexylmethyl)-N-(tetrahydro-2H-pyran-4-yl)-2-(1-trifluoromethylcyclopropyl)imidazo[1,2-a]pyridine-7-carboxamide (Compound 65)

Step 1

Dimethyl methylphosphonate (4.06 mL, 37.9 mmol) was dissolved in THF (70 mL), and the solution was stirred for 30 minutes after adding n-butyllithium (1.63 mol/L-THF solution) (23.3 mL, 37.9 mmol) at −78° C. At the maintained temperature of −78° C., a THF (30 mL) solution of N-methoxy-N-methyl-1-trifluoromethylcyclopropanecarboxamide (6.80 g, 34.5 mmol) obtained according to the method described in WO2008/30466 was gently added to the reaction mixture, and the mixture was stirred at room temperature for 1 hour. The reaction mixture was extracted with ethyl acetate after adding a saturated ammonium chloride aqueous solution. The organic layer was washed with saturated brine, and dried over anhydrous magnesium sulfate. The solvent was then evaporated under reduced pressure. The residue was purified by silica gel column chromatography (chloroform/methanol=98/2→95/5) to give dimethyl 2-oxo-2-(1-trifluoromethylcyclopropyl)ethylphosphonate (7.01 g, yield 78%).

$^1$H NMR (270 MHz, CDCl$_3$, δ): 3.81 (d, J=11.4 Hz, 6H), 3.36 (d, J=21.3 Hz, 2H), 1.58-1.50 (m, 2H), 1.46-1.39 (m, 2H).

Step 2

3-(4,4-Difluorocyclohexyl)-1-(1-trifluoromethylcyclopropyl)propan-2-en-1-one (745 mg, yield 69%) was obtained in the same manner as in step 1 of Example 34, using dimethyl 2-oxo-2-(1-trifluoromethylcyclopropyl)ethylphosphonate obtained in step 1, and 4,4-difluorocyclohexanecarbaldehyde.

$^1$H NMR (270 MHz, CDCl$_3$, δ): 6.93 (dd, J=15.4, 7.0 Hz, 1H), 6.64-6.57 (m, 1H), 2.36-2.24 (m, 1H), 2.19-2.07 (m, 2H), 1.91-1.32 (m, 10H).

Step 3

3-(4,4-Difluorocyclohexyl)-1-(1-trifluoromethylcyclopropyl)propan-2-en-1-one (0.746 g, 2.64 mmol) obtained in step 2 was dissolved in ethanol (10 mL), and allowed to react at 25° C. in the full H2 mode of an H-cube (registered trademark) using 10% Pd/C CatCart (30 mm) (ThalesNano Technologies) to give 3-(4,4-difluorocyclohexyl)-1-(1-trifluoromethylcyclopropyl)propan-1-one (0.715 g, yield 95%).

$^1$H NMR (270 MHz, CDCl$_3$, δ): 2.77 (t, J=7.5 Hz, 2H), 2.15-2.00 (m, 2H), 1.82-1.51 (m, 6H), 1.45-1.18 (m, 7H).

Step 4

3-(4,4-Difluorocyclohexyl)-1-(1-trifluoromethylcyclopropyl)propan-1-one (0.200 g, 0.704 mmol) obtained in step 3 was dissolved in THF (2.0 mL). Under ice-cooled condition, DBU (0.117 mL, 0.774 mmol) and chlorotriethylsilane (0.130 mL, 0.774 mmol) were added, and the mixture was stirred at room temperature for 2 hours. The reaction mixture was extracted with heptane after adding a saturated sodium hydrogen carbonate aqueous solution. The organic layer was washed with saturated brine, and dried over anhydrous magnesium sulfate. The solvent was then evaporated under reduced pressure. The residue was purified by silica gel column chromatography (hexane/ethyl acetate=95/5→90/10) to give {3-(4,4-difluorocyclohexyl)-1-(1-trifluoromethylcyclopropyl)prop-1-enyloxy}triethylsilane (0.253 g, yield 90%).

$^1$H NMR (270 MHz, CDCl$_3$, δ): 4.84 (t, J=7.2 Hz, 1H), 2.12-0.63 (m, 30H).

Step 5

{3-(4,4-Difluorocyclohexyl)-1-(1-trifluoromethylcyclopropyl)prop-1-enyloxy}triethylsilane (3.00 g, 7.53 mmol) obtained in step 4 was dissolved in dichloromethane (30 mL). Under ice-cooled condition, a dichloromethane solution (10 mL) of bromine (1.32 g, 8.28 mmol) was added, and the mixture was stirred at room temperature for 1 hour. The reaction mixture was extracted with hexane after adding a saturated sodium hydrogen carbonate aqueous solution, and a sodium thiosulfate aqueous solution. The organic layer was washed with saturated brine, and dried over anhydrous magnesium sulfate. The solvent was then evaporated under reduced pressure. The residue was purified by silica gel column chromatography (hexane/ethyl acetate=90/10→80/20) to give 2-bromo-3-(4,4-difluorocyclohexyl)-1-(1-trifluoromethylcyclopropyl)propan-1-one (2.69 g, yield 98%).

$^1$H NMR (270 MHz, CDCl$_3$, δ): 4.79 (t, J=7.3 Hz, 1H), 2.16-2.04 (m, 2H), 2.00-1.93 (m, 2H), 1.85-1.20 (m, 11H).

Step 6

2-Bromo-3-(4,4-difluorocyclohexyl)-1-(1-trifluoromethylcyclopropyl)propan-1-one (0.512 g, 1.41 mmol) obtained in step 5,2-amino-4-cyanopyridine (0.185 g, 1.55 mmol), and molecular sieve 4A (0.40 g) were suspended in n-butanol (3.0 mL), and the mixture was stirred under heat and reflux for 3 days. The reaction mixture was allowed to cool to room temperature, filtered through Celite (registered trademark) after adding a sodium hydrogen carbonate aqueous solution, and extracted with ethyl acetate. The organic layer was washed with saturated brine, and dried over anhydrous magnesium sulfate. The solvent was then evaporated under reduced pressure. The residue was purified by silica gel column chromatography (hexane/ethyl acetate=80/20→65/35) to give 3-(4,4-difluorocyclohexylmethyl)-2-(1-trifluoromethylcyclopropyl)imidazo[1,2-a]pyridine-7-carbonitrile (0.0999 g, yield 18%).

$^1$H NMR (270 MHz, CDCl$_3$, δ): 8.03-7.99 (m, 2H), 6.99 (dd, J=7.1, 1.6 Hz, 1H), 3.01 (d, J=7.3 Hz, 2H), 2.20-2.04 (m, 2H), 1.98-1.38 (m, 9H), 1.28-1.17 (m, 2H).

Step 7

3-(4,4-Difluorocyclohexylmethyl)-2-(1-trifluoromethylcyclopropyl)imidazo[1,2-a]pyridine-7-carboxylic acid (103 mg, yield 99%) was obtained in the same manner as in step 2 of Example 7, using 3-(4,4-difluorocyclohexylmethyl)-2-(1-trifluoromethylcyclopropyl)imidazo[1,2-a]pyridine-7-carbonitrile obtained in step 6.

$^1$H NMR (270 MHz, DMSO-d$^6$, δ): 13.33 (br s, 1H), 8.52 (d, J=7.3 Hz, 1H), 8.07 (d, J=1.5 Hz, 1H), 7.32 (dd, J=7.3, 1.5 Hz, 1H), 3.02 (d, J=7.3 Hz, 2H), 2.07-1.12 (m, 13H); ESIMS m/z: [M+H]$^+$ 403.

Step 8

Compound 65 (60.8 mg, yield 72%) was obtained in the same manner as in step 4 of Example 49, using 3-(4,4-difluorocyclohexylmethyl)-2-(1-trifluoromethylcyclopropyl)imidazo[1,2-a]pyridine-7-carboxylic acid obtained in step 7, and 4 aminotetrahydropyran hydrochloride.

$^1$H NMR (270 MHz, CDCl$_3$, δ): 7.97 (d, J=7.1 Hz, 1H), 7.89 (d, J=1.6 Hz, 1H), 7.31 (dd, J=7.1, 1.6 Hz, 1H), 6.03 (d, J=7.7 Hz, 1H), 4.28-4.13 (m, 1H), 4.06-3.96 (m, 2H), 3.60-3.49 (m, 2H), 2.99 (d, J=7.3 Hz, 2H), 2.11-1.91 (m, 5H), 1.81-1.38 (m, 10H), 1.29-1.19 (m, 2H); ESIMS m/z: [M+H]$^+$ 486.

Example 53

N-{(1,4-Dioxepan-6-yl)methyl}-3-(4,4-difluorocyclohexylmethyl)-5-methyl-2-trifluoromethylimidazo[1,2-a]pyridine-7-carboxamide (Compound 93)

Step 1

2-{(1,4-Dioxepan-6-yl)methylisoindoline-1,3-dione (251 mg, yield 85%) was obtained in the same manner as in step 2 of Example 49, using 1,4-dioxepan-6-ylmethanol obtained according to the method described in WO2008/29825.

$^1$H NMR (270 MHz, CDCl$_3$, δ): 7.87-7.83 (m, 2H), 7.75-7.70 (m, 2H), 3.96-3.88 (m, 2H), 3.76 (s, 4H), 3.73-3.65 (m, 4H), 2.64-2.51 (m, 1H).

Step 2

A crude product of (1,4-dioxepan-6-yl)methylamine hydrochloride was obtained in the same manner as in step for compound 62, using 2-{(1,4-dioxepan-6-yl)methylisoindoline-1,3-dione obtained in step 1, and it was directly used for the next reaction.

Step 3

Compound 93 (39.9 mg, yield 44%) was obtained in the same manner as in step 4 of Example 49, using 3-(4,4-difluorocyclohexylmethyl)-5-methyl-2-trifluoromethylimidazo[1,2-a]pyridine-7-carboxylic acid obtained in step 2 of Example 44, and (1,4-dioxepan-6-yl)methylamine hydrochloride obtained in step 2.

$^1$H NMR (270 MHz, CDCl$_3$, δ): 7.80 (d, J=1.3 Hz, 1H), 7.16 (d, J=1.3 Hz, 1H), 6.97 (br s, 1H), 4.03 (dd, J=12.8, 5.6 Hz, 2H), 3.79 (s, 4H), 3.78 (dd, J=12.8, 5.6 Hz, 2H), 3.53 (t, J=5.6 Hz, 2H), 3.22 (d, J=6.3 Hz, 2H), 2.88 (s, 3H), 2.46-2.36 (m, 1H), 2.17-2.04 (m, 2H), 1.76-1.36 (m, 7H); ESIMS m/z: [M+H]$^+$ 490.

Example 54

3-(4,4-Difluorocyclohexylmethyl)-N-(1,1-dioxotetrahydro-2H-thiopyran-4-yl)-5-methyl-2-trifluoromethylimidazo[1,2-a]pyridine-7-carboxamide (Compound 94)

Compound 94 (70.0 mg, yield 66%) was obtained in the same manner as in Example 13, using compound 74.

$^1$H NMR (300 MHz, CDCl$_3$, δ): 7.86 (s, 1H), 7.11 (s, 1H), 6.64 (d, J=7.7 Hz, 1H), 4.35-4.24 (m, 1H), 3.24-3.13 (m, 6H), 2.90 (s, 3H), 2.49-2.03 (m, 6H), 1.74-1.38 (m, 7H); ESIMS m/z: [M+H]$^+$ 508.

Example 55

3-(4,4-Difluorocyclohexylmethyl)-5-methyl-N-{(3-methyloxetan-3-yl)methyl}-2-trifluoromethylimidazo[1,2-a]pyridine-7-carboxamide (Compound 95)

Step 1

3-(4,4-Difluorocyclohexylmethyl)-5-methyl-2-trifluoromethylimidazo[1,2-a]pyridine-7-carboxamide (83.8 mg, yield 95%) was obtained in the same manner as in step 2 of Example 2, using 3-(4,4-difluorocyclohexylmethyl)-5-methyl-2-trifluoromethylimidazo[1,2-a]pyridine-7-carboxylic acid obtained in step 2 of Example 44, and aqueous ammonia.

$^1$H NMR (300 MHz, CDCl$_3$, δ): 7.87 (d, J=1.1 Hz, 1H), 7.18 (d, J=1.1 Hz, 1H), 3.23 (d, J=6.6 Hz, 2H), 2.90 (s, 3H), 2.14-2.06 (m, 2H), 1.72-1.41 (m, 7H). ESIMS m/z: [M+H]$^+$ 376.

Step 2

3-(4,4-Difluorocyclohexylmethyl)-5-methyl-2-trifluoromethylimidazo[1,2-a]pyridine-7-carboxamide (150 mg, 0.400 mmol) obtained in step 1 was dissolved in DMF (1.0 mL), and the solution was stirred overnight at 50° C. after adding (3-methyloxetan-3-yl)methyl methane sulfonic acid (86.0 mg, 0.480 mmol) obtained according to the method described in WO2004/113322, and cesium carbonate (651 mg, 2.00 mmol). After adding a saturated sodium hydrogen carbonate aqueous solution to the reaction mixture, the mixture was filtered through a Presep (registered trademark; diatomaceous earth, granular type M, 4.5 g/25 mL), and the solvent was evaporated under reduced pressure. The residue was purified by silica gel column chromatography (chloroform/methanol=98/2→95/5). The resulting white amorphous was reslurried in tert-butyl methyl ether to give compound 95 (39.6 mg, yield 22%).

$^1$H NMR (300 MHz, CDCl$_3$, δ): 7.85 (d, J=1.3 Hz, 1H), 7.14 (d, J=1.3 Hz, 1H), 6.63-6.55 (br m, 1H) 4.52 (d, J=6.3 Hz, 2H), 4.48 (d, J=6.3 Hz, 2H), 3.66 (d, J=5.9 Hz, 2H), 3.22 (d, J=5.9 Hz, 2H), 2.89 (s, 3H), 2.19-2.03 (m, 2H), 1.72-1.41 (m, 7H), 1.36 (s, 3H); ESIMS m/z: [M+H]$^+$ 460.

Example 56

3-(4,4-Difluorocyclohexylmethyl)-2-(1,1-difluoroethyl)-5-methyl-N-(tetrahydro-2H-pyran-4-yl)imidazo[1,2-a]pyridine-7-carboxamide (Compound 96)

Step 1

Dimethyl 3,3-difluoro-2-oxobutylphosphonate (6.11 g, yield 57%) was obtained in the same manner as in step 1 of Example 52, using ethyl 2,2-difluoropropionate.

$^1$H NMR (300 MHz, CDCl$_3$, δ): 3.82 (d, J=11.4 Hz, 6H), 3.36 (dt, J=22.1, 1.2 Hz, 2H), 1.74 (t, J=19.2 Hz, 3H).

Step 2

1-(4,4-Difluorocyclohexyl)-4,4-difluoropenta-1-en-3-one (113 mg, yield 21%) was obtained in the same manner as in step 1 of Example 34, using dimethyl 3,3-difluoro-2-oxobutylphosphonate obtained in step 1, and 4,4-difluorocyclohexanecarbaldehyde.

$^1$H NMR (300 MHz, CDCl$_3$, δ): 7.14 (dd, J=15.8, 6.6 Hz, 1H), 6.58-6.50 (m, 1H), 2.41-2.26 (m, 1H), 2.24-2.09 (m, 3H), 1.97-1.51 (m, 8H).

Step 3

1-(4,4-Difluorocyclohexyl)-4,4-difluoropentan-3-one (0.973 g, yield 84%) was obtained in the same manner as in step 3 of Example 52, using 1-(4,4-difluorohexyl)-4,4-difluoropenta-1-en-3-one obtained in step 2.

$^1$H NMR (300 MHz, CDCl$_3$, δ): 2.72 (tt, J=7.3, 1.5 Hz, 2H), 2.15-2.01 (m, 2H), 1.82-1.21 (m, 12H).

Step 4

{1-(4,4-Difluorocyclohexyl)-4,4-difluoropenta-2-en-3-yloxy}triethylsilane (31.5 mg, yield 43%) was obtained in the same manner as in step 4 of Example 52, using 1-(4,4-difluorocyclohexyl)-4,4-difluoropentan-3-one obtained in step 3.

$^1$H NMR (300 MHz, CDCl$_3$, δ): 5.12 (t, J=7.3 Hz, 1H), 2.16-1.21 (m, 14H), 0.99 (t, J=7.9 Hz, 9H), 0.71 (q, J=7.9 Hz, 6H).

Step 5

2-Bromo-1-(4,4-difluorocyclohexyl)-4,4-difluoropenta-3-one (39.2 mg, yield 87%) was obtained in the same manner as in step 5 of Example 52, using {1-(4,4-difluorocyclohexyl)-4,4-difluoropenta-2-en-3-yloxy}triethylsilane obtained in step 4.

$^1$H NMR (300 MHz, CDCl$_3$, δ): 4.85-4.78 (m, 1H), 2.18-1.23 (m, 14H).

Step 6

Ethyl 3-(4,4-difluorocyclohexylmethyl)-2-(1,1-difluoroethyl)-5-methylimidazo[1,2-a]pyridine-7-carboxylate (7.90 mg, yield 13%) was obtained in the same manner as in step 6 of Example 52, using 2-bromo-1-(4,4-difluorocyclohexyl)-4,4-difluoropenta-3-one obtained in step 5, and ethyl 2-amino-6-methylpyridine-4-carboxylate obtained according to the method described in WO2008/009750.

$^1$H NMR (300 MHz, CDCl$_3$, δ): 8.22 (d, J=1.1 Hz, 1H), 7.16 (d, J=1.1 Hz, 1H), 4.40 (q, J=7.1 Hz, 3H), 3.28 (d, J=6.6 Hz, 2H), 2.88 (s, 3H), 2.26-1.33 (m, 14H); ESIMS m/z: [M+H]$^+$ 401.

Step 7

3-(4,4-Difluorocyclohexylmethyl)-2-(1,1-difluoroethyl)-5-methylimidazo[1,2-a]pyridine-7-carboxylic acid (179 mg, yield 75%) was obtained in the same manner as in step 7 of Example 52, using ethyl 3-(4,4-difluorocyclohexylmethyl)-2-(1,1-difluoroethyl)-5-methylimidazo[1,2-a]pyridine-7-carboxylate obtained in step 6.

$^1$H NMR (300 MHz, DMSO-d$^6$, δ): 13.30 (br s, 1H), 7.97 (d, J=1.1 Hz, 1H), 7.19 (d, J=1.1 Hz, 1H), 3.21 (d, J=7.0 Hz, 2H), 2.91 (s, 3H), 2.10 (t, J=19.1 Hz, 3H), 2.02-1.18 (m, 9H); ESIMS m/z: [M+H]$^+$ 373.

Step 8

Compound 96 (44.4 mg, yield 45%) was obtained in the same manner as in step 4 of Example 49, using 3-(4,4-difluorocyclohexylmethyl)-2-(1,1-difluoroethyl)-5-methylimidazo[1,2-a]pyridine-7-carboxylic acid obtained in step 7, and 4-aminotetrahydropyran hydrochloride.

$^1$H NMR (300 MHz, CDCl$_3$, δ): 7.77 (d, J=1.8 Hz, 1H), 7.06 (d, J=1.8 Hz, 1H), 6.05 (d, J=8.1 Hz, 1H), 4.26-4.12 (m, 1H), 4.06-3.96 (m, 2H), 3.61-3.48 (m, 2H), 3.26 (d, J=6.2 Hz,

2H), 2.88 (s, 3H), 2.15 (t, J=18.9 Hz, 3H), 2.11-1.96 (m, 4H), 1.72-1.39 (m, 9H); ESIMS m/z: [M+H]+ 456.

Example 57

3-(4,4-Difluorocyclohexylmethyl)-2-(2-methoxypropan-2-yl)-5-methyl-N-(tetrahydro-2H-pyran-4-yl) imidazo[1,2-a]pyridine-7-carboxamide (Compound 97)

Step 1

Ethyl 3-(4,4-difluorocyclohexyl)propionate (0.550 g, 2.50 mmol) obtained in step 2 of Example 34 was dissolved in ethanol (1.0 mL), and the solution was stirred under heat and reflux for 2 hours after adding sodium ethoxide (20% ethanol solution) (1.16 mL, 3.00 mmol) and diethyl oxalate (0.405 mL, 3.00 mmol). The solvent was evaporated under reduced pressure. The residue was extracted with water after adding diethyl ether. Then, concentrated sulfuric acid (0.160 mL, 3.00 mmol) was added to the aqueous layer, and the mixture was extracted with ethyl acetate. The organic layer was washed with saturated brine, and dried over anhydrous magnesium sulfate. The solvent was then evaporated under reduced pressure. The residue was dissolved in a DMSO-$H_2O$ (10:1) mixed solvent (3.3 mL), and the solution was stirred at 150° C. for 30 minutes after adding sodium chloride (0.117 g, 3.03 mmol). The reaction mixture was allowed to cool to room temperature, and, after adding water, extracted with diethyl ether. The organic layer was washed with saturated brine, and dried over anhydrous magnesium sulfate. The solvent was then evaporated under reduced pressure. The residue was purified by silica gel column chromatography (hexane/ethyl acetate=90/10→80/20) to give ethyl 4-(4,4-difluorocyclohexyl)-2-oxobutanoate (0.146 g, yield 39%).

$^1$H NMR (270 MHz, $CDCl_2$, δ): 4.33 (q, J=7.1 Hz, 2H), 2.87 (t, J=7.6 Hz, 2H), 2.16-2.01 (m, 2H), 1.82-1.53 (m, 6H), 1.42-1.21 (m, 6H).

Step 2

Ethyl 3-bromo-4-(4,4-difluorocyclohexyl)-2-oxobutanoate (0.206 g, yield 65%) was obtained in the same manner as in step 1 of Example 1, using ethyl 4-(4,4-difluorocyclohexyl)-2-oxobutanoate obtained in step 1.

$^1$H NMR (300 MHz, $CDCl_2$, δ): 5.11 (dd, J=8.8, 6.2 Hz, 1H), 4.39 (q, J=7.1 Hz, 2H), 2.17-1.18 (m, 14H).

Step 3

Ethyl 7-cyano-3-(4,4-difluorocyclohexylmethyl)-5-methylimidazo[1,2-a]pyridine-2-carboxylate (0.106 g, yield 24%) was obtained in the same manner as in step 6 of Example 52, using ethyl 3-bromo-4-(4,4-difluorocyclohexyl)-2-oxobutanoate obtained in step 2, and 2-amino-6-methyl-4-cyanopyridine obtained according to the method described in WO2010/90716.

$^1$H NMR (300 MHz, $CDCl_3$, δ): 7.97 (s, 1H), 6.71 (s, 1H), 4.48 (q, J=7.2 Hz, 2H), 3.60 (d, J=6.2 Hz, 2H), 2.89 (s, 3H), 2.16-2.04 (m, 2H), 1.74-1.51 (m, 7H), 1.46 (t, J=7.2 Hz, 3H).

Step 4

Ethyl 7-cyano-3-(4,4-difluorocyclohexylmethyl)-5-methylimidazo[1,2-a]pyridine-2-carboxylate (0.0410 g, 0.113 mmol) obtained in step 3 was dissolved in THF (1.0 mL), and the solution was stirred at −50° C. for 2 hours and then at 0° C. for 30 minutes after adding a THF solution of methylmagnesium bromide (1.1 mol/L) (0.446 mL, 0.500 mmol) at −50° C. Under ice-cooled condition, a saturated ammonium chloride aqueous solution was added to the reaction mixture, and the mixture was filtered through a Presep (registered trademark; diatomaceous earth, granular type M, 4.5 g/25 mL). The solvent was then evaporated under reduced pressure. The residue was purified by silica gel column chromatography (heptane/ethyl acetate=80/20→65/35) to give 3-(4,4-difluorocyclohexylmethyl)-2-(2-hydroxypropan-2-yl)-5-methylimidazo[1,2-a]pyridine-7-carbonitrile (20.4 mg, yield 52%).

$^1$H NMR (300 MHz, $CDCl_3$, δ): 7.81 (s, 1H), 6.63 (s, 1H), 3.39 (d, J=6.6 Hz, 2H), 2.84 (s, 3H), 2.41 (br s, 1H), 2.14-2.02 (m, 2H), 1.71 (s, 6H), 1.67-1.39 (m, 7H); ESIMS m/z: [M+H]+ 347.

Step 5

3-(4,4-Difluorocyclohexylmethyl)-2-(2-methoxypropan-2-yl)-5-methylimidazo[1,2-a]pyridine-7-carbonitrile (17.5 mg, yield 73%) was obtained in the same manner as in Example 9, using 3-(4,4-difluorocyclohexylmethyl)-2-(2-hydroxypropan-2-yl)-5-methylimidazo[1,2-a]pyridine-7-carbonitrile obtained in step 4.

$^1$H NMR (300 MHz, $CDCl_3$, δ): 7.82 (d, J=1.5 Hz, 1H), 6.62 (d, J=1.5 Hz, 1H), 3.36 (d, J=7.3 Hz, 2H), 3.25 (s, 3H), 2.83 (s, 3H), 2.18-1.99 (m, 2H), 1.59-1.34 (m, 13H); ESIMS m/z: [M+H]+ 362.

Step 6

3-(4,4-Difluorocyclohexylmethyl)-2-(2-methoxypropan-2-yl)-5-methylimidazo[1,2-a]pyridine-7-carboxylic acid (16.9 mg, yield 94%) was obtained in the same manner as in step 2 of Example 7, using 3-(4,4-difluorocyclohexylmethyl)-2-(2-methoxypropan-2-yl)-5-methylimidazo[1,2-a]pyridine-7-carbonitrile obtained in step 5.

$^1$H NMR (300 MHz, $CDCl_3$, δ): 8.27 (s, 1H), 7.11 (s, 1H), 3.37 (d, J=7.3 Hz, 2H), 3.25 (s, 3H), 2.84 (s, 3H), 2.13-1.96 (m, 2H), 1.60-1.31 (m, 13H); ESIMS m/z: [M+H]+ 381.

Step 7

Compound 97 (6.10 mg, yield 30%) was obtained in the same manner as in step 4 of Example 49, using 3-(4,4-difluorocyclohexylmethyl)-2-(2-methoxypropan-2-yl)-5-methylimidazo[1,2-a]pyridine-7-carboxylic acid obtained in step 6, and 4-aminotetrahydropyran hydrochloride.

$^1$H NMR (300 MHz, $CDCl_3$, δ): 7.74 (d, J=1.5 Hz, 1H), 6.99 (d, J=1.5 Hz, 1H), 5.99 (d, J=8.1 Hz, 1H), 4.26-4.12 (m, 1H), 4.04-3.94 (m, 2H), 3.60-3.48 (m, 2H), 3.34 (d, J=7.3 Hz, 2H), 3.24 (s, 3H), 2.83 (s, 3H), 2.16-1.97 (m, 4H), 1.68 (s, 6H), 1.64-1.34 (m, 9H); ESIMS m/z: [M+H]+ 464.

Example 58

2-(Cyclopropanecarbonyl)-3-(4,4-difluorocyclohexylmethyl)-N,N-diethyl-5-methylimidazo[1,2-a]pyridine-7-carboxamide (Compound 98)

Step 1

2-Amino-N,N-diethyl-6-methylisonicotinamide (2.22 g, yield 81%) was obtained in the same manner as in step 1 of Example 4, using 2-amino-6-methylisonicotinic acid obtained according to the method described in US Patent Application 2010/261687, and diethylamine.

$^1$H NMR (300 MHz, $CDCl_3$, δ): 6.46 (s, 1H), 6.25 (s, 1H), 4.46 (br s, 2H), 3.51 (q, J=7.1 Hz, 2H), 3.23 (q, J=7.1 Hz, 2H), 2.39 (s, 3H), 1.23 (t, J=7.1 Hz, 3H), 1.10 (t, J=7.1 Hz, 3H).

Step 2

Butyl 7-(diethylcarbamoyl)-3-(4,4-difluorocyclohexylmethyl)-5-methylimidazo[1,2-a]pyridine-2-carboxylate (294 mg, yield 23%) was obtained in the same manner as in step 6 of Example 52, using 2-amino-N,N-diethyl-6-methylisonicotinamide obtained in step 1, and ethyl 3-bromo-4-(4,4-difluorocyclohexyl)-2-oxobutanoate obtained in step 2 of Example 57.

$^1$H NMR (300 MHz, $CDCl_3$, δ): 7.53 (d, J=1.5 Hz, 1H), 6.67 (d, J=1.5 Hz, 1H), 4.41 (t, J=7.0 Hz, 2H), 3.57 (d, J=6.2

Hz, 2H), 3.55-3.34 (m, 4H), 2.85 (s, 3H), 2.15-2.02 (m, 2H), 1.88-1.77 (m, 2H), 1.72-1.15 (m, 15H), 0.97 (t, J=7.3 Hz, 3H); ESIMS m/z: [M+H]⁺ 464.

Step 3

7-(Diethylcarbamoyl)-3-(4,4-difluorocyclohexylmethyl)-5-methylimidazo[1,2-a]pyridine-2-carboxylic acid (245 mg, yield 96%) was obtained in the same manner as in step 1 of Example 2, using butyl 7-(diethylcarbamoyl)-3-(4,4-difluorocyclohexylmethyl)-5-methylimidazo[1,2-a]pyridine-2-carboxylate obtained in step 2.

¹H NMR (300 MHz, CDCl₃, δ): 7.67 (br s, 1H), 6.71 (s, 1H), 3.59 (d, J=5.9 Hz, 2H), 3.55-3.36 (m, 4H), 2.88 (s, 3H), 2.17-1.50 (m, 9H), 1.29-1.22 (m, 6H); ESIMS m/z: [M+H]⁺ 408.

Step 4

3-(4,4-Difluorocyclohexylmethyl)-7-(N,N-diethylcarbamoyl)-N,5-dimethyl-N-methoxyimidazo[1,2-a]pyridine-2-carboxamide (95.7 mg, yield 87%) was obtained in the same manner as in step 1 of Example 4, using 7-(diethylcarbamoyl)-3-(4,4-difluorocyclohexylmethyl)-5-methylimidazo[1,2-a]pyridine-2-carboxylic acid obtained in step 3.

¹H NMR (300 MHz, CDCl₃, δ): 7.45 (s, 1H), 6.63 (s, 1H), 3.85 (s, 3H), 3.54-3.42 (m, 7H), 3.33 (d, J=6.6 Hz, 2H), 2.84 (s, 3H), 2.13-2.00 (m, 2H), 1.75-1.18 (m, 13H); ESIMS m/z: [M+H]⁺ 451.

Step 5

Compound 98 (19.1 mg, yield 40%) was obtained in the same manner as in step 2 of Example 4, using 3-(4,4-difluorocyclohexylmethyl)-7-(N,N-diethylcarbamoyl)-N,5-dimethyl-N-methoxyimidazo[1,2-a]pyridine-2-carboxamide obtained in step 4, and a THF solution of cyclopropylmagnesium bromide (0.5 mol/L).

¹H NMR (300 MHz, CDCl₃, δ): 7.51 (s, 1H), 6.64 (s, 1H), 3.63-3.31 (m, 7H), 2.85 (s, 3H), 2.12-1.99 (m, 2H), 1.73-1.16 (m, 15H), 1.10-1.01 (m, 2H); ESIMS m/z: [M+H]⁺ 432.

Example 59

3-(4,4-Difluorocyclohexylmethyl)-5-methyl-2-(1-methylcyclopropyl)-N-(tetrahydro-2H-pyran-4-yl) imidazo[1,2-a]pyridine-7-carboxamide (Compound 100)

Step 1

Butyl 5-methyl-2-(1-methylcyclopropyl)imidazo[1,2-a]pyridine-7-carboxylate (380 mg, yield 10%) was obtained in the same manner as in step 6 of Example 52, using 2-bromo-1-(1-methylcyclopropyl)ethanone obtained according to the method described in WO2004/26868, and ethyl 2-amino-6-methylpyridine-4-carboxylate.

¹H NMR (300 MHz, CDCl₃, δ): 8.19 (s, 1H), 7.35 (s, 1H), 7.19 (s, 1H), 4.32 (t, J=6.4 Hz, 2H), 2.61 (s, 3H), 1.80-1.69 (m, 2H), 1.60-0.81 (m, 12H); ESIMS m/z: [M+H]⁺ 287.

Step 2

Butyl 5-methyl-2-(1-methylcyclopropyl)imidazo[1,2-a]pyridine-7-carboxylate (370 mg, 1.29 mmol) obtained in step 1 was dissolved in DMF (3.0 mL), and the solution was stirred at room temperature for 3 hours after adding N-iodosuccinimide (320 mg, 1.42 mmol). Then, a saturated sodium hydrogen carbonate aqueous solution was added to the reaction mixture, and the mixture was filtered through a Presep (registered trademark; diatomaceous earth, granular type M, 4.5 g/25 mL). The solvent was then evaporated under reduced pressure. The residue was purified by silica gel column chromatography (heptane/ethyl acetate=80/20) to give butyl 3-iodo-5-methyl-2-(1-methylcyclopropyl)imidazo[1,2-a]pyridine-7-carboxylate (351 mg, yield 66%).

¹H NMR (300 MHz, CDCl₃, δ): 8.16 (d, J=1.1 Hz, 1H), 7.08 (d, J=1.1 Hz, 1H), 4.32 (t, J=6.4 Hz, 2H), 3.22 (s, 3H), 1.79-1.69 (m, 2H), 1.49-1.43 (m, 5H), 1.04-0.92 (m, 5H), 0.88-0.82 (m, 2H).

Step 3

Butyl 3-{(4,4-difluorocyclohexyl) (hydroxy)methyl}-5-methyl-2-(1-methylcyclopropyl)imidazo[1,2-a]pyridine-7-carboxylate (109 mg, yield 38%) was obtained in the same manner as in step 4 of Example 7, using butyl 3-iodo-5-methyl-2-(1-methylcyclopropyl)imidazo[1,2-a]pyridine-7-carboxylate obtained in step 2, and 4,4-difluorocyclohexanecarbaldehyde.

¹H NMR (300 MHz, CDCl₃, δ): 8.17 (s, 1H), 7.19 (s, 1H), 5.35 (d, J=9.9 Hz, 1H), 4.34 (t, J=6.4 Hz, 2H), 2.97 (s, 3H), 2.52-2.43 (m, 1H), 2.34-0.80 (m, 23H).

Step 4

Sodium iodide (121 mg, 0.805 mmol) was suspended in a dichloromethane-acetonitrile (1:1) mixed solvent (0.8 mL). Under ice-cooled condition, dichlorodimethylsilane (52.0 mg, 0.403 mmol) was added, and the mixture was stirred for 20 minutes. The reaction mixture was stirred at room temperature for 30 minutes after adding a dichloromethane solution (0.4 mL) of butyl 3-{(4,4-difluorocyclohexyl) (hydroxy)methyl}-5-methyl-2-(1-methylcyclopropyl)imidazo[1,2-a]pyridine-7-carboxylate (35.0 mg, 0.0810 mmol) obtained in step 3. Then, a saturated sodium hydrogen carbonate aqueous solution and a saturated sodium thiosulfate aqueous solution were added to the reaction mixture, and the mixture was filtered through a Presep (registered trademark; diatomaceous earth, granular type M, 4.5 g/25 mL). The solvent was then evaporated under reduced pressure. The residue was purified by silica gel column chromatography (heptane/ethyl acetate=80/20→65/35) to give butyl 3-(4,4-difluorocyclohexylmethyl)-5-methyl-2-(1-methylcyclopropyl)imidazo[1,2-a]pyridine-7-carboxylate (24.6 mg, yield 73%).

¹H NMR (300 MHz, CDCl₃, δ): 8.15 (s, 1H), 7.07 (s, 1H), 4.32 (t, J=6.4 Hz, 2H), 3.17 (d, J=7.0 Hz, 2H), 2.81 (s, 3H), 2.17-2.02 (m, 2H), 1.82-1.20 (m, 14H), 1.04-0.93 (m, 5H), 0.84-0.78 (m, 2H); ESIMS m/z: [M+H]⁺ 419.

Step 5

3-(4,4-Difluorocyclohexylmethyl)-5-methyl-2-(1-methylcyclopropyl)imidazo[1,2-a]pyridine-7-carboxylic acid (20.5 mg, yield 99%) was obtained in the same manner as in step 1 of Example 2, using butyl 3-(4,4-difluorocyclohexylmethyl)-5-methyl-2-(1-methylcyclopropyl)imidazo[1,2-a]pyridine-7-carboxylate obtained in step 4.

¹H NMR (300 MHz, DMSO-d⁶, δ): 7.89 (s, 1H), 7.23 (s, 1H), 3.15 (d, J=6.6 Hz, 2H), 2.88 (s, 3H), 2.01-1.92 (m, 2H), 1.88-1.58 (m, 5H), 1.43 (s, 3H), 1.37-1.21 (m, 2H), 0.99-0.94 (m, 2H), 0.84-0.78 (m, 2H); ESIMS m/z: [M+H]⁺ 363.

Step 6

Compound 100 (11.5 mg, yield 59%) was obtained in the same manner as in step 4 of Example 49, using 3-(4,4-difluorocyclohexylmethyl)-5-methyl-2-(1-methylcyclopropyl) imidazo[1,2-a]pyridine-7-carboxylic acid obtained in step 5, and 4-aminotetrahydropyran hydrochloride.

¹H NMR (300 MHz, CDCl₃, δ): 7.70 (d, J=1.5 Hz, 1H), 6.96 (d, J=1.5 Hz, 1H), 6.00 (d, J=7.7 Hz, 1H), 4.24-4.13 (m, 1H), 4.04-3.95 (m, 2H), 3.59-3.49 (m, 2H), 3.16 (d, J=7.0 Hz, 2H), 2.80 (s, 3H), 2.16-1.97 (m, 4H), 1.79-1.21 (m, 12H), 1.02-0.97 (m, 2H), 0.83-0.78 (m, 2H); ESIMS m/z: [M+H]⁺ 446.

Example 60

3-(4,4-Difluorocyclohexylmethyl)-2-isopropyl-5-methyl-N-(tetrahydro-2H-pyran-4-yl)imidazo[1,2-a]pyridine-7-carboxamide (Compound 101)

Step 1

1-Bromo-3-methylbutan-2-one (4.43 g, 26.8 mmol) was dissolved in ethanol (10 mL), and the solution was stirred under heat and reflux for 2 days after adding ethyl 2-amino-6-methylpyridine-4-carboxylate (3.00 g, 16.7 mmol). The reaction mixture was allowed to cool to room temperature, and extracted with ethyl acetate after adding a sodium hydrogen carbonate aqueous solution. The organic layer was washed with saturated brine, and dried over anhydrous sodium sulfate. The solvent was then evaporated under reduced pressure. The residue was purified by silica gel column chromatography (heptane/ethyl acetate=80/20→65/35) to give ethyl 5-methyl-2-(1-methylcyclopropyl)imidazo[1,2-a]pyridine-7-carboxylate (835 mg, yield 21%).

$^1$H NMR (300 MHz, CDCl$_3$, δ): 8.24-8.22 (m, 1H), 7.32-7.31 (m, 1H), 7.21-7.20 (m, 1H), 4.39 (q, J=7.2 Hz, 2H), 3.22-3.13 (m, 1H), 2.61 (s, 3H), 1.43-1.38 (m, 9H).

Step 2

Ethyl 3-iodo-5-methyl-2-(1-methylcyclopropyl)imidazo[1,2-a]pyridine-7-carboxylate (971 mg, yield 77%) was obtained in the same manner as in step 2 of Example 59, using ethyl 5-methyl-2-(1-methylcyclopropyl)imidazo[1,2-a]pyridine-7-carboxylate obtained in step 1.

$^1$H NMR (300 MHz, CDCl$_3$, δ): 8.23 (d, J=1.0 Hz, 1H), 7.08 (d, J=1.0 Hz, 1H), 4.37 (q, J=7.1 Hz, 2H), 3.30-3.19 (m, 1H), 3.22 (s, 3H), 1.39 (t, J=7.1 Hz, 3H), 1.35 (d, J=6.9 Hz, 6H).

Step 3

Ethyl 3-{(4,4-difluorocyclohexyl)(hydroxy)methyl}-2-isopropyl-5-methylimidazo[1,2-a]pyridine-7-carboxylate (276 mg, yield 52%) was obtained in the same manner as in step 4 of Example 7, using ethyl 3-iodo-5-methyl-2-(1-methylcyclopropyl)imidazo[1,2-a]pyridine-7-carboxylate obtained in step 2, and 4,4-difluorocyclohexanecarbaldehyde.

$^1$H NMR (300 MHz, CDCl$_3$, δ): 8.22 (d, J=1.8 Hz, 1H), 7.14 (d, J=1.8 Hz, 1H), 5.25 (d, J=9.2 Hz, 1H), 4.38 (q, J=7.1 Hz, 2H), 3.50-3.38 (m, 1H), 2.87 (s, 3H), 2.50-0.73 (m, 19H); ESIMS m/z: [M+H]$^+$ 395.

Step 4

Ethyl 3-(4,4-difluorocyclohexylmethyl)-2-isopropyl-5-methylimidazo[1,2-a]pyridine-7-carboxylate (78.1 mg, yield 37%) was obtained in the same manner as in step 4 of Example 59, using ethyl 3-{(4,4-difluorocyclohexyl)(hydroxy)methyl}-2-isopropyl-5-methylimidazo[1,2-a]pyridine-7-carboxylate obtained in step 3.

$^1$H NMR (300 MHz, CDCl$_3$, δ): 8.21 (d, J=1.8 Hz, 1H), 7.07 (d, J=1.8 Hz, 1H), 4.37 (q, J=7.1 Hz, 2H), 3.14-3.05 (m, 1H), 3.03 (d, J=7.0 Hz, 2H), 2.83 (s, 3H), 2.16-2.03 (m, 2H), 1.77-1.32 (m, 16H); ESIMS m/z: [M+H]$^+$ 379.

Step 5

3-(4,4-Difluorocyclohexylmethyl)-2-isopropyl-5-methylimidazo[1,2-a]pyridine-7-carboxylic acid (123 mg, yield 83%) was obtained in the same manner as in step 1 of Example 2, using ethyl 3-(4,4-difluorocyclohexylmethyl)-2-isopropyl-5-methylimidazo[1,2-a]pyridine-7-carboxylate obtained in step 4.

$^1$H NMR (300 MHz, DMSO-d$^6$, δ): 7.86 (s, 1H), 7.05 (s, 1H), 3.17-3.08 (m, 1H), 3.03 (d, J=7.0 Hz, 2H), 2.86 (s, 3H), 2.03-1.59 (m, 7H), 1.33-1.25 (m, 8H); ESIMS m/z: [M+H]$^+$ 351.

Step 6

Compound 100 (62.0 mg, yield 72%) was obtained in the same manner as in step 4 of Example 49, using 3-(4,4-difluorocyclohexylmethyl)-2-isopropyl-5-methylimidazo[1,2-a]pyridine-7-carboxylic acid obtained in step 5, and 4-aminotetrahydropyran hydrochloride.

$^1$H NMR (300 MHz, CDCl$_3$, δ): 7.75 (d, J=1.5 Hz, 1H), 6.98 (d, J=1.5 Hz, 1H), 6.00 (d, J=7.7 Hz, 1H), 4.25-4.12 (m, 1H), 4.03-3.94 (m, 2H), 3.59-3.49 (m, 2H), 3.13-2.99 (m, 3H), 2.84 (s, 3H), 2.17-1.96 (m, 4H), 1.77-1.66 (m, 2H), 1.58-1.52 (m, 7H), 1.35 (d, J=6.6 Hz, 6H); ESIMS m/z: [M+H]$^+$ 434.

Example 61

5-Chloro-3-(4,4-difluorocyclohexylmethyl)-N-phenyl-2-trifluoromethylimidazo[1,2-a]pyridine-7-carboxamide (Compound 102)

Step 1

2-Amino-6-chloroisonicotinic acid (500 mg, 2.90 mmol) was dissolved in ethanol (29.0 mL), and the solution was stirred under heat and reflux for 3 hours after adding thionyl chloride (1.06 mL, 14.5 mmol). The solvent was then evaporated under reduced pressure. The residue was extracted with chloroform after adding a sodium hydrogen carbonate aqueous solution. The organic layer was dried over anhydrous sodium sulfate, and the solvent was evaporated under reduced pressure to give ethyl 2-amino-6-chloroisonicotinate (510 mg, yield 88%).

$^1$H NMR (400 MHz, CDCl$_3$, δ): 7.18 (d, J=1.0 Hz, 1H), 6.96 (d, J=1.0 Hz, 1H), 4.70 (s, 2H), 4.37 (q, J=7.2 Hz, 2H), 1.39 (t, J=7.1 Hz, 3H).

Step 2

Ethyl 2-amino-6-chloroisonicotinate (510 mg, 2.54 mmol) obtained in step 1 was suspended in n-butanol (5.08 mL), and the suspension was stirred overnight at 130° C. after adding 3-bromo-4-(4,4-difluorocyclohexyl)-1,1,1-trifluorobutan-2-one (821 mg, 2.54 mmol) obtained in step 2 of Example 36, and molecular sieve 4A (510 mg). The reaction mixture was allowed to cool to room temperature, and, after adding a sodium hydrogen carbonate aqueous solution, the mixture was filtered through Celite (registered trademark), and extracted with ethyl acetate. The organic layer was washed with water and saturated brine, and dried over anhydrous sodium sulfate. The solvent was then evaporated under reduced pressure. The residue was purified by silica gel column chromatography (hexane/ethyl acetate=9/1→2/1), amino silica gel column chromatography (hexane/ethyl acetate=20/1→9/1), and preparative thin-layer chromatography (hexane/ethyl acetate=9/1) to give ethyl 5-chloro-3-{(4,4-difluorocyclohexyl)methyl}-2-(trifluoromethyl)imidazo[1,2-a]pyridine-7-carboxylate (62.0 mg, yield 5.7%).

$^1$H NMR (400 MHz, CDCl$_3$, δ): 8.35-8.33 (m, 1H), 7.53-7.52 (m, 1H), 4.43 (q, J=7.1 Hz, 2H), 3.36 (d, J=6.8 Hz, 2H), 2.12-1.40 (m, 12H); ESIMS m/z: [M+H]$^+$ 425.

Step 3

Ethyl 5-chloro-3-(4,4-difluorocyclohexylmethyl)-2-trifluoromethylimidazo[1,2-a]pyridine-7-carboxylate (62 mg, 0.146 mmol) obtained in step 2 was suspended in a mixed solvent of THF (2.0 mL) and water (2.0 mL), and the suspension was stirred under heat and reflux for 3 hours after adding sodium hydroxide (29 mg, 0.730 mmol). The reaction mixture was allowed to cool to room temperature, and the solvent was then evaporated under reduced pressure. The residue was extracted with water after adding chloroform. Following neutralization with 1 mol/L hydrochloric acid, the solvent was evaporated under reduced pressure. After adding a mixed solution of chloroform/methanol=4/1 to the residue, the insoluble matter was removed by filtration. The filtrate solvent was evaporated under reduced pressure to give a crude product of 5-chloro-3-(4,4-difluorocyclohexylmethyl)-2-trifluoromethylimidazo[1,2-a]pyridine-7-carboxylic acid (66 mg).

ESIMS m/z: [M–H]⁻ 395.

Step 4

A part of the crude product of 5-chloro-3-(4,4-difluorocyclohexylmethyl)-2-trifluoromethylimidazo[1,2-a]pyridine-7-carboxylic acid obtained in step 3 (28 mg) was dissolved in DMF (2.0 mL), and the solution was stirred overnight at room temperature after adding EDC.HCl (27 mg, 0.141 mmol), HOBt.H$_2$O (22 mg, 0.141 mmol), and aniline (13 mg, 0.141 mmol). The reaction mixture was extracted with ethyl acetate after adding a sodium hydrogen carbonate aqueous solution. The organic layer was washed with water and saturated brine, and dried over anhydrous sodium sulfate. The solvent was then evaporated under reduced pressure. The residue was purified by preparative thin-layer chromatography (chloroform/methanol=9/1) to give 5-chloro-3-(4,4-difluorocyclohexylmethyl)-N-phenyl-2-trifluoromethylimidazo[1,2-a]pyridine-7-carboxamide (18.0 mg, two-step yield 62%).

¹H NMR (400 MHz, CDCl$_3$, δ): 8.02 (d, J=1.6 Hz, 1H), 7.82 (s, 1H), 7.62 (d, J=8.2 Hz, 2H), 7.53 (d, J=1.6 Hz, 1H), 7.41 (t, J=7.9 Hz, 2H), 7.20 (d, J=7.6 Hz, 1H), 3.37 (d, J=6.6 Hz, 2H), 2.10-1.25 (m, 9H); ESIMS m/z: [M+H]⁺ 472.

Example 62

6-Chloro-3-(4,4-difluorocyclohexylmethyl)-N-phenyl-2-trifluoromethylimidazo[1,2-a]pyridine-7-carboxamide (Compound 107)

Step 1

2-Amino-4-cyanopyridine (8.00 g, 67.2 mmol) was dissolved in DMF (40 mL), and the solution was stirred at 50° C. for 1 hour after adding N-chlorosuccinimide (8.97 g, 67.2 mmol). After the reaction was completed, a sodium hydrogen carbonate aqueous solution was added under ice-cooled condition, and the precipitated solid was collected by filteration. The resulting solid was purified by silica gel column chromatography (chloroform/methanol=95/5→90/10, heptane/ethyl acetate=65/35→50/50) to give 2-amino-5-chloro-4-cyanopyridine (6.23 g, yield 60%) and 2-amino-3-chloro-4-cyanopyridine (0.254 g, yield 2%).

2-Amino-5-chloro-4-cyanopyridine

¹H NMR (300 MHz, CDCl$_3$, δ): 8.20 (s, 1H), 6.73 (s, 1H), 4.71 (s, 2H).

2-Amino-3-chloro-4-cyanopyridine

¹H NMR (300 MHz, CDCl$_3$, δ): 8.10 (d, J=5.1 Hz, 1H), 6.89 (d, J=5.1 Hz, 1H), 5.14 (s, 2H).

Step 2

6-Chloro-3-(4,4-difluorocyclohexylmethyl)-2-trifluoromethylimidazo[1,2-a]pyridine-7-carbonitrile (273 mg, yield 23%) was obtained in the same manner as in step 6 of Example 52, using 2-amino-5-chloro-4-cyanopyridine obtained in step 1, and 3-bromo-4-(4,4-difluorocyclohexyl)-1,1,1-trifluorobutan-2-one obtained in step 2 of Example 36.

¹H NMR (300 MHz, CDCl$_3$, δ): 8.12 (s, 1H), 8.11 (s, 1H), 3.02 (d, J=7.0 Hz, 2H), 2.16-2.07 (m, 2H), 1.66-1.49 (m, 7H).

Step 3

6-Chloro-3-(4,4-difluorocyclohexylmethyl)-2-trifluoromethylimidazo[1,2-a]pyridine-7-carboxylic acid (567 mg, yield 76%) was obtained in the same manner as in step 2 of Example 7, using 6-chloro-3-(4,4-difluorocyclohexylmethyl)-2-trifluoromethylimidazo[1,2-a]pyridine-7-carbonitrile obtained in step 2.

¹H NMR (300 MHz, DMSO-d⁶, δ): 8.97 (s, 1H), 8.14 (s, 1H), 3.08 (d, J=7.3 Hz, 2H), 2.06-1.55 (m, 8H), 1.41-1.21 (m, 2H); ESIMS m/z: [M+H]⁺ 397.

Step 4

Compound 107 (40.9 mg, yield 69%) was obtained in the same manner as in step 4 of Example 21, using 6-chloro-3-(4,4-difluorocyclohexylmethyl)-2-trifluoromethylimidazo[1,2-a]pyridine-7-carboxylic acid obtained in step 3, and aniline.

¹H NMR (300 MHz, CDCl$_3$, δ): 8.07 (s, 1H), 8.04 (s, 1H), 7.86 (br s, 1H), 7.68-7.62 (m, 2H), 7.46-7.37 (m, 2H), 7.25-7.19 (m, 1H), 3.02 (d, J=7.0 Hz, 2H), 2.20-2.07 (m, 2H), 1.79-1.43 (m, 7H); ESIMS m/z: [M+H]⁺ 472, 474.

Example 63

6-Chloro-3-(4,4-difluorocyclohexylmethyl)-2-(1,1-difluoroethyl)-N-(tetrahydro-2H-pyran-4-yl)imidazo[1,2-a]pyridine-7-carboxamide (Compound 109)

Step 1

6-Chloro-3-(4,4-difluorocyclohexylmethyl)-2-(1,1-difluoroethyl)imidazo[1,2-a]pyridine-7-carbonitrile (491 mg, yield 45%) was obtained in the same manner as in step 6 of Example 52, using 2-amino-5-chloro-4-cyanopyridine obtained in step 1 of Example 62, and 2-bromo-1-(4,4-difluorocyclohexyl)-4,4-difluoropenta-3-one obtained in step 5 of Example 56.

¹H NMR (300 MHz, CDCl$_3$, δ): 8.08 (s, 1H), 8.05 (s, 1H), 3.03 (d, J=7.0 Hz, 2H), 2.20-2.07 (m, 5H), 1.80-1.40 (m, 7H); ESIMS m/z: [M+H]⁺ 374, 376.

Step 2

6-Chloro-3-(4,4-difluorocyclohexylmethyl)-2-(1,1-difluoroethyl)imidazo[1,2-a]pyridine-7-carboxylic acid (480 mg, yield 94%) was obtained in the same manner as in step 2 of Example 7, using 6-chloro-3-(4,4-difluorocyclohexylmethyl)-2-(1,1-difluoroethyl)imidazo[1,2-a]pyridine-7-carbonitrile obtained in step 1.

¹H NMR (300 MHz, DMSO-d⁶, δ): 8.85 (s, 1H), 8.03 (s, 1H), 3.06 (d, J=7.3 Hz, 2H), 2.08 (t, J=19.1 Hz, 3H), 2.04-1.56 (m, 7H), 1.41-1.21 (m, 2H); ESIMS m/z: [M+H]⁺ 393, 395.

Step 3

Compound 109 (72.0 mg, yield 74%) was obtained in the same manner as in step 4 of Example 49, using 6-chloro-3-(4,4-difluorocyclohexylmethyl)-2-(1,1-difluoroethyl)imidazo[1,2-a]pyridine-7-carboxylic acid obtained in step 2, and 4-aminotetrahydropyran hydrochloride.

¹H NMR (300 MHz, CDCl$_3$, δ): 8.01 (s, 1H), 7.91 (s, 1H), 6.04 (d, J=8.1 Hz, 1H), 4.30-4.19 (m, 1H), 4.04-3.97 (m, 2H), 3.61-3.49 (m, 2H), 3.02 (d, J=7.3 Hz, 2H), 2.13 (t, J=18.7 Hz, 3H), 2.13-2.01 (m, 4H), 1.83-1.39 (m, 9H); ESIMS m/z: [M+H]⁺ 476, 478.

Example 64

6-Chloro-3-(4,4-difluorocyclohexylmethyl)-2-isopropyl-N-(tetrahydro-2H-pyran-4-yl)imidazo[1,2-a]pyridine-7-carboxamide (Compound 111)

Step 1

1-(4,4-Difluorocyclohexyl)-4-methylpenta-1-en-3-one (2.34 g, yield 70%) was obtained in the same manner as in step 1 of Example 34, using dimethyl 3-methyl-oxobutylphosphate obtained according to the method described in U.S. Pat. No. 4,775,692, and 4,4-difluorocyclohexanecarbaldehyde.

$^1$H NMR (300 MHz, CDCl$_3$, δ): 6.80 (dd, J=15.8, 6.6 Hz, 1H), 6.18 (d, J=15.8 Hz, 1H), 2.85-2.76 (m, 1H), 2.43-0.99 (m, 15H).

Step 2

1-(4,4-Difluorocyclohexyl)-4-methylpentan-3-one (1.46 g, yield 62%) was obtained in the same manner as in step 3 of Example 52, using 1-(4,4-difluorocyclohexyl)-4-methylpenta-1-en-3-one obtained in step 2.

$^1$H NMR (300 MHz, CDCl$_3$, δ): 2.67-2.53 (m, 1H), 2.47 (t, J=7.7 Hz, 2H), 2.13-2.00 (m, 2H), 1.80-1.18 (m, 9H), 1.10 (d, J=7.0 Hz, 6H).

Step 3

2-Bromo-1-(4,4-difluorocyclohexyl)-4-methylpentan-3-one (1.84 g, yield 93%) was obtained in the same manner as in step 3 of Example 6, using 1-(4,4-difluorocyclohexyl)-4-methylpentan-3-one obtained in step 2.

$^1$H NMR (300 MHz, CDCl$_3$, δ): 4.46 (dd, J=8.8, 6.2 Hz, 1H), 3.11-3.01 (m, 1H), 2.19-1.25 (m, 11H), 1.19 (d, J=6.6 Hz, 3H), 1.14 (d, J=7.0 Hz, 3H).

Step 4

6-Chloro-3-(4,4-difluorocyclohexylmethyl)-2-isopropylimidazo[1,2-a]pyridine-7-carbonitrile (128 mg, yield 8%) was obtained in the same manner as in step 6 of Example 52, using 2-bromo-1-(4,4-difluorocyclohexyl)-4-methylpentan-3-one obtained in step 3, and 2-amino-5-chloro-4-cyanopyridine.

$^1$H NMR (300 MHz, CDCl$_3$, δ): 7.98 (s, 1H), 7.97 (s, 1H), 3.15-3.06 (m, 1H), 2.84 (d, J=6.6 Hz, 2H), 2.17-2.05 (m, 2H), 1.82-1.41 (m, 7H), 1.35 (d, J=7.0 Hz, 6H).

Step 5

6-Chloro-3-(4,4-difluorocyclohexylmethyl)-2-isopropylimidazo[1,2-a]pyridine-7-carboxylic acid (114 mg, yield 90%) was obtained in the same manner as in step 2 of Example 7, using 6-chloro-3-(4,4-difluorocyclohexylmethyl)-2-isopropylimidazo[1,2-a]pyridine-7-carbonitrile obtained in step 4.

$^1$H NMR (300 MHz, DMSO-d$^6$, δ): 13.38 (br s, 1H), 8.66 (s, 1H), 7.99 (s, 1H), 3.18-3.08 (m, 1H), 2.92 (d, J=6.9 Hz, 2H), 2.01-1.57 (m, 7H), 1.40-1.28 (m, 2H), 1.25 (d, J=6.6 Hz, 6H); ESIMS m/z: [M+H]$^+$ 371, 373.

Step 6

Compound 111 (41.5 mg, yield 51%) was obtained in the same manner as in step 4 of Example 49, using 6-chloro-3-(4,4-difluorocyclohexylmethyl)-2-isopropylimidazo[1,2-a]pyridine-7-carboxylic acid obtained in step 5, and 4-aminotetrahydropyran hydrochloride.

$^1$H NMR (300 MHz, CDCl$_3$, δ): 7.91 (s, 1H), 7.90 (s, 1H), 6.04 (d, J=7.7 Hz, 1H), 4.31-4.16 (m, 1H), 4.04-3.95 (m, 2H), 3.59-3.49 (m, 2H), 3.15-3.03 (m, 1H), 2.83 (d, J=6.6 Hz, 2H), 2.16-2.00 (m, 4H), 1.81-1.31 (m, 9H), 1.35 (d, J=6.6 Hz, 6H); ESIMS m/z: [M+H]$^+$ 454, 456.

Example 65

2-tert-Butyl-6-chloro-3-(4,4-difluorocyclohexylmethyl)-N-(tetrahydro-2H-pyran-4-yl)imidazo[1,2-a]pyridine-7-carboxamide (Compound 113)

Step 1

2-tert-Butyl-6-chloro-3-(4,4-difluorocyclohexylmethyl)imidazo[1,2-a]pyridine-7-carbonitrile (161 mg, yield 9%) was obtained in the same manner as in step 6 of Example 52, using 2-bromo-1-(4,4-difluorocyclohexylmethyl)-4,4-dimethylpentan-3-one obtained in step 4 of Example 34, and 2-amino-5-chloro-4-cyanopyridine obtained in step 1 of Example 62.

$^1$H NMR (300 MHz, CDCl$_3$, δ): 7.97 (s, 2H), 3.00 (d, J=7.3 Hz, 2H), 2.20-2.09 (m, 2H), 1.81-1.16 (m, 16H).

Step 2

2-tert-Butyl-6-chloro-3-(4,4-difluorocyclohexylmethyl)imidazo[1,2-a]pyridine-7-carboxylic acid (139 mg, yield 88%) was obtained in the same manner as in step 2 of Example 7, using 2-tert-butyl-6-chloro-3-(4,4-difluorocyclohexylmethyl)imidazo[1,2-a]pyridine-7-carbonitrile obtained in step 1.

$^1$H NMR (300 MHz, DMSO-d$^6$, δ): 8.66 (s, 1H), 7.96 (s, 1H), 3.06 (d, J=7.3 Hz, 2H), 2.06-1.19 (m, 18H); ESIMS m/z: [M+H]$^+$ 385, 387.

Step 3

Compound 113 (62.8 mg, yield 65%) was obtained in the same manner as in step 4 of Example 49, using 2-tert-butyl-6-chloro-3-(4,4-difluorocyclohexylmethyl)imidazo[1,2-a]pyridine-7-carboxylic acid obtained in step 2, and 4 aminotetrahydropyran hydrochloride.

$^1$H NMR (300 MHz, CDCl$_3$, δ): 7.91 (s, 1H), 7.89 (s, 1H), 6.05 (d, J=7.7 Hz, 1H), 4.28-4.17 (m, 1H), 4.04-3.94 (m, 2H), 3.59-3.48 (m, 2H), 2.98 (d, J=7.3 Hz, 2H), 2.18-2.00 (m, 4H), 1.72-1.19 (m, 18H); ESIMS m/z: [M+H]$^+$ 468, 470.

Example 66

6-Chloro-3-(4,4-difluorocyclohexylmethyl-2-(propa-1-en-2-yl)-N-(tetrahydro-2H-pyran-4-yl)imidazo[1,2-a]pyridine-7-carboxamide (Compound 116)

Step 1

Dimethyl 3-fluoro-3-methyl-2-oxobutylphosphate (7.71 g, yield 73%) was obtained in the same manner as in step 1 of Example 52, using ethyl 2-fluoro-2-methylpropionate.

$^1$H NMR (300 MHz, CDCl$_3$, δ): 3.81 (d, J=11.4 Hz, 6H), 3.36 (dd, J=22.4, 4.0 Hz, 2H), 1.50 (d, J=21.3 Hz, 6H).

Step 2

1-(4,4-Difluorocyclohexyl)-4-fluoro-4-methylpenta-1-en-3-one (93.2 mg, yield 17%) was obtained in the same manner as in step 1 of Example 34, using dimethyl 3-fluoro-3-methyl-2-oxobutylphosphate obtained in step 1, and 4,4-difluorocyclohexanecarbaldehyde.

$^1$H NMR (300 MHz, CDCl$_3$, δ): 7.00 (dd, J=15.8, 7.0 Hz, 1H), 6.68 (ddd, J=15.8, 3.7, 1.5 Hz, 1H), 2.36-2.23 (m, 1H), 2.22-2.07 (m, 2H), 1.94-1.53 (m, 6H), 1.49 (t, J=12.6 Hz, 6H).

Step 3

1-(4,4-Difluorocyclohexyl)-4-fluoro-4-methylpentan-3-one (1.24 g, yield 81%) was obtained in the same manner as in step 3 of Example 52, using 1-(4,4-difluorocyclohexyl)-4-fluoro-4-methylpenta-1-en-3-one obtained in step 2.

$^1$H NMR (300 MHz, CDCl$_3$, δ): 2.69 (td, J=7.6, 3.2 Hz, 2H), 2.16-2.01 (m, 2H), 1.85-1.51 (m, 6H), 1.45 (d, J=21.6 Hz, 6H), 1.39-1.20 (m, 3H).

Step 4

2-Bromo-1-(4,4-difluorocyclohexyl)-4-fluoro-4-methylpentan-3-one (44.5 mg, yield 67%) was obtained in the same manner as in step 1 of Example 1, using 1-(4,4-difluorocyclohexyl)-4-fluoro-4-methylpentan-3-one obtained in step 3.

$^1$H NMR (300 MHz, CDCl$_3$, δ): 4.97-4.90 (m, 1H), 2.17-1.18 (m, 17H).

Step 5

6-Chloro-3-(4,4-difluorocyclohexylmethyl)-2-(propa-1-en-2-yl)imidazo[1,2-a]pyridine-7-carbonitrile (202 mg, yield 18%) was obtained in the same manner as in step 6 of Example 52, using 2-bromo-1-(4,4-difluorocyclohexyl)-4-fluoro-4-methylpentan-3-one obtained in step 4, and 2-amino-5-chloro-4-cyanopyridine obtained in step 1 of Example 62.

$^1$H NMR (300 MHz, CDCl$_3$, δ): 8.02 (s, 1H), 7.99 (s, 1H), 5.43-5.39 (m, 2H), 3.01 (d, J=7.0 Hz, 2H), 2.26-2.24 (m, 3H), 2.17-2.02 (m, 2H), 1.83-1.18 (m, 7H); ESIMS m/z: [M+H]$^+$ 350, 352.

Step 6

6-Chloro-3-(4,4-difluorocyclohexylmethyl)-2-(propa-1-en-2-yl)imidazo[1,2-a]pyridine-7-carboxylic acid (146 mg, yield 69%) was obtained in the same manner as in step 2 of Example 7, using 6-chloro-3-(4,4-difluorocyclohexylmethyl)-2-(propa-1-en-2-yl)imidazo[1,2-a]pyridine-7-carbonitrile obtained in step 5.

$^1$H NMR (300 MHz, DMSO-d$^6$, δ): 8.90 (s, 1H), 8.06 (s, 1H), 5.52 (s, 1H), 5.40 (s, 1H), 3.11 (d, J=7.3 Hz, 2H), 2.19 (s, 3H), 2.07-0.83 (m, 9H); ESIMS m/z: [M+H]$^+$ 369, 371.

Step 7

Compound 116 (42.9 mg, yield 35%) was obtained in the same manner as in step 4 of Example 49, using 6-chloro-3-(4,4-difluorocyclohexylmethyl)-2-(propa-1-en-2-yl)imidazo[1,2-a]pyridine-7-carboxylic acid obtained in step 6, and 4-aminotetrahydropyran hydrochloride.

$^1$H NMR (300 MHz, CDCl$_3$, δ): 7.95 (s, 1H), 7.90 (s, 1H), 6.05 (d, J=7.0 Hz, 1H), 5.40-5.38 (m, 1H), 5.37-5.34 (m, 1H), 4.31-4.17 (m, 1H), 4.05-3.96 (m, 2H), 3.60-3.49 (m, 2H), 2.99 (d, J=7.0 Hz, 2H), 2.26-2.24 (m, 3H), 2.17-2.02 (m, 4H), 1.88-1.33 (m, 9H); ESIMS m/z: [M+H]$^+$ 452, 454.

Example 67

6-Bromo-3-(4,4-difluorocyclohexylmethyl)-N-phenyl-2-trifluoromethylimidazo[1,2-a]pyridine-7-carboxamide (Compound 117)

Step 1

6-Bromo-3-(4,4-difluorocyclohexylmethyl)-2-trifluoromethylimidazo[1,2-a]pyridine-7-carbonitrile (141 mg, yield 18%) was obtained in the same manner as in step 6 of Example 52, using 2-amino-5-bromoisonicotinonitrile, and 3-bromo-4-(4,4-difluorocyclohexyl)-1,1,1-trifluorobutan-2-one obtained in step 2 of Example 36.

$^1$H NMR (300 MHz, CDCl$_3$, δ): 8.22 (s, 1H), 8.11 (s, 1H), 3.02 (d, J=7.3 Hz, 2H), 2.20-2.01 (m, 2H), 1.83-1.44 (m, 7H); ESIMS m/z: [M+H]$^+$ 422, 424.

Step 2

6-Bromo-3-(4,4-difluorocyclohexylmethyl)-2-trifluoromethylimidazo[1,2-a]pyridine-7-carboxylic acid (56.8 mg, yield 50%) was obtained in the same manner as in step 2 of Example 7, using 6-bromo-3-(4,4-difluorocyclohexylmethyl)-2-trifluoromethylimidazo[1,2-a]pyridine-7-carbonitrile obtained in step 1.

$^1$H NMR (300 MHz, CDCl$_3$, δ): 9.02 (s, 1H), 8.09 (s, 1H), 3.08 (d, J=7.3 Hz, 2H), 2.04-1.21 (m, 9H); ESIMS m/z: [M+H]$^+$ 441, 443.

Step 3

Compound 117 (8.20 mg, yield 23%) was obtained in the same manner as in step 4 of Example 21, using 6-bromo-3-(4,4-difluorocyclohexylmethyl)-2-trifluoromethylimidazo[1,2-a]pyridine-7-carboxylic acid obtained in step 2, and aniline.

$^1$H NMR (300 MHz, CDCl$_3$, δ): 8.17 (s, 1H), 7.92 (s, 1H), 7.81 (s, 1H), 7.65 (d, J=8.1 Hz, 2H), 7.41 (t, J=7.9 Hz, 2H), 7.22 (t, J=7.3 Hz, 1H), 3.02 (d, J=7.3 Hz, 2H), 2.19-1.38 (m, 9H); ESIMS m/z: [M+H]$^+$ 516, 518.

Example 68

3-(4,4-Difluorocyclohexylmethyl)-6-methyl-N-(tetrahydro-2H-pyran-4-yl)-2-trifluoromethylimidazo[1,2-a]pyridine-7-carboxamide (Compound 118)

Step 1

3-(4,4-Difluorocyclohexylmethyl)-6-methyl-2-trifluoromethylimidazo[1,2-a]pyridine-7-carbonitrile (24.1 mg, yield 22%) was obtained in the same manner as in step 2 of Example 39, using 6-bromo-3-(4,4-difluorocyclohexylmethyl)-2-trifluoromethylimidazo[1,2-a]pyridine-7-carbonitrile obtained in step 1 of Example 67.

$^1$H NMR (300 MHz, CDCl$_3$, δ): 8.05 (s, 1H), 7.84 (s, 1H), 3.01 (d, J=7.3 Hz, 2H), 2.57 (d, J=0.7 Hz, 3H), 2.16-2.06 (m, 2H), 1.43-1.40 (m, 7H); ESIMS m/z: [M+H]$^+$ 358.

Step 2

3-(4,4-Difluorocyclohexylmethyl)-6-methyl-2-trifluoromethylimidazo[1,2-a]pyridine-7-carboxylic acid (24.9 mg, yield 98%) was obtained in the same manner as in step 2 of Example 7, using 3-(4,4-difluorocyclohexylmethyl)-6-methyl-2-trifluoromethylimidazo[1,2-a]pyridine-7-carbonitrile obtained in step 1.

$^1$H NMR (300 MHz, CDOD3, δ): 8.25 (s, 1H), 8.14 (s, 1H), 3.08 (d, J=7.0 Hz, 2H), 2.58 (d, J=0.7 Hz, 3H), 2.17-1.36 (m, 9H); ESIMS m/z: [M+H]$^+$ 377.

Step 3

Compound 118 (57.4 mg, yield 67%) was obtained in the same manner as in step 4 of Example 49, using 3-(4,4-difluorocyclohexylmethyl)-6-methyl-2-trifluoromethylimidazo[1,2-a]pyridine-7-carboxylic acid obtained in step 2, and 4-aminotetrahydropyran hydrochloride.

$^1$H NMR (300 MHz, CDCl$_3$, δ): 7.73 (s, 1H), 7.66 (s, 1H), 5.83 (d, J=7.7 Hz, 1H), 4.27-4.13 (m, 1H), 4.06-3.97 (m, 2H), 3.60-3.49 (m, 2H), 2.99 (d, J=7.0 Hz, 2H), 2.46 (s, 3H), 2.18-1.99 (m, 5H), 1.82-1.37 (m, 8H); ESIMS m/z: [M−H]$^−$ 458.

Example 69

3-(4,4-Dicyclohexylmethyl)-6-methoxy-N-(tetrahydro-2H-pyran-4-yl)-2-trifluoromethylimidazo[1,2-a]pyridine-7-carboxamide (Compound 119)

Step 1

2-Bromo-5-fluoroisonicotinic acid (500 mg, 2.27 mmol) was dissolved in ethanol (22.7 mL), and the solution was stirred under heat and reflux for 1 hour after adding thionyl chloride (0.829 mL, 11.3 mmol). The solvent was then evaporated under reduced pressure. The residue was extracted with chloroform after adding a sodium hydrogen carbonate aqueous solution. The organic layer was dried over anhydrous sodium sulfate, and the solvent was then evaporated under reduced pressure. The residue was purified by silica gel column chromatography (hexane/ethyl acetate=100/0→4/1) to give ethyl 2 bromo-5-fluoroisonicotinate (434 mg, yield 77%).

$^1$H NMR (400 MHz, CDCl$_3$, δ): 8.38-8.38 (m, 1H), 7.92-7.78 (m, 1H), 4.48-4.40 (m, 2H), 1.40-1.35 (m, 3H).

Step 2

Ethyl 2-bromo-5-fluoroisonicotinate (434 mg, 1.75 mmol) obtained in step 1 was dissolved in methanol (3.50 mL), and the solution was stirred at room temperature for 30 minutes after adding a 28% sodium methoxide-methanol solution (1.69 g, 8.75 mmol). The reaction mixture was extracted with ethyl acetate after adding water. The organic layer was washed with water and saturated brine, and dried over anhydrous sodium sulfate. The solvent was evaporated under reduced pressure to give methyl 2-bromo-5-methoxyisonicotinate (154 mg, yield 36%).

$^1$H NMR (400 MHz, CDCl$_3$, δ): 8.18 (s, 1H), 7.73-7.60 (m, 1H), 3.99-3.99 (m, 3H), 3.93-3.93 (m, 3H); ESIMS m/z: [M+H]$^+$ 246, 248.

Step 3

Tris(dibenzylideneacetone)dipalladium(0) (9.30 mg, 0.0102 mmol), 2-(dicyclohexylphosphino)biphenyl (3.56 mg, 0.0102 mmol), and methyl 2-bromo-5-methoxyisonicotinate (50 mg, 0.203 mmol) obtained in step 2 were suspended in toluene (0.5 mL), and the suspension was stirred at room temperature for 3 hours after adding lithium bis(trimethylsilyl)amide (1 mol/L THF solution) (0.224 mL, 0.224 mmol). The reaction mixture was stirred at room temperature for 10 minutes after adding diethyl ether (10 mL) and 1 mol/L hydrochloric acid (0.1 mL). Then, a 1 mol/L sodium hydroxide aqueous solution (5.0 mL) was added to the mixture, and the mixture was extracted with diethyl ether. The organic layer was washed with water and saturated brine, and dried over anhydrous sodium sulfate. The solvent was then evaporated under reduced pressure. The residue was purified by preparative thin-layer chromatography (chloroform/methanol=9/1) to give methyl 2-amino-5-methoxyisonicotinate (20.0 mg, yield 54%).

$^1$H NMR (400 MHz, CDCl$_3$, δ): 7.90 (s, 1H), 6.83 (s, 1H), 4.36-4.30 (m, 2H), 3.91 (s, 3H), 3.88 (s, 3H); ESIMS m/z: [M+H]$^+$ 183.

Step 4

Methyl 2-amino-5-methoxyisonicotinate (20 mg, 0.110 mmol) obtained in step 3 was suspended in n-butanol (1.10 mL), and the suspension was stirred overnight at 130° C. after adding 3-bromo-4-(4,4-difluorocyclohexyl)-1,1,1-trifluorobutan-2-one (53 mg, 0.165 mmol) obtained in step 2 of Example 36, and molecular sieve 4A (20 mg). The reaction mixture was allowed to cool to room temperature, filtered through Celite (registered trademark) after adding a sodium hydrogen carbonate aqueous solution, and extracted with ethyl acetate. The organic layer was washed with water and saturated brine, and dried over anhydrous sodium sulfate. The solvent was then evaporated under reduced pressure. The residue was purified by preparative thin-layer chromatography (chloroform/methanol=15/1) to give methyl 3-(4,4-difluorocyclohexylmethyl)-6-methoxy-2-(trifluoromethyl)imidazo[1,2-a]pyridine-7-carboxylate (23.0 mg, yield 52%).

$^1$H NMR (400 MHz, CDCl$_3$, δ): 8.11 (s, 1H), 7.42 (s, 1H), 3.95 (s, 3H), 3.94 (s, 3H), 3.55-3.50 (m, 2H), 2.10-1.26 (m, 9H); ESIMS m/z: [M+H]$^+$ 407.

Step 5

Methyl 3-(4,4-difluorocyclohexylmethyl)-6-methoxy-2-(trifluoromethyl)imidazo[1,2-a]pyridine-7-carboxylate (23 mg, 0.057 mmol) obtained in step 4 was suspended in a mixed solvent of THF (1.0 mL) and water (1.0 mL), and the suspension was stirred under heat and reflux for 3 hours after adding sodium hydroxide (11 mg, 0.283 mmol). The reaction mixture was allowed to cool to room temperature, and the solvent was evaporated under reduced pressure. The residue was extracted with water after adding chloroform, then neutralized with 1 mol/L hydrochloric acid, the solvent was evaporated under reduced pressure. After adding a mixed solution of chloroform/methanol=4/1 to the residue, the insoluble matter was removed by filtration. The filtrate solvent was evaporated under reduced pressure to give 3-(4,4-difluorocyclohexylmethyl)-6-methoxy-2-(trifluoromethyl)imidazo[1,2-a]pyridine-7-carboxylic acid (22.0 mg, yield 99%).

$^1$H NMR (400 MHz, CD$_3$OD, δ): 7.77 (s, 1H), 7.49 (s, 1H), 3.92 (s, 3H), 3.07 (d, J=7.6 Hz, 2H), 2.00-0.90 (m, 9H); ESIMS m/z: [M–H]$^-$ 391.

Step 6

3-(4,4-Difluorocyclohexylmethyl)-6-methoxy-2-(trifluoromethyl)imidazo[1,2-a]pyridine-7-carboxylic acid (22 mg, 0.056 mmol) obtained in step 5 was dissolved in DMF (2.0 mL), and the solution was stirred overnight at room temperature after adding EDC.HCl (21 mg, 0.112 mmol), HOBt.H$_2$O (17 mg, 0.112 mmol), triethylamine (0.016 mL, 0.112 mmol), and tetrahydro-2H-pyran-4-amine hydrochloride (15 mg, 0.112 mmol). The reaction mixture was allowed to cool to room temperature, and extracted with ethyl acetate after adding a sodium hydrogen carbonate aqueous solution. The organic layer was washed with water and saturated brine, and dried over anhydrous sodium sulfate. The solvent was then evaporated under reduced pressure. The residue was purified by preparative thin-layer chromatography (chloroform/methanol=9/1) to give 3-(4,4-dicyclohexylmethyl)-6-methoxy-N-(tetrahydro-2H-pyran-4-yl)-2-trifluoromethylimidazo[1,2-a]pyridine-7-carboxamide (10.0 mg, yield 38%).

$^1$H NMR (400 MHz, CDCl$_3$, δ): 8.54 (s, 1H), 7.52 (d, J=6.9 Hz, 1H), 7.45 (s, 1H), 4.31-4.19 (m, 1H), 4.02-3.98 (m, 5H), 3.60-3.52 (m, 2H), 2.99 (d, J=6.9 Hz, 2H), 2.06-0.85 (m, 13H); ESIMS m/z: [M+H]$^+$ 476.

Example 70

3-(4,4-Difluorocyclohexylmethyl)-N-phenyl-2-trifluoromethyl-6-vinylimidazo[1,2-a]pyridine-7-carboxamide (Compound 120)

Step 1

2-Amino-4-cyano-5-iodopyridine (597 mg, yield 29%) was obtained in the same manner as in step 2 of Example 59, using 2-amino-4-cyanopyridine.

$^1$H NMR (300 MHz, CDCl$_3$, δ): 8.44 (s, 1H), 6.76 (d, J=0.7 Hz, 1H), 4.72 (br s, 2H).

Step 2

3-(4,4-Difluorocyclohexylmethyl)-6-iodo-2-trifluoromethylimidazo[1,2-a]pyridine-7-carbonitrile (401 mg, yield 36%) was obtained in the same manner as in step 6 of Example 52, using 2-amino-4-cyano-5-iodopyridine obtained in step 1, and 3-bromo-4-(4,4-difluorocyclohexyl)-1,1,1-trifluorobutan-2-one obtained in step 2 of Example 36.

$^1$H NMR (300 MHz, CDCl$_3$, δ): 8.33 (s, 1H), 8.07 (s, 1H), 3.01 (d, J=7.0 Hz, 2H), 2.24-2.02 (m, 4H), 1.83-1.22 (m, 5H); ESIMS m/z: [M+H]$^-$ 468.

Step 3

3-(4,4-Difluorocyclohexylmethyl)-6-iodo-2-trifluoromethylimidazo[1,2-a]pyridine-7-carbonitrile (20.0 mg, 0.0430 mmol) obtained in step 2 was dissolved in 1,2-dichloromethane (0.60 mL), and the solution was stirred at 60° C. for 1 hour after adding 4,4,5,5-tetramethyl-2-vinyl-1,3,2-dioxaborolane (24.0 mg, 0.153 mmol), tetrakis(triphenylphosphine)palladium(0) (4.93 mg, 0.00426 mmol), and water (0.2 mL). The reaction mixture was filtered through Celite (registered trademark), and the solvent was evaporated under reduced pressure. The residue was purified by silica gel column chromatography (hexane/ethyl acetate=90/10→50/50) to give 3-(4,4-difluorocyclohexylmethyl)-2-trifluoromethyl-6-vinylimidazo[1,2-a]pyridine-7-carbonitrile (11.0 mg, yield 70%).

$^1$H NMR (300 MHz, CDCl$_3$, δ): 8.08 (s, 1H), 8.05 (s, 1H), 6.93 (dd, J=17.4, 11.2 Hz, 1H), 5.94 (d, J=17.2 Hz, 1H), 5.65 (d, J=11.0 Hz, 1H), 3.05 (d, J=7.0 Hz, 2H), 2.24-2.03 (m, 2H), 1.87-1.21 (m, 7H); ESIMS m/z: [M+H]$^+$ 370.

Step 4

3-(4,4-Difluorocyclohexylmethyl)-2-trifluoromethyl-6-vinylimidazo[1,2-a]pyridine-7-carboxylic acid (32.3 mg, yield 61%) was obtained in the same manner as in step 2 of Example 7, using 3-(4,4-difluorocyclohexylmethyl)-2-trifluoromethyl-6-vinylimidazo[1,2-a]pyridine-7-carbonitrile obtained in step 3.

$^1$H NMR (300 MHz, DMSO-d$^6$, δ): 8.57 (s, 1H), 8.10 (s, 1H), 7.23 (dd, J=17.2, 11.0 Hz, 1H), 5.78 (dd, J=17.2, 1.1 Hz, 1H), 5.39 (dd, J=11.0, 1.1 Hz, 1H), 3.15 (d, J=7.0 Hz, 2H), 2.02-1.26 (m, 9H); ESIMS m/z: [M+H]$^+$ 389.

Step 5

Compound 120 (16.1 mg, yield 54%) was obtained in the same manner as in step 4 of Example 21, using 3-(4,4-difluorocyclohexylmethyl)-2-trifluoromethyl-6-vinylimidazo[1,2-a]pyridine-7-carboxylic acid obtained in step 4, and aniline.

$^1$H NMR (300 MHz, CDCl$_3$, δ): 8.02-7.84 (m, 3H), 7.64 (d, J=7.7 Hz, 2H), 7.39 (dd, J=7.7, 7.5 Hz, 2H), 7.20 (t, J=7.5 Hz, 1H), 7.05 (dd, J=17.2, 11.0 Hz, 1H), 5.68 (d, J=17.2 Hz, 1H), 5.48 (d, J=11.0 Hz, 1H), 3.03 (d, J=7.0 Hz, 2H), 2.20-1.39 (m, 9H); ESIMS m/z: [M+H]$^+$ 464.

Example 71

8-Chloro-3-(4,4-difluorocyclohexylmethyl)-N-(tetrahydro-2H-pyran-4-yl)-2-trifluoromethylimidazo[1,2-a]pyridine-7-carboxamide (Compound 123)

Step 1

8-Chloro-3-(4,4-difluorocyclohexylmethyl)-2-trifluoromethylimidazo[1,2-a]pyridine-7-carbonitrile (110 mg, yield 31%) was obtained in the same manner as in step 6 of Example 52, using 2-amino-3-chloro-4-cyanopyridine obtained in step 1 of Example 62, and 3-bromo-4-(4,4-difluorocyclohexyl)-1,1,1-trifluorobutan-2-one obtained in step 2 of Example 36.

$^1$H NMR (300 MHz, CDCl$_3$, δ): 7.99 (d, J=7.3 Hz, 1H), 7.10 (d, J=7.3 Hz, 1H), 3.04 (d, J=7.0 Hz, 2H), 2.17-2.05 (m, 2H), 1.78-1.43 (m, 7H).

Step 2

8-Chloro-3-(4,4-difluorocyclohexylmethyl)-2-trifluoromethylimidazo[1,2-a]pyridine-7-carboxylic acid (100 mg, yield 85%) was obtained in the same manner as in step 2 of Example 7, using 8-chloro-3-(4,4-difluorocyclohexylmethyl)-2-trifluoromethylimidazo[1,2-a]pyridine-7-carbonitrile obtained in step 1.

$^1$H NMR (300 MHz, DMSO-d$^6$, δ): 8.65 (d, J=7.2 Hz, 1H), 7.37 (d, J=7.2 Hz, 1H), 3.07 (d, J=7.2 Hz, 2H), 1.89-1.39 (m, 9H); ESIMS m/z: [M+H]$^+$ 397.

Step 3

Compound 123 (46.7 mg, yield 48%) was obtained in the same manner as in step 4 of Example 49, using 8-chloro-3-(4,4-difluorocyclohexylmethyl)-2-trifluoromethylimidazo[1,2-a]pyridine-7-carboxylic acid obtained in step 2, and 4-aminotetrahydropyran hydrochloride.

$^1$H NMR (300 MHz, CDCl$_3$, δ): 7.94 (d, J=7.1 Hz, 1H), 7.38 (d, J=7.1 Hz, 1H), 6.50 (d, J=6.6 Hz, 1H), 4.33-4.21 (m, 1H), 4.07-3.97 (m, 2H), 3.62-3.50 (m, 2H), 3.02 (d, J=7.1 Hz, 2H), 2.18-2.02 (m, 4H), 1.81-1.41 (m, 9H); ESIMS m/z: [M+H]$^+$ 480, 482.

Example 72

6-Chloro-3-(4,4-difluorocyclohexylmethyl)-5-methyl-N-(tetrahydro-2H-pyran-4-yl)-2-trifluoromethylimidazo[1,2-a]pyridine-7-carboxamide (Compound 124)

Step 1

Ethyl 6-amino-2-methylisonicotinate (2.00 g, 11.1 mmol) was dissolved in DMF (20 mL), and the solution was stirred at 50° C. for 1 hour after adding N-chlorosuccinimide (1.48 g, 11.1 mmol). The reaction mixture was allowed to cool to room temperature, and a sodium hydrogen carbonate aqueous solution was added. The precipitated solid was collected by filteration to give ethyl 6-amino-3-chloro-2-methylisonicotinate (1.36 g, yield 57%).

$^1$H NMR (300 MHz, CDCl$_3$, δ): 6.58 (s, 1H), 4.48 (s, 2H), 4.39 (q, J=7.1 Hz, 2H), 2.50 (s, 3H), 1.39 (t, J=7.1 Hz, 3H).

Step 2

Ethyl 6-chloro-3-(4,4-difluorocyclohexylmethyl)-5-methyl-2-trifluoromethylimidazo[1,2-a]pyridine-7-carboxylate (491 mg, yield 24%) was obtained in the same manner as in step 6 of Example 52, using ethyl 6-amino-3-chloro-2-methylisonicotinate obtained in step 1, and 3-bromo-4-(4,4-difluorocyclohexyl)-1,1,1-trifluorobutan-2-one obtained in step 2 of Example 36.

$^1$H NMR (300 MHz, CDCl$_3$, δ): 7.99 (s, 1H), 4.43 (q, J=7.1 Hz, 2H), 3.23 (d, J=6.2 Hz, 2H), 2.99 (s, 3H), 2.03-2.18 (m, 3H), 1.65-1.26 (m, 9H).

Step 3

6-Chloro-3-(4,4-difluorocyclohexylmethyl)-5-methyl-2-trifluoromethylimidazo[1,2-a]pyridine-7-carboxylic acid (315 mg, yield 69%) was obtained in the same manner as in step 3 of Example 61, using ethyl 6-chloro-3-(4,4-difluorocyclohexylmethyl)-5-methyl-2-trifluoromethylimidazo[1,2-a]pyridine-7-carboxylate obtained in step 2.

$^1$H NMR (300 MHz, DMSO-d$^6$, δ): 13.80 (s, 1H), 7.91 (s, 1H), 3.18 (d, J=6.8 Hz, 2H), 2.99 (s, 3H), 2.06-1.51 (m, 9H); ESIMS m/z: [M+H]$^+$ 411.

Step 4

Compound 124 (63.5 mg, yield 75%) was obtained in the same manner as in step 4 of Example 21, using 6-chloro-3-(4,4-difluorocyclohexylmethyl)-5-methyl-2-trifluoromethylimidazo[1,2-a]pyridine-7-carboxylic acid obtained in step 3, and 4-aminotetrahydropyran.

$^1$H NMR (300 MHz, CDCl$_3$, δ): 7.65 (s, 1H), 5.84 (d, J=7.7 Hz, 1H), 4.26-4.21 (m, 1H), 4.02-3.99 (m, 2H), 3.59-3.49 (m, 2H), 3.22 (d, J=5.9 Hz, 2H), 2.97 (s, 3H), 2.08-2.04 (m, 4H), 1.72-1.41 (m, 9H); ESIMS m/z: [M+H]$^+$ 494.

Example 73

3-(4,4-Difluorocyclohexylmethyl)-6-iodo-5-methyl-N-phenyl-2-trifluoromethylimidazo[1,2-a]pyridine-7-carboxamide (Compound 125)

Step 1

Ethyl 6-amino-2-methylisonicotinate (2.00 g, 11.1 mmol) was dissolved in DMF (20 mL), and the solution was stirred overnight at 60° C. after adding N-iodosuccinimide (2.50 g, 11.1 mmol). The reaction mixture was stirred at 60° C. for 5 hours after adding N-iodosuccinimide (1.25 g, 5.55 mmol). The reaction mixture was allowed to cool to room temperature, and extracted with a mixed solvent of ethyl acetate and hexane after adding a sodium hydrogen carbonate aqueous solution. The organic layer was washed with saturated brine, and dried over anhydrous magnesium sulfate. The solvent was then evaporated under reduced pressure. The residue was purified by silica gel column chromatography (hexane/ethyl acetate=80/20→50/50) to give ethyl 6-amino-3-iodo-2-methylisonicotinate (1.92 g, yield 57%).

$^1$H NMR (300 MHz, CDCl$_3$, δ): 6.44 (s, 1H), 4.52 (s, 2H), 4.39 (q, J=7.1 Hz, 2H), 2.65 (s, 3H), 1.40 (t, J=7.1 Hz, 3H).

Step 2

Ethyl 3-(4,4-difluorocyclohexylmethyl)-6-iodo-5-methyl-2-trifluoromethylimidazo[1,2-a]pyridine-7-carboxylate (179 mg, yield 10%) was obtained in the same manner as in step 6 of Example 52, using ethyl 6-amino-3-iodo-2-methylisonicotinate obtained in step 1, and 3-bromo-4-(4,4-difluorocyclohexyl)-1,1,1-trifluorobutan-2-one obtained in step 2 of Example 36.

$^1$H NMR (300 MHz, CDCl$_3$, δ): 7.83 (s, 1H), 4.43 (q, J=7.1 Hz, 2H), 3.19 (d, J=5.9 Hz, 2H), 3.17 (s, 3H), 2.11-2.09 (m, 2H), 1.71-1.24 (m, 10H).

Step 3

3-(4,4-Difluorocyclohexylmethyl)-6-iodo-5-methyl-2-trifluoromethylimidazo[1,2-a]pyridine-7-carboxylic acid (149 mg, yield 90%) was obtained in the same manner as in step 3 of Example 61, using ethyl 3-(4,4-difluorocyclohexylmethyl)-6-iodo-5-methyl-2-trifluoromethylimidazo[1,2-a]pyridine-7-carboxylate obtained in step 2.

$^1$H NMR (300 MHz, DMSO-d$^6$, δ): 13.68 (s, 1H), 7.71 (s, 1H), 3.15-3.12 (m, 5H), 2.03-1.56 (m, 9H); ESIMS m/z: [M+H]$^+$ 503.

Step 4

Compound 125 (56.2 mg, yield 83%) was obtained in the same manner as in step 4 of Example 21, using 6-chloro-3-(4,4-difluorocyclohexylmethyl)-5-methyl-2-trifluoromethylimidazo[1,2-a]pyridine-7-carboxylic acid obtained in step 3, and aniline.

$^1$H NMR (300 MHz, CDCl$_3$, δ): 7.66-7.60 (m, 3H), 7.49 (s, 1H), 7.45-7.38 (m, 2H), 7.27-7.18 (m, 1H), 3.23-3.14 (m, 5H), 2.15-2.04 (m, 2H), 1.73-1.40 (m, 5H), 1.31-1.23 (m, 2H); ESIMS m/z: [M+H]$^+$ 578.

Example 74

3-(N-Cyclohexylsulfamoyl)-2-isopropyl-N-phenylimidazo[1,2-a]pyridine-7-carboxamide (Compound 128)

Step 1

2-Isopropylimidazo[1,2-a]pyridine-7-carbonitrile (300 mg, 1.62 mmol) obtained in step 1 of Example 7 was dissolved in 1,2-dichloroethane (3.0 mL), and the solution was stirred at 90° C. for 3 hours after adding chlorosulfonic acid (0.215 mL, 3.24 mmol). Under ice-cooled condition, triethylamine (0.451 mL, 3.24 mmol) was added to the reaction mixture, and the mixture was stirred at 90° C. for 15 minutes. Under ice-cooled condition, phosphoryl chloride (0.302 mL, 3.24 mmol) was added to the reaction mixture, and the mixture was stirred at 95° C. for 1 hour. After adding water, the reaction mixture was extracted with dichloromethane under ice-cooled condition. The organic layer was dried over anhydrous magnesium sulfate, and the solvent was evaporated under reduced pressure. The residue was dissolved in acetonitrile (3.0 mL). Under ice-cooled condition, cyclohexylamine (371 mL, 3.24 mmol) was added, and the mixture was stirred at room temperature for 40 minutes. The reaction mixture was extracted with ethyl acetate after adding water. The organic layer was washed with saturated brine, and dried over anhydrous magnesium sulfate. The solvent was then evaporated under reduced pressure. The residue was purified by silica gel column chromatography (hexane/ethyl acetate=80/20) to give 7-cyano-N-cyclohexyl-2-isopropylimidazo[1,2-a]pyridine-3-sulfoneamide (358 mg, yield 64.2%).

$^1$H NMR (300 MHz, CDCl$_3$, δ): 8.77 (d, J=7.3 Hz, 1H), 8.06 (s, 1H), 7.14 (d, J=7.3 Hz, 1H), 4.95 (br s, 1H), 3.87-3.77 (m, 1H), 3.18-3.08 (m, 1H), 1.74-1.50 (m, 4H), 1.40 (d, J=6.9 Hz, 6H), 1.22-1.13 (m, 6H); ESIMS m/z: [M+H]$^+$ 347.

Step 2

3-(N-Cyclohexylsulfamoyl)-2-isopropyl-N-phenylimidazo[1,2-a]pyridine-7-carboxylic acid (324 mg, yield 87%) was obtained in the same manner as in step 2 of Example 7, using 7-cyano-N-cyclohexyl-2-isopropylimidazo[1,2-a]pyridine-3-sulfoneamide obtained in step 1.

$^1$H NMR (300 MHz, DMSO-d$^6$, δ): 8.75 (d, J=7.0 Hz, 1H), 8.35 (br s, 1H), 8.20 (s, 1H), 7.57 (d, J=7.0 Hz, 1H), 3.78-3.76 (m, 1H), 2.94-2.93 (m, 1H), 1.39-1.12 (m, 10H), 1.29 (d, J=6.6 Hz, 6H); ESIMS m/z: [M+H]$^+$ 366.

Step 3

Compound 128 (83.9 mg, yield 99%) was obtained in the same manner as in step 4 of Example 21, using 3-(N-cyclohexylsulfamoyl)-2-isopropyl-N-phenylimidazo[1,2-a]pyridine-7-carboxylic acid obtained in step 2, and aniline.

$^1$H NMR (300 MHz, CDCl$_3$, δ): 8.70 (d, J=7.0 Hz, 1H), 8.17 (s, 1H), 8.16 (br s, 1H), 7.65 (d, J=7.7 Hz, 2H), 7.47-7.39 (m, 3H), 7.20-7.18 (m, 1H), 5.10 (br s, 1H), 3.89-3.80 (m, 1H), 3.14-3.12 (m, 1H), 1.66-1.49 (m, 4H), 1.40 (d, J=6.6 Hz, 6H), 1.14-1.03 (m, 6H); ESIMS m/z: [M+H]$^+$ 441.

Example 75

3-{N-(Dicyclopropylmethyl)sulfamoyl}-2-isopropyl-N-phenylimidazo[1,2-a]pyridine-7-carboxamide (Compound 129)

Step 1

The 2-isopropylimidazo[1,2-a]pyridine-7-carbonitrile (2.00 g, 10.8 mmol) obtained in step 1 of Example 7 was dissolved in dichloroethane (22 mL). Under ice-cooled condition, trimethylsilyl chlorosulfonate (4.08 g, 21.6 mmol) was added, and the mixture was stirred at 100° C. for hours. The solvent was evaporated under reduced pressure, and the residue was slurried in heptane. The resulting crystals were collected by filtration to give 7-cyano-2-isopropylimidazo[1,2-a]pyridine-3-sulfonic acid (2.71 g, yield 95%).

$^1$H NMR (300 MHz, DMSO-d$^6$, δ): 9.05-9.02 (m, 1H), 8.52-8.51 (m, 1H), 7.68-7.64 (m, 1H), 4.09-3.90 (m, 1H), 1.30 (d, J=7.0 Hz, 6H); ESIMS m/z: [M–H]$^-$ 264.

Step 2

2-Isopropyl-3-sulfoimidazo[1,2-a]pyridine-7-carboxylic acid (2.06 g, yield 63%) was obtained in the same manner as in step 2 of Example 7, using 7-cyano-2-isopropylimidazo[1,2-a]pyridine-3-sulfonic acid obtained in step 1.

$^1$H NMR (300 MHz, DMSO-d$^6$, δ): 9.11 (d, J=7.0 Hz, 1H), 8.22 (s, 1H), 7.90 (d, J=7.0 Hz, 1H), 4.10-4.00 (m, 1H), 1.34 (d, J=7.0 Hz, 6H); ESIMS m/z: [M–H]$^-$ 283.

Step 3

2-Isopropyl-3-sulfoimidazo[1,2-a]pyridine-7-carboxylic acid (0.93 g, 3.25 mmol) obtained in step 2 was dissolved in dichloroethane (30 mL), and the solution was stirred at 100° C. for 4 hours after adding triethylamine (1.13 mL, 8.13 mmol) and phosphorus oxychloride (0.760 mL, 8.13 mmol).

The reaction mixture was allowed to cool to room temperature, and stirred at room temperature for 2.5 hours after adding aniline (0.300 mL, 3.25 mmol). Then, a saturated sodium hydrogen carbonate aqueous solution was added to the reaction mixture, and the mixture was extracted with chloroform. The organic layer was dried over anhydrous magnesium sulfate, and the solvent was then evaporated under reduced pressure. The residue was purified by silica gel column chromatography (hexane/ethyl acetate=80/20→50/50) to give 2-isopropyl-7-phenylcarbamoylimidazo[1,2-a]pyridine-3-sulfonylchloride (1.24 g, yield 97%).

$^1$H NMR (300 MHz, CDCl$_3$, δ): 8.91-8.88 (m, 1H), 8.22-8.20 (m, 1H), 7.87 (s, 1H), 7.68-7.64 (m, 3H), 7.45-7.39 (m, 2H), 7.24-7.21 (m, 1H), 3.87-3.78 (m, 1H), 1.43 (d, J=6.8 Hz, 6H).

Step 4

2-Isopropyl-7-phenylcarbamoylimidazo[1,2-a]pyridine-3-sulfonylchloride (50.0 mg, 0.132 mmol) obtained in step 3 was dissolved in dichloromethane (5 mL), and the solution was stirred at room temperature for 1 hour after adding dicyclopropylmethylamine (74.0 mg, 0.662 mmol) and triethylamine (0.0920 mL, 0.662 mmol). After adding chloroform and a saturated sodium hydrogen carbonate aqueous solution to the reaction mixture, the mixture was filtered through a Presep (registered trademark; diatomaceous earth, granular type M, 4.5 g/25 mL). The solvent was then evaporated under reduced pressure. The residue was purified by silica gel column chromatography (hexane/ethyl acetate=80/20→50/50), and reslurried with a mixed solvent of tert-butyl methyl ether and hexane to give compound 129 (46.0 mg, yield 77%).

$^1$H NMR (300 MHz, CDCl$_3$, δ): 8.74 (d, J=7.3 Hz, 1H), 8.15 (s, 1H), 7.94 (s, 1H), 7.64 (d, J=7.8 Hz, 2H), 7.52 (dd, J=7.3, 2.0 Hz, 1H), 7.40 (t, J=7.8 Hz, 2H), 7.20 (t, J=7.3 Hz, 1H), 5.04 (s, 1H), 3.84-3.75 (m, 1H), 2.34-2.25 (m, 1H), 1.39 (d, J=7.0 Hz, 6H), 0.84-0.72 (m, 2H), 0.49-0.38 (m, 2H), 0.24-0.13 (m, 4H), −0.04-−0.12. (m, 2H); ESIMS m/z: [M+H]$^+$ 453.

Example 76

2-(3,3-Difluoroazetidin-1-yl)-3-(4,4-difluoropiperidin-1-ylsulfonyl)-N-phenylimidazo[1,2-a]pyridine-7-carboxamide (Compound 139)

Step 1

2-Amino-4-cyanopyridine (3.00 g, 25.2 mmol) and ethyl bromoacetate (16.8 mL, 151 mmol) were mixed, and the mixture was stirred at 70° C. for 2 hours. The reaction mixture was allowed to cool to room temperature. The precipitated solid was collected by filtration, and washed with ethyl acetate. The resulting solid was suspended in phosphoryl chloride (30 mL), and stirred overnight at 90° C. The solvent was evaporated under reduced pressure. The residue was suspended in ethanol, and the suspension was dropped on a saturated sodium hydrogen carbonate aqueous solution under ice-cooled condition. The precipitated white crystals were collected by filtration to give 2-chloroimidazo[1,2-a]pyridine-7-carbonitrile (2.26 g, yield 51%).

$^1$H NMR (300 MHz, DMSO-d$^6$, δ): 8.15 (d, J=7.1 Hz, 1H), 7.95 (s, 1H), 7.66 (s, 1H), 7.02 (d, J=7.1 Hz, 1H); ESIMS m/z: [M+H]$^+$ 178.

Step 2

2-Chloro-3-(4,4-difluoropiperidin-1-ylsulfonyl)imidazo[1,2-a]pyridine-7-carbonitrile (2.09 g, yield 43%) was obtained in the same manner as in step 1 of Example 74, using 2-chloroimidazo[1,2-a]pyridine-7-carbonitrile obtained in step 1, and 4,4-difluoropiperidine hydrochloride.

$^1$H NMR (300 MHz, CDCl$_3$, δ): 8.97 (d, J=7.2 Hz, 1H), 8.04 (s, 1H), 7.22 (d, J=7.2 Hz, 1H), 3.51-3.49 (m, 4H), 2.19-2.07 (m, 4H); ESIMS m/z: [M+H]$^+$ 361.

Step 3

2-Chloro-3-(4,4-difluoropiperidin-1-ylsulfonyl)imidazo[1,2-a]pyridine-7-carboxylic acid (2.30 g, yield 99%) was obtained in the same manner as in step 2 of Example 7, using 2-chloro-3-(4,4-difluoropiperidin-1-ylsulfonyl)imidazo[1,2-a]pyridine-7-carbonitrile obtained in step 2.

$^1$H NMR (300 MHz, DMSO-d$^6$, δ): 8.90 (d, J=7.3 Hz, 1H), 8.21 (s, 1H), 7.64 (d, J=7.3 Hz, 1H), 3.45-3.32 (m, 4H), 2.13-2.03 (m, 4H); ESIMS m/z: [M+H]$^+$ 380.

Step 4

2-Chloro-3-(4,4-difluoropiperidin-1-ylsulfonyl)-N-phenylimidazo[1,2-a]pyridine-7-carboxamide (2.53 g, yield 92%) was obtained in the same manner as in step 4 of Example 21, using 2-chloro-3-(4,4-difluoropiperidin-1-ylsulfonyl)imidazo[1,2-a]pyridine-7-carboxylic acid obtained in step 3, and aniline.

$^1$H NMR (300 MHz, DMSO-d$^6$, δ): 10.58 (s, 1H), 8.94 (d, J=7.3 Hz, 1H), 8.45 (s, 1H), 7.80 (d, J=7.8 Hz, 2H), 7.73 (d, J=7.3 Hz, 1H), 7.40 (dd, J=7.9, 3.8 Hz, 2H), 7.17-7.14 (m, 1H), 3.41-3.38 (m, 4H), 2.12-2.09 (m, 4H); ESIMS m/z: [M+H]$^+$ 455.

Step 5

3,3-Difluoroazetidine hydrochloride (43.0 mg, 0.330 mmol) was dissolved in DMF (1.0 mL). Under ice-cooled condition, 60% sodium hydride (0.0260 g, 0.660 mmol), and 2-chloro-3-(4,4-difluoropiperidin-1-ylsulfonyl)-N-phenylimidazo[1,2-a]pyridine-7-carboxamide (50.0 mg, 110 mmol) obtained in step 4 were added, and the mixture was stirred at 70° C. for 2 hours, and then 120° C. for 5 hours. At the maintained temperature of 120° C., the mixture was stirred overnight after adding 3,3-difluoroazetidinehydrochloride (142 mg, 1.10 mmol). The reaction mixture was allowed to cool to room temperature, and, after adding water, filtered through a Presep (registered trademark; diatomaceous earth, granular type M, 4.5 g/25 mL). The solvent was then evaporated under reduced pressure. The residue was purified by silica gel column chromatography (hexane/ethyl acetate=85/15→40/60) to give compound 139 (3.2 mg, yield 6%).

$^1$H NMR (300 MHz, CDCl$_3$, δ): 8.65 (d, J=7.3 Hz, 1H), 7.91 (s, 1H), 7.82 (s, 1H), 7.63 (dd, J=8.4, 4.2 Hz, 2H), 7.45-7.38 (m, 3H), 7.22-7.20 (m, 1H), 4.64-4.60 (m, 4H), 3.36-3.34 (m, 4H), 2.10-1.98 (m, 4H); ESIMS m/z: [M+H]$^+$ 512.

Example 77

3-(4,4-Difluoropiperidin-1-ylsulfonyl)-N-phenyl-2-(1H-pyrrol-1-yl)imidazo[1,2-a]pyridine-7-carboxamide (Compound 140)

2-Chloro-3-(4,4-difluoropiperidin-1-ylsulfonyl)-N-phenylimidazo[1,2-a]pyridine-7-carboxamide (0.0500 mg, 0.110 mmol) obtained in step 4 of Example 76 was dissolved in DMF (1.0 mL), and the solution was stirred at 120° C. for 5 hours after adding pyrrole (22.0 mg, 0.330 mmol) and potassium tert-butoxide (37.0 mg, 0.330 mmol). After adding pyrrole (37.0 mg, 0.550 mmol) and potassium tert-butoxide (62.0 mg, 0.550 mmol) to the reaction mixture, the mixture was stirred at 150° C. for 1 hour. After adding water, the reaction mixture was filtered through a Presep (registered trademark; diatomaceous earth, granular type M, 4.5 g/25 mL), and the solvent was evaporated under reduced pressure.

The residue was purified by silica gel column chromatography (hexane/ethyl acetate=85/15→40/60) to give compound 140 (9.0 mg, yield 17%).

$^1$H NMR (300 MHz, CDCl$_3$, δ): 9.14 (d, J=7.3 Hz, 1H), 8.12 (s, 1H), 7.90 (s, 1H), 7.67-7.64 (m, 2H), 7.57 (d, J=7.5 Hz, 1H), 7.45-7.39 (m, 4H), 7.24-7.20 (m, 1H), 6.40-6.39 (m, 2H), 3.18-3.16 (m, 4H), 1.89-1.76 (m, 4H); ESIMS m/z: [M+H]$^+$ 486.

Example 78

3-(4,4-Difluoropiperidin-1-ylsulfonyl)-2-(methylthio)-N-phenylimidazo[1,2-a]pyridine-7-carboxamide (Compound 141)

2-Chloro-3-(4,4-difluoropiperidin-1-ylsulfonyl)-N-phenylimidazo[1,2-a]pyridine-7-carboxamide (0.0520 mg, 0.114 mmol) obtained in step 4 of Example 76 was dissolved in DMF (1.0 mL), and the solution was stirred at 120° C. for 1 hour after adding sodium thiomethoxide (28.0 mg, 0.399 mmol). The reaction mixture was allowed to cool to room temperature, and, after adding a saturated sodium hydrogen carbonate aqueous solution, filtered through a Presep (registered trademark; diatomaceous earth, granular type M, 4.5 g/25 mL). The solvent was then evaporated under reduced pressure. The residue was purified by silica gel column chromatography (hexane/ethyl acetate=80/20→50/50) to give compound 141 (43.9 mg, yield 82%).

$^1$H NMR (300 MHz, CDCl$_3$, δ): 8.71 (d, J=6.8 Hz, 1H), 8.05-8.03 (m, 2H), 7.67-7.64 (m, 2H), 7.48 (d, J=7.8 Hz, 1H), 7.42-7.40 (m, 2H), 7.22-7.20 (m, 1H), 3.46-3.44 (m, 4H), 2.67 (s, 3H), 2.10-2.04 (m, 4H); ESIMS m/z: [M+H]$^+$ 467.

Example 79

3-(4,4-Difluoropiperidin-1-ylsulfonyl)-2-(methylsulfinyl)-N-phenylimidazo[1,2-a]pyridine-7-carboxamide (Compound 142)

Compound 141 (0.05 g, 0.107 mol) was suspended in 1,2-dichloroethane (1 mL). Under ice-cooled condition, m-chloroperbenzoic acid (0.024 g, 0.139 mmol) was added, and the mixture was stirred for 0.5 hours. A sodium hydrogen carbonate aqueous solution was added to the reaction mixture. The precipitated solid was collected by filteration, and washed with water to give compound 142 (0.047 g, yield 91%).

$^1$H NMR (300 MHz, DMSO-d$^6$, δ): 10.60 (s, 1H), 8.92 (d, J=7.8 Hz, 1H), 8.60 (s, 1H), 7.80-7.79 (m, 3H), 7.39-7.37 (m, 2H), 7.14-7.11 (m, 1H), 3.47-3.45 (m, 4H), 3.02 (s, 3H), 2.10-2.07 (m, 4H); ESIMS m/z: [M+H]$^+$ 483.

Example 80

3-(4,4-Difluoropiperidin-1-ylsulfonyl)-2-(methylsulfonyl)-N-phenylimidazo[1,2-a]pyridine-7-carboxamide (Compound 143)

Compound 141 (0.05 g, 0.107 mol) was suspended in 1,2-dichloroethane (1 mL). Under ice-cooled condition, m-chloroperbenzoic acid (0.065 g, 0.375 mmol) was added, and the mixture was stirred at 60° C. for 3 hours. A sodium hydrogen carbonate aqueous solution was added to the reaction mixture. The precipitated solid was collected by filteration, and washed with water to give compound 143 (34.3 mg, yield 64%).

$^1$H NMR (300 MHz, DMSO-d$^6$, δ): 10.61 (s, 1H), 9.05 (d, J=6.8 Hz, 1H), 8.65-8.63 (m, 1H), 7.82-7.79 (m, 3H), 7.42-7.39 (m, 2H), 7.18-7.15 (m, 1H), 3.58-3.56 (m, 4H), 3.51 (s, 3H), 2.08-2.05 (m, 4H); ESIMS m/z: [M+H]$^+$ 499.

Example 81

6-Chloro-3-(3,3-difluoroazetidin-1-ylsulfonyl)-2-isopropyl-N-(3-methylisooxazol-5-yl)imidazo[1,2-a]pyridine-7-carboxamide (Compound 148)

Step 1

6-Chloro-2-isopropylimidazo[1,2-a]pyridine-7-carbonitrile (1.46 g, yield 51%) was obtained in the same manner as in step 2 of Example 1, using 2-amino-5-chloroisonicotinonitrile, and 1-bromo-3-methylbutan-2-one.

$^1$H NMR (300 MHz, CDCl$_3$, δ): 8.23-8.22 (m, 1H), 7.97-7.96 (m, 1H), 7.48-7.46 (m, 1H), 3.16-3.11 (m, 1H), 1.37 (d, J=6.9 Hz, 6H).

Step 2

6-Chloro-7-cyano-2-isopropylimidazo[1,2-a]pyridine-3-sulfonic acid (1.83 g, yield 99%) was obtained in the same manner as in step 1 of Example 75, using 6-chloro-2-isopropylimidazo[1,2-a]pyridine-7-carbonitrile obtained in step 1.

$^1$H NMR (300 MHz, DMSO-d$^6$, δ): 8.98 (s, 1H), 8.57 (s, 1H), 3.90-3.84 (m, 1H), 1.25 (d, J=6.6 Hz, 6H).

Step 3

6-Chloro-7-cyano-2-isopropylimidazo[1,2-a]pyridine-3-sulfonic acid (2.16 g, 7.21 mmol) obtained in step 2 was dissolved in dichloroethane (20 mL), and the solution was stirred at 100° C. for 4 hours after adding triethylamine (2.01 mL, 14.4 mmol) and phosphorus oxychloride (1.34 mL, 14.4 mL). The reaction mixture was extracted with chloroform after adding water. The organic layer was dried over anhydrous magnesium sulfate, and the solvent was then evaporated under reduced pressure. The residue was purified by silica gel column chromatography (hexane/ethyl acetate=90/10→80/20) to give 6-chloro-7-cyano-2-isopropylimidazo[1,2-a]pyridine-3-sulfonylchloride (1.73 g, yield 75%).

$^1$H NMR (300 MHz, CDCl$_3$, δ): 8.96 (d, J=0.9 Hz, 1H), 8.15 (d, J=0.9 Hz, 1H), 3.84-3.75 (m, 1H), 1.41 (d, J=7.0 Hz, 6H).

Step 4

6-Chloro-7-cyano-2-isopropylimidazo[1,2-a]pyridine-3-sulfonylchloride (1.00 g, 3.14 mmol) obtained in step 3 was dissolved in acetonitrile (10 mL), and the solution was stirred at room temperature for 1.25 hours after adding 3,3-difluoroazetidinehydrochloride (611 mg, 4.71 mmol) and triethylamine (1.31 mL, 9.43 mmol). A saturated sodium hydrogen carbonate aqueous solution was added to the reaction mixture. The precipitated crystals were collected by filteration, and washed with water. The resulting crude product was purified by silica gel column chromatography (heptane/ethyl acetate=80/20→50/50) to give 6-chloro-3-(3,3-difluoroazetidin-1-ylsulfonyl)-2-isopropylimidazo[1,2-a]pyridine-7-carbonitrile (1.10 g, yield 93%).

$^1$H NMR (300 MHz, CDCl$_3$, δ): 8.78 (s, 1H), 8.09 (s, 1H), 4.31 (t, J=11.7 Hz, 4H), 3.75-3.68 (m, 1H), 1.37 (d, J=6.8 Hz, 6H).

Step 5

6-Chloro-3-(3,3-difluoroazetidin-1-ylsulfonyl)-2-isopropylimidazo[1,2-a]pyridine-7-carboxylic acid (462 mg, yield 76%) was obtained in the same manner as in step 3 of Example 61, using 6-chloro-3-(3,3-difluoroazetidin-1-ylsulfonyl)-2-isopropylimidazo[1,2-a]pyridine-7-carbonitrile obtained in step 4.

¹H NMR (300 MHz, DMSO-d⁶, δ): 8.72 (s, 1H), 8.23 (s, 1H), 4.41 (t, J=12.5 Hz, 4H), 3.68-3.55 (m, 1H), 1.31 (d, J=7.0 Hz, 6H).

Step 6

Compound 148 (173 mg, yield 29%) was obtained in the same manner as in Example 48, using 6-chloro-3-(3,3-difluoroazetidin-1-ylsulfonyl)-2-isopropylimidazo[1,2-a]pyridine-7-carboxylic acid obtained in step 5, and 3-methylisooxazole-5-amine.

¹H NMR (300 MHz, CDCl₃, δ): 8.90 (s, 1H), 8.78 (s, 1H), 8.21 (s, 1H), 6.44 (s, 1H), 4.30 (t, J=11.7 Hz, 4H), 3.77-3.68 (m, 1H), 2.33 (s, 3H), 1.38 (d, J=7.0 Hz, 6H); ESIMS m/z: [M+H]⁺ 474.

Example 82

6-Chloro-2-isopropyl-N-phenyl-3-(N-phenylsulfamoyl)imidazo[1,2-a]pyridine-7-carboxamide (Compound 155)

Step 1

6-Chloro-2-isopropyl-3-sulfoimidazo[1,2-a]pyridine-7-carboxylic acid (754 mg, yield 79%) was obtained in the same manner as in step 2 of Example 7, using 6-chloro-7-cyano-2-isopropylimidazo[1,2-a]pyridine-3-sulfonic acid obtained in step 2 of Example 81.

¹H NMR (300 MHz, DMSO-d⁶, δ): 9.02 (s, 1H), 8.20 (s, 1H), 4.00-3.93 (m, 1H), 1.30 (d, J=6.8 Hz, 6H).

Step 2

6-Chloro-2-isopropyl-3-sulfoimidazo[1,2-a]pyridine-7-carboxylic acid (743 mg, 2.33 mmol) obtained in step 1 was dissolved in dichloroethane (10 mL), and the solution was stirred at 100° C. for 4 hours after adding triethylamine (0.975 mL, 6.99 mmol) and phosphorus oxychloride (0.652 mL, 6.99 mmol). The reaction mixture was allowed to cool to room temperature, and, after adding aniline (0.123 mL, 3.25 mmol), stirred overnight at room temperature. After adding a saturated sodium hydrogen carbonate aqueous solution to the reaction mixture, the mixture was extracted with chloroform. The organic layer was dried over anhydrous magnesium sulfate, and the solvent was then evaporated under reduced pressure. The residue was purified by silica gel column chromatography (hexane/ethyl acetate=80/20→50/50) to give compound 155 (43.5 mg, yield 4%).

¹H NMR (300 MHz, CDCl₃, δ): 8.72 (s, 1H), 7.99 (s, 1H), 7.88 (s, 1H), 7.62 (d, J=7.7 Hz, 2H), 7.40 (t, J=7.9 Hz, 2H), 7.21 (dd, J=8.6, 4.9 Hz, 4H), 6.99-6.98 (m, 3H), 3.58-3.49 (m, 1H), 1.19 (d, J=6.6 Hz, 6H); ESIMS m/z: [M+H]⁺ 469.

Example 83

N-{3-(3,3-Difluoroazetidin-1-ylsulfonyl)-2-isopropylimidazo[1,2-a]pyridin-7-yl}benzamide (Compound 169)

Step 1

7-Bromo-2-isopropylimidazo[1,2-a]pyridine (1.00 g, 4.18 mmol) obtained in step 1 of Example 28 was dissolved in 1,2-dichloroethane (10 mL). Under ice-cooled condition, trimethylsilyl chlorosulfonate (1.20 mL, 8.36 mmol) was added, and the mixture was stirred at 90° C. for 3 hours. Under ice-cooled condition, triethylamine (1.17 mL, 8.36 mmol) and phosphoryl chloride (0.779 mL, 8.36 mmol) were added, and the mixture was stirred at 100° C. for 1.5 hours. The solvent was evaporated under reduced pressure, and the residue was dissolved in acetonitrile. After adding a sodium hydrogen carbonate aqueous solution, the precipitated solid was collected by filteration to give 7-bromo-2-isopropylimidazo[1,2-a]pyridine-3-sulfonylchloride (1.31 g, yield 93%).

¹H NMR (270 MHz, CDCl₃, δ): 8.64 (dd, J=7.2, 0.7 Hz, 1H), 7.97 (dd, J=2.0, 0.7 Hz, 1H), 7.27 (dd, J=7.2, 2.0 Hz, 1H), 3.83-3.71 (m, 1H), 1.39 (d, J=6.9 Hz, 6H).

Step 2

7-Bromo-2-isopropylimidazo[1,2-a]pyridine-3-sulfonylchloride (500 mg, 1.481 mmol) obtained in step 1 was dissolved in acetonitrile (5.0 mL), and the solution was stirred at 50° C. for 30 minutes after adding 3,3-difluoroazetidine hydrochloride (230 mg, 1.78 mmol) and triethylamine (0.413 ml, 2.96 mmol). The reaction mixture was allowed to cool to room temperature, and a sodium hydrogen carbonate aqueous solution was added. The precipitated solid was collected by filteration to give 7-bromo-3-(3,3-difluoroazetidin-1-ylsulfonyl)-2-isopropylimidazo[1,2-a]pyridine (546 mg, yield 94%).

¹H NMR (270 MHz, CDCl₃, δ): 8.48 (dd, J=7.6, 0.8 Hz, 1H), 7.90 (dd, J=2.0, 0.8 Hz, 1H), 7.13 (dd, J=7.6, 2.0 Hz, 1H), 4.24 (t, J=11.7 Hz, 4H), 3.77-3.67 (m, 1H), 1.36 (d, J=6.9 Hz, 6H).

Step 3

Compound 169 (7.40 mg, yield 13%) was obtained in the same manner as in step 4 of Example 28, using 7-bromo-3-(3,3-difluoroazetidin-1-ylsulfonyl)-2-isopropylimidazo[1,2-a]pyridine obtained in step 2, and benzamide.

¹H NMR (270 MHz, CDCl₃, δ): 8.58 (d, J=7.6 Hz, 1H), 8.07 (d, J=2.3 Hz, 1H), 7.93-7.88 (m, 2H), 7.65-7.44 (m, 5H), 4.23 (t, J=11.8 Hz, 4H), 3.77-3.68 (m, 1H), 1.39 (d, J=6.9 Hz, 6H); ESIMS m/z: [M+H]⁺ 435.

Example 84

2-{6-Chloro-3-(3,3-difluoroazetidin-1-ylsulfonyl)-2-isopropylimidazo[1,2-a]pyridin-7-yl}-1H-benzimidazole (Compound 170)

Compound 170 (68.5 mg, yield 89%) was obtained in the same manner as in Example 33, using compound 149.

¹H NMR (300 MHz, CDCl₃, δ): 10.21 (s, 1H), 8.80 (d, J=0.7 Hz, 1H), 8.75 (d, J=0.7 Hz, 1H), 7.89-7.88 (m, 1H), 7.58-7.56 (m, 1H), 7.37-7.36 (m, 2H), 4.31 (t, J=11.9 Hz, 4H), 3.77-3.68 (m, 1H), 1.40 (d, J=7.0 Hz, 6H); ESIMS m/z: [M+H]⁺ 466.

Example 85

3-(4,4-Difluoropiperidin-1-ylsulfonyl)-2-isopropyl-N-phenylimidazo[1,2-a]pyrimidine-7-carboxamide (Compound 171)

2-(4,4-Difluoropiperidin-1-ylsulfonyl)-3-isopropyl-N-phenylimidazo[1,2-a]pyrimidine-7-carboxamide (Compound 176)

Step 1

N,N-Diethyl-2-isopropylimidazo[1,2-a]pyrimidine-7-carboxamide (2.11 g, yield 40%) was obtained in the same manner as in step 1 of Example 60, using 2-amino-N,N-diethylpyrimidine-4-carboxamide obtained in step 1 of Example 45, and 1-bromo-3-methylbutan-2-one.

¹H NMR (300 MHz, CDCl₃, δ): 8.41 (d, J=6.8 Hz, 1H), 7.37 (s, 1H), 7.26 (1, J=6.8 Hz, 1H), 3.70 (q, J=7.2 Hz, 2H), 3.58 (q, J=7.2 Hz, 2H), 3.18 (sep, J=6.8 Hz, 1H), 1.39 (d, J=6.8 Hz, 6H), 1.28 (q, J=7.2 Hz, 6H); ESIMS m/z: [M+H]⁺ 261.

Step 2

2-Isopropylimidazo[1,2-a]pyrimidine-7-carboxylic acid (272 mg, yield quantitative) was obtained in the same manner as in step 3 of Example 61, using N,N-diethyl 2-isopropylimidazo[1,2-a]pyrimidine-7-carboxamide obtained in step 1.

$^1$H NMR (300 MHz, DMSO-d$^6$, δ): 8.79 (d, J=7.0 Hz, 1H), 7.66 (s, 1H), 7.46 (d, J=7.0 Hz, 1H), 3.03 (sep, J=7.0 Hz, 1H), 1.30 (d, J=7.0 Hz, 6H).

Step 3

Ethyl 2-isopropylimidazo[1,2-a]pyrimidine-7-carboxylate (65.1 mg, yield 73%) was obtained in the same manner as in step 2 of Example 2, using 2-isopropylimidazo[1,2-a]pyrimidine-7-carboxylic acid obtained in step 2, and ethanol.

$^1$H NMR (300 MHz, CDCl$_3$, δ): 8.46 (d, J=7.0 Hz, 1H), 7.60 (d, J=7.0 Hz, 1H), 7.46 (s, 1H), 4.47 (q, J=7.0 Hz, 2H), 3.21 (sep, J=7.0 Hz, 1H), 1.45 (t, J=7.0 Hz, 3H), 1.40 (d, J=7.0 Hz, 6H); ESIMS m/z: [M+H]$^+$ 234.

Step 4

7-(ethoxycarbonyl)-2-isopropylimidazo[1,2-a]pyrimidine-3-sulfonic acid (470 mg, yield 98%) was obtained in the same manner as in step 1 of Example 75, using ethyl 2-isopropylimidazo[1,2-a]pyrimidine-7-carboxylate obtained in step 3.

$^1$H NMR (300 MHz, DMSO-d$^6$, δ): 9.43 (d, J=7.3 Hz, 1H), 8.01 (d, J=7.3 Hz, 1H), 4.43 (q, J=7.2 Hz, 2H), 4.00 (sep, J=7.0 Hz, 1H), 1.38 (t, J=7.2 Hz, 3H), 1.31 (d, J=7.0 Hz, 6H); ESIMS m/z: [M+H]$^+$ 314.

Step 5

Ethyl 3-(chlorosulfonyl)-2-isopropylimidazo[1,2-a]pyrimidine-7-carboxylate (314 mg, yield 63%) was obtained in the same manner as in step 3 of Example 75, using 7-(ethoxycarbonyl)-2-isopropylimidazo[1,2-a]pyrimidine-3-sulfonic acid obtained in step 4, and 4,4-difluoropiperidine hydrochloride.

Step 6

Ethyl 3-(4,4-difluoropiperidin-1-ylsulfonyl)-2-isopropylimidazo[1,2-a]pyrimidine-7-carboxylate (310 mg, two-step yield 79%) was obtained in the same manner as in step 4 of Example 75, using ethyl 3-(chlorosulfonyl)-isopropylimidazo[1,2-a]pyrimidine-7-carboxylate obtained in step 5, and 4,4-difluoropiperidine hydrochloride.

$^1$H NMR (300 MHz, CDCl$_3$, δ): 9.12 (d, J=7.0 Hz, 1H), 7.80 (d, J=7.0 Hz, 1H), 4.50 (q, J=7.2 Hz, 2H), 3.68 (sep, J=6.6 Hz, 1H), 3.40-3.34 (m, 4H), 2.18-2.03 (m, 4H), 1.46 (t, J=7.2 Hz, 3H), 1.42 (d, J=6.6 Hz, 6H); ESIMS m/z: [M+H]$^+$ 417.

Step 7

3-(4,4-Difluoropiperidin-1-ylsulfonyl)-2-isopropylimidazo[1,2-a]pyrimidine-7-carboxylic acid (112 mg, yield 60%) and 2-(4,4-difluoropiperidin-1-ylsulfonyl)-3-isopropylimidazo[1,2-a]pyrimidine-7-carboxylic acid (54.9 mg, yield 29%) were obtained as a mixture in the same manner as in step 3 of Example 61, using ethyl 3-(4,4-difluoropiperidin-1-ylsulfonyl)-2-isopropylimidazo[1,2-a]pyrimidine-7-carboxylate obtained in step 6.

3-(4,4-Difluoropiperidin-1-ylsulfonyl)-2-isopropylimidazo[1,2-a]pyrimidine-7-carboxylic acid $^1$H NMR (300 MHz, DMSO-d$^6$, δ): 9.22 (d, J=6.8 Hz, 1H), 7.72 (d, J=6.8 Hz, 1H), 3.66 (sep, J=6.8 Hz, 1H), 3.36-3.30 (m, 4H), 2.14-2.02 (m, 4H), 1.33 (d, J=6.8 Hz, 6H); ESIMS m/z: [M+H]$^+$ 389.

2-(4,4-Difluoropiperidin-1-ylsulfonyl)-3-isopropylimidazo[1,2-a]pyrimidine-7-carboxylic acid $^1$H NMR (300 MHz, DMSO-d$^6$, δ): 9.27 (d, J=7.8 Hz, 1H), 7.60 (d, J=7.8 Hz, 1H), 4.08 (sep, J=6.8 Hz, 1H), 3.49-3.42 (m, 4H), 2.17-2.05 (m, 4H), 1.44 (d, J=6.8 Hz, 6H); ESIMS m/z: [M+H]$^+$ 389.

Step 8

Compound 171 (5.4 mg, yield 9%) and compound 176 (2.6 mg, yield 4%) were obtained in the same manner as in step 4 of Example 21, using the mixture of 3-(4,4-difluoropiperidin-1-ylsulfonyl)-2-isopropylimidazo[1,2-a]pyrimidine-7-carboxylic acid and 2-(4,4-difluoropiperidin-1-ylsulfonyl)-3-isopropylimidazo[1,2-a]pyrimidine-7-carboxylic acid obtained in step 7, and aniline.

Compound 171

$^1$H NMR (400 MHz, CDCl$_3$, δ): 9.83 (br s, 1H), 9.19 (d, J=7.8 Hz, 1H), 8.06 (d, J=7.8 Hz, 1H), 7.78 (d, J=7.8 Hz, 2H), 7.42 (dd, J=7.8, 7.8 Hz, 2H), 7.21 (dd, J=7.8, 7.8 Hz, 1H), 3.73 (sep, J=6.8 Hz, 1H), 3.45-3.37 (m, 4H), 2.20-2.07 (m, 4H), 1.46 (d, J=6.8 Hz, 6H); ESIMS m/z: [M+H]$^+$ 464.

Compound 176

$^1$H NMR (400 MHz, CDCl$_3$, δ): 9.76 (br s, 1H), 8.72 (d, J=7.8 Hz, 1H), 7.99 (d, J=7.8 Hz, 1H), 7.80 (d, J=7.8 Hz, 2H), 7.42 (dd, J=7.8, 7.8 Hz, 2H), 7.21 (dd, J=7.8, 7.8 Hz, 1H), 4.31 (sep, J=6.8 Hz, 1H), 3.70-3.61 (m, 4H), 2.23-2.10 (m, 4H), 1.53 (d, J=6.8 Hz, 6H); ESIMS m/z: [M+H]$^+$ 464.

Example 86

N-{3-(4,4-Difluoropiperidin-1-ylsulfonyl)-2-isopropylimidazo[1,2-c]pyrimidin-7-yl}benzamide (Compound 174)

Step 1

4-Amino-6-chloropyrimidine (100 mg, 0.772 mmol) was suspended in DMF (0.5 mL), and the suspension was stirred overnight at 50° C. after adding 1-bromo-3-methylbutan-2-one (153 mg, 0.920 mmol) and molecular sieve 4A (200 mg). The reaction mixture was allowed to cool to room temperature. After adding a sodium hydrogen carbonate aqueous solution, the mixture was filtered through Celite (registered trademark), and extracted with ethyl acetate. The organic layer was washed with water and saturated brine, and dried over anhydrous sodium sulfate. The solvent was then evaporated under reduced pressure. The residue was purified by preparative thin-layer chromatography (chloroform/methanol=98/2) to give 7-chloro-2-isopropylimidazo[1,2-c]pyrimidine (64.7 mg, yield 43%).

$^1$H NMR (300 MHz, CDCl$_3$, δ): 8.80 (s, 1H), 7.48 (s, 1H), 7.39 (s, 1H), 3.18-3.06 (m, 1H), 1.36 (d, J=7.0 Hz, 6H); ESIMS m/z: [M+H]$^+$ 196, 198.

Step 2

7-Chloro-2-isopropylimidazo[1,2-c]pyrimidine-3-sulfonic acid (641 mg, yield 91%) was obtained in the same manner as in step 1 of Example 75, using 7-chloro-2-isopropylimidazo[1,2-c]pyrimidine obtained in step 1.

$^1$H NMR (300 MHz, DMSO-d$^6$, δ): 9.47 (d, J=1.1 Hz, 1H), 8.00 (d, J=1.1 Hz, 1H), 3.88 (sep, J=7.0 Hz, 1H), 1.25 (d, J=7.0 Hz, 6H).

Step 3

7-Chloro-2-isopropylimidazo[1,2-c]pyrimidine-3-sulfonylchloride (83.8 mg, yield 79%) was obtained in the same manner as in step 3 of Example 75, using 7-chloro-2-isopropylimidazo[1,2-c]pyrimidine-3-sulfonic acid obtained in step 2.

¹H NMR (300 MHz, CDCl₃, δ): 9.43 (d, J=1.1 Hz, 1H), 7.71 (d, J=1.1 Hz, 1H), 3.80 (sep, J=6.6 Hz, 1H), 1.40 (d, J=6.6 Hz, 6H).

Step 4

7-Chloro-3-(4,4-difluoropiperidin-1-ylsulfonyl)-2-isopropylimidazo[1,2-c]pyrimidine (98.4 mg, yield 91%) was obtained in the same manner as in step 4 of Example 75, using 7-chloro-2-isopropylimidazo[1,2-c]pyrimidine-3-sulfonylchloride obtained in step 3, and 4,4-difluoropiperidine hydrochloride.

¹H NMR (300 MHz, CDCl₃, δ): 9.34 (s, 1H), 7.62 (s, 1H), 3.66 (sep, J=6.8 Hz, 1H), 3.42-3.35 (m, 4H), 2.19-2.06 (m, 4H), 1.37 (d, J=6.8 Hz, 6H); ESIMS m/z: [M+H]⁺ 379, 381.

Step 5

Compound 174 (25.8 mg, yield 53%) was obtained in the same manner as in step 4 of Example 28, using 7-chloro-3-(4,4-difluoropiperidin-1-ylsulfonyl)-2-isopropylimidazo[1,2-c]pyrimidine obtained in step 4, and benzamide.

¹H NMR (300 MHz, CDCl₃, δ): 9.27 (d, J=1.5 Hz, 1H), 8.64 (d, J=1.5 Hz, 1H), 8.51 (br s, 1H), 7.97-7.91 (m, 2H), 7.65-7.51 (m, 3H), 3.65 (sep, J=7.0 Hz, 1H), 3.44-3.35 (m, 4H), 2.19-2.04 (m, 4H), 1.39 (d, J=7.0 Hz, 6H); ESIMS m/z: [M+H]⁺ 464.

Example 87

N-(Cyclohex-3-enyl)-3-(4,4-difluorocyclohexylmethyl)-2-trifluoromethylimidazo[1,2-a]pyridine-7-carboxamide (Compound 180)

Step 1

3-(4,4-Difluorocyclohexylmethyl)-N-(4-hydroxycyclohexyl)-2-trifluoromethylimidazo[1,2-a]pyridine-7-carboxamide (0.224 g, yield 88%) was obtained in the same manner as in Example 63, using 3-(4,4-difluorocyclohexylmethyl)-2-trifluoromethylimidazo[1,2-a]pyridine-7-carboxylic acid obtained in step 4 of Example 36, and trans-4-hydroxycyclohexaneamine.

¹H NMR (300 MHz, CDCl₃, δ): 8.01 (dd, J=7.3, 0.7 Hz, 1H), 7.91 (dd, J=1.8, 0.7 Hz, 1H), 7.42 (dd, J=7.3, 1.8 Hz, 1H), 6.00 (d, J=7.7 Hz, 1H), 4.04-3.91 (m, 1H), 3.73-3.64 (m, 1H), 3.03 (d, J=7.0 Hz, 2H), 2.19-2.01 (m, 6H), 1.85-1.26 (m, 12H); ESIMS m/z: [M+H]⁺ 460.

Step 2

3-(4,4-Difluorocyclohexylmethyl)-N-(4-hydroxycyclohexyl)-2-trifluoromethylimidazo[1,2-a]pyridine-7-carboxamide (0.050 g, 0.109 mmol) obtained in step 1 was dissolved in 1,2-dichloromethane (1.0 mL). Under ice-cooled condition, bis(2-methoxyethyl)aminosulfur trifluoride (0.060 g, 0.271 mmol) was added, and the mixture was stirred overnight at room temperature. After adding a saturated sodium hydrogen carbonate aqueous solution to the reaction mixture, the mixture was filtered through a Presep (registered trademark; diatomaceous earth, granular type M, 4.5 g/25 mL), and the solvent was evaporated under reduced pressure. The residue was purified by silica gel column chromatography (chloroform/methanol=95/5→90/10) to give compound 180 (16.0 mg, yield 27%).

¹H NMR (300 MHz, CDCl₃, δ): 8.02 (d, J=7.3 Hz, 1H), 7.94 (d, J=1.5 Hz, 1H), 7.46 (dd, J=7.3, 1.5 Hz, 1H), 6.28 (d, J=8.1 Hz, 1H), 5.82-5.74 (m, 1H), 5.73-5.63 (m, 1H), 4.47-4.33 (m, 1H), 3.04 (d, J=7.0 Hz, 2H), 2.35-1.40 (m, 15H); ESIMS m/z: [M+H]⁺ 442.

Example 88

5-Chloro-3-(4,4-difluorocyclohexylmethyl)-N-(2-hydroxy-2-methylpropyl)-2-trifluoromethylimidazo[1,2-a]pyridine-7-carboxamide (Compound 182)

5-Chloro-3-(4,4-difluorocyclohexylmethyl)-2-trifluoromethylimidazo[1,2-a]pyridine-7-carboxylic acid (28 mg, 0.093 mmol) obtained in step 3 of Example 61 was dissolved in N,N-dimethylformamide (2.0 mL), and the solution was stirred overnight at room temperature after adding EDC.HCl (36 mg, 0.187 mmol), HOBt.H₂O (29 mg, 0.187 mmol), and 1-amino-2-methylpropan-2-ol (17 mg, 0.187 mmol). The mixture was extracted with ethyl acetate after adding a sodium hydrogen carbonate aqueous solution. The organic layer was washed with water and saturated brine, and dried over anhydrous sodium sulfate. The solvent was then evaporated under reduced pressure. The residue was purified by preparative thin-layer chromatography (chloroform/methanol=9/1) to give compound 182 (40.4 mg, 85%).

¹H NMR (400 MHz, CDCl₃, δ): 7.95 (s, 1H), 7.46 (s, 1H), 6.60 (br s, 1H), 3.49 (d, J=5.9 Hz, 2H), 3.35 (d, J=6.9 Hz, 2H), 1.97-1.56 (m, 9H), 1.31 (s, 6H); ESIMS m/z: [M+H]⁺ 468.

Example 89

3-(4,4-Difluorocyclohexylmethyl)-5-methyl-2-propionyl-N-(tetrahydro-2H-pyran-4-yl)imidazo[1,2-a]pyridine-7-carboxamide (Compound 183)

Step 1

Compound 99 (0.175 g, 0.417 mmol) was dissolved in isobutyl alcohol (1 mL), and the solution was stirred overnight under heat and reflux after adding a 10 mol/L potassium hydroxide aqueous solution (0.417 mL, 4.27 mmol). The reaction mixture was extracted with water after adding diethyl ether. Then, 3 mol/L hydrochloric acid (1.4 mL) was added to the aqueous layer, and the mixture was extracted with a chloroform-isopropanol mixed solvent (6:1). The organic layer was washed with saturated brine, and dried over anhydrous sodium sulfate. The solvent was evaporated under reduced pressure to give a crude product of 3-(4,4-difluorocyclohexylmethyl)-5-methyl-2-propionylimidazo[1,2-a]pyridine-7-carboxylic acid (53.8 mg, yield 35%).

¹H NMR (300 MHz, CDCl₃, δ): 8.33 (s, 1H), 7.16 (s, 1H), 3.59 (d, J=6.6 Hz, 2H), 3.26 (q, J=7.3 Hz, 2H), 2.89 (s, 3H), 2.14-1.45 (m, 10H), 1.23 (t, J=7.3 Hz, 3H); ESIMS m/z: [M+H]⁺ 365.

Step 2

Compound 183 (58.0 mg, yield 94%) was obtained in the same manner as in step 4 of Example 49, using 3-(4,4-difluorocyclohexylmethyl)-5-methyl-2-propionylimidazo[1,2-a]pyridine-7-carboxylic acid obtained in step 1, and 4-aminotetrahydropyran hydrochloride.

¹H NMR (300 MHz, CDCl₃, δ): 7.83 (s, 1H), 7.04 (s, 1H), 6.22 (d, J=7.3 Hz, 1H), 4.27-4.09 (m, 1H), 4.06-3.96 (m, 2H), 3.61-3.44 (m, 4H), 3.28-3.17 (m, 2H), 2.88 (s, 3H), 2.13-1.96 (m, 4H), 1.73-1.41 (m, 9H), 1.26-1.17 (m, 3H); ESIMS m/z: [M+H]⁺ 448.

The following compounds were synthesized according to the synthesis method of the above compound 14.

2-tert-Butyl-3-cyclohexylmethyl-N-(1-methylpyridin-2(1H)-on-5-yl)imidazo[1,2-a]pyridine-7-carboxamide (compound 66); ESIMS m/z: [M+H]⁺ 421.

2-tert-Butyl-N-(4,4-difluorocyclohexyl)-3-{(4-tetrahydro-2H-pyran-4-yl)methyl}imidazo[1,2-a]pyridine-7-carboxamide (compound 67); ESIMS m/z: [M+H]⁺ 434.

The following compound was synthesized according to the synthesis method of the above compound 28.

N-{3-(4,4-Difluorocyclohexylmethyl)-2-trifluoromethylimidazo[1,2-a]pyridin-7-yl}benzamide (compound 126); ESIMS m/z: [M+H]+ 438.

The following compound was synthesized according to the synthesis method of the above compound 33.

2-{3-(4,4-Difluorocyclohexylmethyl)-5-methyl-2-trifluoromethylimidazo[1,2-a]pyridin-7-yl}-1H-benzimidazole (compound 127); ESIMS m/z: [M+H]+ 449.

The following compounds were synthesized according to the synthesis method of the above compound 36.

N-(3-Cyclopropylisooxazol-5-yl)-3-(4,4-difluorocyclohexylmethyl)-2-trifluoromethylimidazo[1,2-a]pyridine-7-carboxamide (compound 49); ESIMS m/z: [M+H]+ 469.

N-Cyclobutyl-3-(4,4-difluorocyclohexylmethyl)-2-trifluoromethylimidazo[1,2-a]pyridine-7-carboxamide (compound 50); ESIMS m/z: [M+H]+ 416.

N-(3,3-Difluorocyclobutyl)-3-(4,4-difluorocyclohexylmethyl)-2-trifluoromethylimidazo[1,2-a]pyridine-7-carboxamide (compound 51); ESIMS m/z: [M+H]+ 452.

3-(4,4-Difluorocyclohexylmethyl)-N-(4-methyltetrahydro-2H-pyran-4-yl)-2-trifluoromethylimidazo[1,2-a]pyridine-7-carboxamide (compound 52); ESIMS m/z: [M+H]+ 460.

3-(4,4-Difluorocyclohexylmethyl)-N-(3,3-dimethyltetrahydro-2H-pyran-4-yl)-2-trifluoromethylimidazo[1,2-a]pyridine-7-carboxamide (compound 53); ESIMS m/z: [M+H]+ 474.

3-(4,4-Difluorocyclohexylmethyl)-N-(2,2-dimethyltetrahydro-2H-pyran-4-yl)-2-trifluoromethylimidazo[1,2-a]pyridine-7-carboxamide (compound 54); ESIMS m/z: [M+H]+ 474.

N-Cyclopropylmethyl-3-(4,4-difluorocyclohexylmethyl)-2-trifluoromethylimidazo[1,2-a]pyridine-7-carboxamide (compound 55); ESIMS m/z: [M+H]+ 416.

3-(4,4-Difluorocyclohexylmethyl)-N-{(3-ethyloxetan-3-yl)methyl}-2-trifluoromethylimidazo[1,2-a]pyridine-7-carboxamide (compound 56); ESIMS m/z: [M+H]+ 460.

3-(4,4-Difluorocyclohexylmethyl)-N-{(2-methyltetrahydrofuran-2-yl)methyl}-2-trifluoromethylimidazo[1,2-a]pyridine-7-carboxamide (compound 57); ESIMS m/z: [M+H]+ 460.

N-{(4-Cyanotetrahydro-2H-pyran-4-yl)methyl}-3-(4,4-difluorocyclohexylmethyl)-2-trifluoromethylimidazo[1,2-a]pyridine-7-carboxamide (compound 58); ESIMS m/z: [M+H]+ 485.

3-(4,4-Difluorocyclohexylmethyl)-N-[{4-(methoxymethyl)tetrahydro-2H-pyran-4-yl}methyl]-2-trifluoromethylimidazo[1,2-a]pyridine-7-carboxamide (compound 59); ESIMS m/z: [M+H]+ 504.

3-(4,4-Difluorocyclohexylmethyl)-N-{(4-methanesulfonyltetrahydro-2H-pyran-4-yl)methyl}-2-trifluoromethylimidazo[1,2-a]pyridine-7-carboxamide (compound 60); ESIMS m/z: [M+H]+ 538.

3-(4,4-difluorocyclohexylmethyl)-N-methyl-N-(tetrahydro-2H-pyran-4-yl)-2-trifluoromethylimidazo[1,2-a]pyridine-7-carboxamide (compound 61); ESIMS m/z: [M+H]+ 460.

The following compounds were synthesized according to the synthesis method of the above compound 44.

N-(2-Aminophenyl)-3-(4,4-difluorocyclohexylmethyl)-5-methyl-2-trifluoromethylimidazo[1,2-a]pyridine-7-carboxamide (compound 68); ESIMS m/z: [M+H]+ 467.

3-(4,4-Difluorocyclohexylmethyl)-5-methyl-N-(pyrazin-2-yl)-2-trifluoromethylimidazo[1,2-a]pyridine-7-carboxamide (compound 69); ESIMS m/z: [M+H]+ 454.

3-(4,4-Difluorocyclohexylmethyl)-N-(4-hydroxycyclohexyl)-5-methyl-2-trifluoromethylimidazo[1,2-a]pyridine-7-carboxamide (compound 70); ESIMS m/z: [M+H]+ 474.

3-(4,4-Difluorocyclohexylmethyl)-5-methyl-N-(4-oxocyclohexyl)-2-trifluoromethylimidazo[1,2-a]pyridine-7-carboxamide (compound 71); ESIMS m/z: [M+H]+ 472.

N-(4,4-Difluorocyclohexyl)-3-(4,4-difluorocyclohexylmethyl)-5-methyl-2-trifluoromethylimidazo[1,2-a]pyridine-7-carboxamide (compound 72); ESIMS m/z: [M+H]+ 494.

3-(4,4-Difluorocyclohexylmethyl)-5-methyl-N-(tetrahydrofuran-3-yl)-2-trifluoromethylimidazo[1,2-a]pyridine-7-carboxamide (compound 73); ESIMS m/z: [M+H]+ 446.

3-(4,4-Difluorocyclohexylmethyl)-5-methyl-N-(tetrahydro-2H-thiopyran-4-yl)-2-trifluoromethylimidazo[1,2-a]pyridine-7-carboxamide (compound 74); ESIMS m/z: [M+H]+ 476.

3-(4,4-Difluorocyclohexylmethyl)-N-(2,2-dimethyltetrahydro-2H-pyran-4-yl)-5-methyl-2-trifluoromethylimidazo[1,2-a]pyridine-7-carboxamide (compound 75); ESIMS m/z: [M+H]+ 488.

3-(4,4-Difluorocyclohexylmethyl)-5-methyl-N-(tetrahydro-2H-pyran-3-yl)-2-trifluoromethylimidazo[1,2-a]pyridine-7-carboxamide (compound 76); ESIMS m/z: [M+H]+ 460.

3-(4,4-Difluorocyclohexylmethyl)-N-{4-(hydroxymethyl)tetrahydro-2H-pyran-4-yl}-5-methyl-2-trifluoromethylimidazo[1,2-a]pyridine-7-carboxamide (compound 77); ESIMS m/z: [M+H]+ 490.

3-(4,4-Difluorocyclohexylmethyl)-N-(2-hydroxy-2-methylpropyl)-5-methyl-2-trifluoromethylimidazo[1,2-a]pyridine-7-carboxamide (compound 78); ESIMS m/z: [M+H]+ 448.

3-(4,4-Difluorocyclohexylmethyl)-N-(2-methoxy-2-methylpropyl)-5-methyl-2-trifluoromethylimidazo[1,2-a]pyridine-7-carboxamide (compound 79); ESIMS m/z: [M+H]+ 462.

3-(4,4-Difluorocyclohexylmethyl)-N-{(tetrahydrofuran-3-yl)methyl}-5-methyl-2-trifluoromethylimidazo[1,2-a]pyridine-7-carboxamide (compound 80); ESIMS m/z: [M+H]+ 460.

3-(4,4-Difluorocyclohexylmethyl)-5-methyl-N-{(tetrahydro-2H-pyran-4-yl)methyl}-2-trifluoromethylimidazo[1,2-a]pyridine-7-carboxamide (compound 81); ESIMS m/z: [M+H]+ 474.

3-(4,4-Difluorocyclohexylmethyl)-N-{(4-hydroxytetrahydro-2H-pyran-4-ylidyne-7-carboxamide (compound 82); ESIMS m/z: [M+H]+ 490.

3-(4,4-Difluorocyclohexylmethyl)-N-[{4-(dimethylamino)tetrahydro-2H-pyran-4-yl}methyl]-5-methyl-2-trifluoromethylimidazo[1,2-a]pyridine-7-carboxamide (compound 83); ESIMS m/z: [M+H]+ 517.

N-{(4-Cyanotetrahydro-2H-pyran-4-yl)methyl}-3-(4,4-difluorocyclohexylmethyl)-5-methyl-2-trifluoromethylimidazo[1,2-a]pyridine-7-carboxamide (compound 84); ESIMS m/z: [M+H]+ 499.

3-(4,4-Difluorocyclohexylmethyl)-N-[{4-(hydroxymethyl)tetrahydro-2H-pyran-4-yl}methyl]-5-methyl-2-trifluoromethylimidazo[1,2-a]pyridine-7-carboxamide (compound 85); ESIMS m/z: [M+H]+ 504.

3-(4,4-Difluorocyclohexylmethyl)-N-{(4-methoxytetrahydro-2H-pyran-4-yl)methyl}-5-methyl-2-trifluoromethylimidazo[1,2-a]pyridine-7-carboxamide (compound 86); ESIMS m/z: [M+H]+ 504.

3-(4,4-Difluorocyclohexylmethyl)-N-{(4-fluorotetrahydro-2H-pyran-4-yl)methyl}-5-methyl-2-trifluoromethylimidazo[1,2-a]pyridine-7-carboxamide (compound 87); ESIMS m/z: [M+H]+ 492.

3-(4,4-Difluorocyclohexylmethyl)-N-(1,3-dihydroxy-2-methylpropan-2-yl)-5-methyl-2-trifluoromethylimidazo[1,2-a]pyridine-7-carboxamide (compound 88); ESIMS m/z: [M+H]+ 464.

3-(4,4-Difluorocyclohexylmethyl)-5-methyl-N-(tetrahydro-2H-pyran-4-yloxy)-2-trifluoromethylimidazo[1,2-a]pyridine-7-carboxamide (compound 90); ESIMS m/z: [M+H]+ 476.

3-(4,4-Difluorocyclohexylmethyl)-N,5-dimethyl-N-(tetrahydro-2H-pyran-4-yl)-2-trifluoromethylimidazo[1,2-a]pyridine-7-carboxamide (compound 91); ESIMS m/z: [M+H]+ 474.

{3-(4,4-Difluorocyclohexylmethyl)-5-methyl-2-trifluoromethylimidazo[1,2-a]pyridin-7-yl}(4-hydroxypiperidin-1-yl)methanone (compound 92); ESIMS m/z: [M+H]+ 460.

3-(4,4-Difluorocyclohexylmethyl)-8-methyl-N-(tetrahydro-2H-pyran-4-yl)-2-trifluoromethylimidazo[1,2-a]pyridine-7-carboxamide (compound 122); ESIMS m/z: [M+H]+ 460.

The following compound was synthesized according to the synthesis method of the above compound 64.

{3-(4,4-Difluorocyclohexylmethyl)-5-methyl-2-trifluoromethylimidazoimidazo[1,2-a]pyridin-7-yl}{(2-hydroxymethyl)-2-methylaziridin-1-yl}methanone (compound 89); ESIMS m/z: [M+H]+ 446.

The following compounds were synthesized according to the synthesis method of the above compound 65.

6-Chloro-2-cyclobutyl-3-(4,4-difluorocyclohexylmethyl)-N-(tetrahydro-2H-pyran-4-yl)imidazo[1,2-a]pyridine-7-carboxamide (compound 112); ESIMS m/z: [M+H]+ 466, 468.

6-Chloro-3-(4,4-difluorocyclohexylmethyl)-N-(tetrahydro-2H-pyran-4-yl)-2-{1-(trifluoromethyl)cyclopropyl}imidazo[1,2-a]pyridine-7-carboxamide (compound 110); ESIMS m/z: [M+H]+ 520, 522.

6-Chloro-3-(4,4-difluorocyclohexylmethyl)-2-(1-methylcyclopropyl)-N-(tetrahydro-2H-pyran-4-yl)imidazo[1,2-a]pyridine-7-carboxamide (compound 114); ESIMS m/z: [M+H]+ 466, 468.

6-Chloro-3-(4,4-difluorocyclohexylmethyl)-N-(tetrahydro-2H-pyran-4-yl)-2-(1,1,1-trifluoro-2-methylpropan-2-yl)imidazo[1,2-a]pyridine-7-carboxamide (compound 115); ESIMS m/z: [M+H]+ 522, 524.

The following compound was synthesized according to the synthesis method of the above compound 98.

3-(4,4-Difluorocyclohexylmethyl)-N,N-diethyl-5-methyl-2-propionylimidazo[1,2-a]pyridine-7-carboxamide (compound 99); ESIMS m/z: [M+H]+ 420.

The following compounds were synthesized according to the synthesis method of the above compound 102.

5-Chloro-3-(4,4-difluorocyclohexylmethyl)-N-(trans-4-hydroxycyclohexyl)-2-trifluoromethylimidazo[1,2-a]pyridine-7-carboxamide (compound 103); ESIMS m/z: [M+H]+ 494.

5-Chloro-3-(4,4-difluorocyclohexylmethyl)-N-(tetrahydro-2H-pyran-4-yl)-2-trifluoromethylimidazo[1,2-a]pyridine-7-carboxamide (compound 104); ESIMS m/z: [M+H]+ 480.

5-Chloro-3-(4,4-difluorocyclohexylmethyl)-N-(2,2-dimethyltetrahydro-2H-pyran-4-yl)-2-trifluoromethylimidazo[1,2-a]pyridine-7-carboxamide (compound 105); ESIMS m/z: [M+H]+ 508.

5-Chloro-3-(4,4-difluorocyclohexylmethyl)-N-{(tetrahydrofuran-3-yl)methyl}-2-trifluoromethylimidazo[1,2-a]pyridine-7-carboxamide (compound 106); ESIMS m/z: [M+H]+ 480.

The following compounds were synthesized according to the synthesis method of the above compound 107.

6-Chloro-3-(4,4-difluorocyclohexylmethyl)-N-(tetrahydro-2H-pyran-4-yl)-2-trifluoromethylimidazo[1,2-a]pyridine-7-carboxamide (compound 108); ESIMS m/z: [M+H]+ 480, 482.

6-Chloro-3-(4,4-difluorocyclohexylmethyl)-N-(tetrahydro-2H-pyran-4-yloxy)-2-trifluoromethylimidazo[1,2-a]pyridine-7-carboxamide (compound 181); ESIMS m/z: [M+H]+ 496.

The following compound was synthesized according to the synthesis method of the above compound 120.

3-(4,4-Difluorocyclohexylmethyl)-N-(tetrahydro-2H-pyran-4-yl)-2-trifluoromethyl-6-vinylimidazo[1,2-a]pyridine-7-carboxamide (compound 121); ESIMS m/z: [M+H]+ 472.

The following compounds were synthesized according to the synthesis method of the above compound 128.

3-(3,3-Difluoroazetidin-1-ylsulfonyl)-N-(2,2-dimethyltetrahydro-2H-pyran-4-yl)-2-isopropylimidazo[1,2-a]pyridine-7-carboxamide (compound 134); ESIMS m/z: [M+H]+ 471.

N-(Benzyloxy)-3-(3,3-difluoroazetidin-1-ylsulfonyl)-2-isopropylimidazo[1,2-a]pyridine-7-carboxamide (compound 135); ESIMS m/z: [M+H]+ 465.

Indolin-1-yl{2-isopropyl-3-(piperidin-1-ylsulfonyl)imidazo[1,2-a]pyridin-7-yl}methanone (compound 136); ESIMS m/z: [M+H]+ 453.

3-(N-tert-Butylsulfamoyl)-2-isopropyl-N-(4-methyltetrahydro-2H-pyran-4-ylmethyl)imidazo[1,2-a]pyridine-7-carboxamide (compound 137); ESIMS m/z: [M+H]+ 451.

2-Cyclopropyl-3-(3,3-difluoroazetidin-1-ylsulfonyl)-N-phenylimidazo[1,2-a]pyridine-7-carboxamide (compound 138); ESIMS m/z: [M+H]+ 433.

N-Phenyl-3-{N-(tetrahydro-2H-pyran-4-yl)sulfamoyl}-2-trifluoromethylimidazo[1,2-a]pyridine-7-carboxamide (compound 145); ESIMS m/z: [M+H]+ 469.

3-(3,3-Difluoroazetidin-1-ylsulfonyl)-N-phenyl-2-trifluoromethylimidazo[1,2-a]pyridine-7-carboxamide (compound 146); ESIMS m/z: [M+H]+ 461.

3-(N-tert-Butyl-N-methylsulfamoyl)-N-phenyl-2-trifluoromethylimidazo[1,2-a]pyridine-7-carboxamide (compound 147); ESIMS m/z: [M+H]+ 455.

3-(N-tert-Butylsulfamoyl)-6-chloro-2-isopropyl-N-phenylimidazo[1,2-a]pyridine-7-carboxamide (compound 156); ESIMS m/z: [M+H]+ 449.

3-(N-tert-Butylsulfamoyl)-6-chloro-2-isopropyl-N-(3-methylisooxazol-5-yl)imidazo[1,2-a]pyridine-7-carboxamide (compound 157); ESIMS m/z: [M+H]+ 454.

3-(N-tert-Butylsulfamoyl)-6-chloro-N-(3,3-difluorocyclobutyl)-2-isopropylimidazo[1,2-a]pyridine-7-carboxamide (compound 158); ESIMS m/z: [M+H]+ 463.

N-Benzyloxy-3-(N-tert-butylsulfamoyl)-6-chloro-2-isopropylimidazo[1,2-a]pyridine-7-carboxamide (compound 159); ESIMS m/z: [M+H]+ 479.

N-tert-Butyl-6-chloro-7-(indoline-1-carbonyl)-2-trifluoromethylimidazo[1,2-a]pyridine-3-sulfoneamide (compound 160); ESIMS m/z: [M+H]+ 501.

3-(N-tert-Butylsulfamoyl)-6-chloro-N-methyl-N-(tetrahydro-2H-pyran-4-yl)-2-trifluoromethylimidazo[1,2-a]pyridine-7-carboxamide (compound 161); ESIMS m/z: [M+H]+ 497.

2-tert-Butyl-3-(N-tert-butylsulfamoyl)-6-chloro-N-(tetrahydro-2H-pyran-4-yl)imidazo[1,2-a]pyridine-7-carboxamide (compound 162); ESIMS m/z: [M+H]+ 471.

3-(Cyclohexylsulfonyl)-2-isopropyl-6-methyl-N-phenylimidazo[1,2-a]pyridine-7-carboxamide (compound 163); ESIMS m/z: [M+H]+ 440.

3-(4,4-Difluoropiperidin-1-ylsulfonyl)-2-isopropyl-N-methoxy-N,6-dimethylimidazo[1,2-a]pyridine-7-carboxamide (compound 164); ESIMS m/z: [M+H]$^+$ 445.

3-(4,4-Difluoropiperidin-1-ylsulfonyl)-2-isopropyl-6-methyl-N-(pyridin-4-yl)imidazo[1,2-a]pyridine-7-carboxamide (compound 165); ESIMS m/z: [M+H]$^+$ 478.

3-(2-Oxa-6-azaspiro[3.3]heptan-6-ylsulfonyl)-2-isopropyl-6-methyl-N-phenylimidazo[1,2-a]pyridine-7-carboxamide (compound 166); ESIMS m/z: [M+H]$^+$ 455.

3-(2-Oxa-6-azaspiro[3.3]heptan-6-ylsulfonyl)-N,N-(4,4-difluorocyclohexyl)-2-isopropyl-6-methylimidazo[1,2-a]pyridine-7-carboxamide (compound 167); ESIMS m/z: [M+H]$^+$ 497.

3-(N-tert-Butylsulfamoyl)-2-isopropyl-6-methyl-N-phenylimidazo[1,2-a]pyridine-7-carboxamide (compound 168); ESIMS m/z: [M+H]$^+$ 429.

The following compounds were synthesized according to the synthesis method of the above compound 129.

3-(N-Cyclopropyl-N-isopropylsulfamoyl)-2-isopropyl-N-phenylimidazo[1,2-a]pyridine-7-carboxamide (compound 130); ESIMS m/z: [M+H]$^+$ 441.

3-(N,N-Dicyclopropylsulfamoyl)-2-isopropyl-N-phenylimidazo[1,2-a]pyridine-7-carboxamide (compound 131); ESIMS m/z: [M+H]$^+$ 439.

2-Isopropyl-3-(N-methyl-N-phenylsulfamoyl)-N-phenylimidazo[1,2-a]pyridine-7-carboxamide (compound 132); ESIMS m/z: [M+H]$^+$ 449.

3-(3,3-Difluoroazetidin-1-ylsulfonyl)-2-isopropyl-N-phenylimidazo[1,2-a]pyridine-7-carboxamide (compound 133); ESIMS m/z: [M+H]$^+$ 435.

6-Chloro-3-{N-(3,3-difluorocyclobutyl)sulfamoyl}-2-isopropyl-N-phenylimidazo[1,2-a]pyridine-7-carboxamide (compound 154); ESIMS m/z: [M+H]$^+$ 483.

6-Chloro-2-isopropyl-3-{N-(2-methylbut-3-yne-2-yl)sulfamoyl}-N-phenylimidazo[1,2-a]pyridine-7-carboxamide (compound 179); ESIMS m/z: [M+H]$^+$ 459.

The following compound was synthesized according to the synthesis method of the above compound 141.

3-(4,4-Difluoropiperidin-1-ylsulfonyl)-2-methoxy-N-phenylimidazo[1,2-a]pyridine-7-carboxamide (compound 144); ESIMS m/z: [M+H]$^+$ 451.

The following compounds were synthesized according to the synthesis method of the above compound 148.

N-(2-Aminophenyl)-6-chloro-3-(3,3-difluoroazetidin-1-ylsulfonyl)-2-isopropylimidazo[1,2-a]pyridine-7-carboxamide (compound 149); ESIMS m/z: [M+H]$^+$ 484.

6-Chloro-N-cyclopropylmethyl-3-(3,3-difluoroazetidin-1-ylsulfonyl)-2-isopropylimidazo[1,2-a]pyridine-7-carboxamide (compound 150); ESIMS m/z: [M+H]$^+$ 447.

6-Chloro-3-(3,3-difluoroazetidin-1-ylsulfonyl)-N-(3,3-difluorocyclobutyl)-2-isopropylimidazo[1,2-a]pyridine-7-carboxamide (compound 151); ESIMS m/z: [M+H]$^+$ 483.

N-Benzyloxy-6-chloro-3-(3,3-difluoroazetidin-1-ylsulfonyl)-2-isopropylimidazo[1,2-a]pyridine-7-carboxamide (compound 152); ESIMS m/z: [M+H]$^+$ 499.

6-Chloro-3-(3,3-difluoroazetidin-1-ylsulfonyl)-N-(2,2-dimethyltetrahydro-2H-pyran-4-yl)-2-isopropylimidazo[1,2-a]pyridine-7-carboxamide (compound 153); ESIMS m/z: [M+H]$^+$ 505.

6-Chloro-3-(3,3-difluoroazetidin-1-ylsulfonyl)-2-isopropyl-N-phenoxyimidazo[1,2-a]pyridine-7-carboxamide (compound 178); ESIMS m/z: [M+H]$^+$ 485.

The following compounds were synthesized according to the synthesis method of the above compound 171.

N-Cyclohexyl-3-(4,4-difluoropiperidin-1-ylsulfonyl)-2-isopropylimidazo[1,2-a]pyrimidine-7-carboxamide (compound 172); ESIMS m/z: [M+H]$^+$ 470.

3-(4,4-Difluoropiperidin-1-ylsulfonyl)-2-isopropyl-N-(tetrahydro-2H-pyran-4-yl)imidazo[1,2-a]pyrimidine-7-carboxamide (compound 173); ESIMS m/z: [M+H]$^+$ 472.

The following compound was synthesized according to the synthesis method of the above compound 174.

N-{3-(4,4-Difluoropiperidin-1-ylsulfonyl)-2-isopropylimidazo[1,2-c]pyrimidin-7-yl}cyclohexanecarboxamide (compound 175); ESIMS m/z: [M+H]$^+$470.

The following compound was synthesized according to the synthesis method of the above compound 176.

2-(4,4-Difluoropiperidin-1-ylsulfonyl)-3-isopropyl-N-(tetrahydro-2H-pyran-4-yl)imidazo[1,2-a]pyrimidine-7-carboxamide (compound 177); ESIMS m/z: [M+H]$^+$ 472.

Example 90

Tablet (Compound 34)

A tablet of the composition below is prepared using an ordinary method. Compound 34 (40 g), lactose (286.8 g), and potato starch (60 g) are mixed, and a 10% aqueous solution of hydroxypropyl cellulose (120 g) is added thereto. The resulting mixture is kneaded using an ordinary method, and granulated and dried. The mixture is then pulverized to form tableting granules. These are mixed with magnesium stearate (1.2 g) added thereto, and punched with a tableting machine (Kikusui; Model RT-15; 8-mm punch diameter) to obtain tablets (containing 20 mg of active ingredient per tablet).

Formulation

| | |
|---|---|
| Compound 34 | 20 Mg |
| Lactose | 143.4 Mg |
| Potato starch | 30 Mg |
| Hydroxypropyl cellulose | 6 Mg |
| Magnesium stearate | 0.6 Mg |
| | 200 Mg |

Example 91

Injection (Compound 34)

An injection of the composition below is prepared using an ordinary method. Compound 34 (1 g) is added to and mixed with distilled water for injection. After adjusting the pH to 7 by adding hydrochloric acid and a sodium hydroxide aqueous solution, distilled water for injection is used to make the total amount 1,000 mL. The resulting mixture is aseptically charged into glass vials in 2-mL portions to obtain an injection (containing 2 mg of active ingredient per vial).

Formulation

| | |
|---|---|
| Compound 34 | 2 mg |
| Hydrochloric acid | appropriate amount |
| Sodium hydroxide aqueous solution | appropriate amount |
| Distilled water for injection | appropriate amount |
| | 2.00 mL |

INDUSTRIAL APPLICABILITY

The present invention can provide a novel ring-fused heterocyclic derivative or a pharmaceutically acceptable salt thereof having a T-type calcium channel regulatory effect and useful as a therapeutic and/or preventive agent for pruritus, and the like. The present invention also can provide a T-type calcium channel inhibitor containing a ring-fused heterocyclic derivative or a pharmaceutically acceptable salt thereof as an active ingredient, and the like.

The invention claimed is:

1. A compound represented by the general formula (IA) or a pharmaceutically acceptable salt thereof, (Chemical Formula 37)

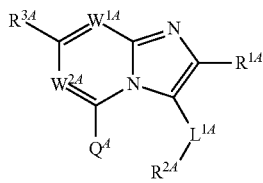

(IA)

wherein $R^{1A}$ represents optionally substituted lower alkyl, optionally substituted lower alkenyl, optionally substituted cycloalkyl, optionally substituted lower alkoxy, an optionally substituted aromatic heterocyclic group, an optionally substituted aliphatic heterocyclic group, optionally substituted aralkyl, —C(=O)R$^4$ (wherein R$^4$ represents optionally substituted lower alkyl, optionally substituted aralkyl, optionally substituted cycloalkyl, or an optionally substituted aliphatic heterocyclic group), —C(=O)OR$^4$ (wherein R$^4$ has the same definition as described above), —C(=O)NR$^5$R$^6$ (wherein R$^5$ and R$^6$ may be the same or different, and each represents a hydrogen atom, optionally substituted lower alkyl, or optionally substituted aralkyl), —NR$^7$C(=O)OR$^4$ (wherein R$^4$ has the same definition as described above, and R$^7$ represents a hydrogen atom, or optionally substituted lower alkyl), or —S(O)nR$^4$ (wherein R$^4$ has the same definition as described above, and n represents an integer of 0 to 2), $R^{2A}$ represents an optionally substituted cycloalkyl, optionally substituted aryl, an optionally substituted aromatic heterocyclic group, or an optionally substituted aliphatic heterocyclic group, $Q^A$ represents a hydrogen atom, halogen, or optionally substituted lower alkyl, $R^{3A}$ represents (i) —C(=O)NHR$^{9A}$, wherein R$^{9A}$ represents a hydrogen atom, optionally substituted lower alkyl, optionally substituted lower alkenyl, optionally substituted cycloalkyl, optionally substituted cycloalkenyl, optionally substituted aralkyl, optionally substituted aryl, an optionally substituted aromatic heterocyclic group, an optionally substituted aliphatic heterocyclic group, or —OR$^{10}$ (wherein R$^{10}$ represents optionally substituted lower alkyl, optionally substituted lower alkenyl, optionally substituted cycloalkyl, optionally substituted aralkyl, optionally substituted aryl, an optionally substituted aromatic heterocyclic group, or an optionally substituted aliphatic heterocyclic group), (ii) —C(=O)NR$^{7A}$—NR$^{7B}$C(=O)R$^{10}$ (wherein R$^{7A}$ and R$^{7B}$ may be the same or different, and each has the same definition as the above R$^7$, and R$^{10}$ has the same definition as described above), (iii) —NHC(=O)R$^{10}$ (wherein R$^{10}$ has the same definition as described above), (iv) —NHC(=O)NR$^{8A}$R$^{9A}$ (wherein R$^{8A}$ and R$^{9A}$ may be the same or different, and have the same definition as the above R$^{9A}$), (v) —NR$^{7A}$C(=O)OR$^{10}$ (wherein R$^{7A}$ and R$^{10}$ have the same definitions as described above, respectively), (vi) —SO$_2$NR$^{8A}$R$^{9A}$ (wherein R$^{8A}$ and R$^{9A}$ may be the same or different, and each has the same definition as the above R$^{9A}$), (vii) —NHSO$_2$R$^{10}$ (wherein R$^{10}$ has the same definition as described above), (viii) —NHSO$_2$NR$^{8A}$R$^{9A}$ (wherein R$^{8A}$ and R$^{9A}$ may be the same or different, and each has the same definition as the above R$^{9A}$), or (ix) optionally substituted benzimidazol-2-yl, $L^{1A}$ represents —CR$^{11A}$R$^{11B}$— (wherein R$^{11A}$ and R$^{11B}$ may be the same or different, and each represents a hydrogen atom, optionally substituted lower alkyl, halogen, optionally substituted lower alkoxy, or hydroxy), or —(CR$^{11A}$R$^{11B}$)n$^1$-L$^2$- (wherein R$^{11A}$ and R$^{11B}$ may be the same or different, and each represents a hydrogen atom, optionally substituted lower alkyl, halogen, optionally substituted lower alkoxy, or hydroxy, n$^1$ represents an integer of 0 to 1, and L$^2$ represents —C(=O)—, —O—, —S(O)n$^2$- (wherein n$^2$ represents an integer of 0 to 1), or —SO$_2$NR$^{7C}$— (wherein R$^{7C}$ represents a hydrogen atom, optionally substituted lower alkyl, or optionally substituted cycloalkyl), and $W^{1A}$ and $W^{2A}$ may be the same or different, and each represents C—R$^{12}$ (wherein R$^{12}$ represents a hydrogen atom, halogen, optionally substituted lower alkyl, optionally substituted cycloalkyl, optionally substituted lower alkoxy, or optionally substituted lower alkenyl).

2. The compound or a pharmaceutically acceptable salt thereof according to claim 1, wherein $R^{1A}$ is optionally substituted lower alkyl or optionally substituted cycloalkyl.

3. The compound or a pharmaceutically acceptable salt thereof according to claim 1, wherein $R^{1A}$ is optionally substituted lower alkyl.

4. The compound or a pharmaceutically acceptable salt thereof according to claim 1, wherein $R^{1A}$ is halogen-substituted lower alkyl.

5. The compound or a pharmaceutically acceptable salt thereof according to claim 1, wherein $R^{1A}$ is optionally substituted cycloalkyl.

6. The compound or a pharmaceutically acceptable salt thereof according to claim 1, wherein $R^{2A}$ is optionally substituted cycloalkyl.

7. The compound or a pharmaceutically acceptable salt thereof according to claim 1, wherein $R^{2A}$ is an optionally substituted aliphatic heterocyclic group.

8. The compound or a pharmaceutically acceptable salt thereof according to claim 1, wherein $L^{1A}$ is —CR$^{11A}$R$^{11B}$— (wherein R$^{11A}$ and R$^{11B}$ may be the same or different, and have the same definitions as described above, respectively).

9. The compound or a pharmaceutically acceptable salt thereof according to claim 8, wherein $R^{11A}$ and $R^{11B}$ are hydrogen atoms.

10. The compound or a pharmaceutically acceptable salt thereof according to claim 1, wherein $L^{1A}$ is —(CR$^{11A}$R$^{11B}$)n$^1$-L$^2$- (wherein R$^{11A}$, R$^{11B}$, n$^1$, and L$^2$ have the same definitions as described above, respectively).

11. The compound or a pharmaceutically acceptable salt thereof according to claim 10, wherein n$^1$ is 0.

12. The compound or a pharmaceutically acceptable salt thereof according to claim 10, wherein n$^1$ is 1.

13. The compound or a pharmaceutically acceptable salt thereof according to claim 10, wherein L$^2$ is —O—.

14. The compound or a pharmaceutically acceptable salt thereof according to claim 10, wherein L$^2$ is —S(O)n$^2$- (wherein n$^2$ has the same definition as described above).

15. The compound or a pharmaceutically acceptable salt thereof according to claim 14, wherein n$^2$ is 2.

16. The compound or a pharmaceutically acceptable salt thereof according to claim 10, wherein $L^2$ is —SO$_2$NR$^{7C}$— (wherein R$^{7c}$ has the same definition as described above).

17. The compound or a pharmaceutically acceptable salt thereof according to claim 1, wherein Q$^4$ is a hydrogen atom.

18. The compound or a pharmaceutically acceptable salt thereof according to claim 1, wherein Q$^4$ is halogen.

19. The compound or a pharmaceutically acceptable salt thereof according to claim 1, wherein Q$^4$ is optionally substituted lower alkyl.

20. The compound or a pharmaceutically acceptable salt thereof according to claim 1, wherein R$^{3A}$ is —NHC(=O)R$^{10}$ (wherein R$^{10}$ has the same definition as described above).

21. The compound or a pharmaceutically acceptable salt thereof according to claim 1, wherein R$^{3A}$ is —C(=O)NHR$^{9A}$ (wherein R$^{9A}$ has the same definition as described above).

22. The compound or a pharmaceutically acceptable salt thereof according to claim 21, wherein R$^{9A}$ is optionally substituted lower alkyl, optionally substituted aryl, an optionally substituted aromatic heterocyclic group, or an optionally substituted aliphatic heterocyclic group.

23. The compound or a pharmaceutically acceptable salt thereof according to claim 21, wherein R$^{9A}$ is optionally substituted lower alkyl.

24. The compound or a pharmaceutically acceptable salt thereof according to claim 21, wherein R$^{9A}$ is optionally substituted aryl.

25. The compound or a pharmaceutically acceptable salt thereof according to claim 21, wherein R$^{9A}$ is an optionally substituted aromatic heterocyclic group.

26. The compound or a pharmaceutically acceptable salt thereof according to claim 21, wherein R$^{9A}$ is an optionally substituted aliphatic heterocyclic group.

27. The compound or a pharmaceutically acceptable salt thereof according to claim 1, wherein W$^{1A}$ is C—R$^{12A}$ (wherein R$^{12A}$ represents a hydrogen atom).

28. The compound or a pharmaceutically acceptable salt thereof according to claim 1, wherein W$^{2A}$ is C—R$^{12B}$ (wherein R$^{12B}$ represents a hydrogen atom).

29. The compound or a pharmaceutically acceptable salt thereof according to claim 1, wherein W$^{2A}$ is C—R$^{12C}$ (wherein R$^{12C}$ represents halogen).

* * * * *